US012668583B2

(12) United States Patent
Lee et al.

(10) Patent No.: US 12,668,583 B2
(45) Date of Patent: Jun. 30, 2026

(54) HETEROCYCLIC COMPOUND AND ORGANIC LIGHT-EMITTING DEVICE COMPRISING SAME

(71) Applicant: LT MATERIALS CO., LTD., Yongin-si (KR)

(72) Inventors: Gi-Back Lee, Yongin-si (KR); Hyun-Ju La, Yongin-si (KR); Won-Jang Jeong, Yongin-si (KR); Dong-Jun Kim, Yongin-si (KR)

(73) Assignee: LT MATERIALS CO., LTD., Yongin-Si (KR)

( * ) Notice: Subject to any disclaimer, the term of this patent is extended or adjusted under 35 U.S.C. 154(b) by 906 days.

(21) Appl. No.: 17/783,448

(22) PCT Filed: Dec. 9, 2020

(86) PCT No.: PCT/KR2020/017902

§ 371 (c)(1),
(2) Date: Jun. 8, 2022

(87) PCT Pub. No.: WO2021/118217

PCT Pub. Date: Jun. 17, 2021

(65) Prior Publication Data

US 2023/0056059 A1 Feb. 23, 2023

(30) Foreign Application Priority Data

Dec. 9, 2019 (KR) ........................ 10-2019-0162705

(51) Int. Cl.
*C07D 401/10* (2006.01)
*C07D 401/14* (2006.01)
(Continued)

(52) U.S. Cl.
CPC ......... *C07D 401/10* (2013.01); *C07D 401/14* (2013.01); *C07D 405/14* (2013.01);
(Continued)

(58) Field of Classification Search
CPC .... C07D 401/10; H10K 85/654; H10K 50/16; H10K 50/18; H10K 50/19
See application file for complete search history.

(56) References Cited

U.S. PATENT DOCUMENTS 4,356,429 A 10/1982 Tang
8,558,223 B2 * 10/2013 Schmid .............. H10K 85/6572 257/40

(Continued)

FOREIGN PATENT DOCUMENTS

CN 110818687 A * 2/2020 ........... C07D 401/10
JP 2006135155 A * 5/2006

(Continued)

OTHER PUBLICATIONS

Machine-generated English-language translation of JP-2006135155-A.*

(Continued)

*Primary Examiner* — Vu A Nguyen
(74) *Attorney, Agent, or Firm* — NKL LAW; Jae Youn Kim

(57) ABSTRACT

The present application provides a heterocyclic compound capable of significantly enhancing lifetime, efficiency, electrochemical stability and thermal stability of an organic light emitting device, and an organic light emitting device comprising the heterocyclic compound in an organic material layer.

7 Claims, 2 Drawing Sheets

(51) Int. Cl.

| | |
|---|---|
| ***C07D 405/14*** | (2006.01) |
| ***C09K 11/06*** | (2006.01) |
| ***H10K 50/16*** | (2023.01) |
| ***H10K 50/18*** | (2023.01) |
| ***H10K 50/19*** | (2023.01) |
| ***H10K 85/60*** | (2023.01) |

(52) U.S. Cl.

CPC ............ *C09K 11/06* (2013.01); *H10K 85/654* (2023.02); *H10K 85/6572* (2023.02); *H10K 85/6574* (2023.02); *C09K 2211/1018* (2013.01); *H10K 50/16* (2023.02); *H10K 50/18* (2023.02); *H10K 50/19* (2023.02)

(56) References Cited

U.S. PATENT DOCUMENTS

| | | | | |
|---|---|---|---|---|
| 9,520,570 | B2 * | 12/2016 | Schmid | H10K 50/165 |
| 2011/0253991 | A1 | 10/2011 | Oyamada et al. | |
| 2011/0309340 | A1 | 12/2011 | Schmid et al. | |
| 2012/0286253 | A1 | 11/2012 | Schmid et al. | |
| 2019/0067593 | A1 | 2/2019 | Cho et al. | |
| 2019/0322642 | A1 * | 10/2019 | Schulze | H10K 50/11 |

FOREIGN PATENT DOCUMENTS

| | | | |
|---|---|---|---|
| JP | 2007-261969 | A | 10/2007 |
| JP | 2016-216421 | A | 12/2016 |
| KR | 10-2011-0084406 | A | 7/2011 |
| KR | 10-2012-0091133 | A | 8/2012 |
| KR | 10-2018-0117650 | A | 10/2018 |

OTHER PUBLICATIONS

International Search Report (PCT/ISA/210) issued in PCT/KR2020/017902, dated Mar. 17, 2021.

Kuwabara et al., “Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenylamino)triphenylamine (m-MTDATA), as Hole-Transport Materials”, Advanced Materials, vol. 6, No. 9, 1994, pp. 677-679.

* cited by examiner

【FIG. 1】
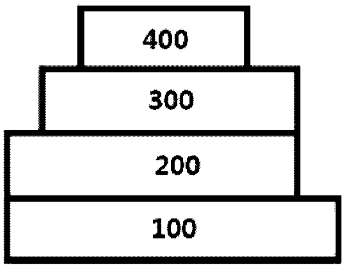
【FIG. 2】
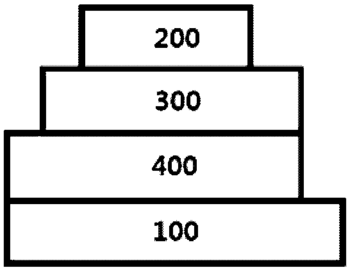

【FIG. 3】
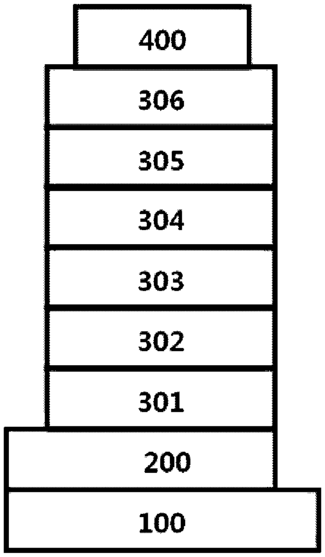
【FIG. 4】
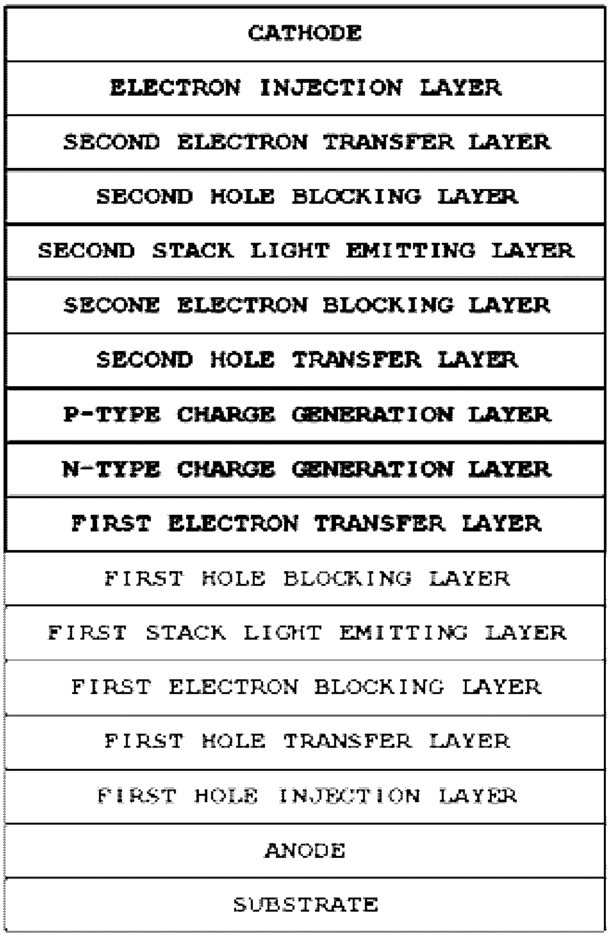

HETEROCYCLIC COMPOUND AND ORGANIC LIGHT-EMITTING DEVICE COMPRISING SAME

TECHNICAL FIELD

The present specification claims priority to and the benefits of Korean Patent Application No. 10-2019-0162705, filed with the Korean Intellectual Property Office on Dec. 9, 2019, the entire contents of which are incorporated herein by reference.

The present specification relates to a heterocyclic compound and an organic light emitting device comprising the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

PRIOR ART DOCUMENTS

Patent Documents (Patent Document 1) U.S. Pat. No. 4,356,429

DISCLOSURE

Technical Problem

The present specification is directed to providing a heterocyclic compound, and an organic light emitting device including the same.

Technical Solution

One embodiment of the present application provides a heterocyclic compound represented by the following Chemical Formula 1.

[Chemical Formula 1]

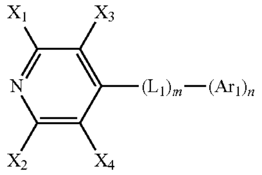

In Chemical Formula 1, $L_1$ is a direct bond; a substituted or unsubstituted arylene group having 6 to 60 carbon atoms; or a substituted or unsubstituted heteroarylene group having 2 to 60 carbon atoms, $X_1$ to $X_4$ are the same as or different from each other, and each independently a substituted or unsubstituted aryl group having 6 to 20 carbon atoms, $Ar_1$ is a substituted or unsubstituted aryl group having 6 to 60 carbon atoms; a substituted or unsubstituted heteroaryl group having 2 to 60 carbon atoms comprising N as a heteroatom; or a substituted or unsubstituted phosphine oxide group, and m and n are each independently an integer of 0 to 2, and when m and n are each 2, substituents in the parentheses are the same as or different from each other.

Another embodiment of the present application provides an organic light emitting device comprising a first electrode; a second electrode; and one or more organic material layers provided between the first electrode and the second electrode, wherein one or more layers of the organic material layers comprise the heterocyclic compound represented by Chemical Formula 1.

Advantageous Effects

A heterocyclic compound described in the present specification can be used as a material of an organic material layer of an organic light emitting device. In the organic light emitting device, the heterocyclic compound is capable of performing a role of a hole injection material, a hole transfer material, a light emitting material, an electron transfer material, an electron injection material or the like. Particularly, the heterocyclic compound can be used as an electron transfer layer material, a hole blocking layer material or a charge generation layer material of the organic light emitting device.

Specifically, when using the heterocyclic compound represented by Chemical Formula 1 in the organic material layer, a driving voltage of the device can be lowered, light efficiency can be enhanced, and lifetime properties of the device can be enhanced.

DESCRIPTION OF DRAWINGS

FIG. 1 to FIG. 4 are diagrams each illustrating a lamination structure of an organic light emitting device according to one embodiment of the present application.

MODE FOR DISCLOSURE

Hereinafter, the present specification will be described in more detail.

In the present specification, a certain part "comprising (including)" certain constituents means capable of further including other constituents, and does not exclude other constituents unless particularly stated on the contrary.

In the present specification, the term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of a linear or branched alkyl group having 1 to 60 carbon atoms; a linear or branched alkenyl group having 2 to 60 carbon atoms; a linear or branched alkynyl group having 2 to 60 carbon atoms; a monocyclic or polycyclic cycloalkyl group having 3 to 60 carbon atoms; a monocyclic or polycyclic heterocycloalkyl group having 2 to 60 carbon atoms; a monocyclic or polycyclic aryl group having 6 to 60 carbon atoms; a monocyclic or polycyclic heteroaryl group having 2 to 60 carbon atoms; a silyl group; a phosphine oxide group; and an amine group, or being unsubstituted, or being substituted with a substituent linking two or more substituents selected from among the substituents illustrated above, or being unsubstituted.

More specifically, "substituted or unsubstituted" in the present specification means being substituted with one or more substituents selected from the group consisting of a monocyclic or polycyclic aryl group having 6 to 60 carbon atoms; or a monocyclic or polycyclic heteroaryl group having 2 to 60 carbon atoms.

In the present specification, the halogen may be fluorine, chlorine, bromine or iodine.

In the present specification, the alkyl group includes linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group includes linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group includes linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may include methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy and the like, but are not limited thereto.

In the present specification, the cycloalkyl group includes monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group includes O, S, Se, N or Si as a heteroatom, includes monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group includes monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group includes a spiro group. The number of carbon atoms of the aryl group may be from 6 to 60, specifically from 6 to 40 and more specifically from 6 to 25. Specific examples of the aryl group may include a phenyl group, a biphenyl group, a terphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the phosphine oxide group is represented by —P(=O)R101R102, and R101 and R102 are the same as or different from each other and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the phosphine oxide may include a diphenylphosphine oxide group, a dinaphthylphosphine oxide group and the like, but are not limited thereto.

In the present specification, the silyl group is a substituent including Si, having the Si atom directly linked as a radical, and is represented by —SiR104R105R106. R104 to R106 are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may include a trimethylsilyl group, a triethylsilyl group, a tert-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

In the present specification, the spiro group is a group including a spiro structure, and may have 15 to 60 carbon atoms. For example, the spiro group may include a structure in which a 2,3-dihydro-1H-indene group or a cyclohexane group spiro bonds to a fluorenyl group. Specifically, the following spiro group may include any one of groups of the following structural formulae.

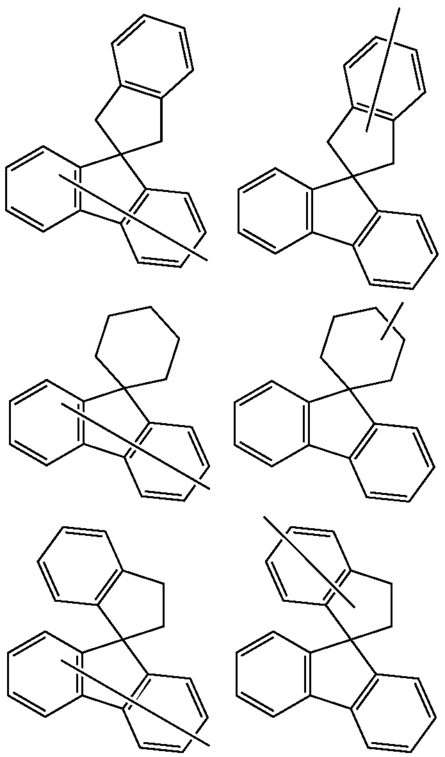

-continued

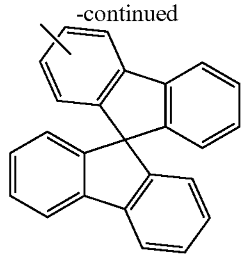

In the present specification, the heteroaryl group includes S, O, Se, N or Si as a heteroatom, includes monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may include a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydro-dibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl group, a pyrazolo[1,5-c]quinazolinyl group, a pyrido[1,2-b]indazolyl group, a pyrido[1,2-a]imidazo[1,2-b]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; $—NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. The descriptions on the aryl group provided above may be applied thereto except for those that are each a divalent group. In addition, the heteroarylene group means the heteroaryl group having two bonding sites, that is, a divalent group. The descriptions on the heteroaryl group provided above may be applied thereto except for those that are each a divalent group.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, a "case of a substituent being not indicated in a chemical formula or compound structure" means that a hydrogen atom bonds to a carbon atom. However, since deuterium ($^2H$) is an isotope of hydrogen, some hydrogen atoms may be deuterium.

In one embodiment of the present application, a "case of a substituent being not indicated in a chemical formula or compound structure" may mean that positions that may come as a substituent may all be hydrogen or deuterium. In other words, since deuterium is an isotope of hydrogen, some hydrogen atoms may be deuterium that is an isotope, and herein, a content of the deuterium may be from 0% to 100%.

In one embodiment of the present application, in a "case of a substituent being not indicated in a chemical formula or compound structure", hydrogen and deuterium may be mixed in the compound when deuterium is not explicitly excluded such as a deuterium content being 0%, a hydrogen content being 100% or substituents being all hydrogen.

In one embodiment of the present application, deuterium is one of isotopes of hydrogen, is an element having deuteron formed with one proton and one neutron as a nucleus, and may be expressed as hydrogen-2, and the elemental symbol may also be written as D or 2H.

In one embodiment of the present application, an isotope means an atom with the same atomic number (Z) but with a different mass number (A), and may also be interpreted as an element with the same number of protons but with a different number of neutrons.

In one embodiment of the present application, a meaning of a content T % of a specific substituent may be defined as T2/T1×100=T % when the total number of substituents that a basic compound may have is defined as T1, and the number of specific substituents among these is defined as T2.

In other words, in one example, having a deuterium content of 20% in a phenyl group represented by

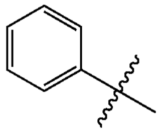 [SMILES: *c1ccccc1]

means that the total number of substituents that the phenyl group may have is 5 (T1 in the formula), and the number of deuterium among these is 1 (T2 in the formula). In other words, having a deuterium content of 20% in a phenyl group may be represented by the following structural formulae.

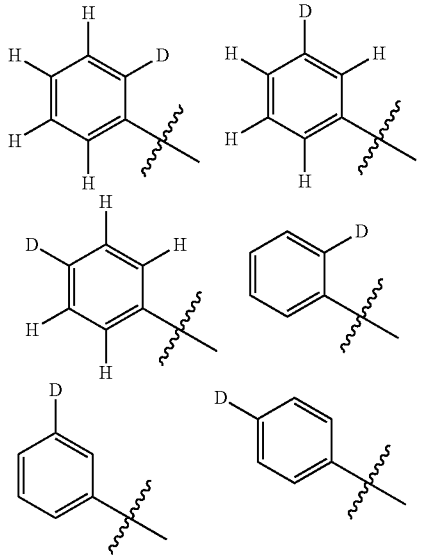

In addition, in one embodiment of the present application, "a phenyl group having a deuterium content of 0%" may mean a phenyl group that does not include a deuterium atom, that is, a phenyl group that has 5 hydrogen atoms.

One embodiment of the present application provides a heterocyclic compound represented by the following Chemical Formula 1.

[Chemical Formula 1]

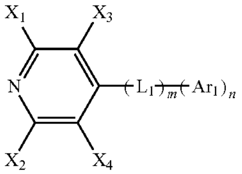

In Chemical Formula 1, $L_1$ is a direct bond; a substituted or unsubstituted arylene group having 6 to 60 carbon atoms; or a substituted or unsubstituted heteroarylene group having 2 to 60 carbon atoms, $X_1$ to $X_4$ are the same as or different from each other, and each independently a substituted or unsubstituted aryl group having 6 to 20 carbon atoms, $Ar_1$ is a substituted or unsubstituted aryl group having 6 to 60 carbon atoms; a substituted or unsubstituted heteroaryl group having 2 to 60 carbon atoms including N as a heteroatom; or a substituted or unsubstituted phosphine oxide group, and m and n are each independently an integer of 0 to 2, and when m and n are each 2, substituents in the parentheses are the same as or different from each other.

The heterocyclic compound represented by Chemical Formula 1 has enhanced hole properties by a specific substituent bonding to the pyridine structure, and accordingly, highest occupied molecular orbital (HOMO) energy level and lowest unoccupied molecular orbital (LUMO) level have an energy level suitable to be used in an organic material layer of a device. In other words, proper energy level and band gap are formed increasing excitons in a light emitting area. Having increased excitons in a light emitting area means being effective in increasing driving voltage and efficiency of a device.

In addition, by having a high T1 value, a device with a long lifetime provided with an excellent hole transfer ability and thermal stability may be obtained. Herein, the T1 value means an energy level value in a triplet state.

In one embodiment of the present application, $L_1$ of Chemical Formula 1 may be a direct bond; a substituted or unsubstituted arylene group; or a substituted or unsubstituted heteroarylene group.

In another embodiment, $L_1$ may be a direct bond; a substituted or unsubstituted arylene group having 6 to 60 carbon atoms; or a substituted or unsubstituted heteroarylene group having 2 to 60 carbon atoms.

In another embodiment, $L_1$ may be a direct bond; a substituted or unsubstituted arylene group having 6 to 40 carbon atoms; or a substituted or unsubstituted heteroarylene group having 2 to 40 carbon atoms.

In another embodiment, $L_1$ may be a direct bond; a substituted or unsubstituted arylene group having 6 to 20 carbon atoms; or a substituted or unsubstituted heteroarylene group having 2 to 20 carbon atoms.

In another embodiment, $L_1$ may be a direct bond; a substituted or unsubstituted phenylene group; a substituted or unsubstituted biphenylene group; a substituted or unsubstituted naphthylene group; or a substituted or unsubstituted anthracenyl group.

In another embodiment, $L_1$ may be a direct bond; a phenylene group; a biphenylene group; a naphthylene group; or an anthracenyl group.

In another embodiment, $L_1$ is a direct bond.

In another embodiment, $L_1$ is a phenylene group.

In another embodiment, $L_1$ is a biphenylene group.

In another embodiment, $L_1$ is a naphthylene group.

In another embodiment, $L_1$ is an anthracenyl group.

In one embodiment of the present application, $X_1$ to $X_4$ of Chemical Formula 1 are the same as or different from each other, and may be each independently a substituted or unsubstituted aryl group having 6 to 20 carbon atoms.

In one embodiment of the present application, $X_1$ to $X_4$ are the same as or different from each other, and may be each independently a substituted or unsubstituted phenyl group; or a substituted or unsubstituted biphenyl group.

In one embodiment of the present application, $X_1$ to $X_4$ are the same as or different from each other, and may be each independently a phenyl group; or a biphenyl group.

In one embodiment of the present application, $X_1$ to $X_4$ are all a phenyl group.

In one embodiment of the present application, $Ar_1$ of Chemical Formula 1 may be a substituted or unsubstituted aryl group having 6 to 60 carbon atoms; a substituted or unsubstituted heteroaryl group having 2 to 60 carbon atoms including N as a heteroatom; or a substituted or unsubstituted phosphine oxide group.

In one embodiment of the present application, $Ar_1$ of Chemical Formula 1 may be a substituted or unsubstituted aryl group having 6 to 40 carbon atoms; a substituted or unsubstituted heteroaryl group having 2 to 60 carbon atoms including N as a heteroatom; or a substituted or unsubstituted phosphine oxide group.

In one embodiment of the present application, $Ar_1$ of Chemical Formula 1 may be a substituted or unsubstituted aryl group having 6 to 40 carbon atoms; a group represented by the following Chemical Formula 2; a substituted or unsubstituted carbazolyl group; or a substituted or unsubstituted phosphine oxide group.

[Chemical Formula 2]

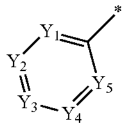

In Chemical Formula 2,

* is a position bonding to $L_1$ of Chemical Formula 1, $Y_1$ to $Y_5$ are the same as or different from each other, and each independently N or CRa, and when CRa is 2 or greater, Ras are the same as or different from each other, and Ras are the same as or different from each other, and each independently selected from the group consisting of hydrogen; deuterium; a substituted or unsubstituted aryl group having 6 to 60 carbon atoms; and a substituted or unsubstituted heteroaryl group having 2 to 60 carbon atoms, or two or more groups adjacent to each other may bond to each other to form a substituted or unsubstituted aromatic hydrocarbon ring having 6 to 60 carbon atoms or a substituted or unsubstituted heteroring having 2 to 60 carbon atoms.

In one embodiment of the present application, at least one or more of $Y_1$ to $Y_5$ of Chemical Formula 2 may be N.

In one embodiment of the present application, when $Y_1$ to $Y_5$ of Chemical Formula 2 are all CRa, the two or more Ras adjacent to each other may bond to each other to form a substituted or unsubstituted aromatic hydrocarbon ring having 6 to 60 carbon atoms or a substituted or unsubstituted heteroring having 2 to 60 carbon atoms, and the aromatic hydrocarbon ring or the heteroring may include at least one or more Ns.

In one embodiment of the present application, Chemical Formula 2 may be represented by any one of the following Chemical Formulae 3 to 5.

[Chemical Formula 3]

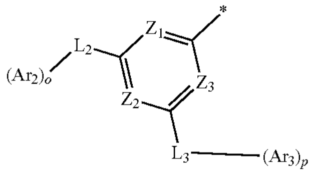

-continued

[Chemical Formula 4]

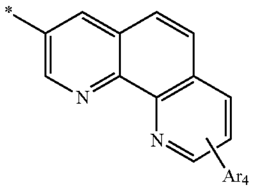

[Chemical Formula 5]

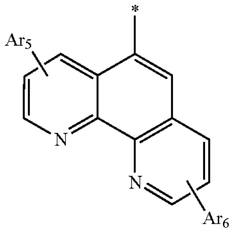

In Chemical Formulae 3 to 5,

* is a position bonding to $L_1$ of Chemical Formula 1, $Z_1$ to $Z_3$ are the same as or different from each other and each independently N or CH, and at least one or more of $Z_1$ to $Z_3$ are N, $L_2$ and $L_3$ are the same as or different from each other, and each independently a direct bond; a substituted or unsubstituted arylene group having 6 to 60 carbon atoms; or a substituted or unsubstituted heteroarylene group having 2 to 60 carbon atoms, $Ar_2$ to $Ar_6$ are the same as or different from each other, and each independently hydrogen; deuterium; a substituted or unsubstituted aryl group having 6 to 60 carbon atoms; or a substituted or unsubstituted heteroaryl group having 2 to 60 carbon atoms, and o and p are each independently an integer of 0 to 2, and when o and p are each 2, substituents in the parentheses are the same as or different from each other.

In one embodiment of the present application, $Z_1$ to $Z_3$ of Chemical Formula 3 are the same as or different from each other and each independently N or CH, and at least one or more of $Z_1$ to $Z_3$ may be N.

In one embodiment of the present application, $Z_1$ is N, and $Z_2$ and $Z_3$ are CH.

In one embodiment of the present application, $Z_2$ is N, and $Z_1$ and $Z_3$ are CH.

In one embodiment of the present application, $Z_3$ is N, and $Z_1$ and $Z_2$ are CH.

In one embodiment of the present application, $Z_1$ is CH, and $Z_2$ and $Z_3$ are N.

In one embodiment of the present application, $Z_2$ is CH, and $Z_1$ and $Z_3$ are N.

In one embodiment of the present application, $Z_3$ is CH, and $Z_1$ and $Z_Z$ are N.

In one embodiment of the present application, $Z_1$ to $Z_3$ are N.

In one embodiment of the present application, $L_2$ and $L_3$ of Chemical Formula 3 are the same as or different from each other, and may be each independently a direct bond; a substituted or unsubstituted arylene group having 6 to 60 carbon atoms; or a substituted or unsubstituted heteroarylene group having 2 to 60 carbon atoms.

In one embodiment of the present application, $L_2$ and $L_3$ are the same as or different from each other, and may be each independently a direct bond; a substituted or unsubstituted arylene group having 6 to 40 carbon atoms; or a substituted or unsubstituted heteroarylene group having 2 to 40 carbon atoms.

In one embodiment of the present application, $L_2$ and $L_3$ are the same as or different from each other, and may be each independently a direct bond; a substituted or unsubstituted arylene group having 6 to 20 carbon atoms; or a substituted or unsubstituted heteroarylene group having 2 to 20 carbon atoms.

In one embodiment of the present application, $L_2$ and $L_3$ are the same as or different from each other, and may be each independently a direct bond; or a substituted or unsubstituted arylene group having 6 to 20 carbon atoms.

In one embodiment of the present application, $L_2$ and $L_3$ are the same as or different from each other, and may be each independently a direct bond; or a substituted or unsubstituted phenylene group.

In one embodiment of the present application, $L_2$ and $L_3$ are the same as or different from each other, and may be each independently a direct bond; or a phenylene group.

In another embodiment, $L_2$ is a direct bond.

In another embodiment, $L_2$ is a phenylene group.

In another embodiment, $L_3$ is a direct bond.

In another embodiment, $L_3$ is a phenylene group.

In one embodiment of the present application, $Ar_2$ and $Ar_3$ of Chemical Formula 3 are the same as or different from each other, and may be each independently hydrogen; deuterium; a substituted or unsubstituted aryl group having 6 to 60 carbon atoms; or a substituted or unsubstituted heteroaryl group having 2 to 60 carbon atoms.

In one embodiment of the present application, $Ar_2$ and $Ar_3$ are the same as or different from each other, and may be each independently a substituted or unsubstituted aryl group having 6 to 60 carbon atoms; or a substituted or unsubstituted heteroaryl group having 2 to 60 carbon atoms.

In one embodiment of the present application, $Ar_2$ and $Ar_3$ are the same as or different from each other, and may be each independently a substituted or unsubstituted aryl group having 6 to 40 carbon atoms; or a substituted or unsubstituted heteroaryl group having 2 to 40 carbon atoms.

In one embodiment of the present application, $Ar_2$ and $Ar_3$ are the same as or different from each other, and may be each independently a substituted or unsubstituted phenyl group; a substituted or unsubstituted biphenyl group; a substituted or unsubstituted terphenyl group; a substituted or unsubstituted triphenyl group; a substituted or unsubstituted dibenzofuran group; a substituted or unsubstituted dibenzothiophene group; or a substituted or unsubstituted carbazolyl group.

In one embodiment of the present application, $Ar_2$ and $Ar_3$ are the same as or different from each other, and may be each independently a phenyl group; a biphenyl group; a terphenyl group; a triphenyl group; a dibenzofuran group; a dibenzothiophene group; or a substituted or unsubstituted carbazolyl group.

In one embodiment of the present application, o and p of Chemical Formula 1 are each independently an integer of 0 to 2, and when o and p are each 2, substituents in the parentheses are the same as or different from each other.

In one embodiment of the present application, o is 2.

In one embodiment of the present application, o is 1.

In one embodiment of the present application, o is 0.

In one embodiment of the present application, when o is 2, substituents in the parentheses are the same as or different from each other.

In one embodiment of the present application, p is 2.

In one embodiment of the present application, p is 1.

In one embodiment of the present application, p is 0.

In one embodiment of the present application, when p is 2, substituents in the parentheses are the same as or different from each other.

In one embodiment of the present application, $Ar_4$ of Chemical Formula 4 may be hydrogen; deuterium; a substituted or unsubstituted aryl group having 6 to 60 carbon atoms; or a substituted or unsubstituted heteroaryl group having 2 to 60 carbon atoms.

In one embodiment of the present application, $Ar_4$ may be hydrogen; deuterium; a substituted or unsubstituted aryl group having 6 to 40 carbon atoms; or a substituted or unsubstituted heteroaryl group having 2 to 40 carbon atoms.

In one embodiment of the present application, $Ar_4$ may be 20 hydrogen; deuterium; a substituted or unsubstituted aryl group having 6 to 20 carbon atoms; or a substituted or unsubstituted heteroaryl group having 2 to 20 carbon atoms.

In one embodiment of the present application, $Ar_4$ may be hydrogen; deuterium; or a substituted or unsubstituted aryl group having 6 to 20 carbon atoms.

In one embodiment of the present application, $Ar_4$ may be hydrogen; deuterium; or a substituted or unsubstituted phenyl group.

In one embodiment of the present application, $Ar_4$ may be hydrogen; deuterium; or a phenyl group.

In one embodiment of the present application, $Ar_5$ and Are of Chemical Formula 5 are the same as or different from each other, and may be each independently hydrogen; deuterium; a substituted or unsubstituted aryl group having 6 to 60 carbon atoms; or a substituted or unsubstituted heteroaryl group having 2 to 60 carbon atoms.

In one embodiment of the present application, $Ar_5$ and Are are the same as or different from each other, and may be each independently hydrogen; deuterium; a substituted or unsubstituted aryl group having 6 to 40 carbon atoms; or a substituted or unsubstituted heteroaryl group having 2 to 40 carbon atoms.

In one embodiment of the present application, $Ar_5$ and $Ar_6$ are the same as or different from each other, and may be each independently hydrogen; deuterium; a substituted or unsubstituted aryl group having 6 to 20 carbon atoms; or a substituted or unsubstituted heteroaryl group having 2 to 20 carbon atoms.

In one embodiment of the present application, $Ar_5$ and $Ar_6$ are the same as or different from each other, and may be each independently hydrogen; deuterium; or a substituted or unsubstituted aryl group having 6 to 20 carbon atoms.

In one embodiment of the present application, $Ar_5$ and $Ar_F$ are the same as or different from each other, and may be each independently hydrogen; deuterium; or a substituted or unsubstituted phenyl group.

In one embodiment of the present application, $Ar_5$ and Are are the same as or different from each other, and may be each independently hydrogen; deuterium; or a phenyl group.

In one embodiment of the present application, m and n of Chemical Formula 1 are each independently an integer of 0 to 2, and when m and n are each 2, substituents in the parentheses are the same as or different from each other.

In one embodiment of the present application, m is 2.

In one embodiment of the present application, m is 1.

In one embodiment of the present application, m is 0.

In one embodiment of the present application, when m is 2, substituents in the parentheses are the same as or different from each other.

In one embodiment of the present application, n is 2.

In one embodiment of the present application, n is 1.

In one embodiment of the present application, n is 0.

In one embodiment of the present application, when n is 2, substituents in the parentheses are the same as or different from each other.

In the heterocyclic compound provided in one embodiment of the present application, Chemical Formula 1 is represented by any one of the following compounds.

1

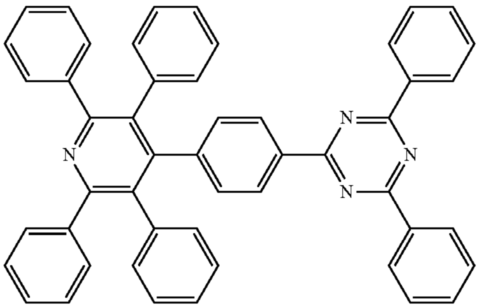

2

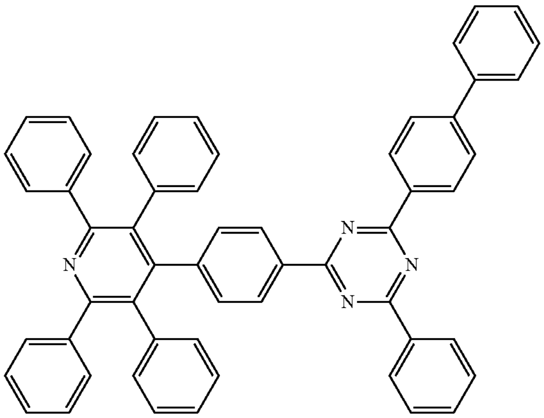

3

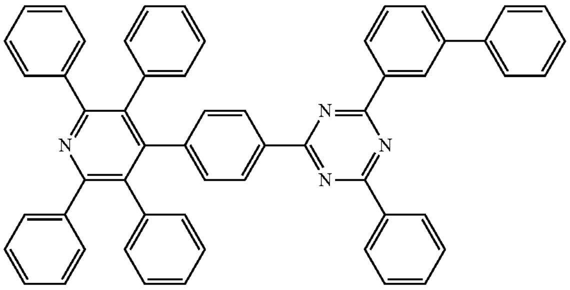

4

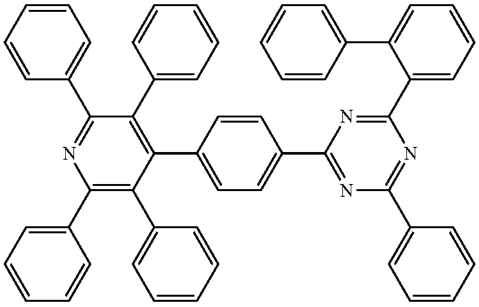

-continued
5
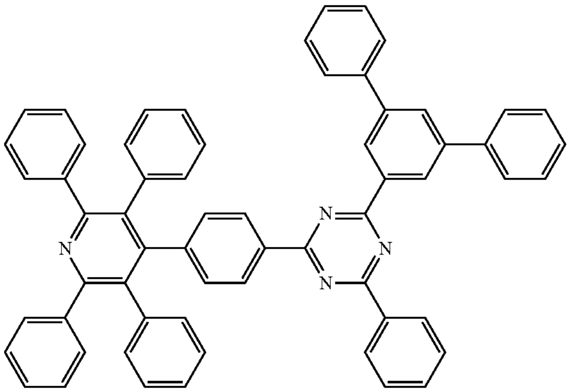
6
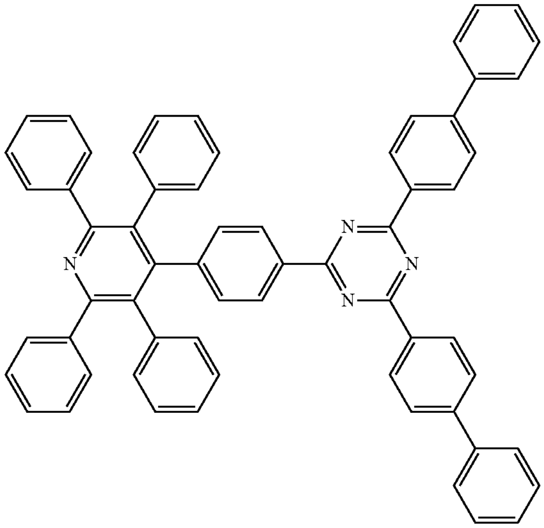
7
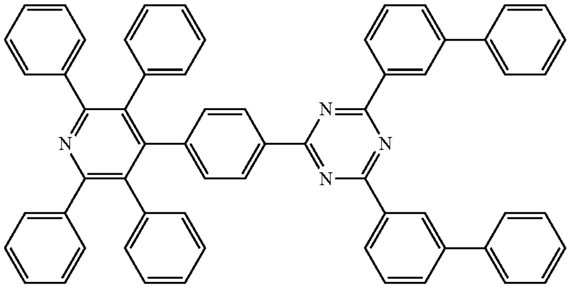
-continued
8
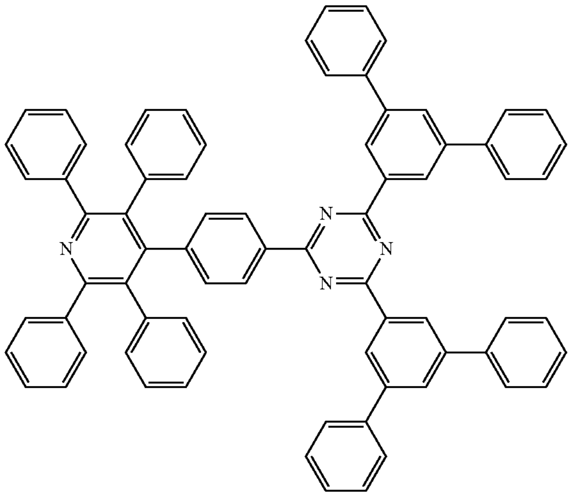
9
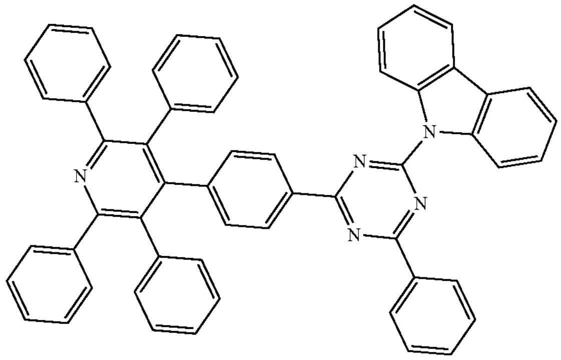
10
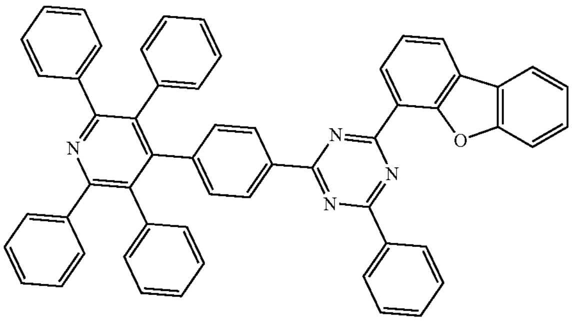
11
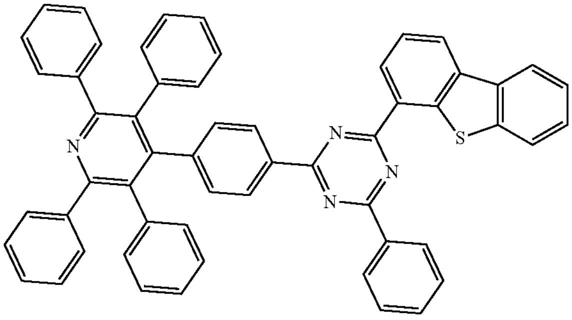

-continued
12
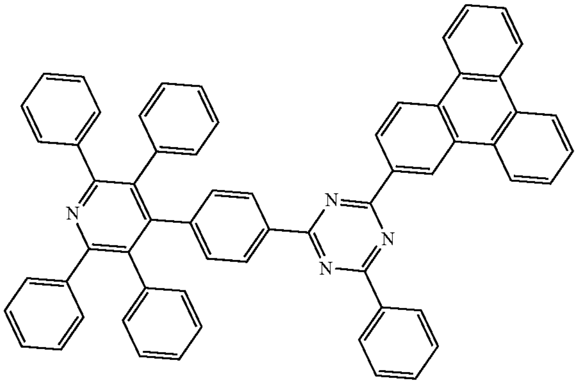
13
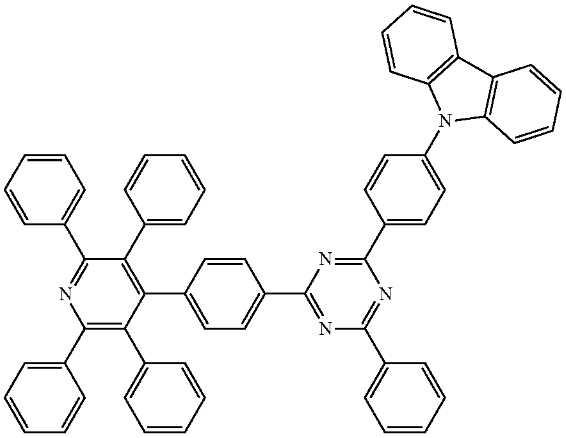
14
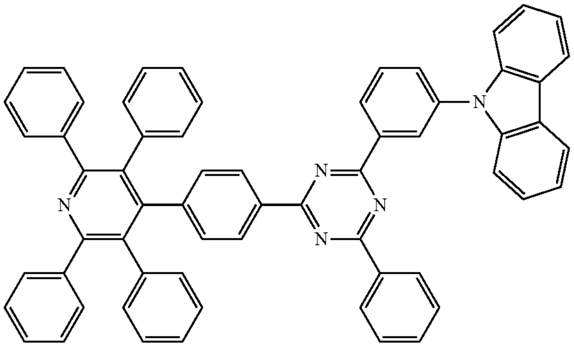
15
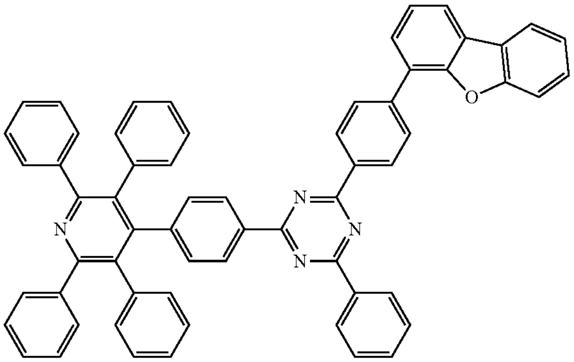
-continued
16
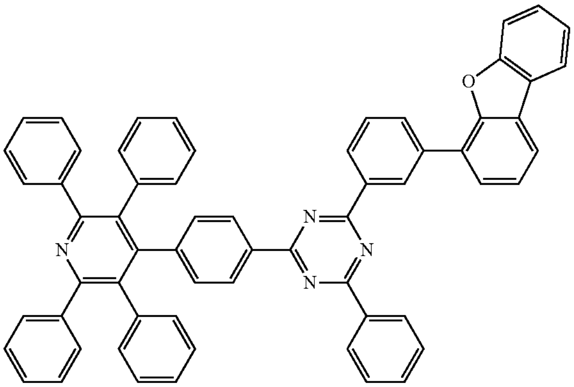
17
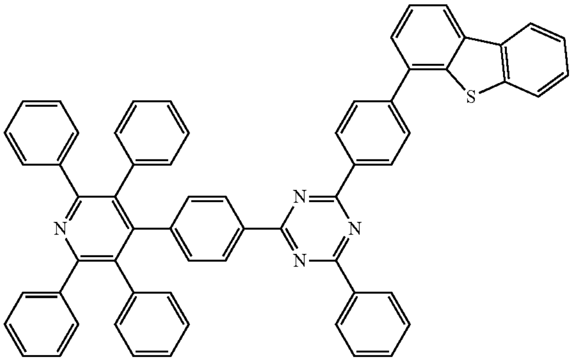
18
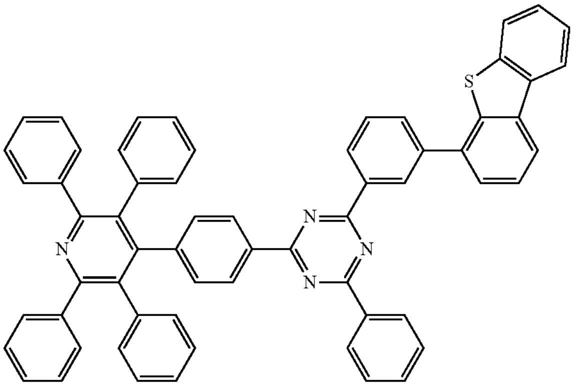
19
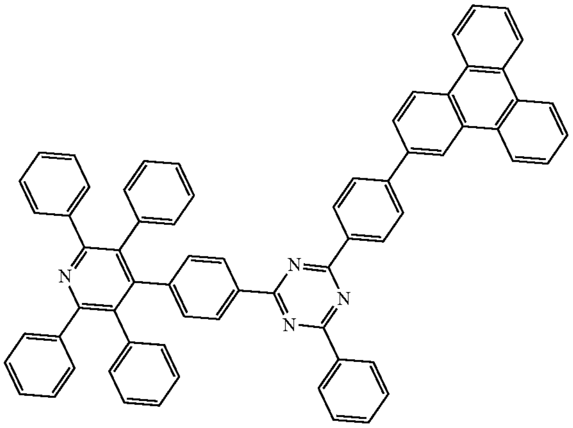

-continued
20
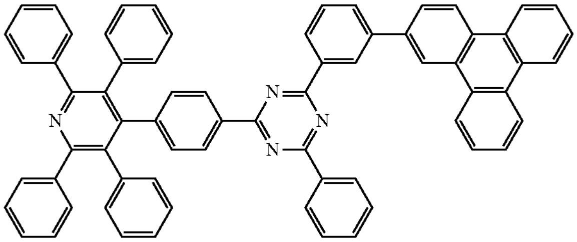
21
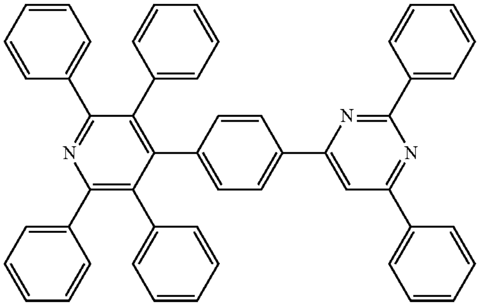
22
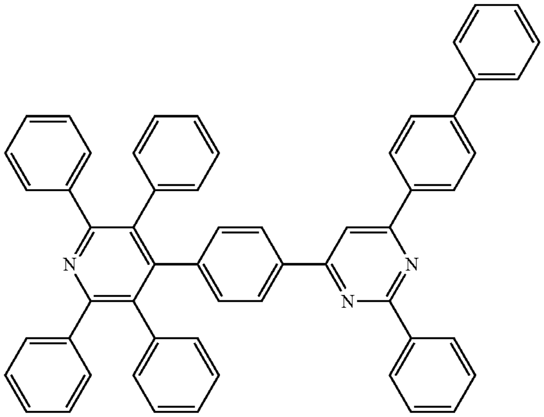
23
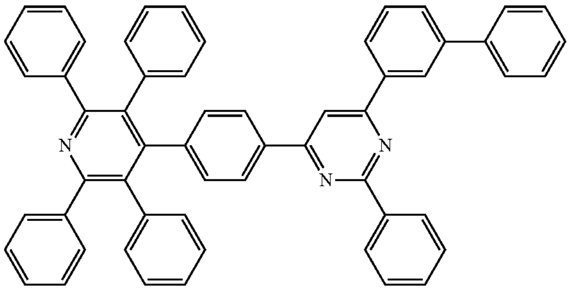
24
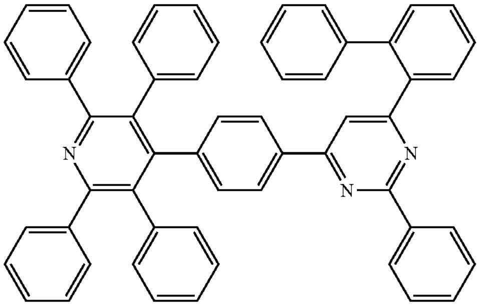
-continued
25
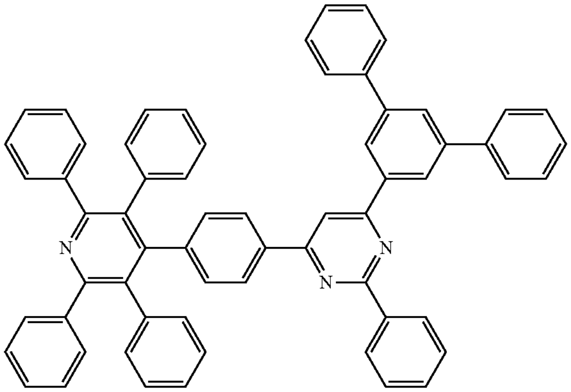
26
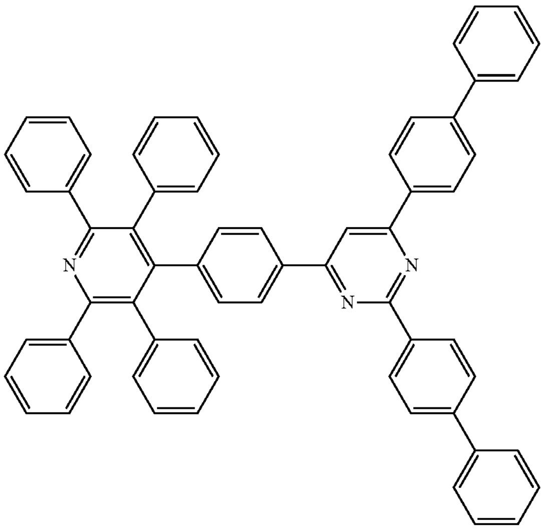
27
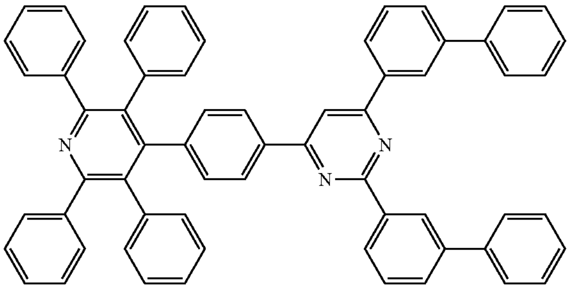

-continued
28
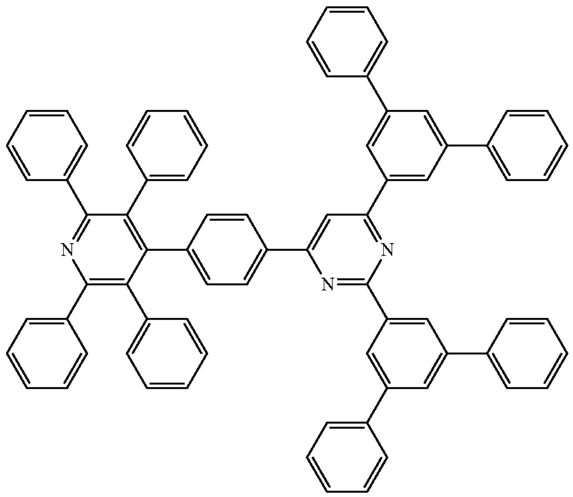
29
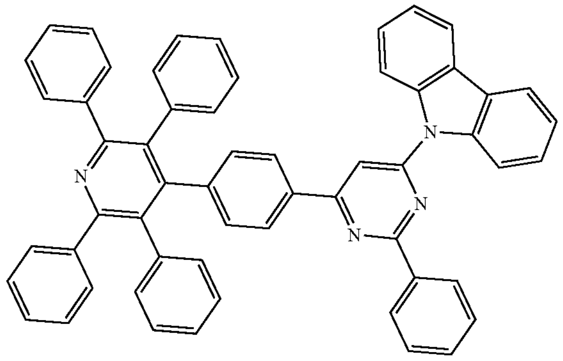
30
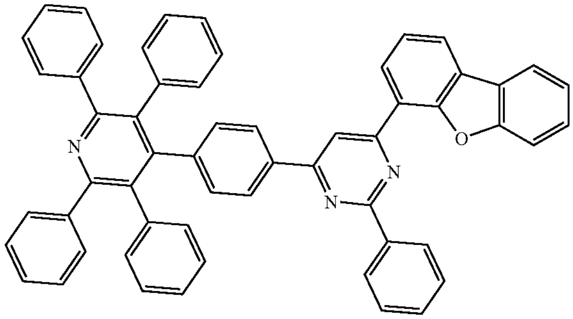
31
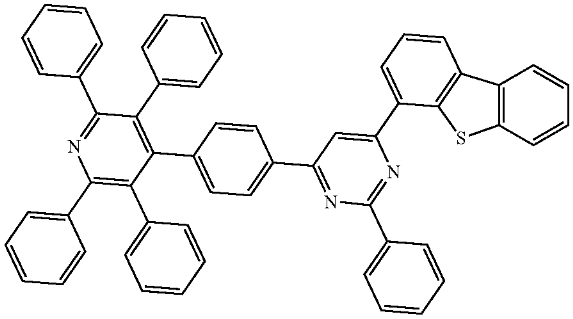
-continued
32
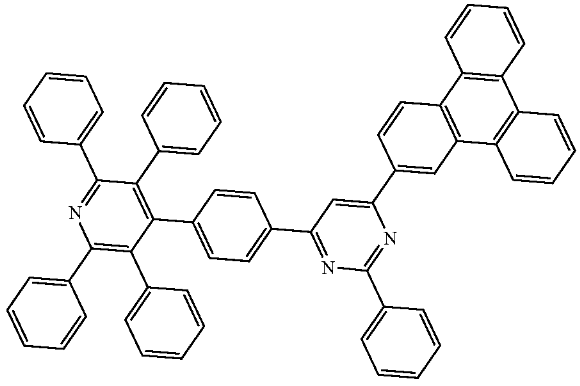
33
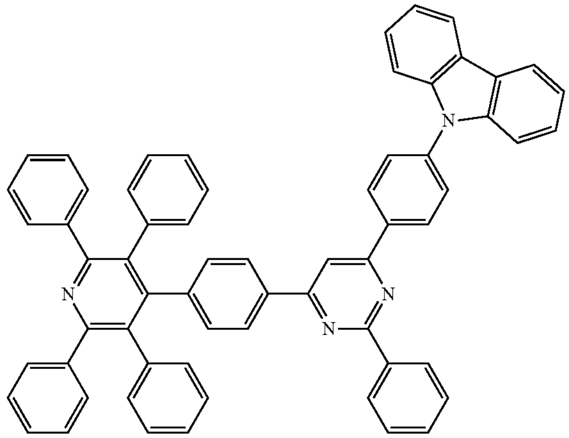
34
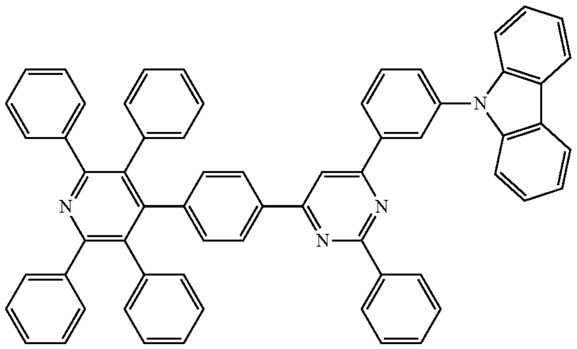
35
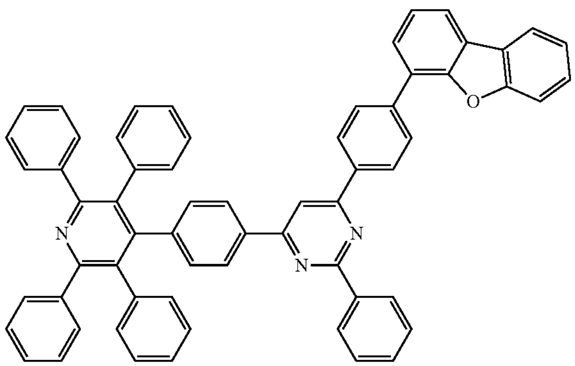

-continued
36
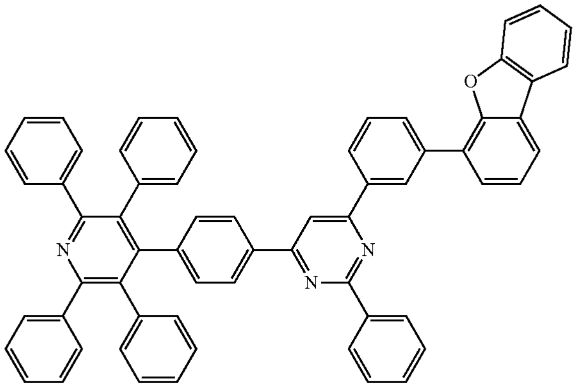
37
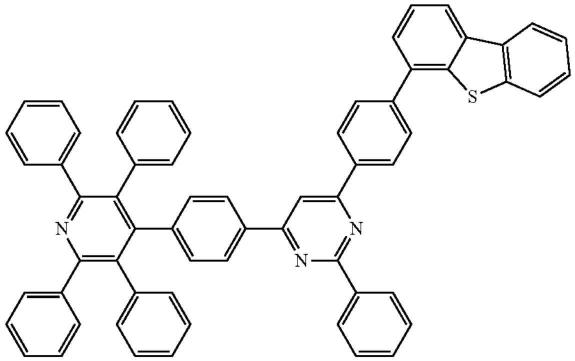
38
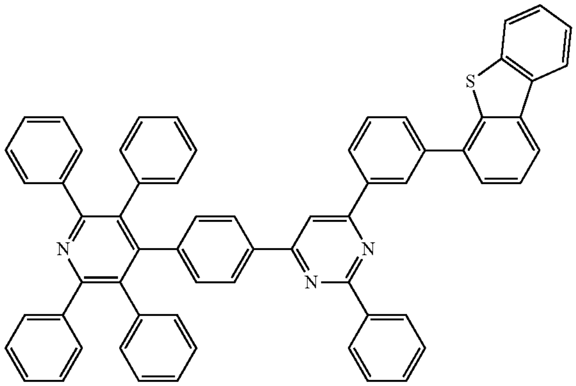
39
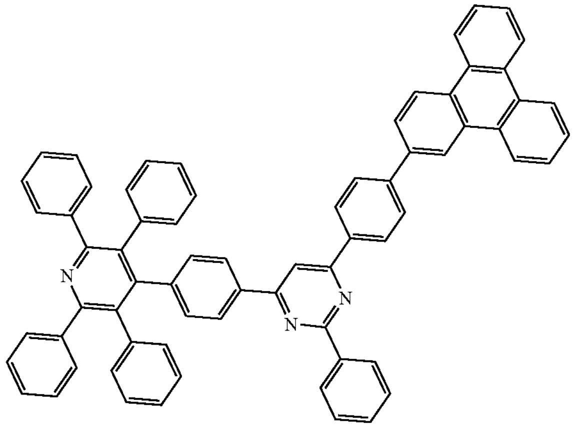
-continued
40
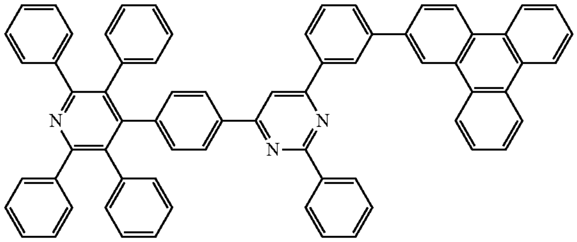
41
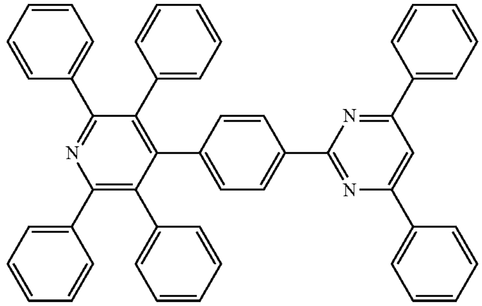
42
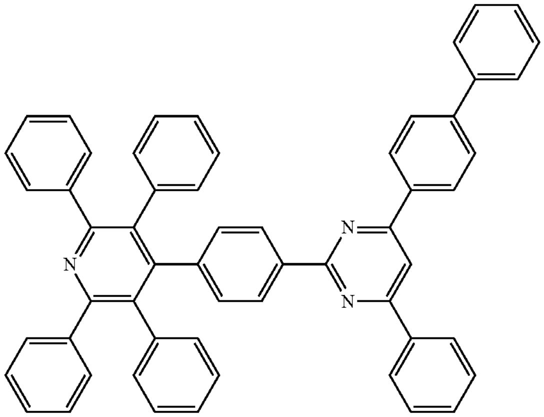
43
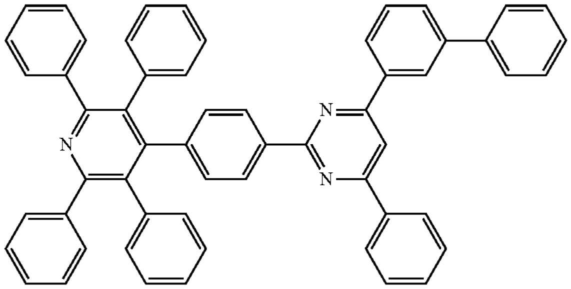
44
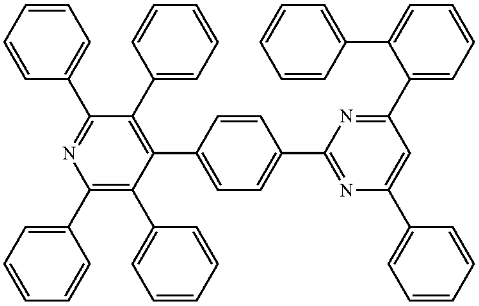

-continued
45
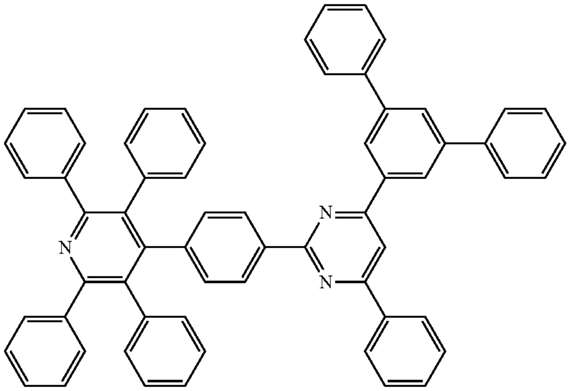
46
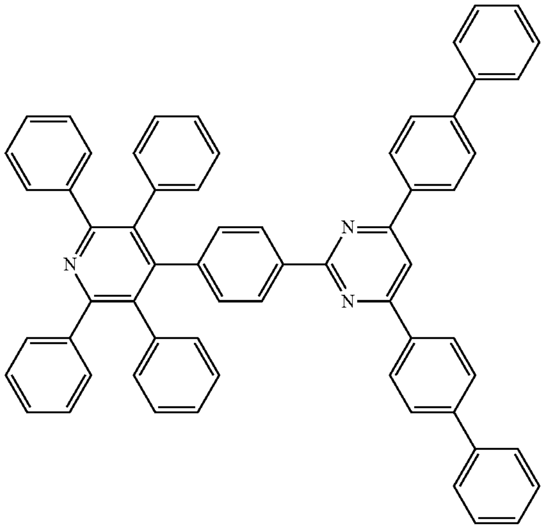
47
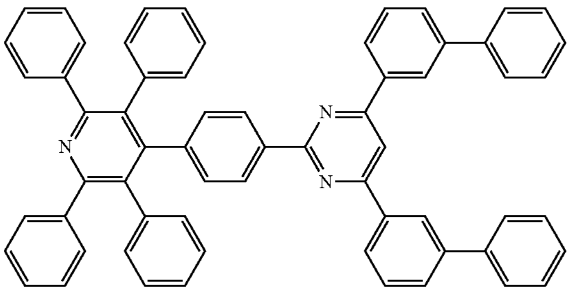
-continued
48
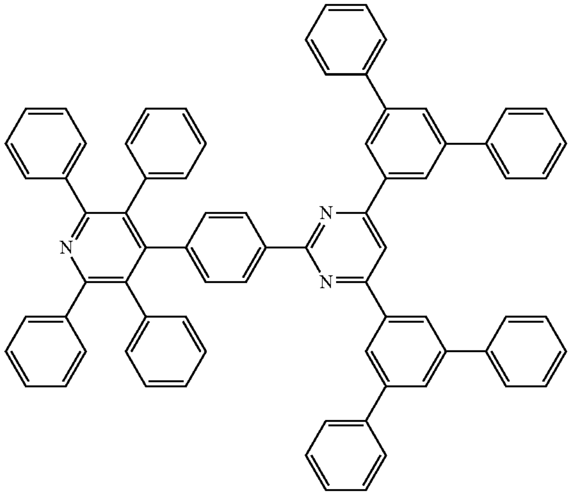
49
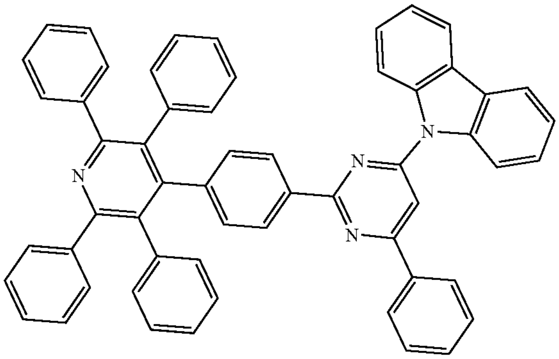
50
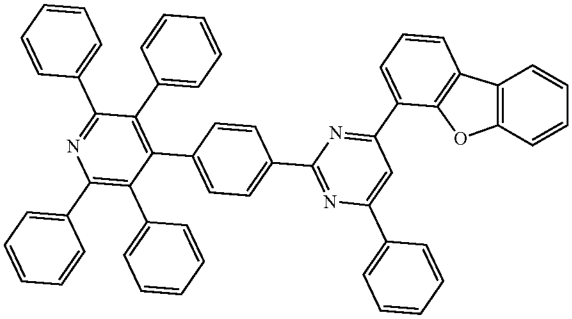
51
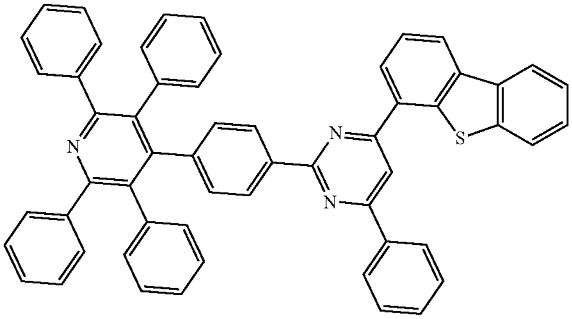

-continued
52
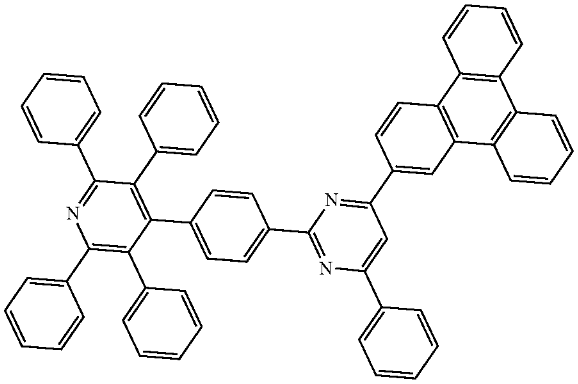
53
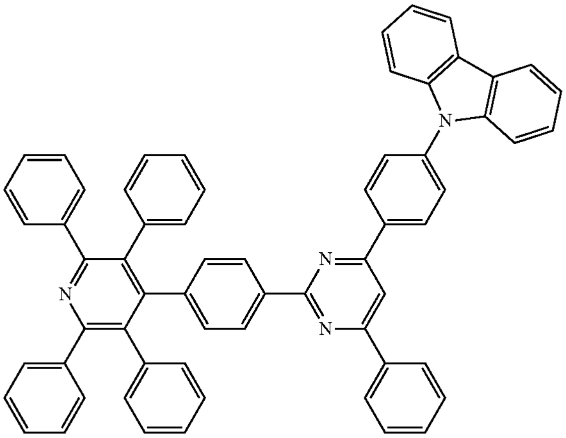
54
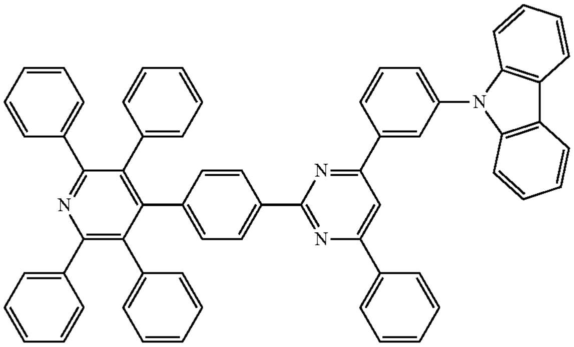
55
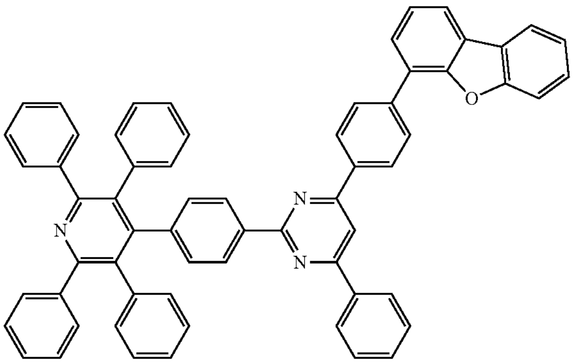
-continued
56
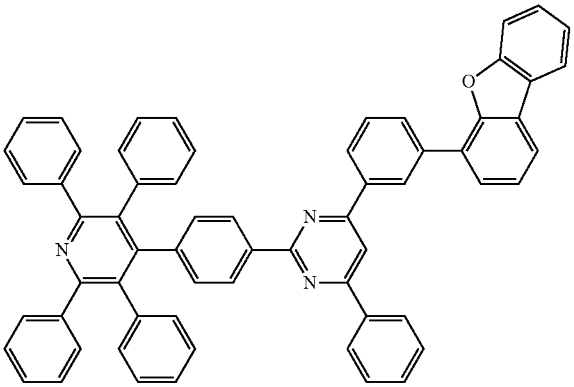
57
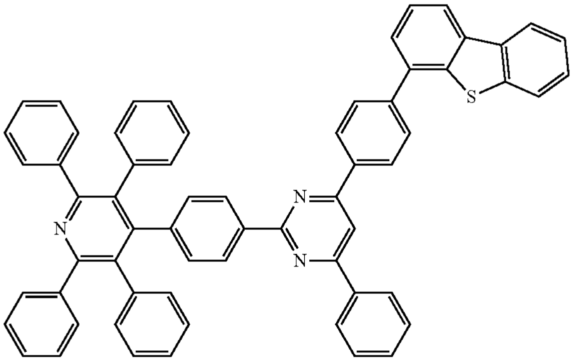
58
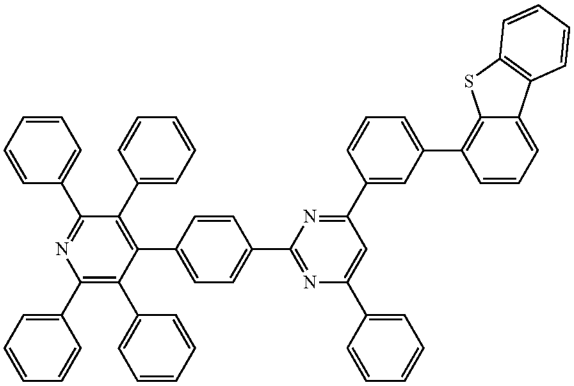
59
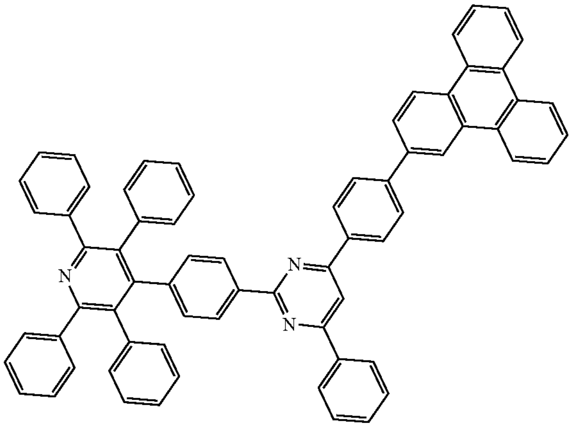

-continued
60
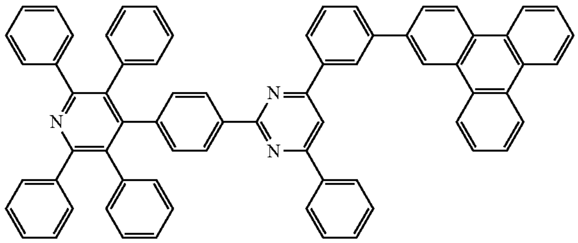
61
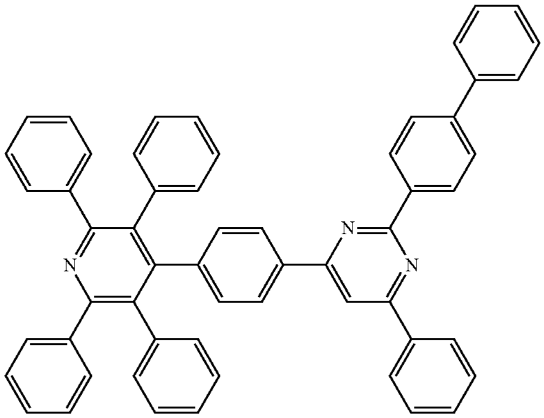
62
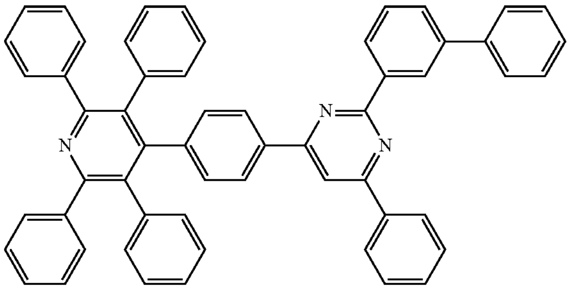
63
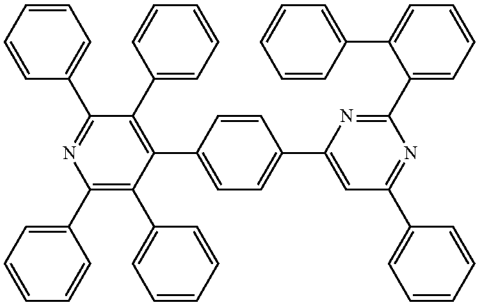
-continued
64
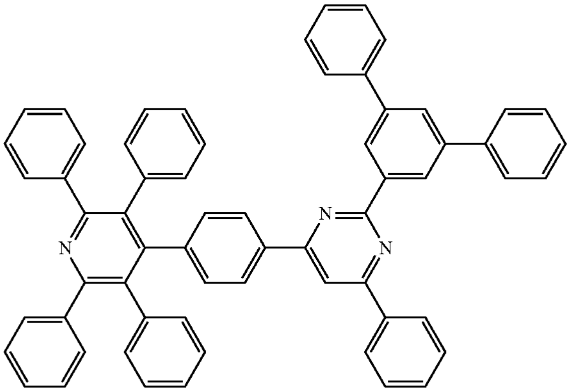
65
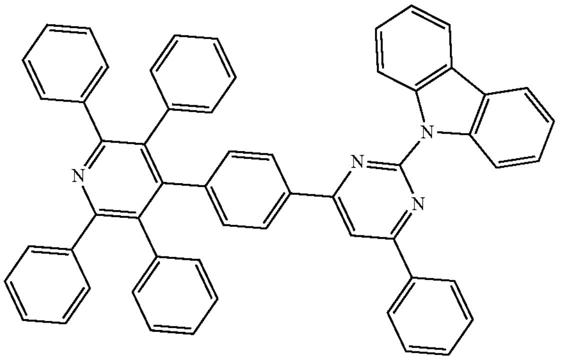
66
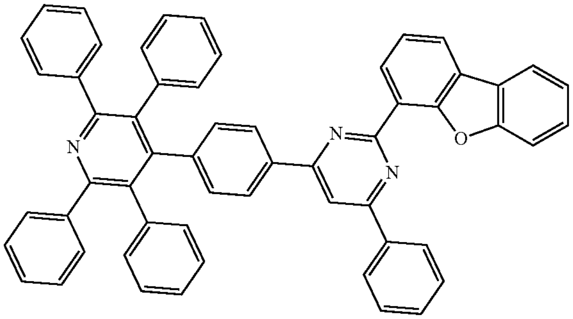
67
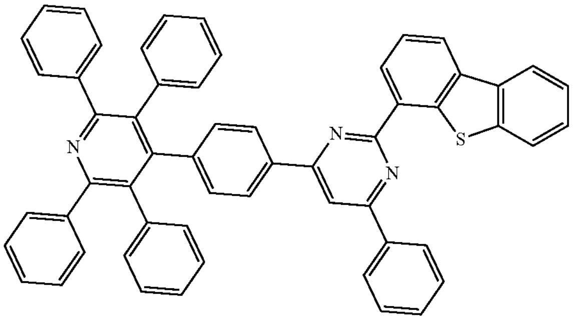

-continued
68
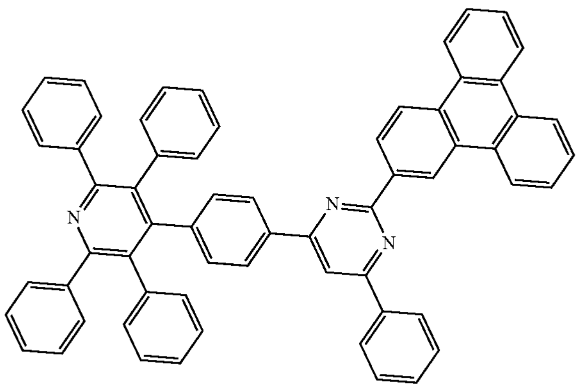
69
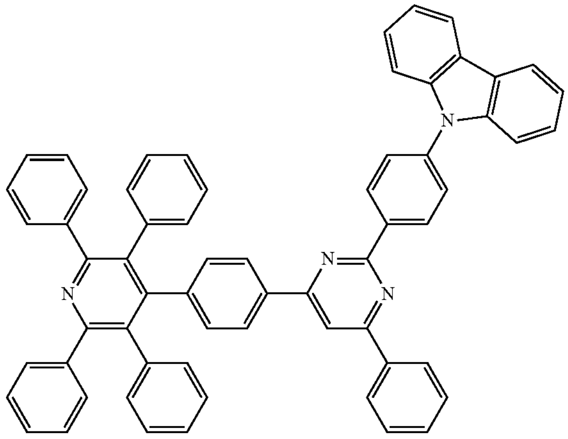
70
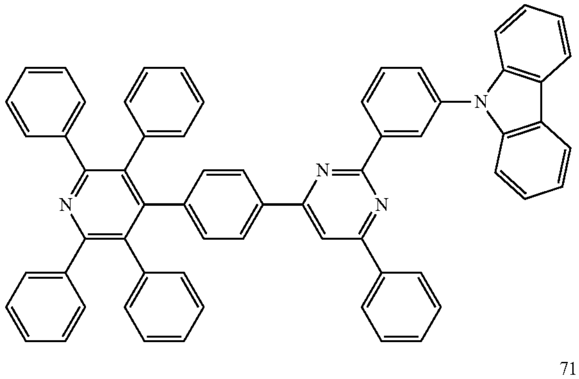
71
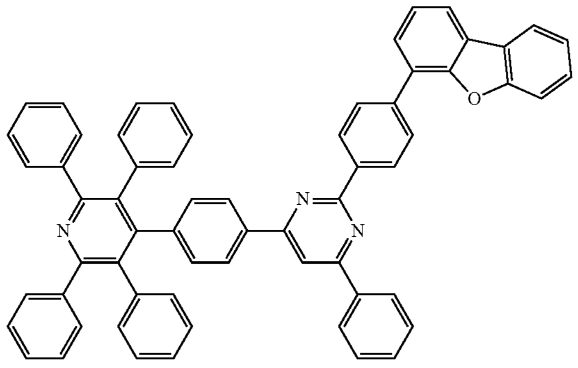
-continued
72
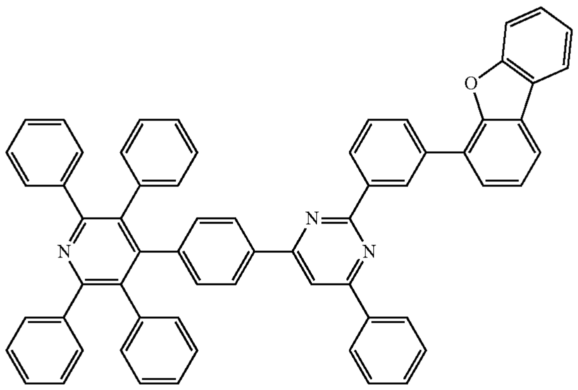
73
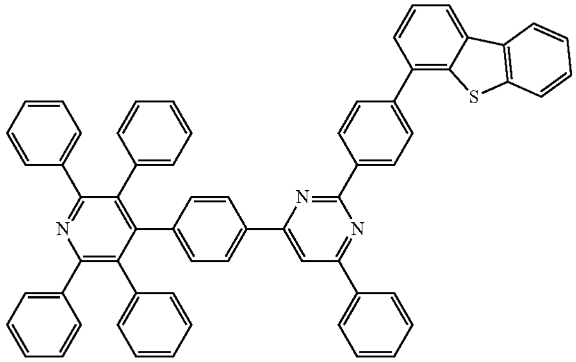
74
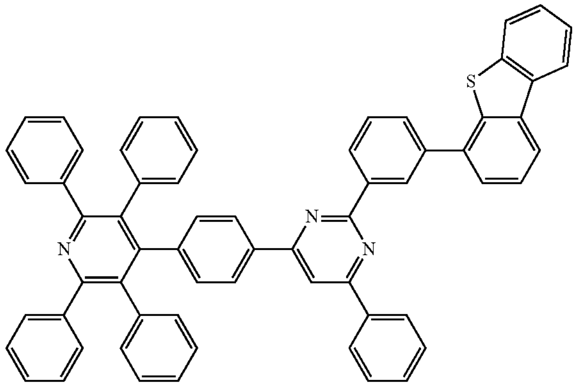
75
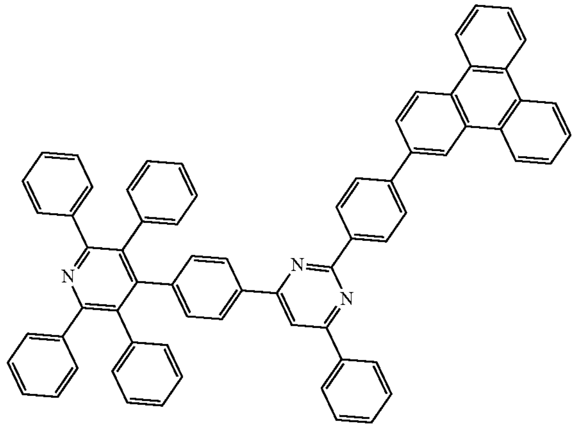

-continued
76
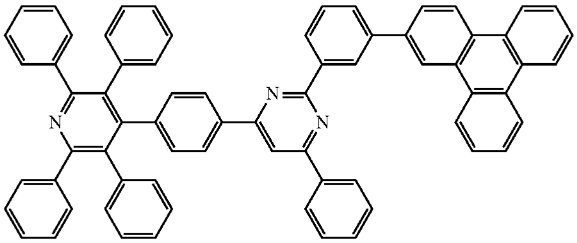
77
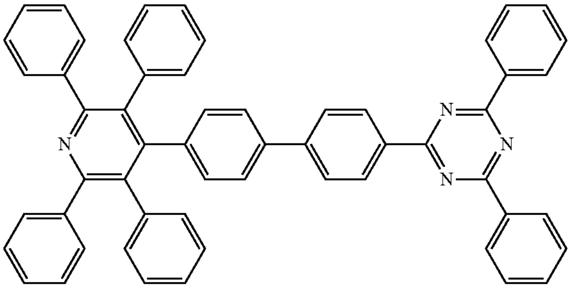
78
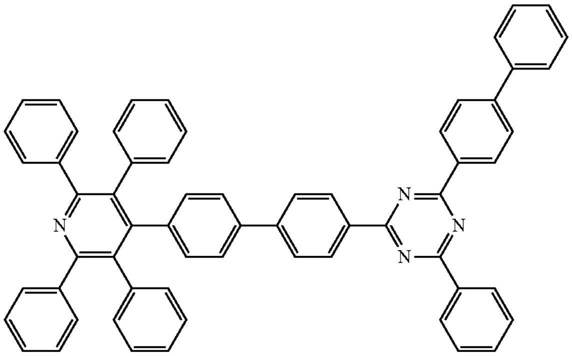
79
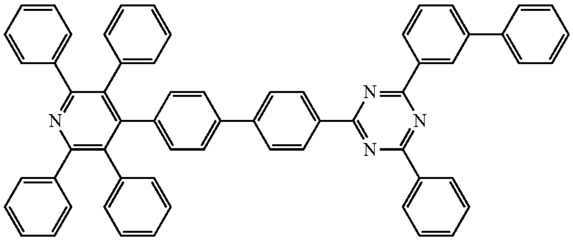
80
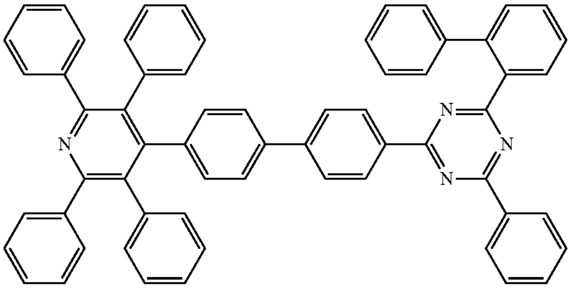
-continued
81
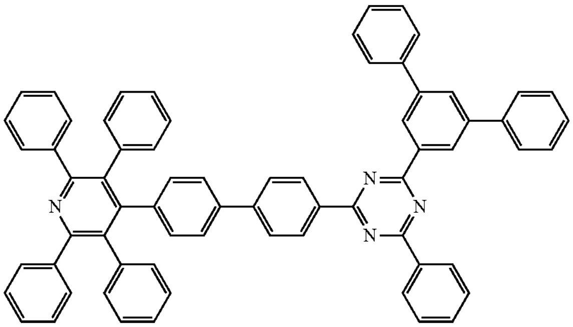
82
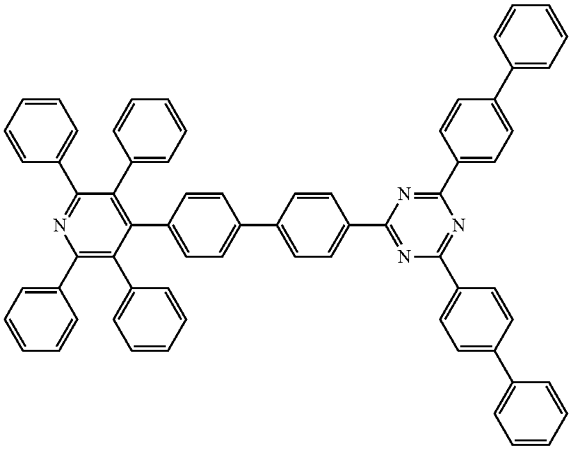
83
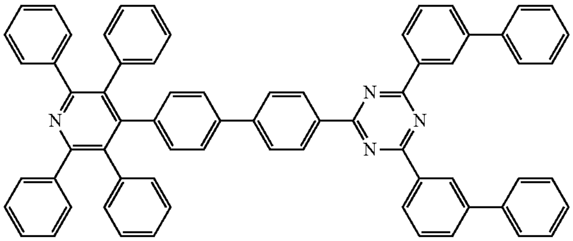
84
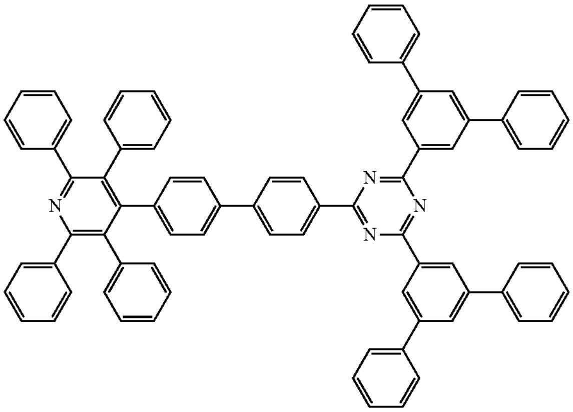

-continued
85
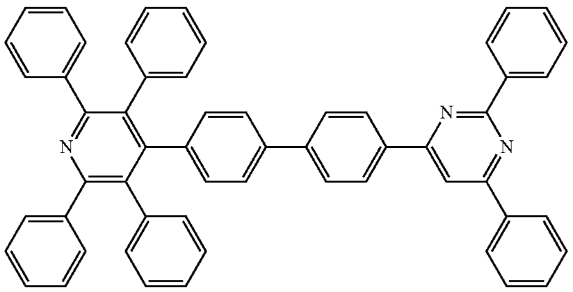
86
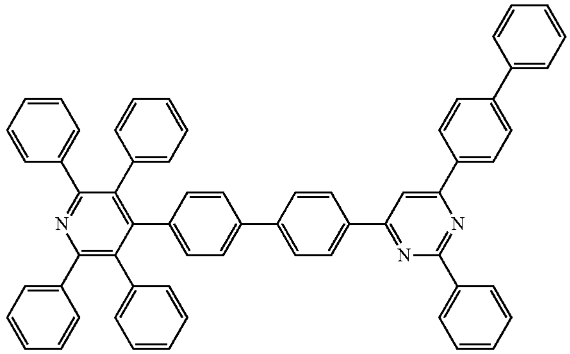
87
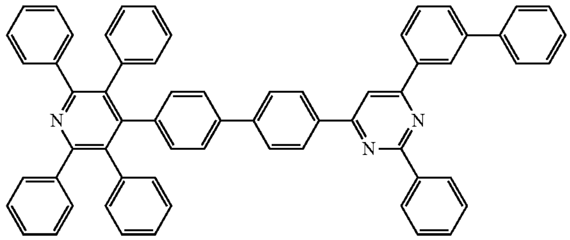
88
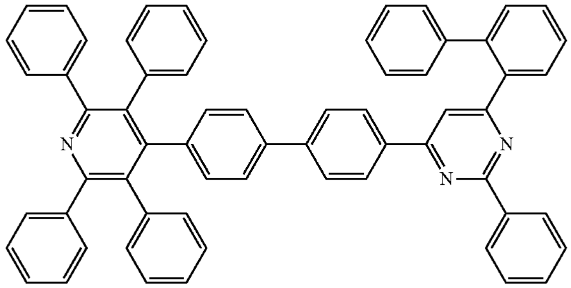
89
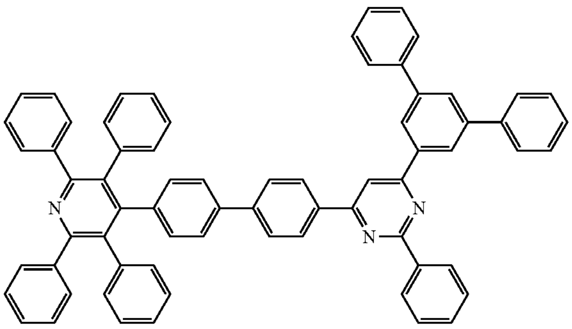
90
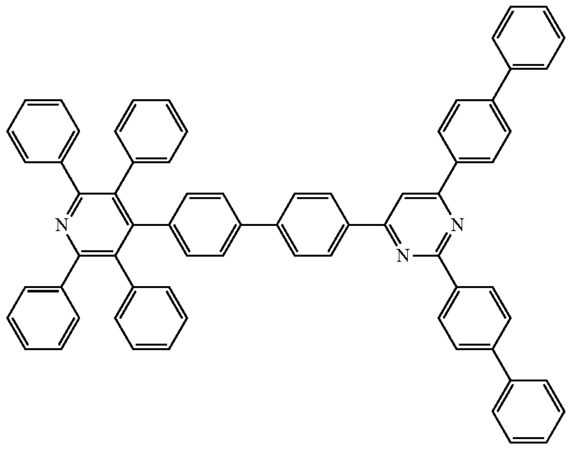
91
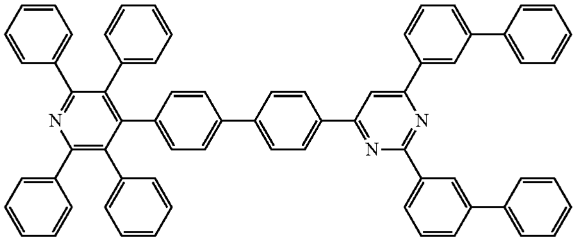
92
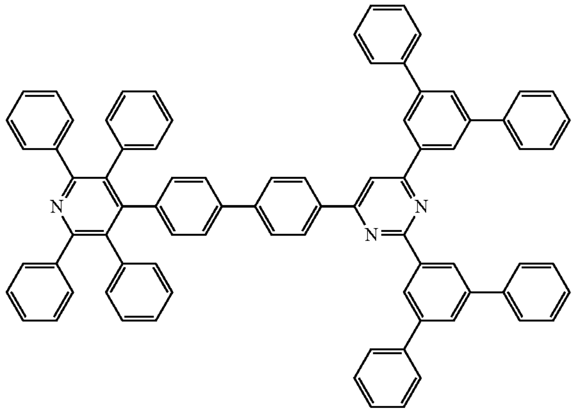
93
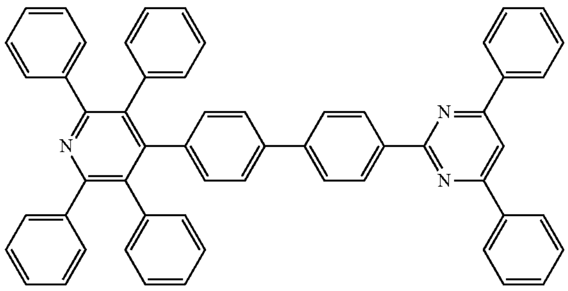

-continued
94
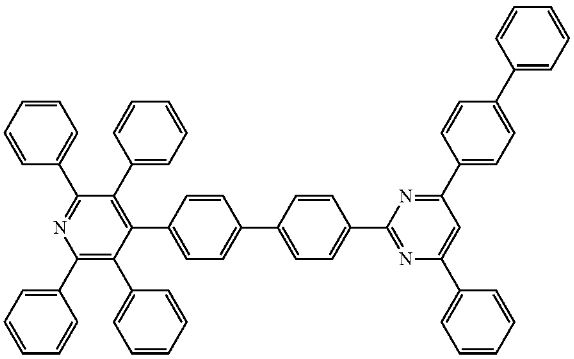
95
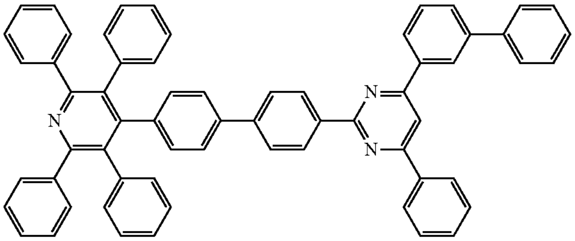
96
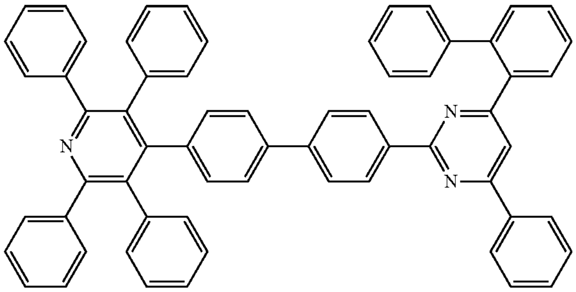
97
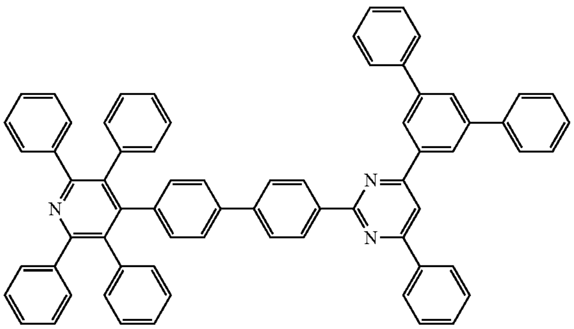
-continued
98
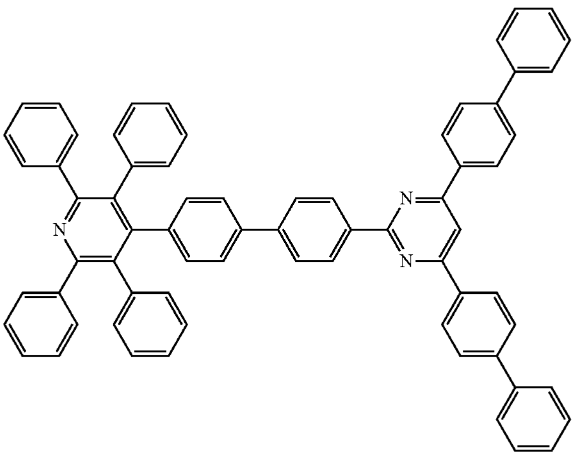
99
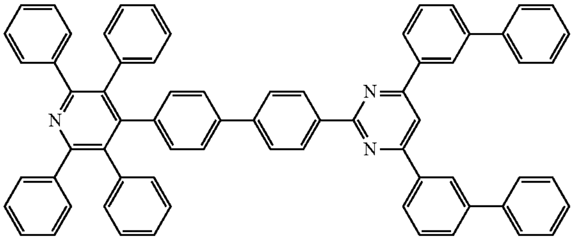
100
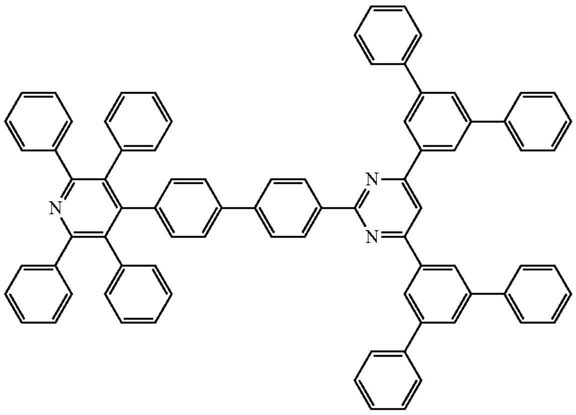
101
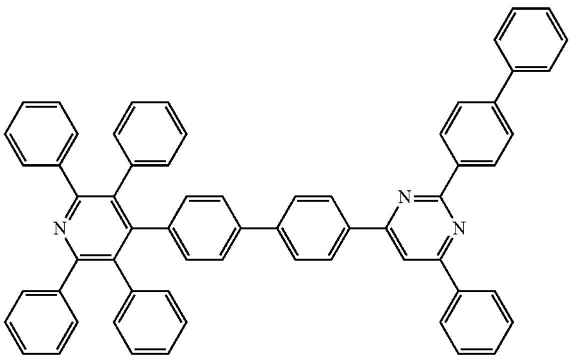

-continued
102
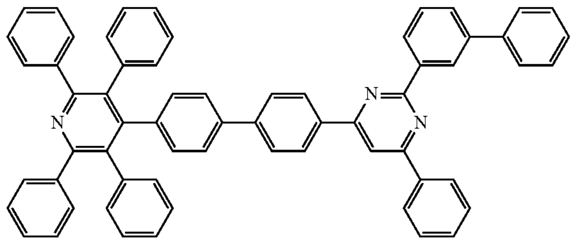
103
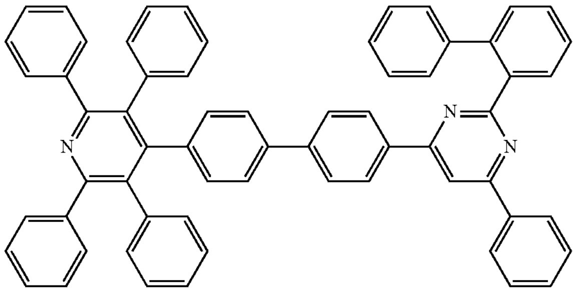
104
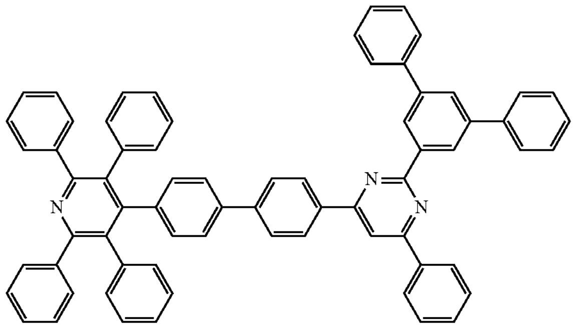
105
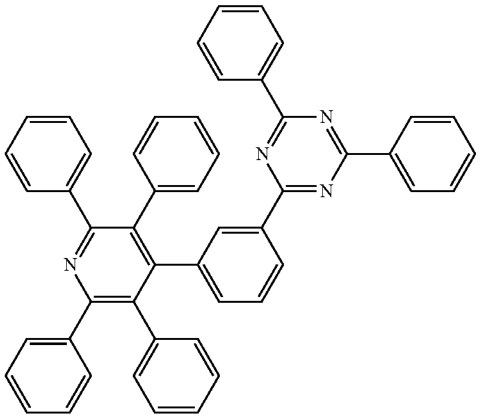
-continued
106
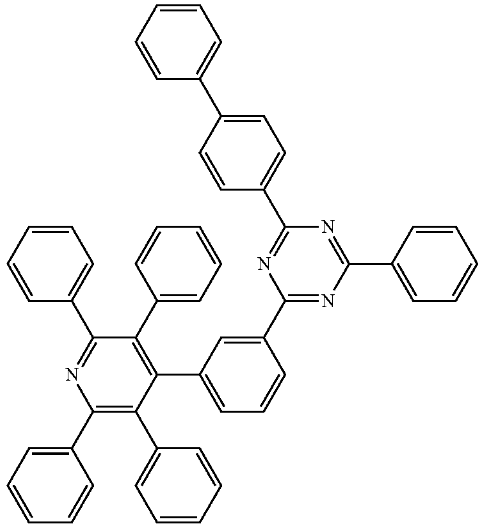
107
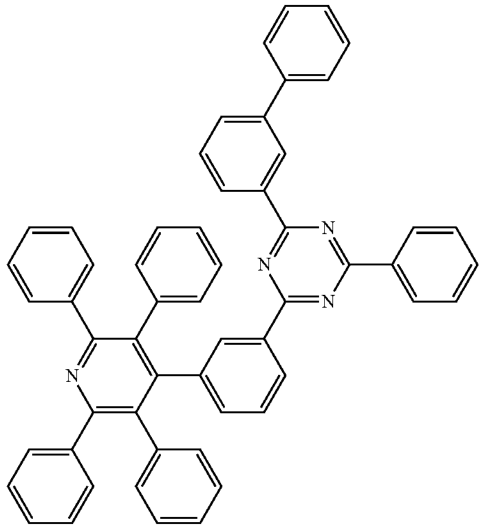
108
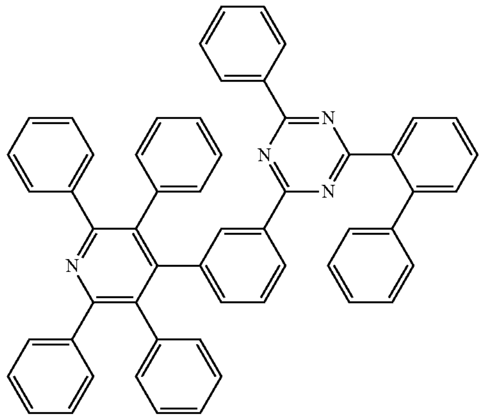

-continued
109
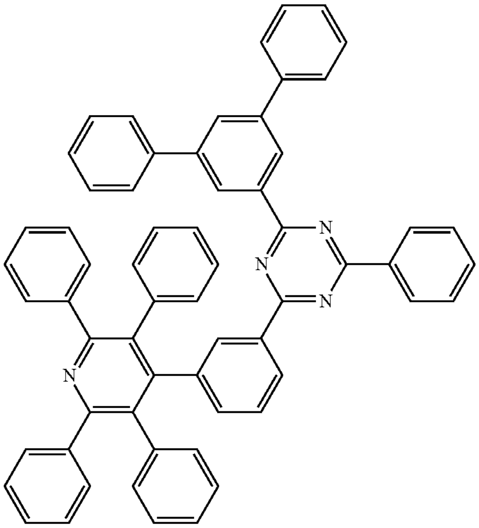
110
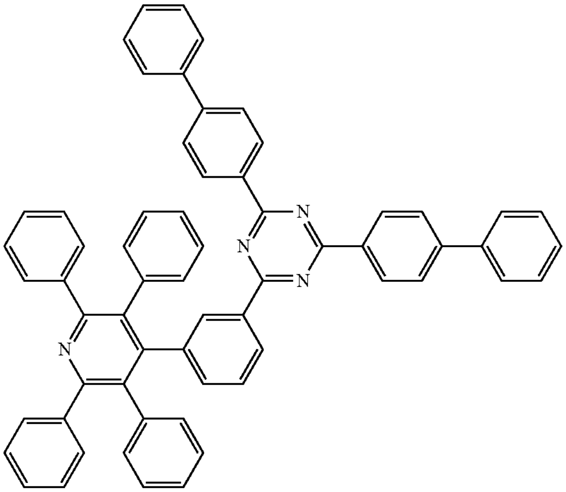
111
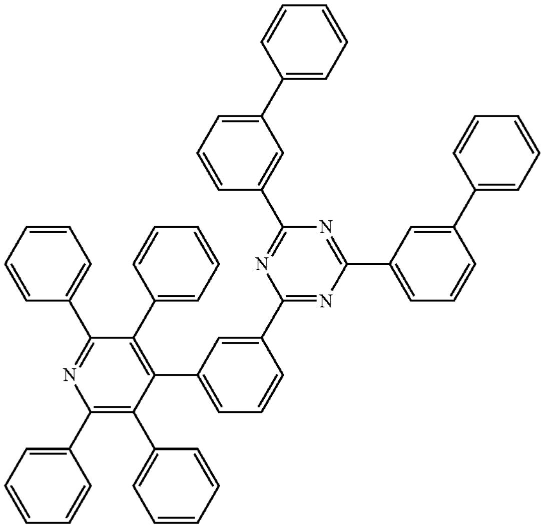
-continued
112
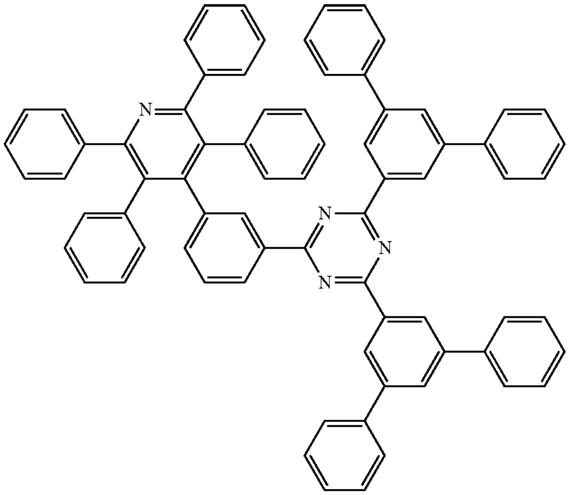
113
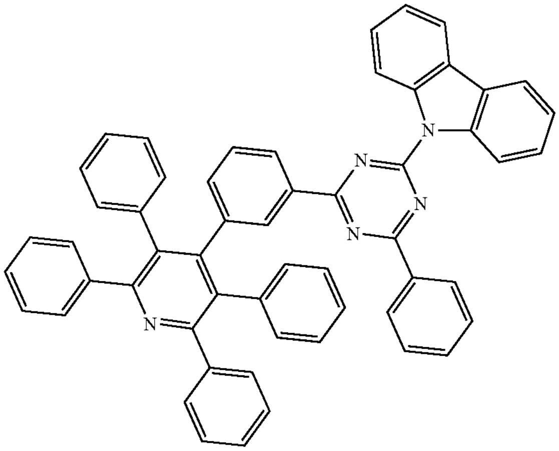
114
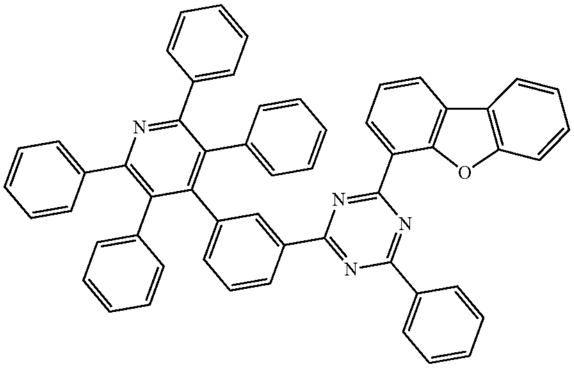

-continued
115
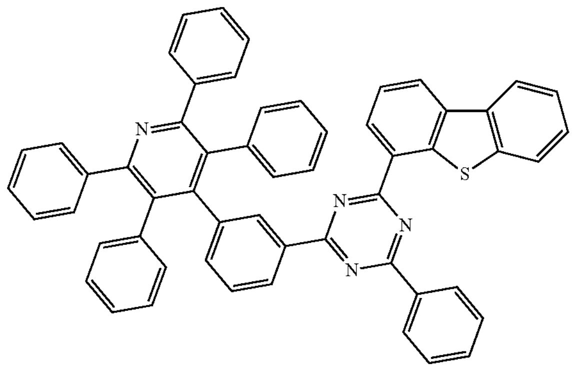
116
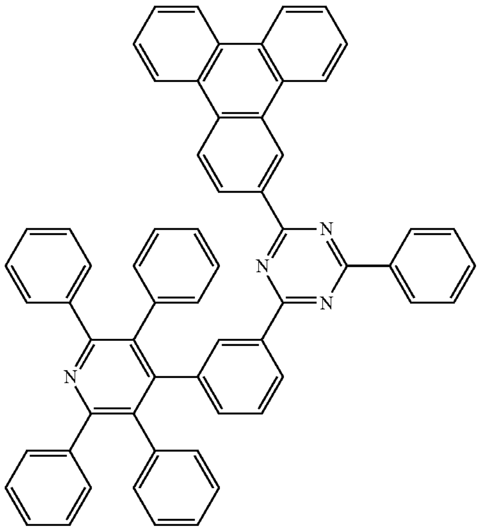
117
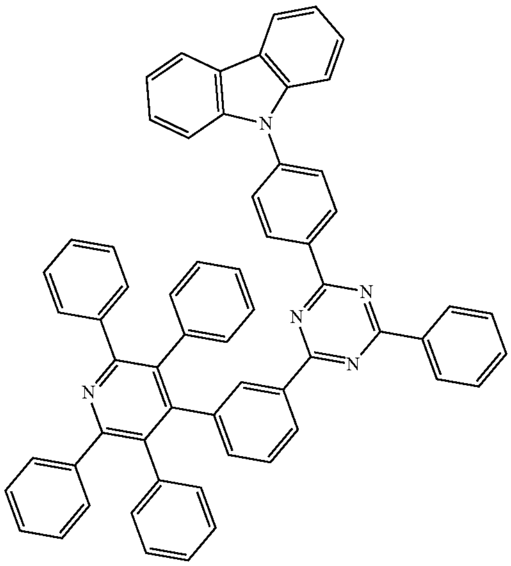
-continued
118
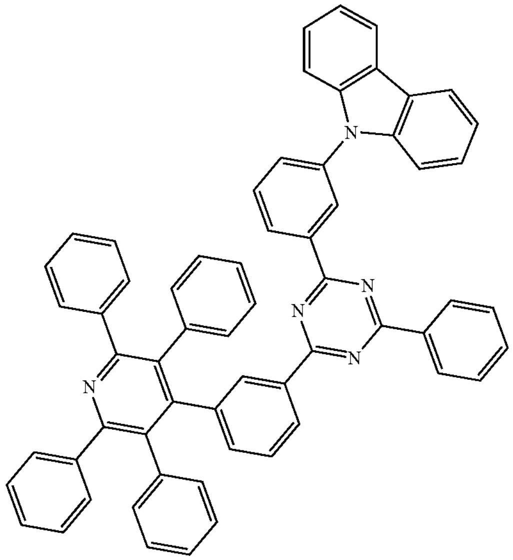
119
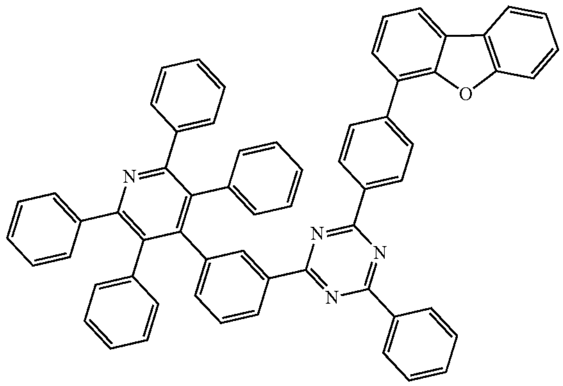
120
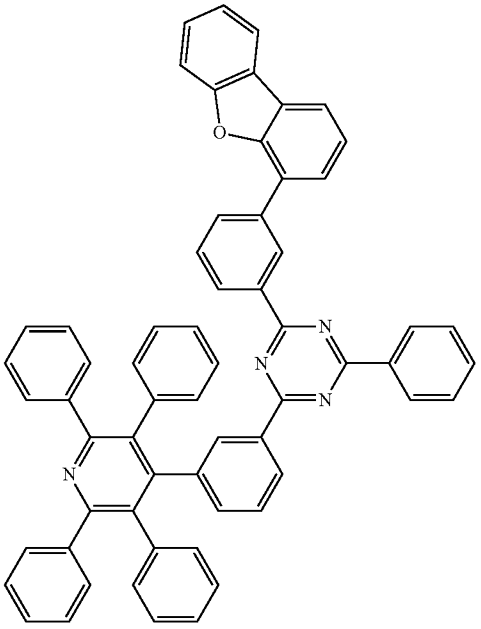

-continued
121
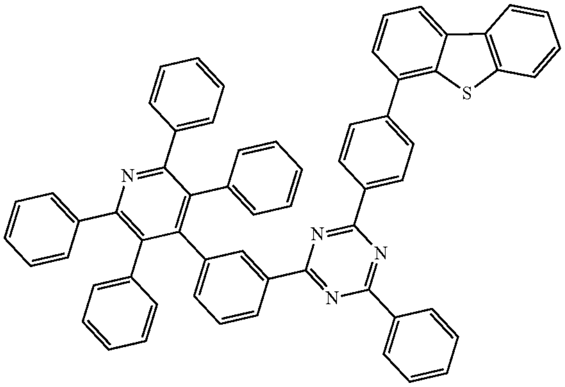
122
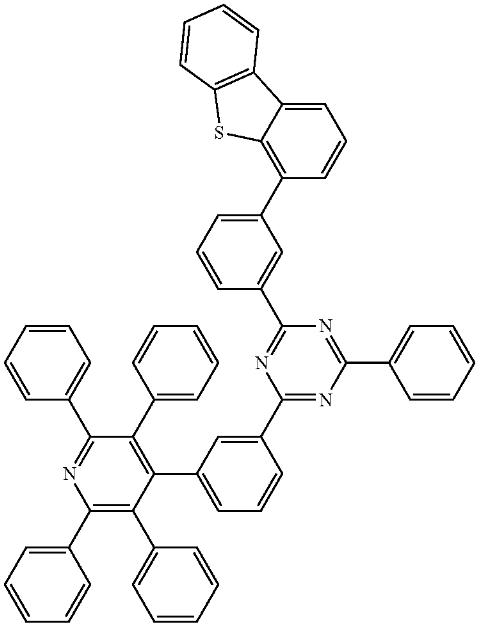
123
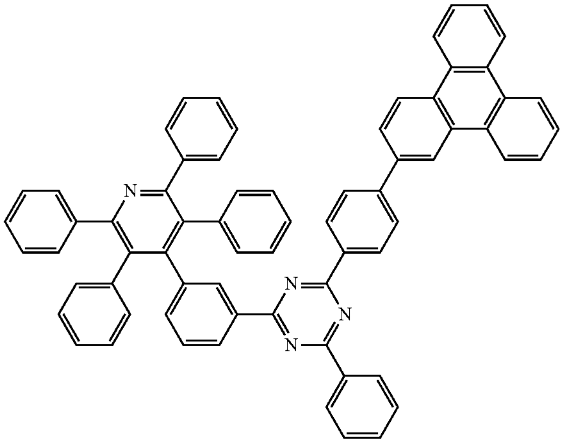
-continued
124
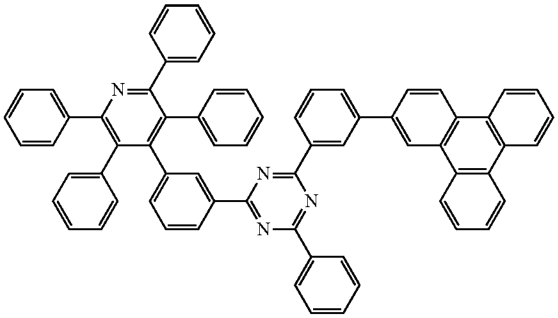
125
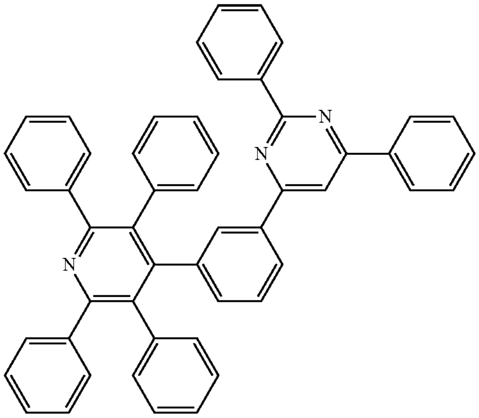
126
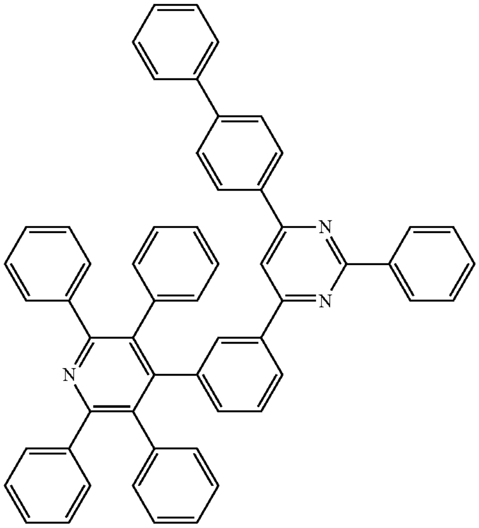

-continued
127
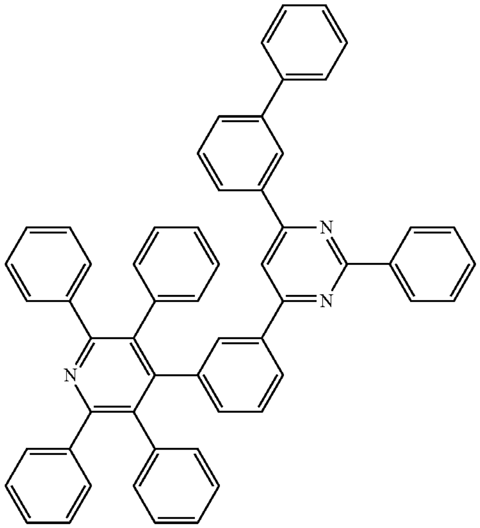
128
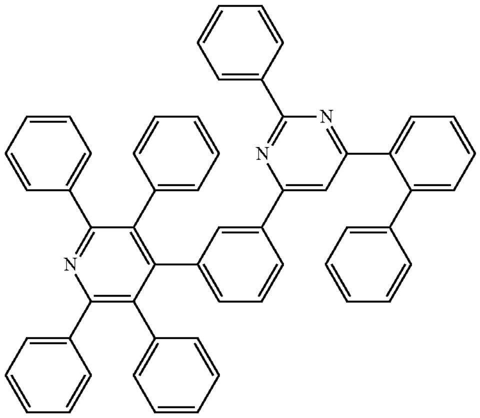
129
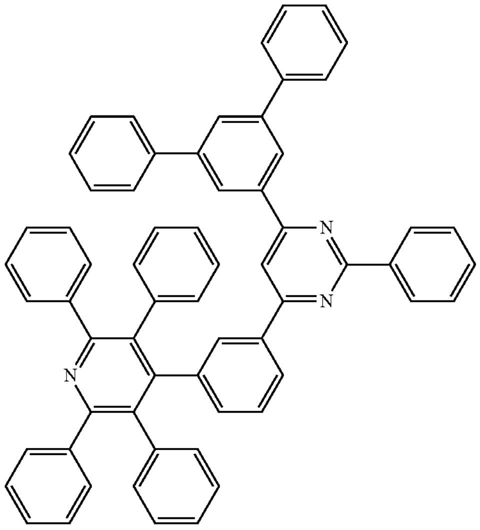
-continued
130
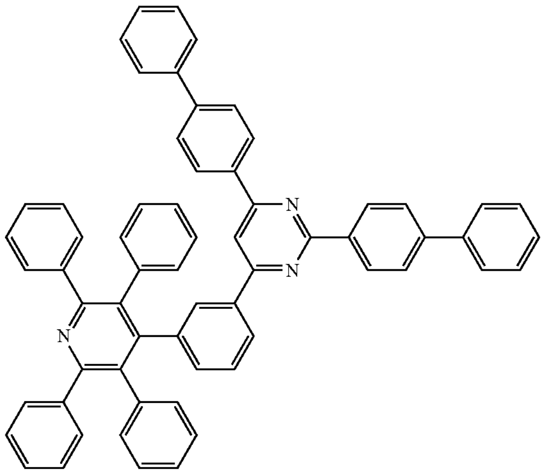
131
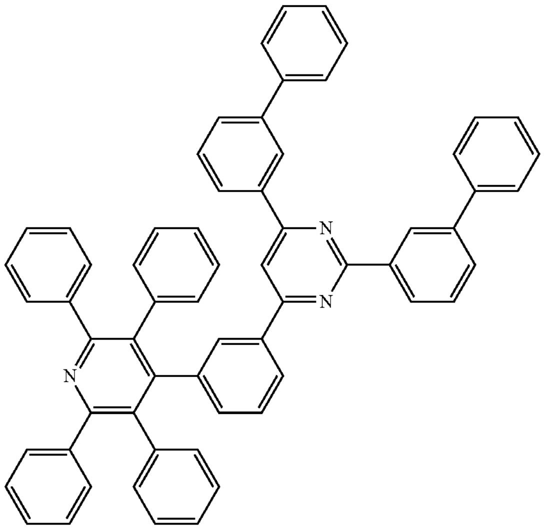
132
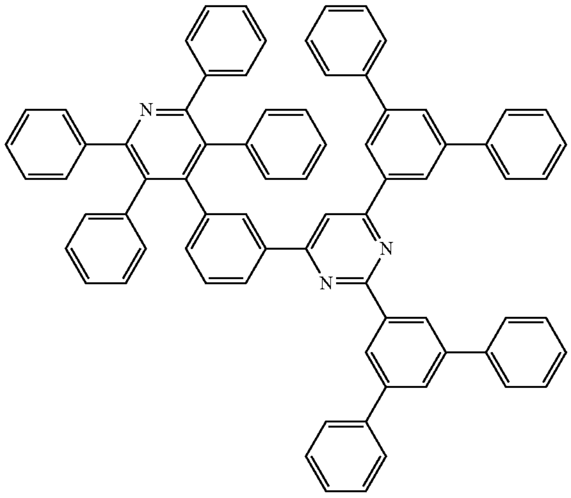

133
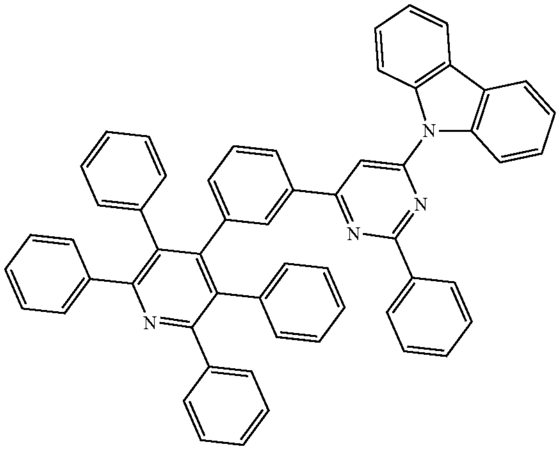
134
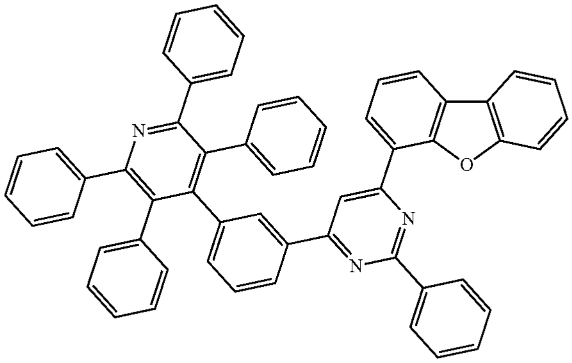
135
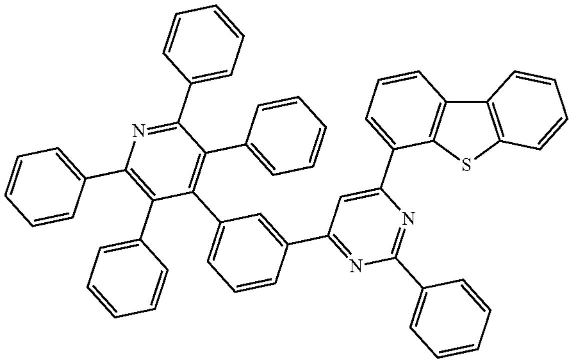
136
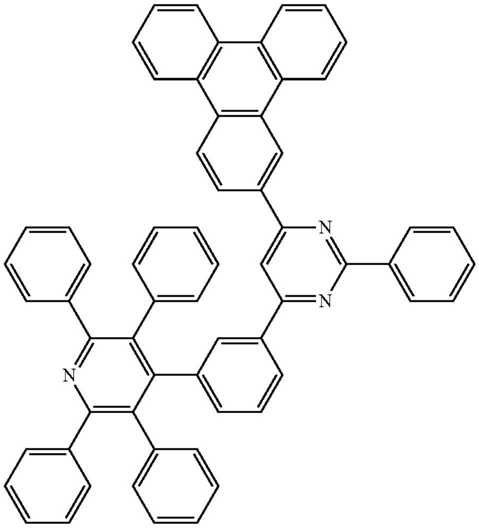
137
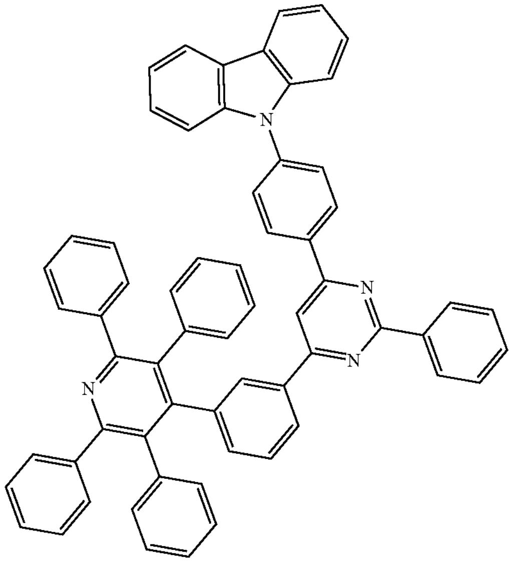
138
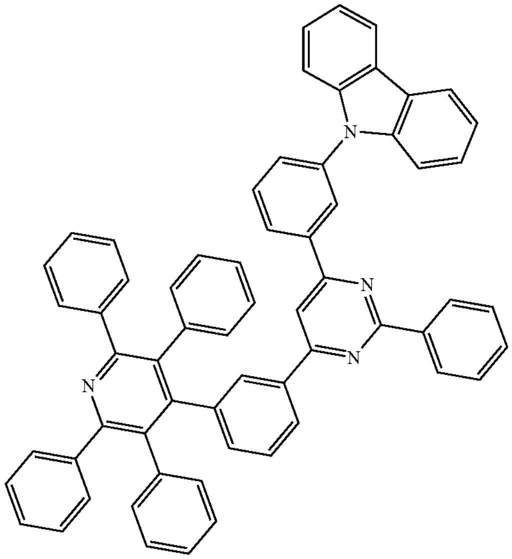

-continued
139
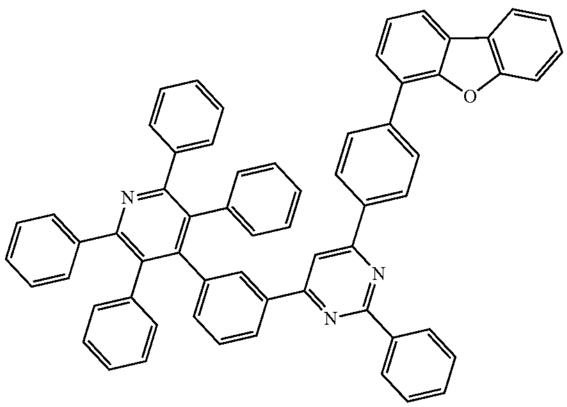
140
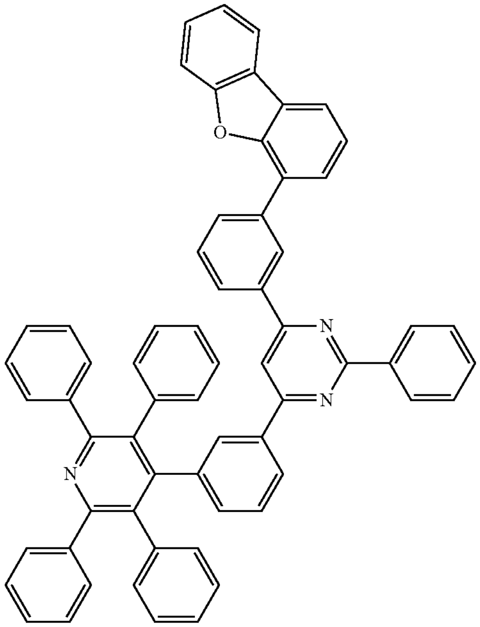
141
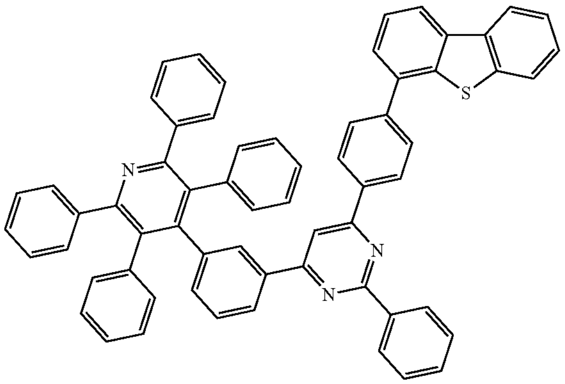
-continued
142
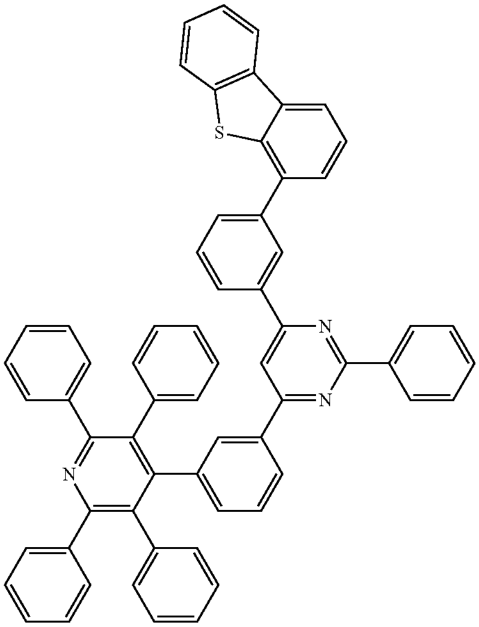
143
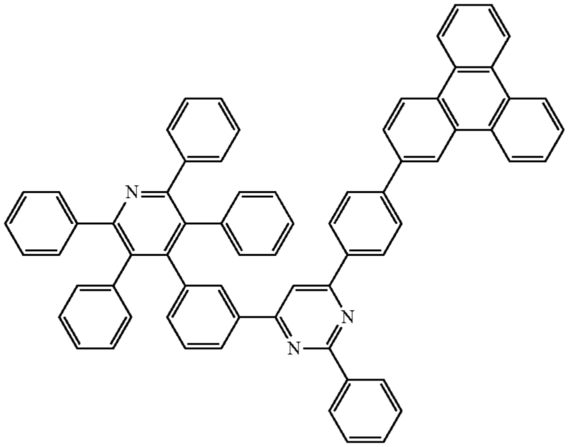
144
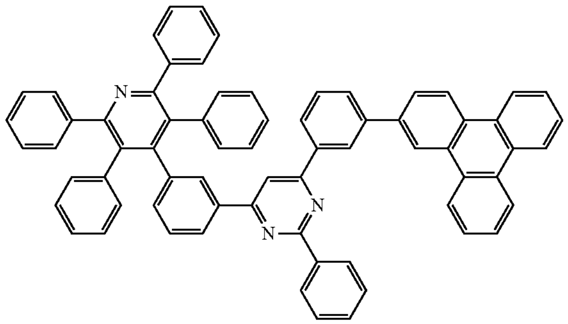

-continued
145
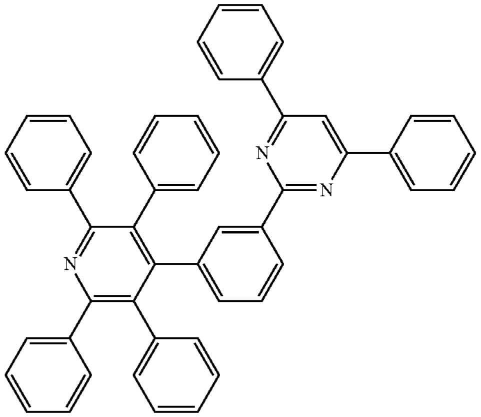
146
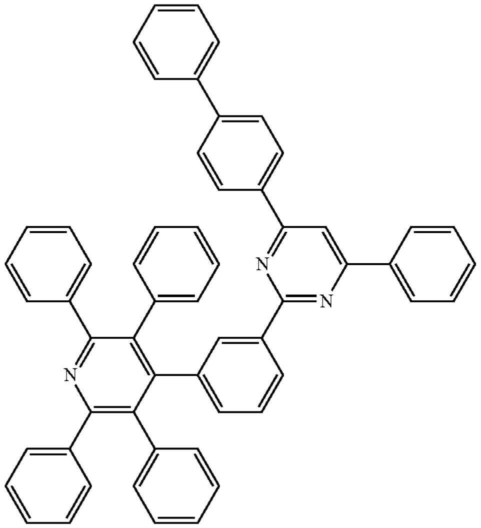
147
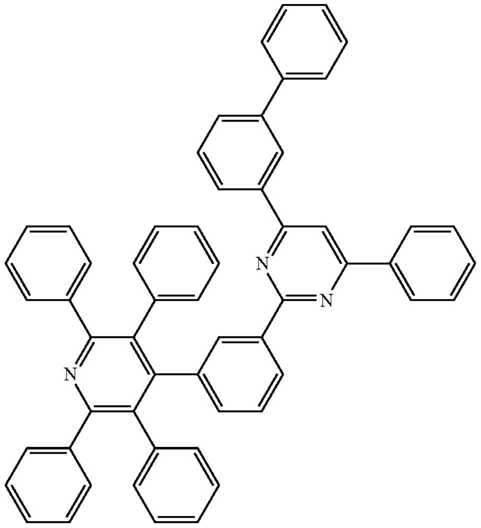
-continued
148
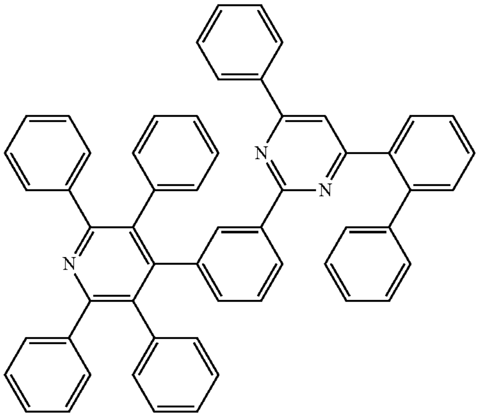
149
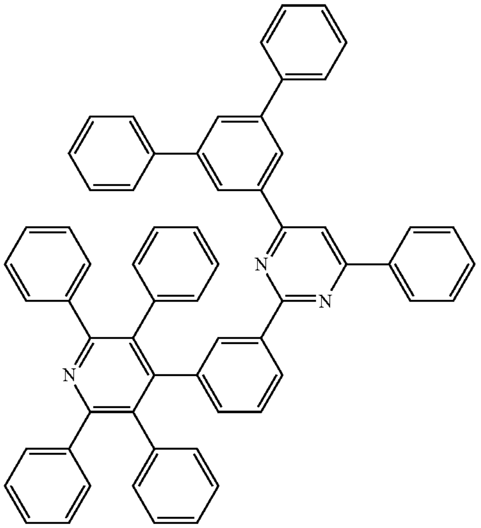
150
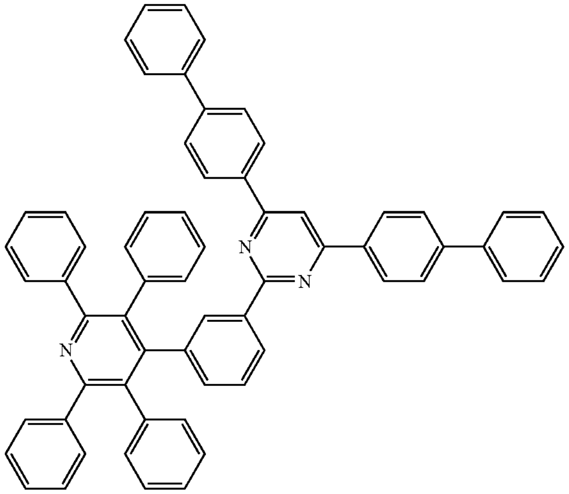

-continued
151
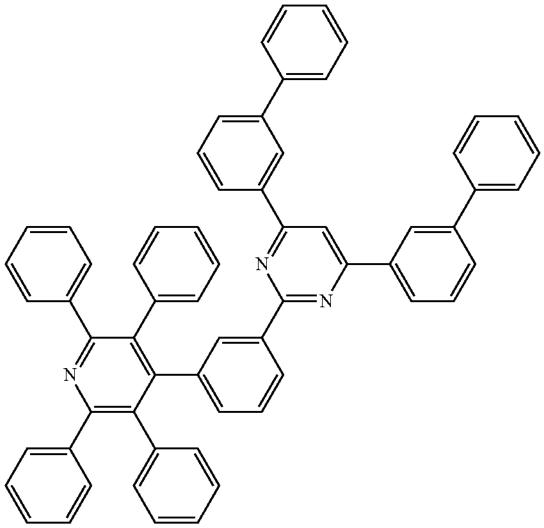
152
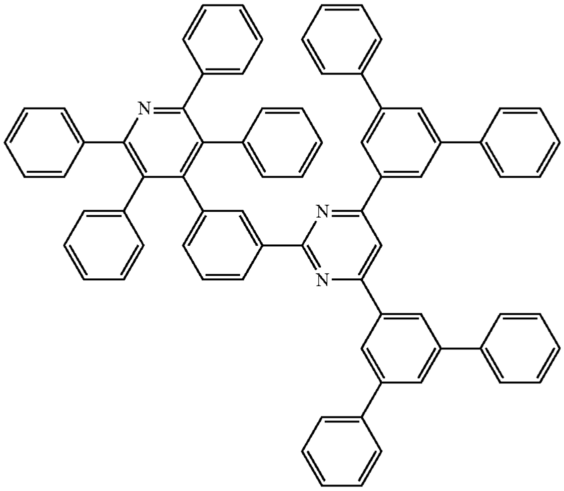
153
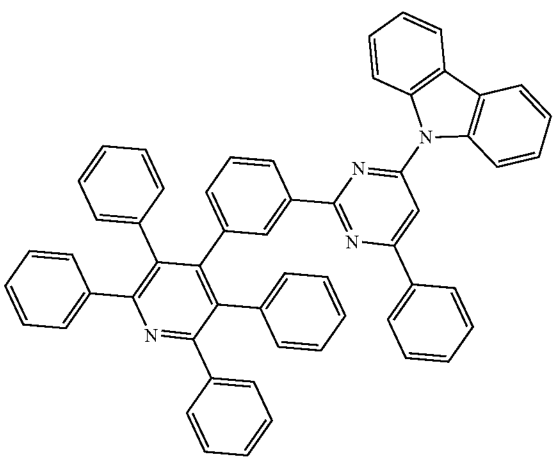
-continued
154
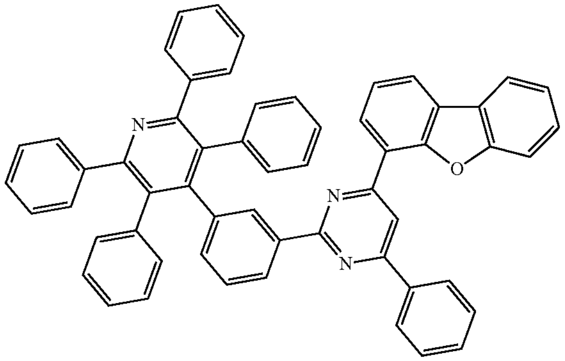
155
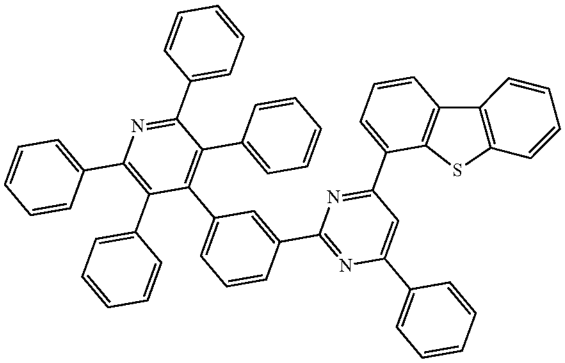
156
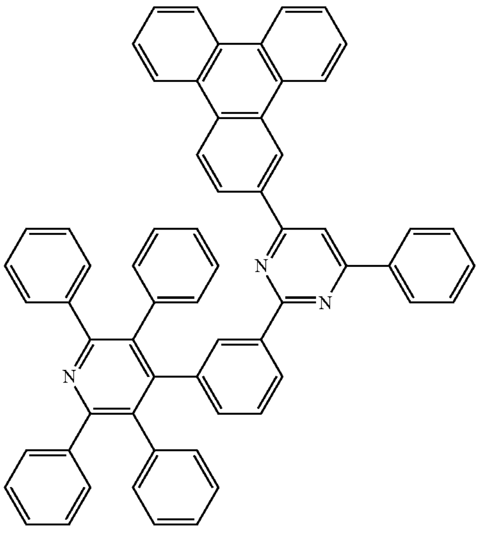

-continued
157
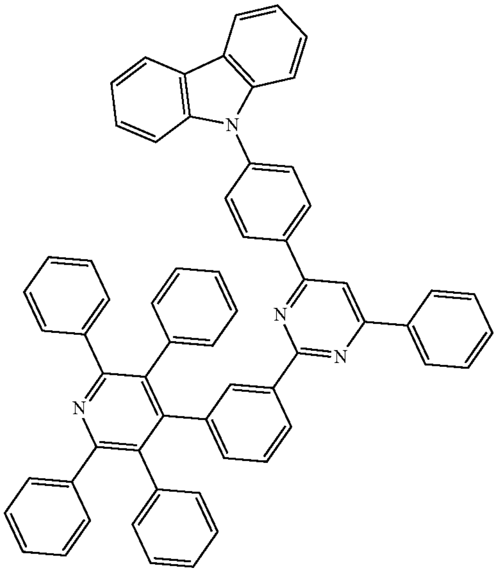
158
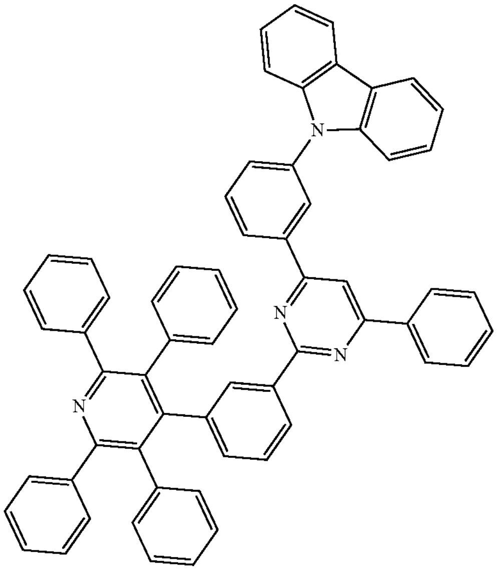
159
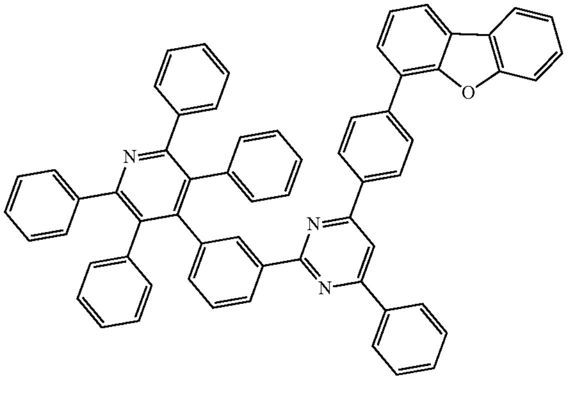
-continued
160
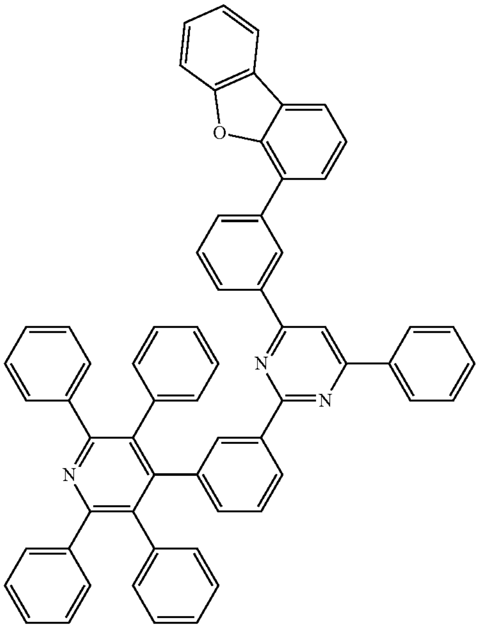
161
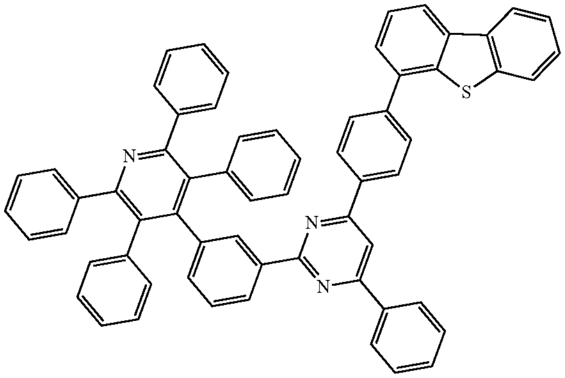
162
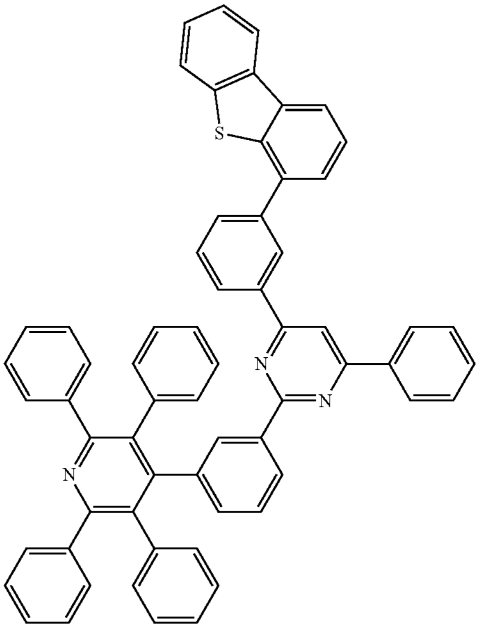

-continued
163
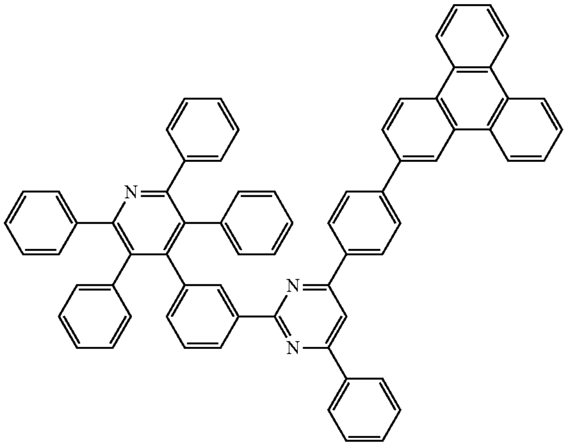
164
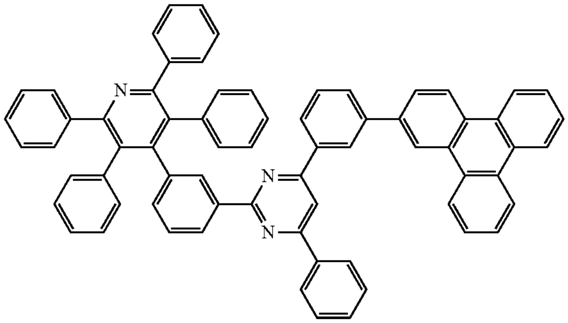
165
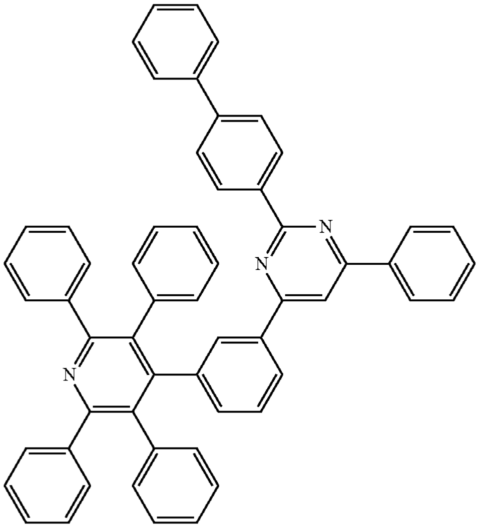
-continued
166
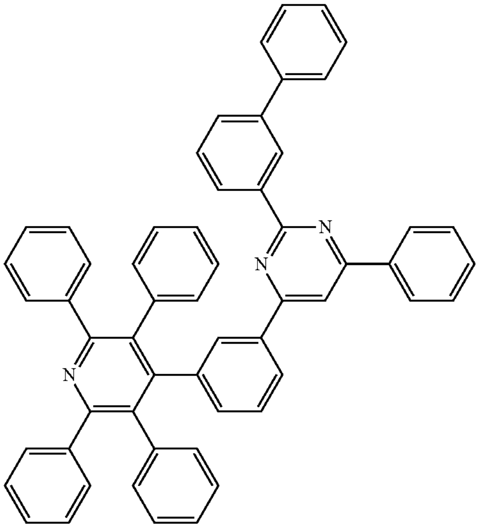
167
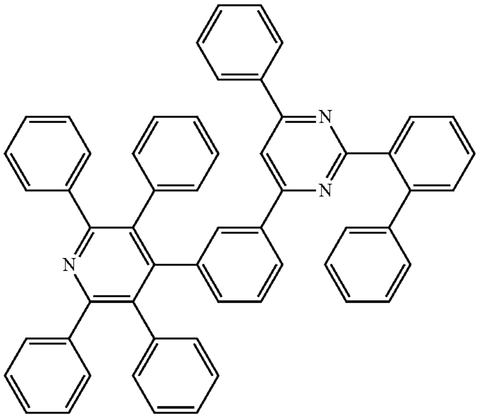
168
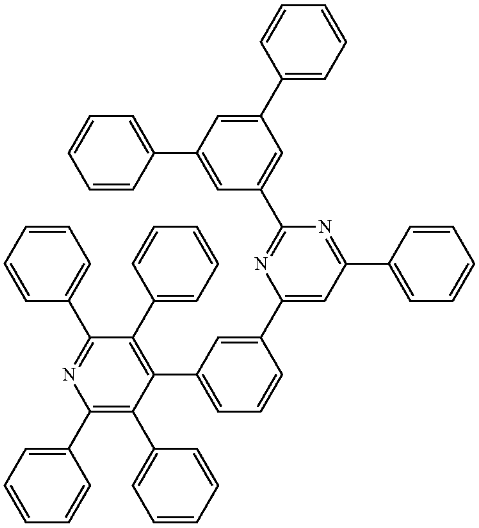

-continued
169
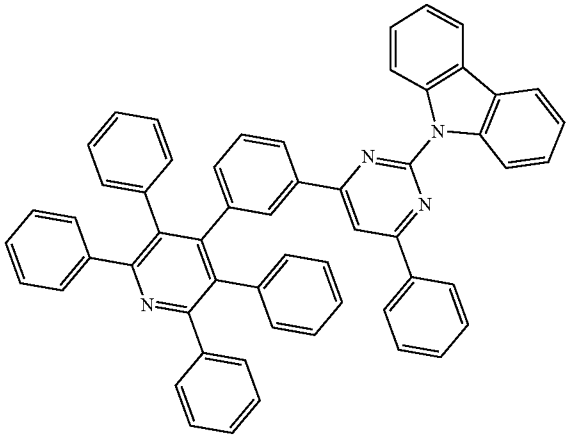
170
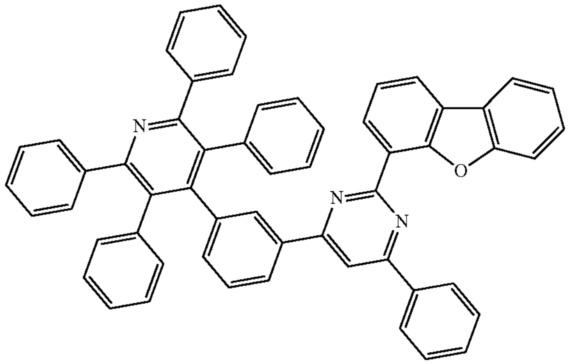
171
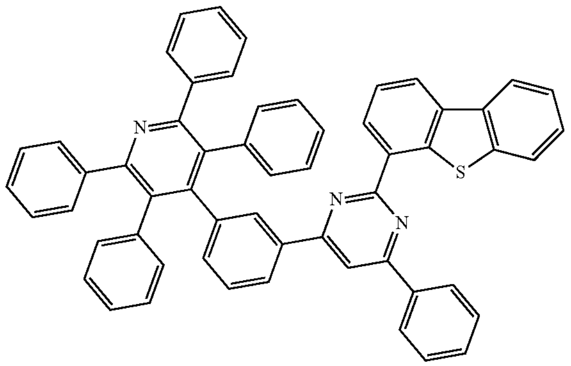
-continued
172
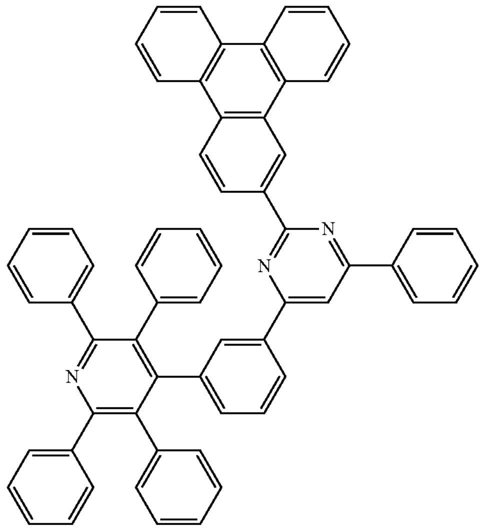
173
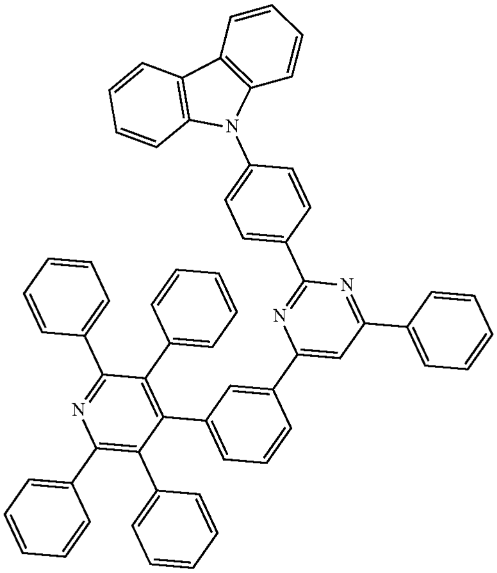
174
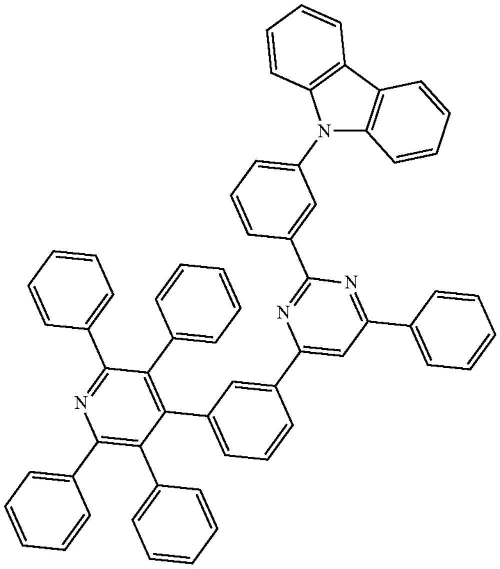

-continued
175
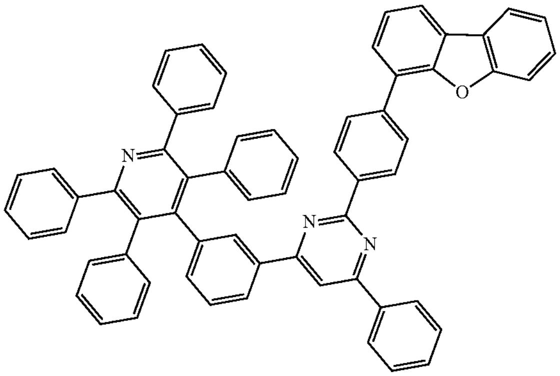
176
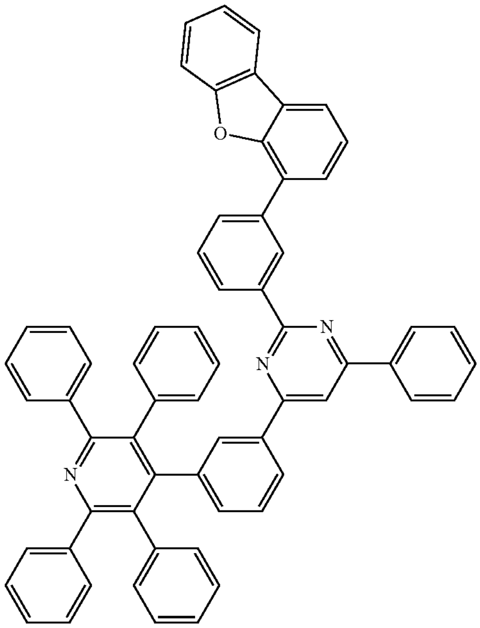
177
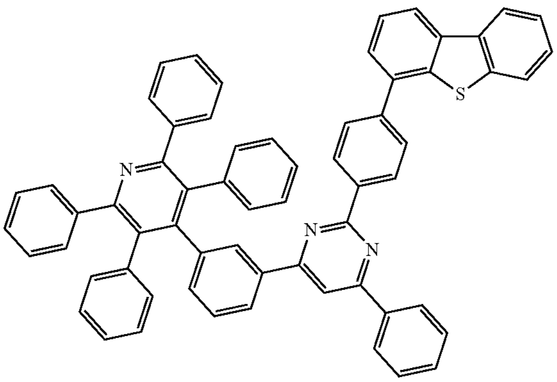
-continued
178
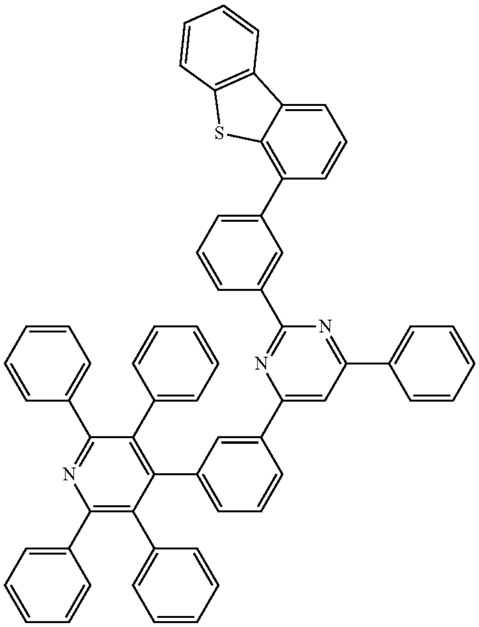
179
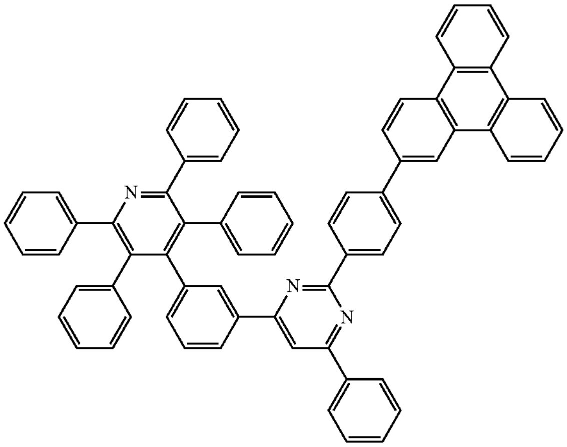
180
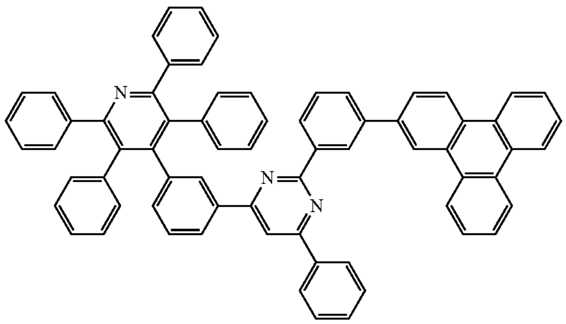

-continued
181
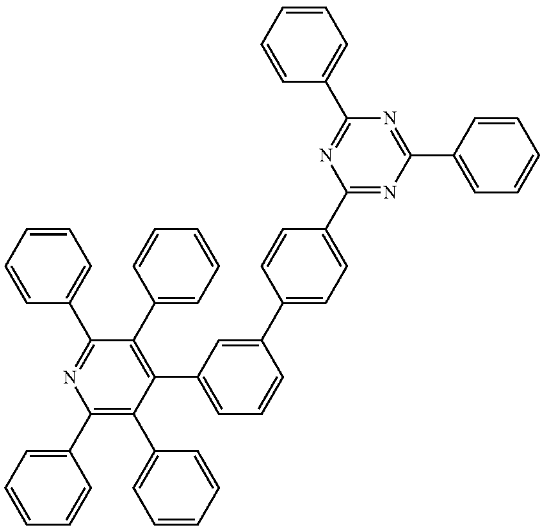
182
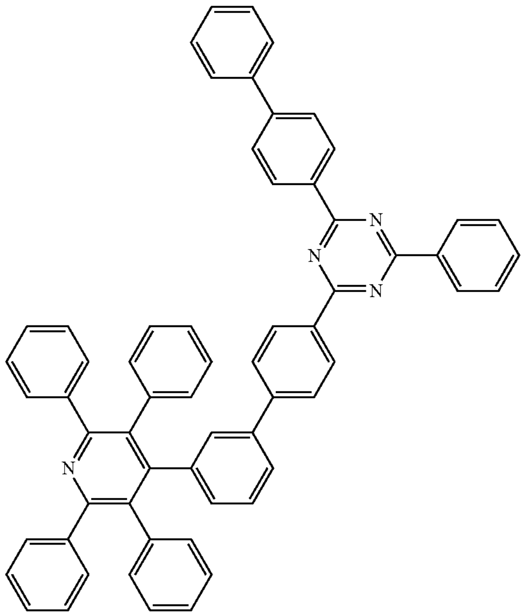
-continued
183
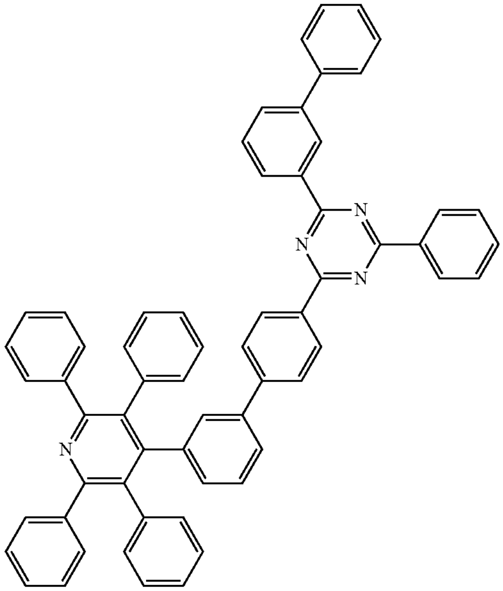
184
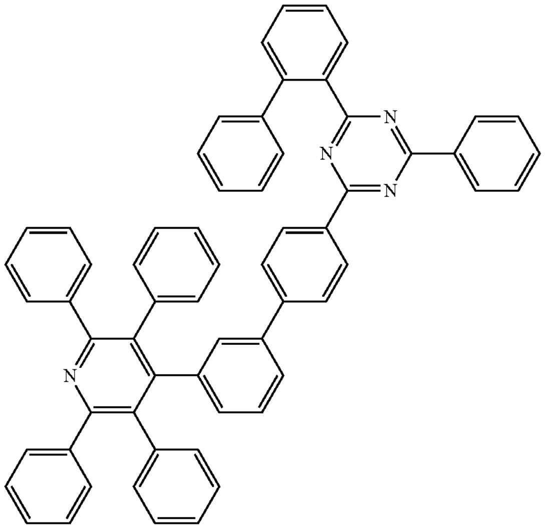

185
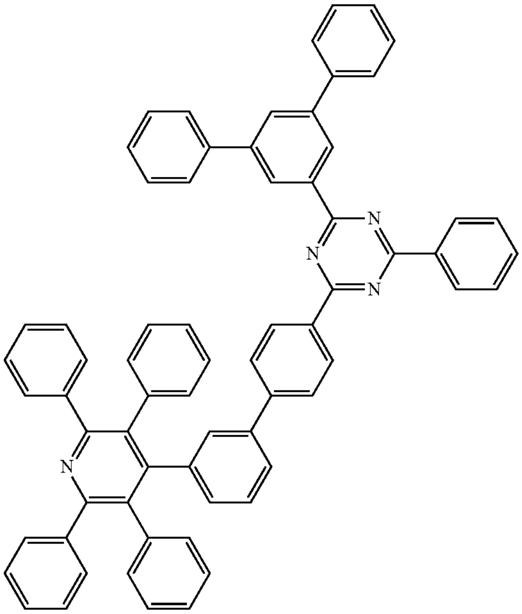
186
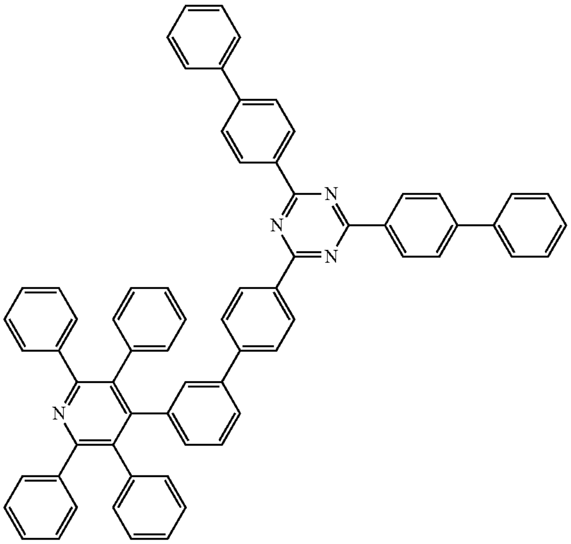
187
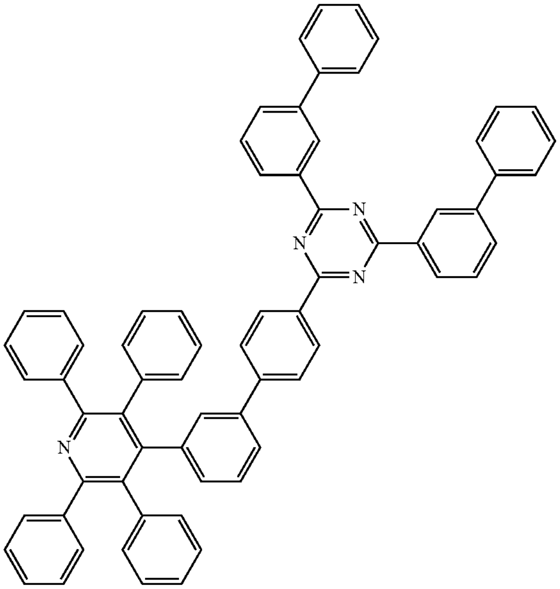
188
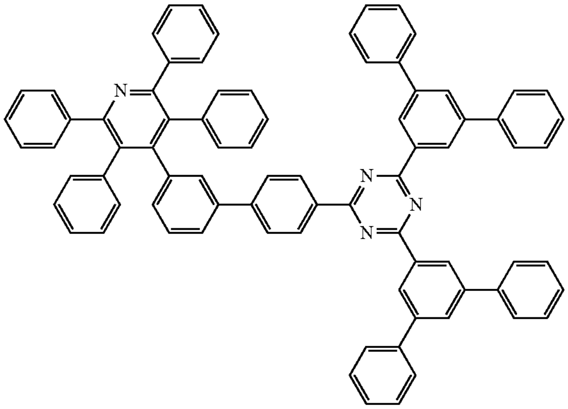
189
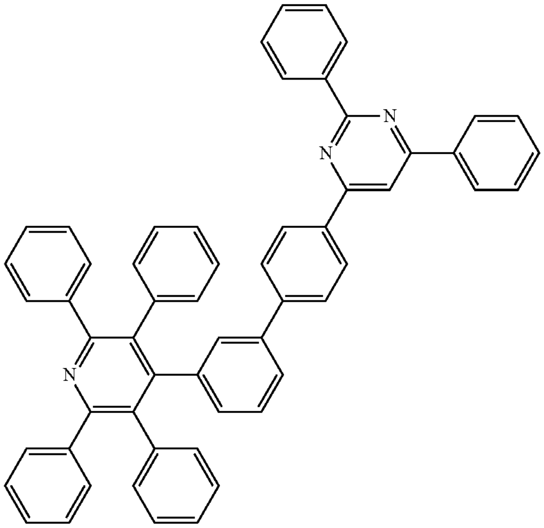

-continued
190
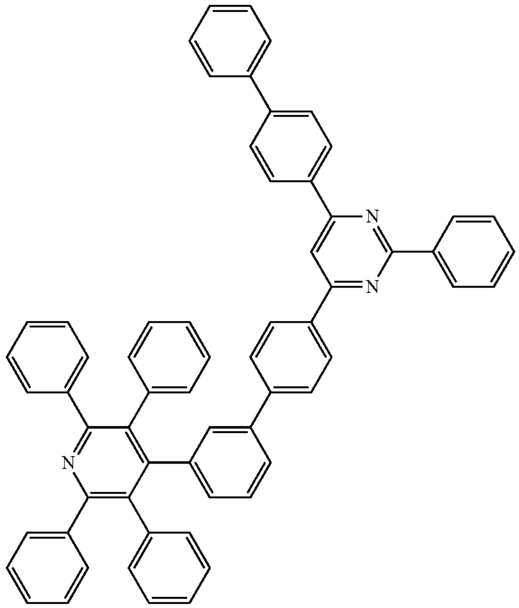
191
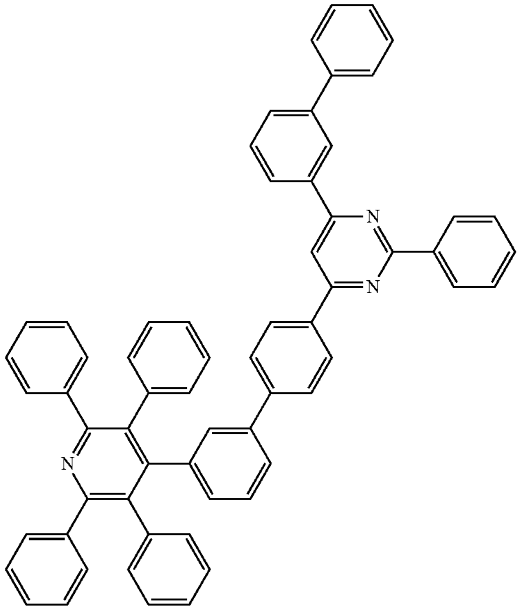
-continued
192
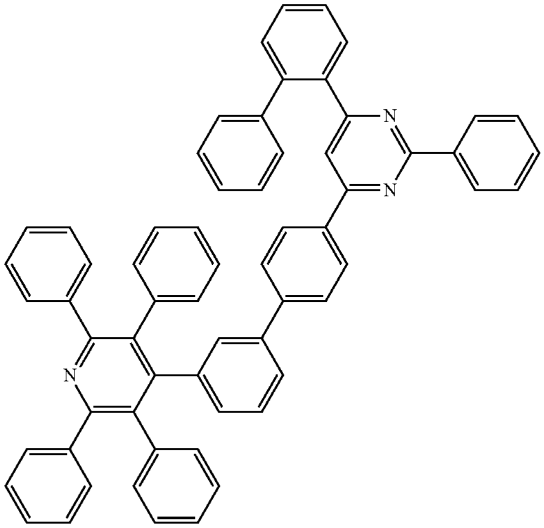
193
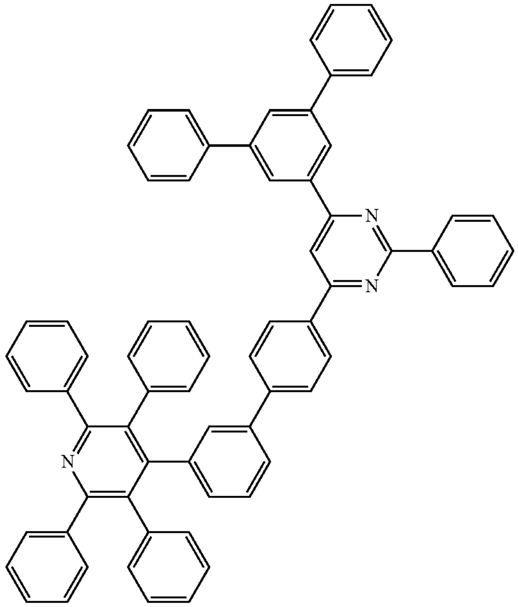

-continued
194
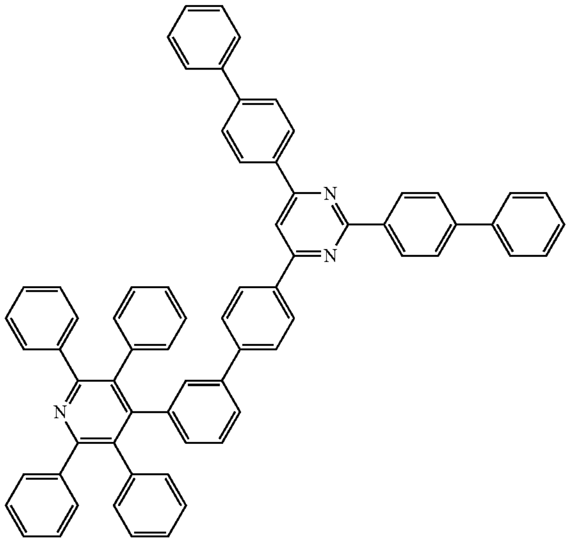
195
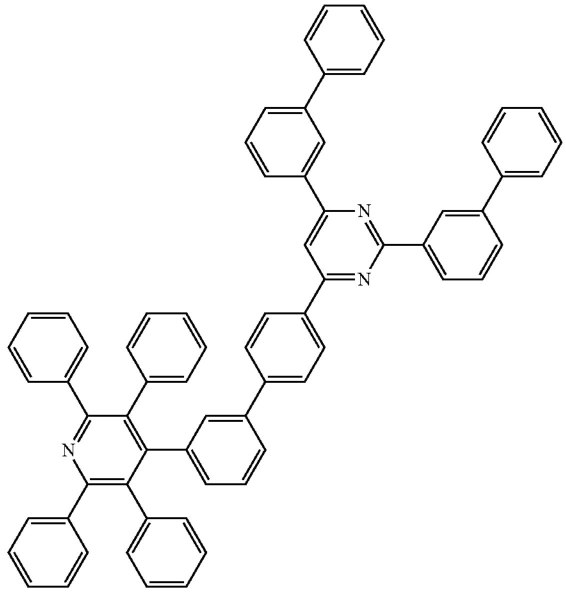
196
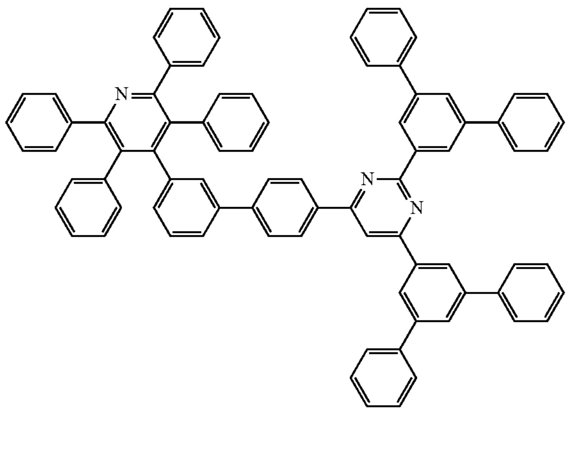
197
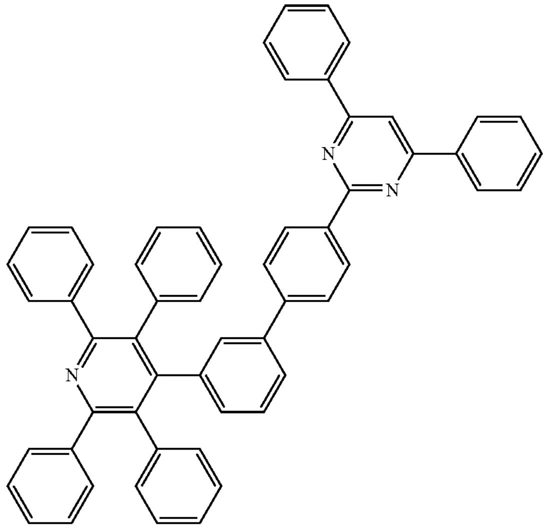
198
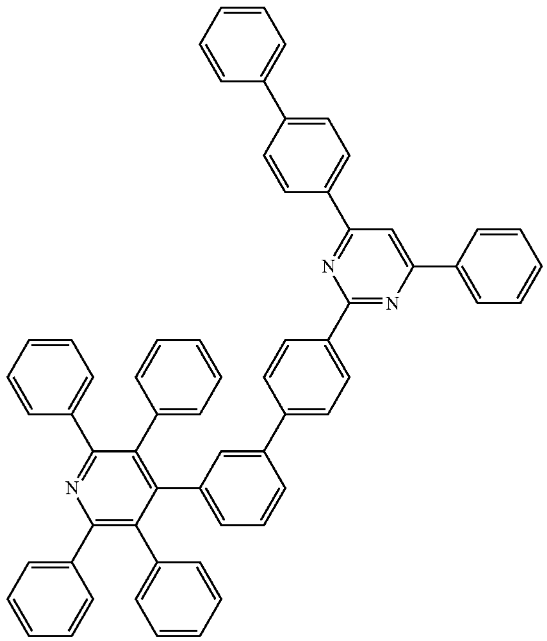

-continued
199
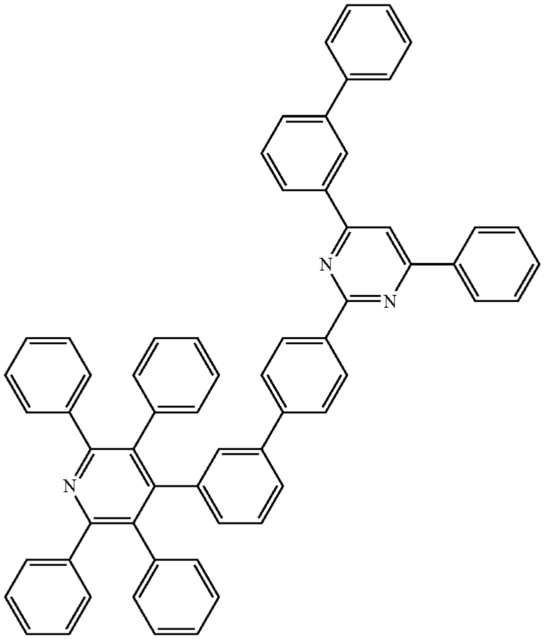
200
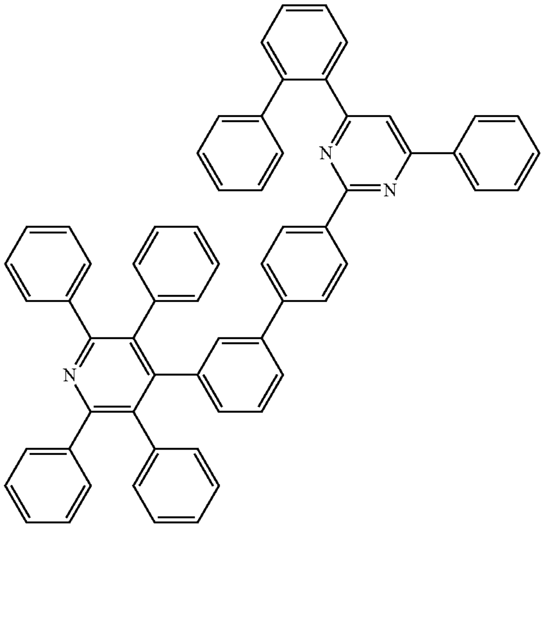
-continued
201
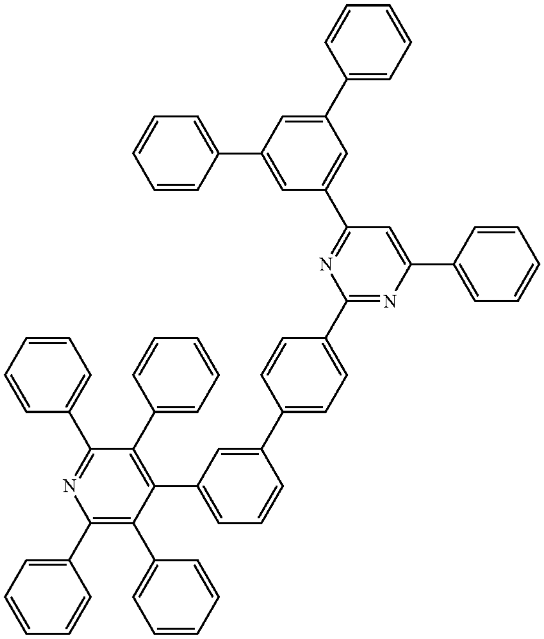
202
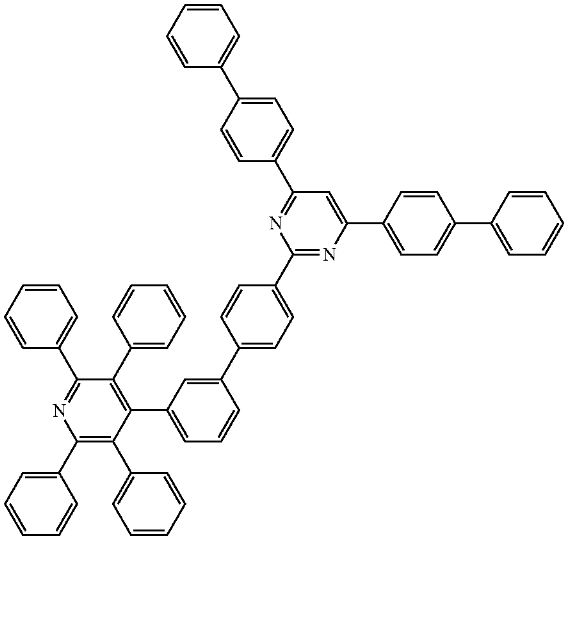

-continued
203
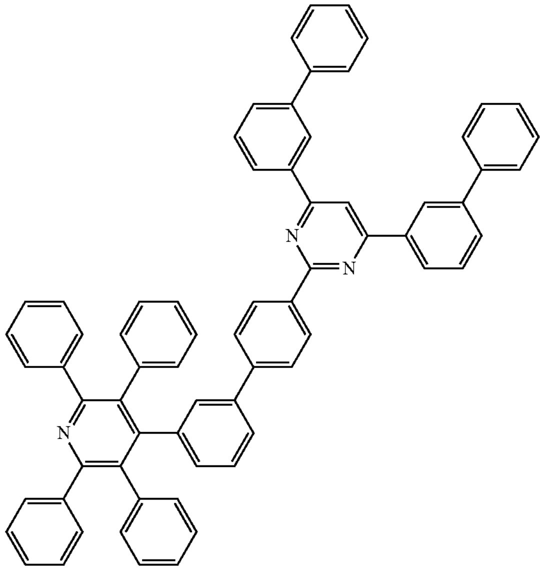
204
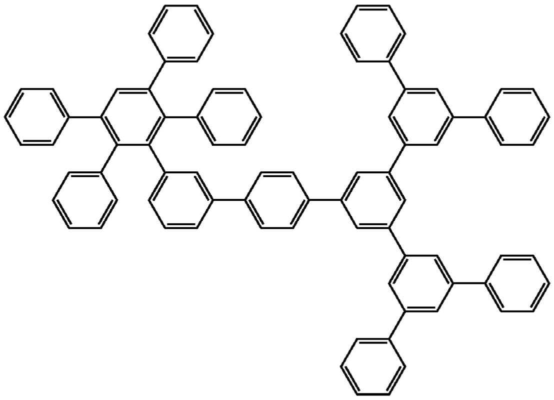
205
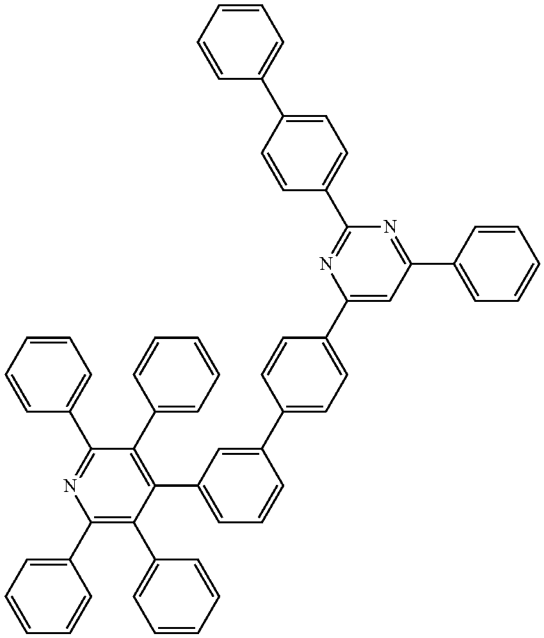
-continued
206
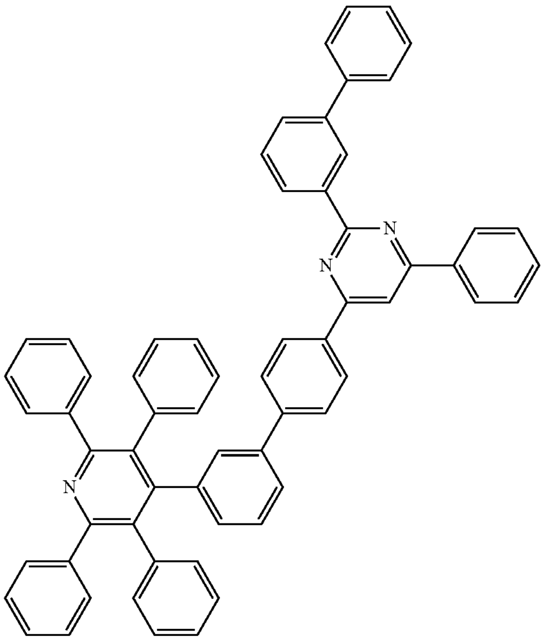
207
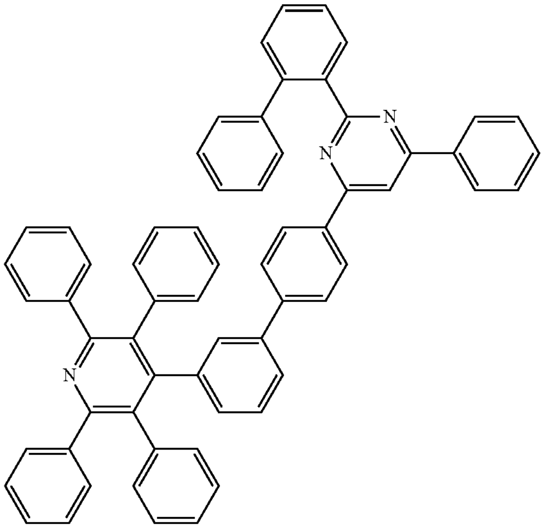

-continued
208
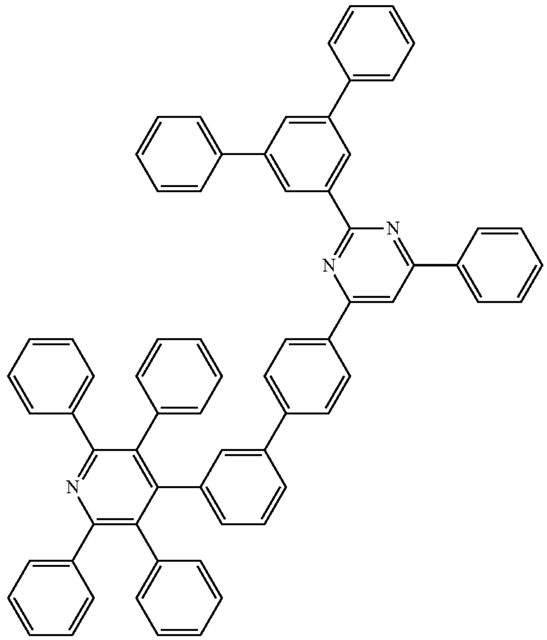
209
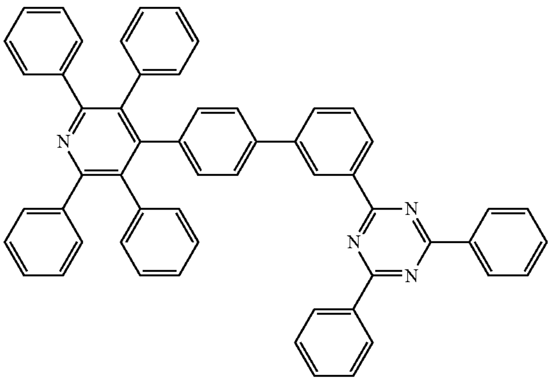
210
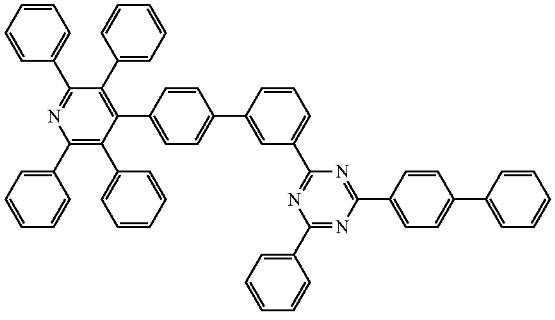
-continued
211
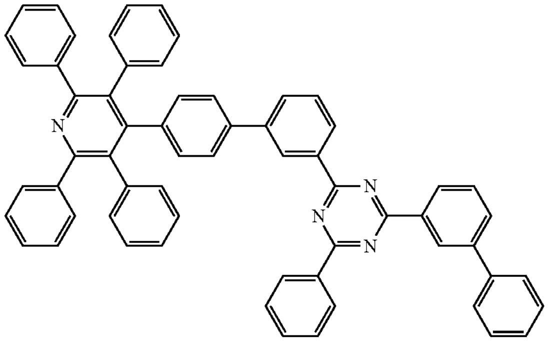
212
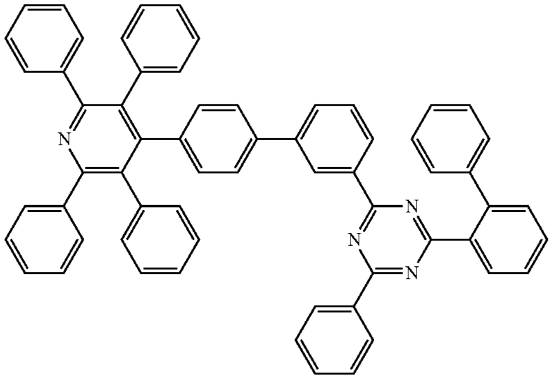
213
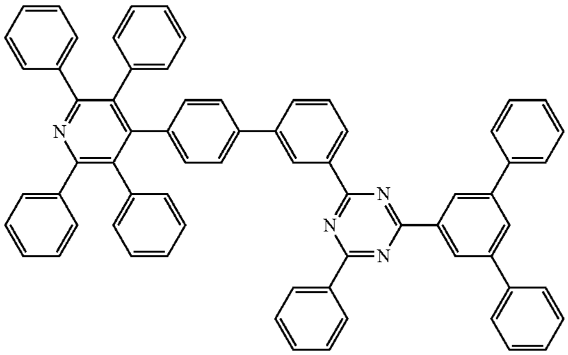
214
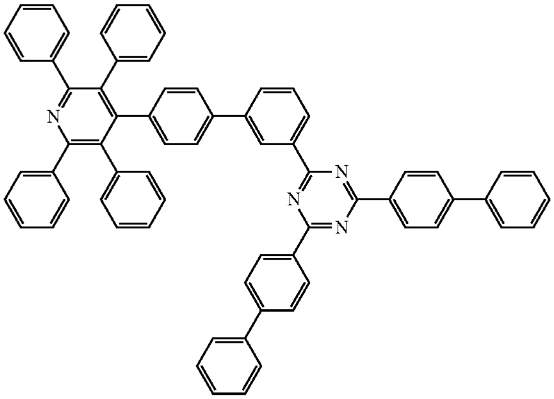

-continued
215
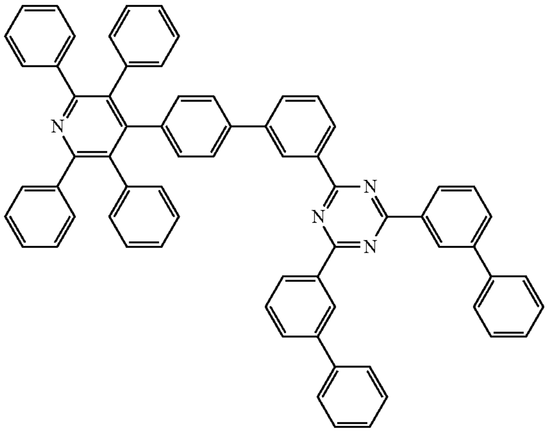
216
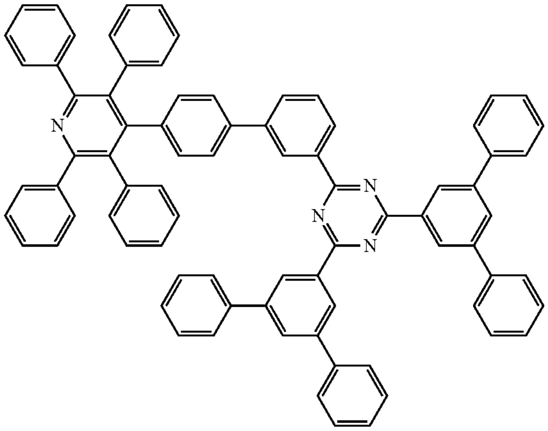
217
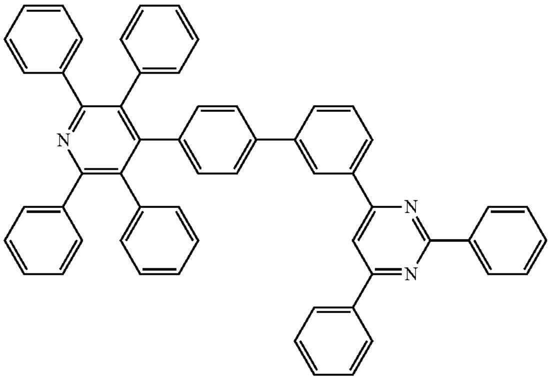
218
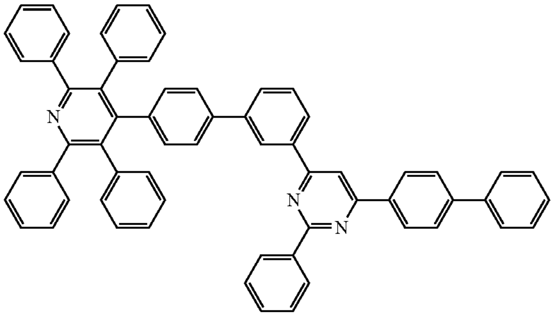
-continued
219
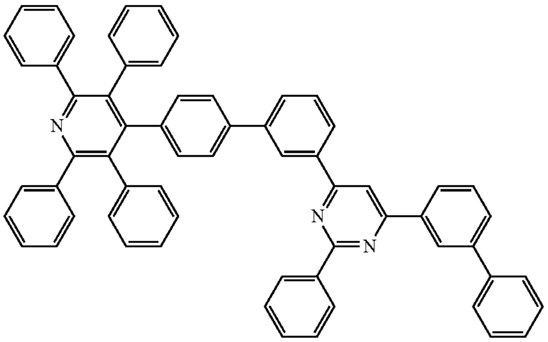
220
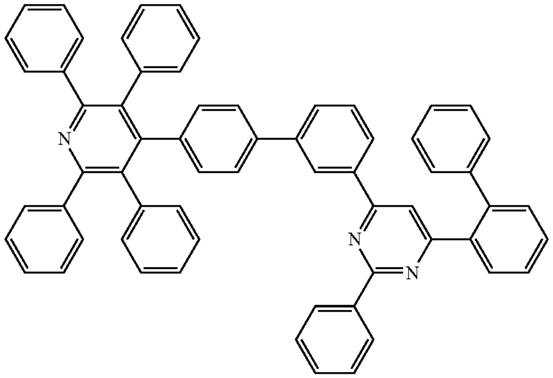
221
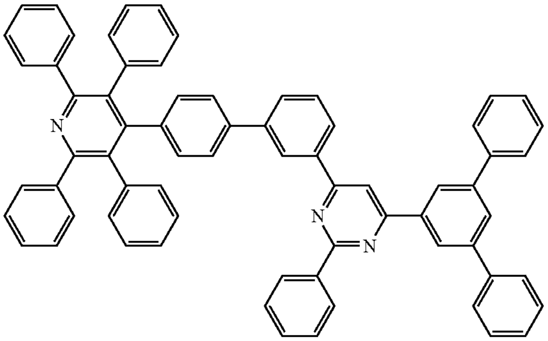
222
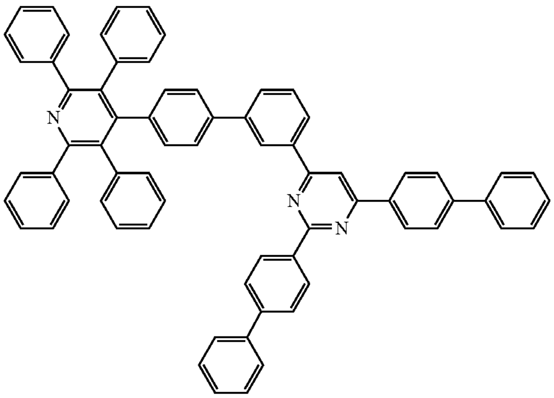

-continued
223
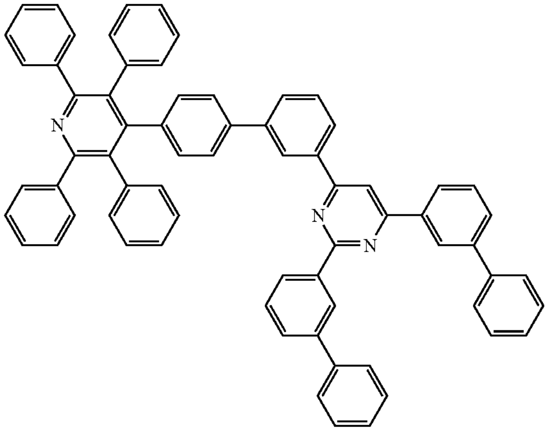
224
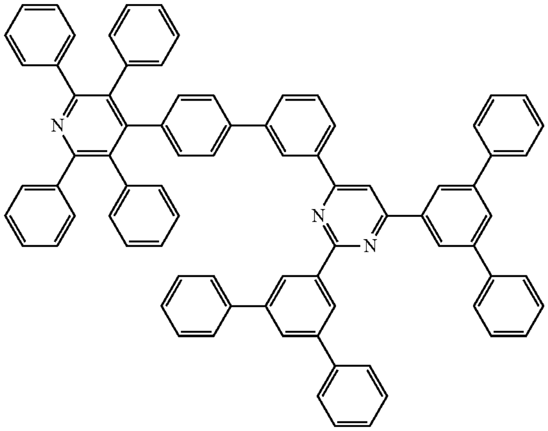
225
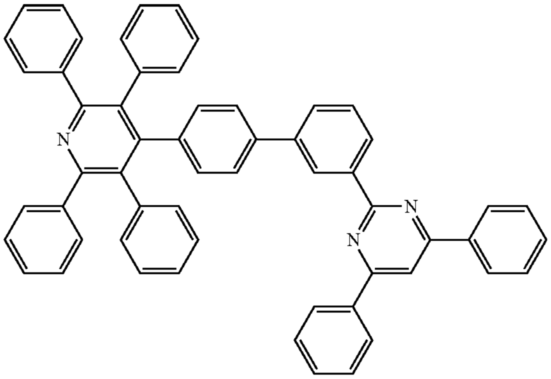
226
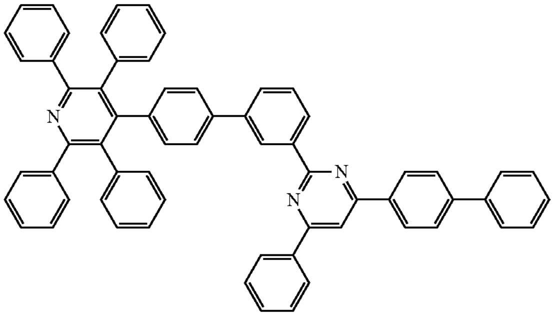
-continued
227
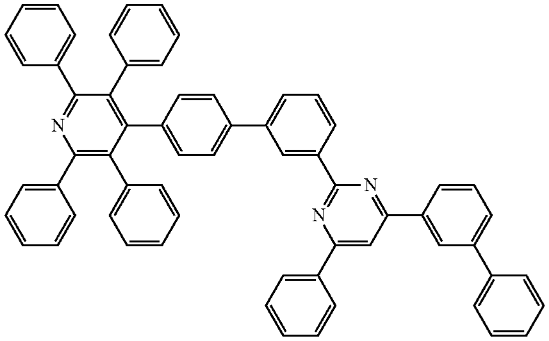
228
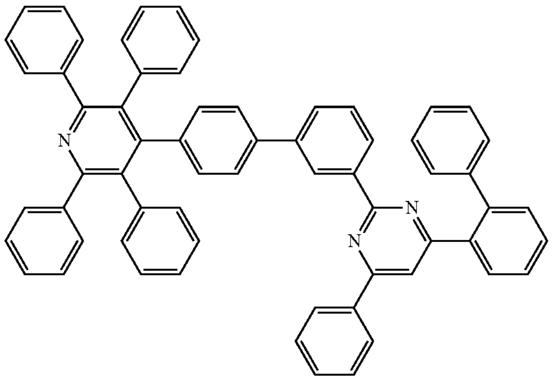
229
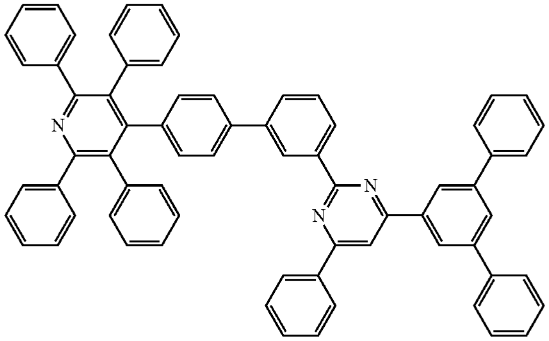
230
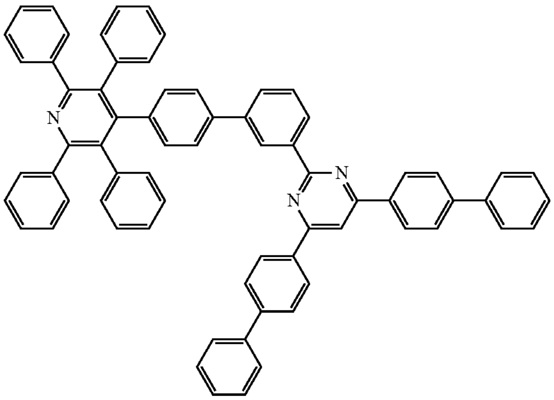

-continued
231
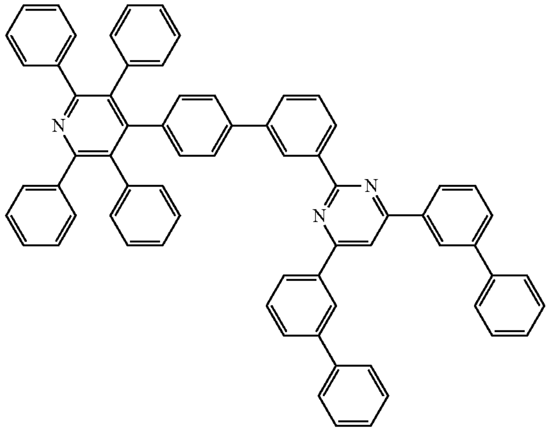
232
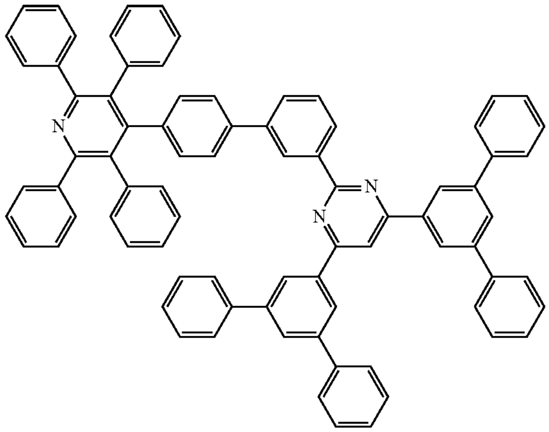
233
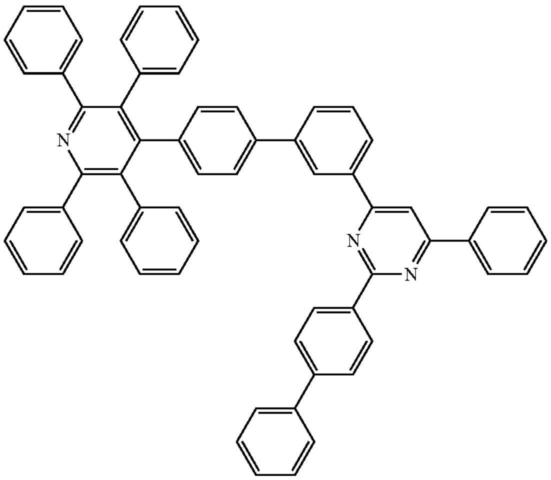
-continued
234
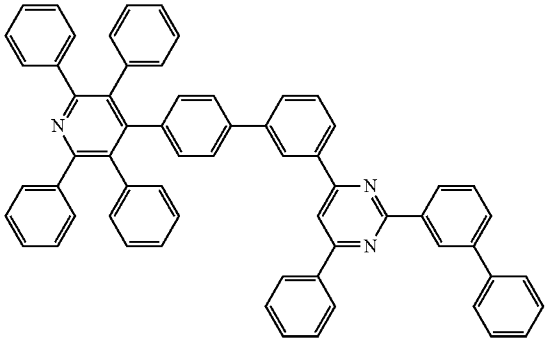
235
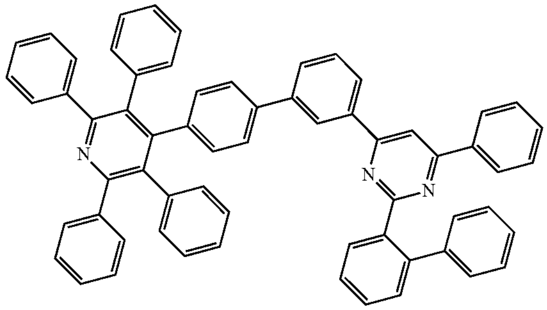
236
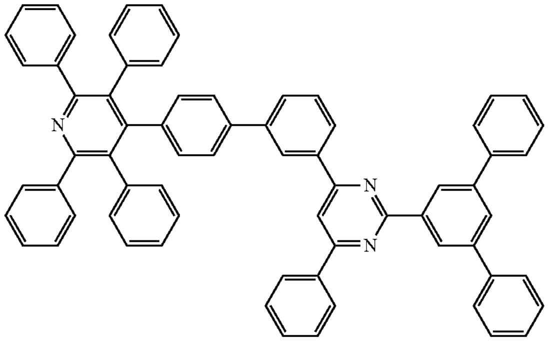
237
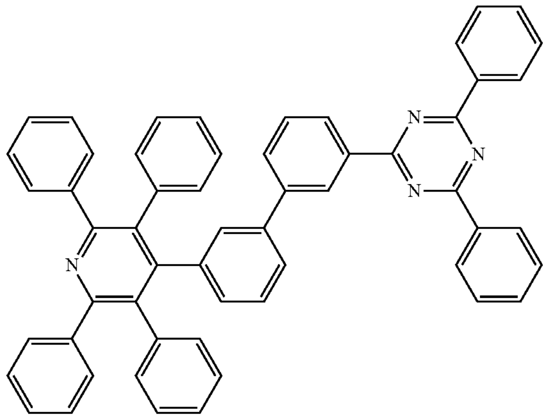

-continued
238
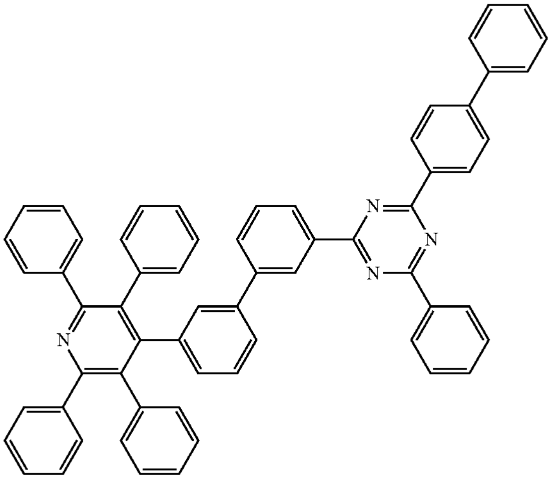
239
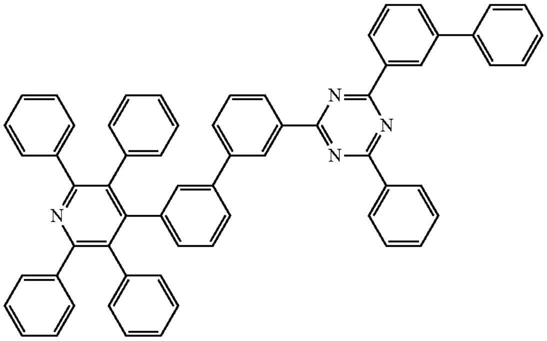
240
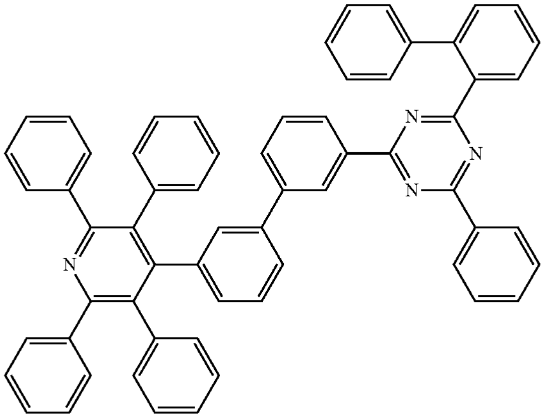
-continued
241
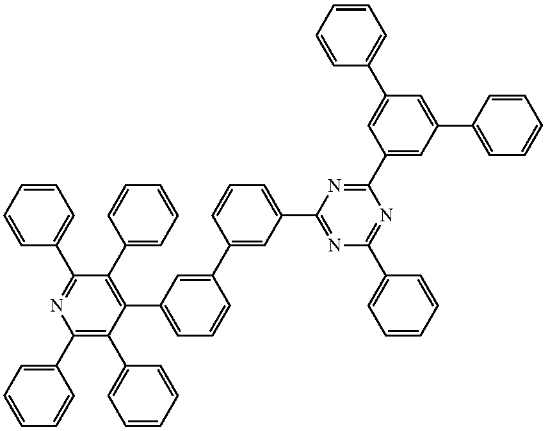
242
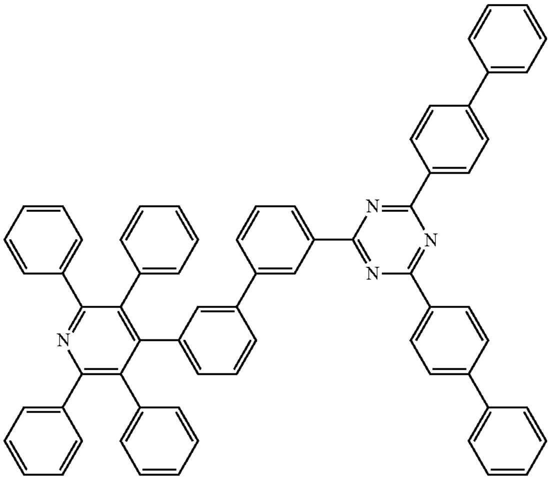
243
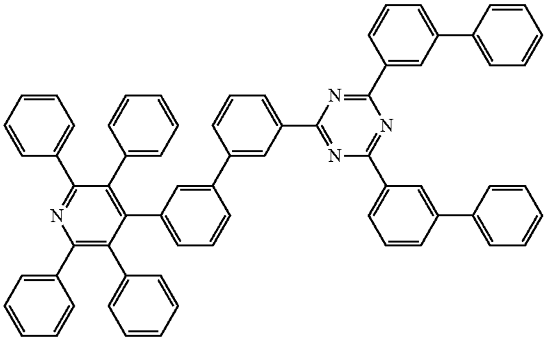

-continued
244
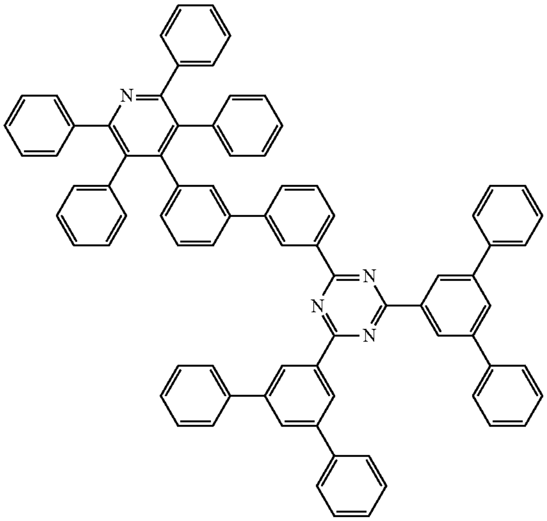
245
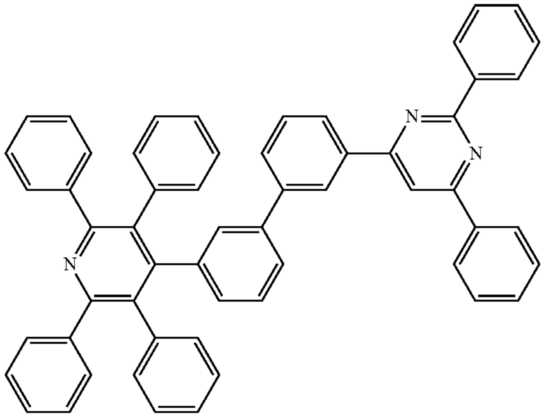
246
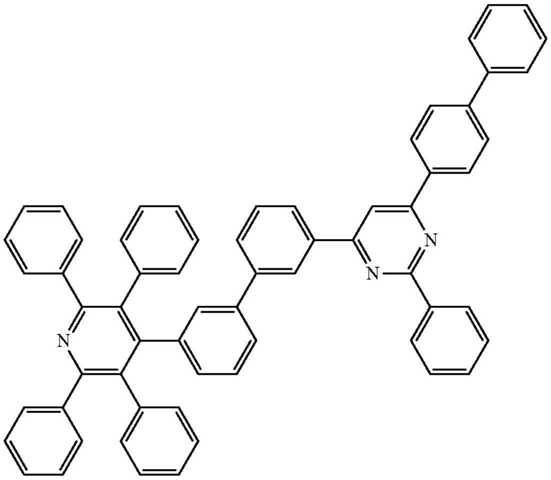
-continued
247
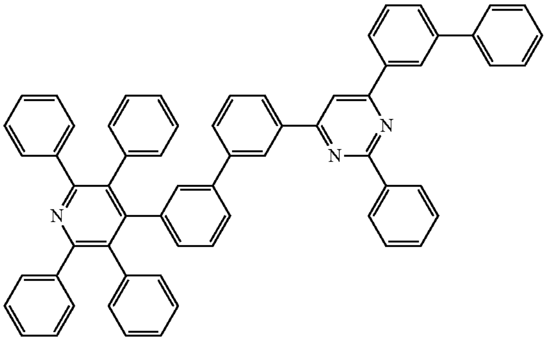
248
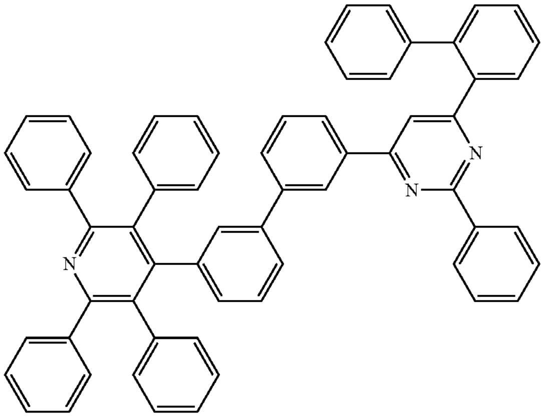
249
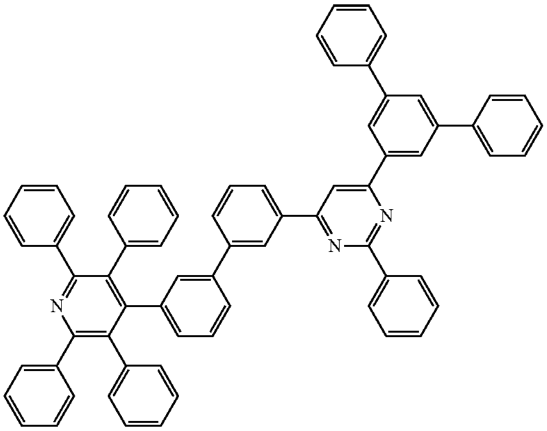

-continued
250
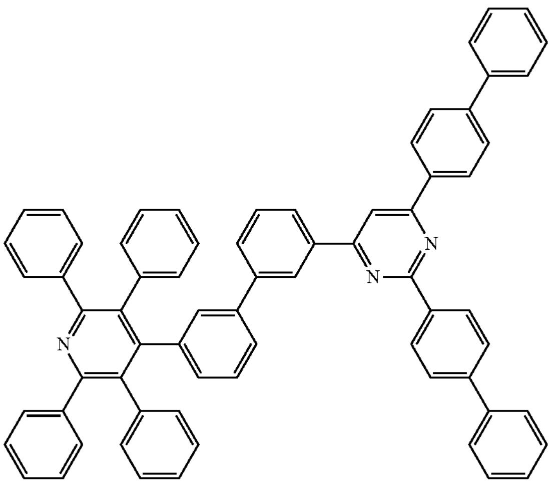
251
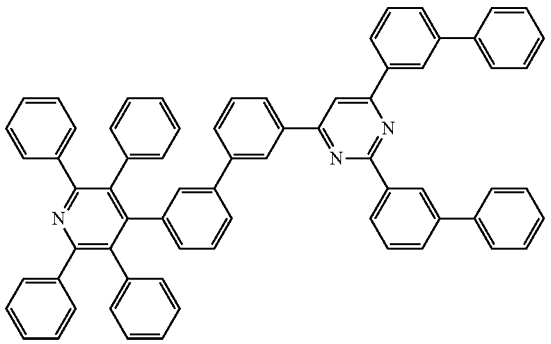
252
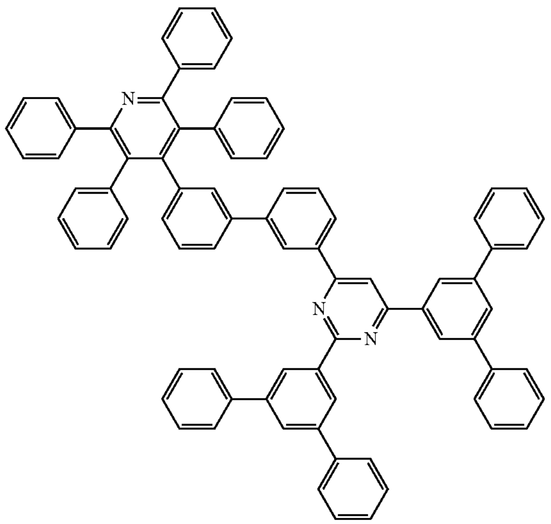
-continued
253
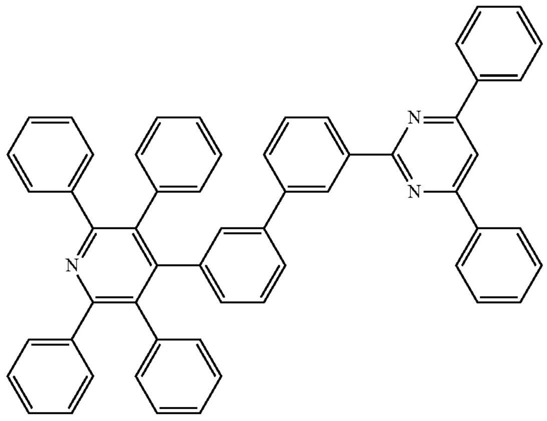
254
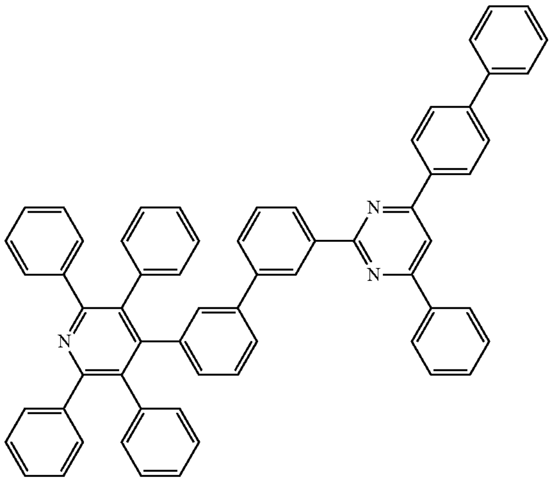
255
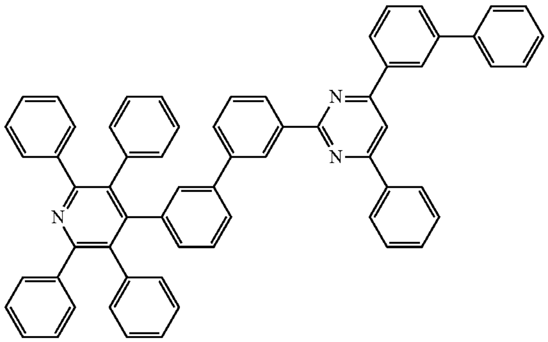

-continued
256
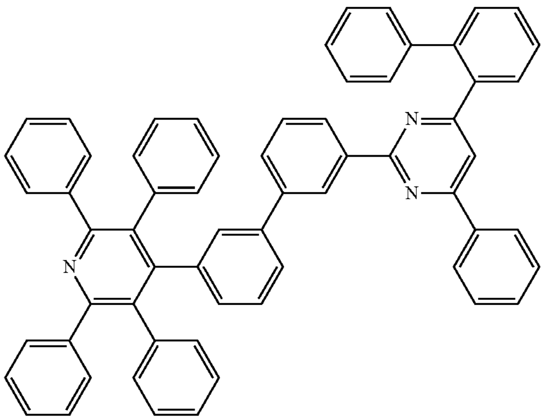
257
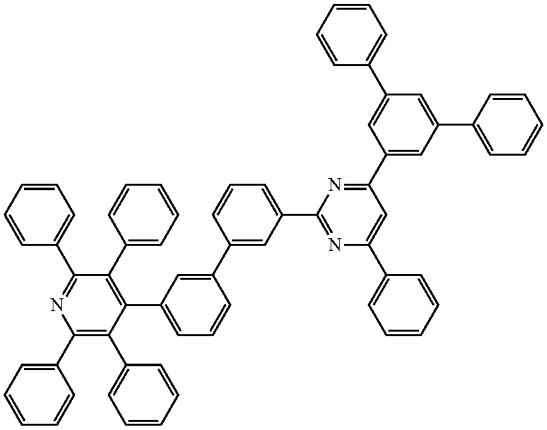
258
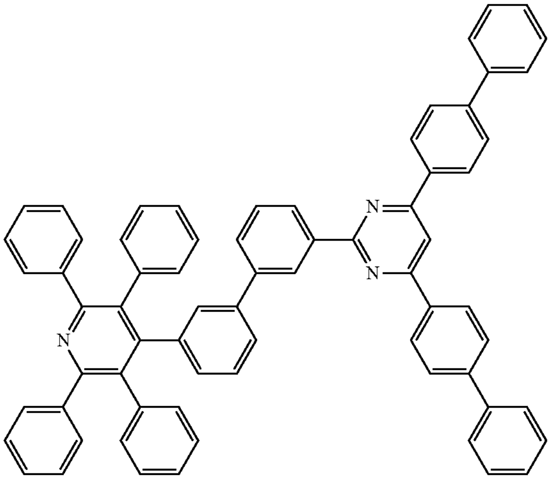
-continued
259
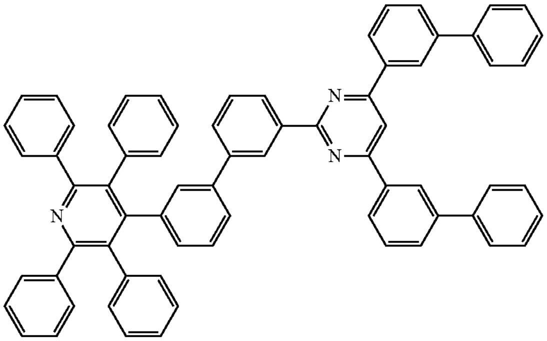
260
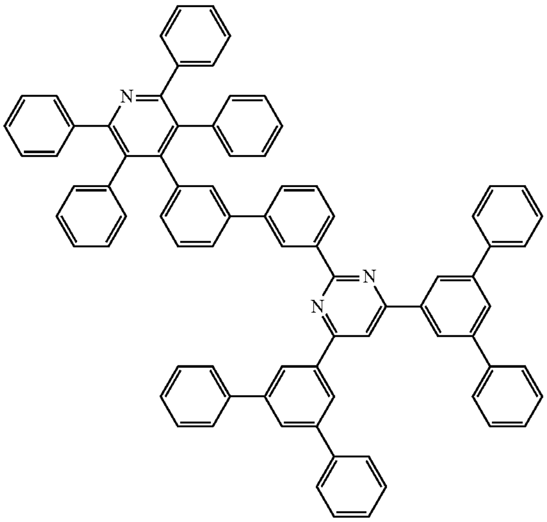
261
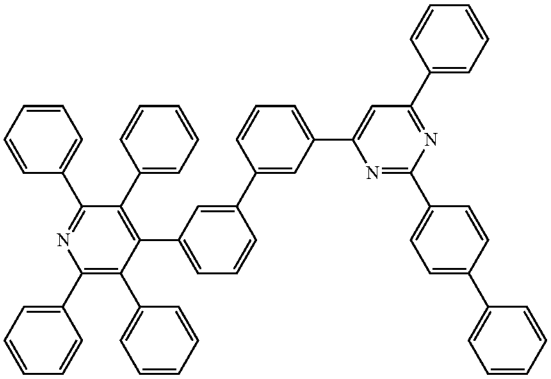

-continued
262
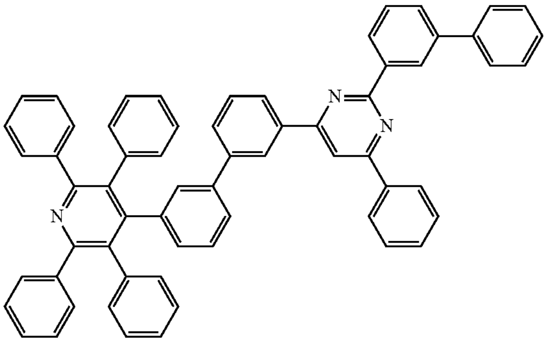
263
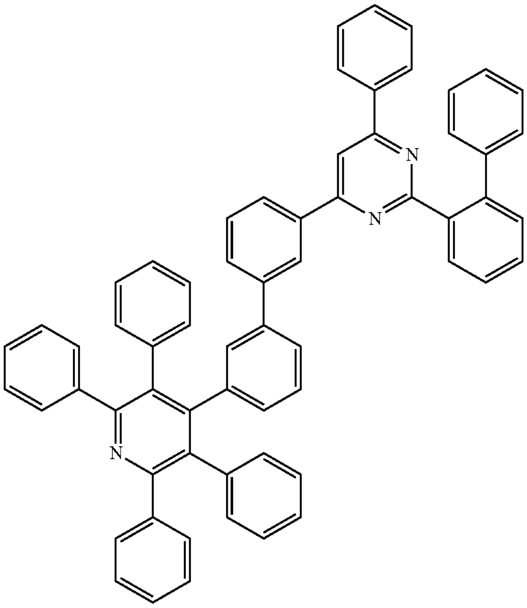
264
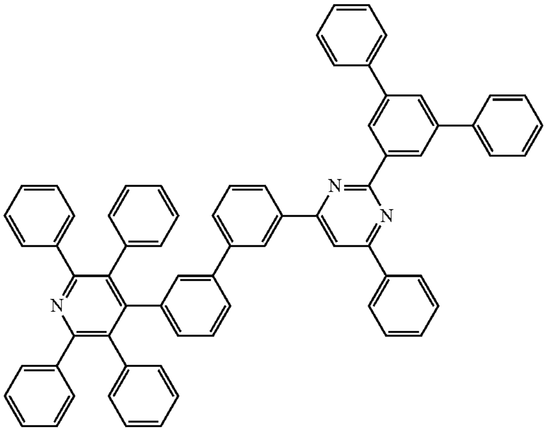
-continued
265
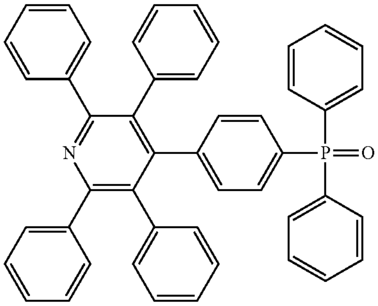
266
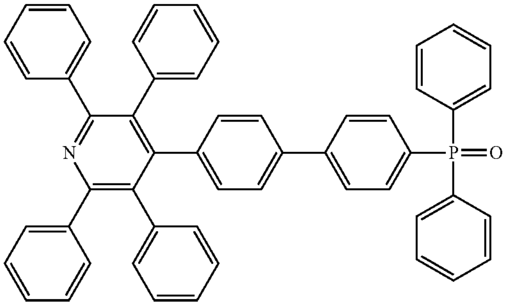
267
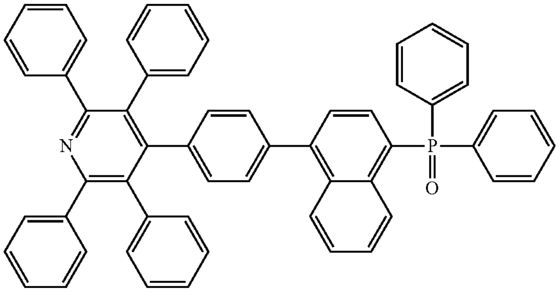
268
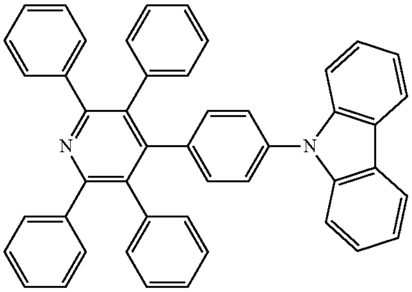
269
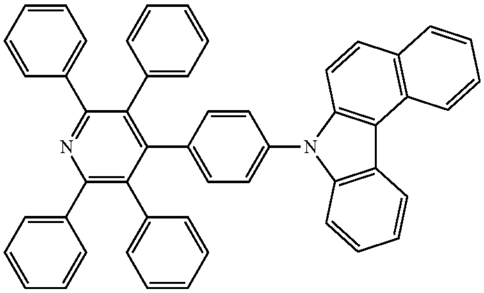

270
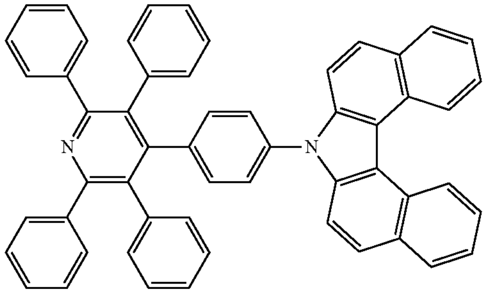
271
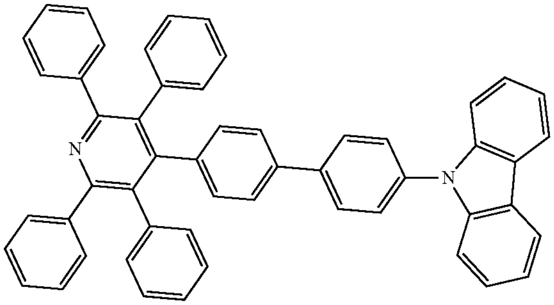
272
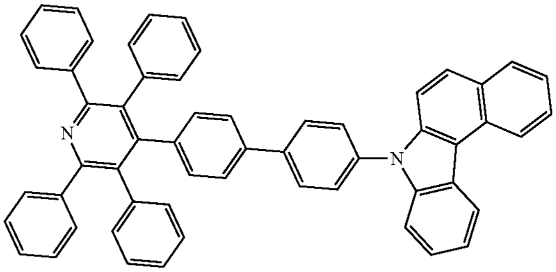
273
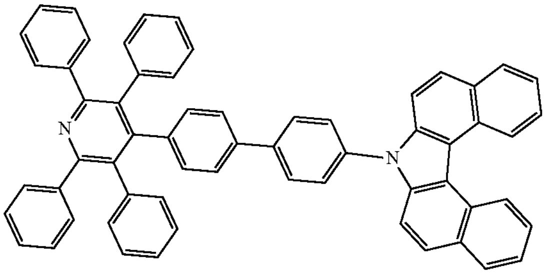
274
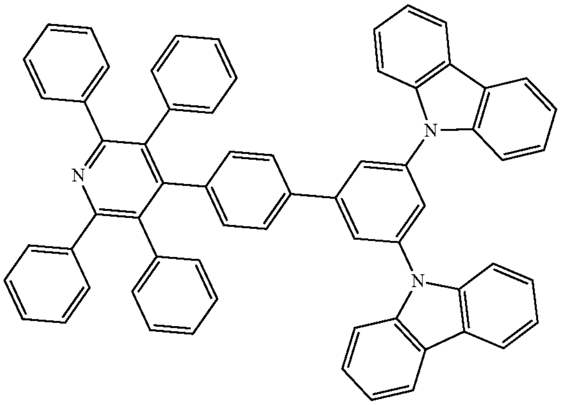
275
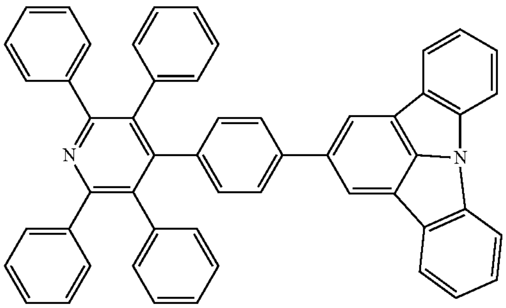
276
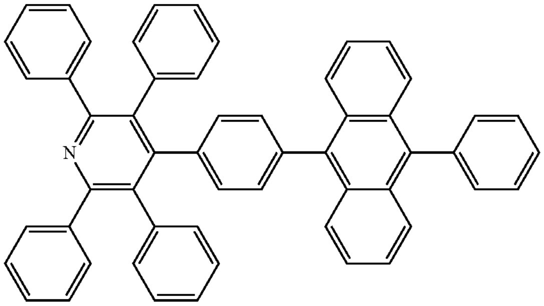
277
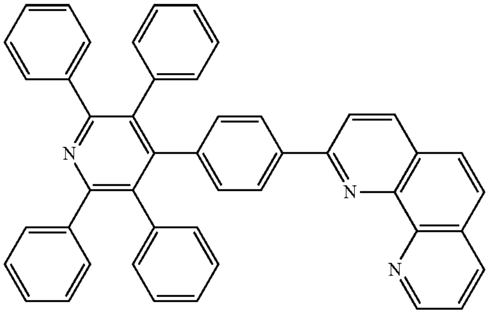
278
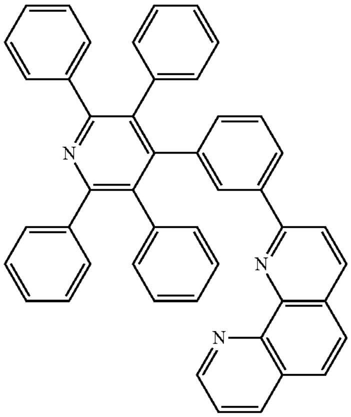

-continued
279
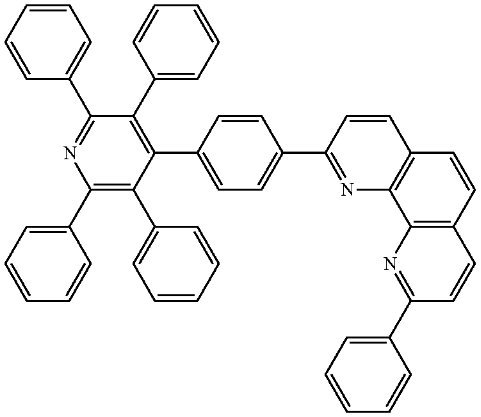
280
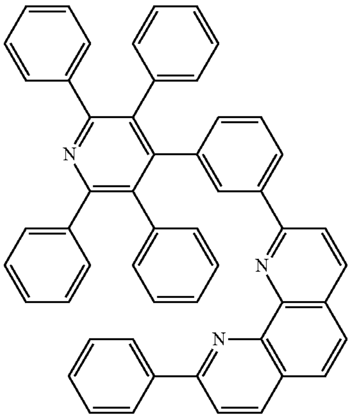
281
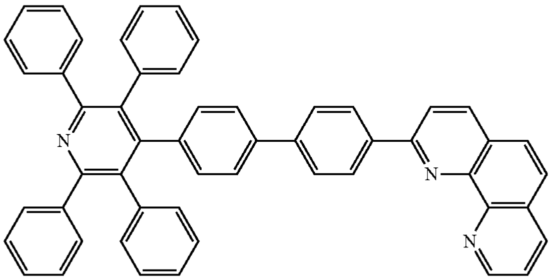
282
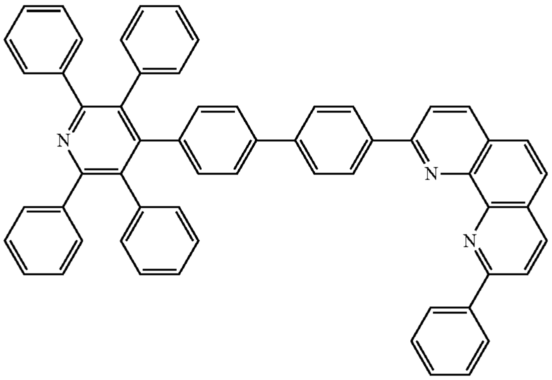
-continued
283
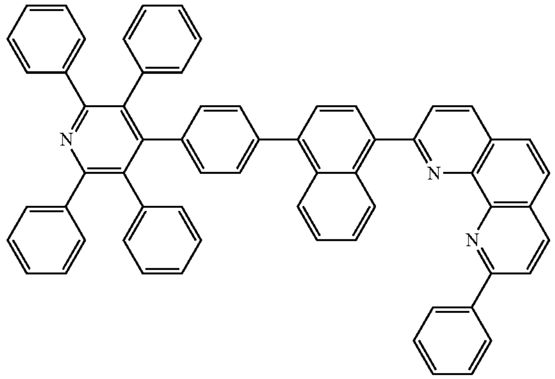
284
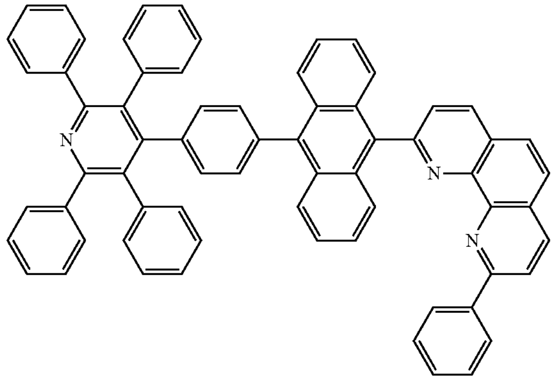
285
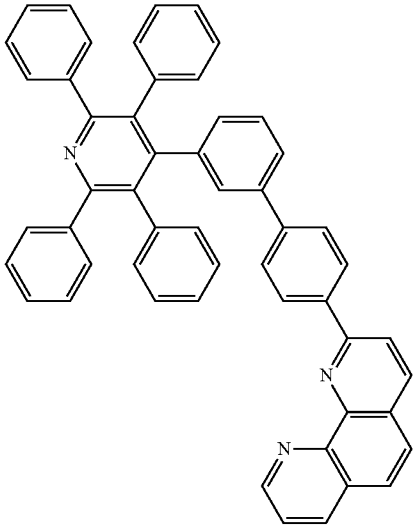

-continued
286
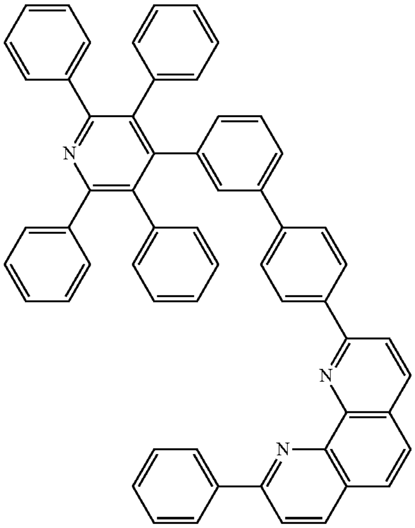
287
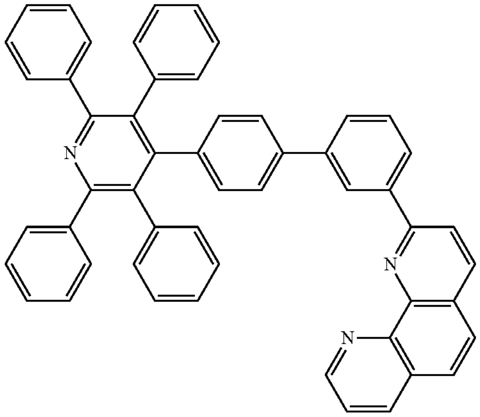
288
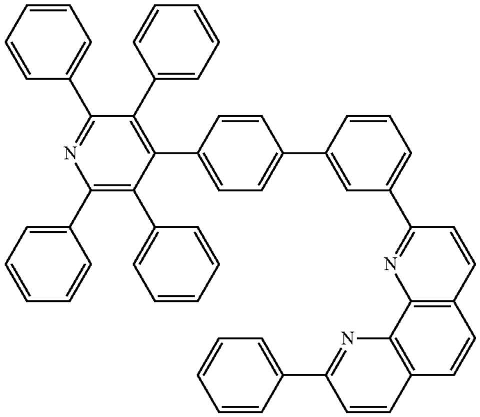
-continued
289
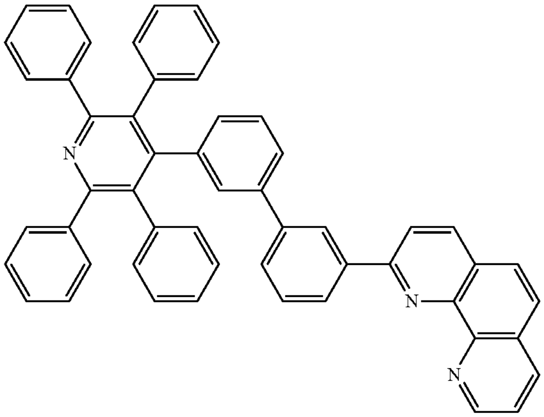
290
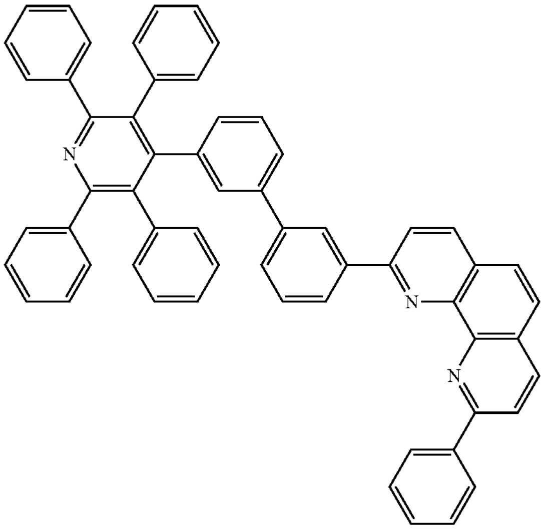
291
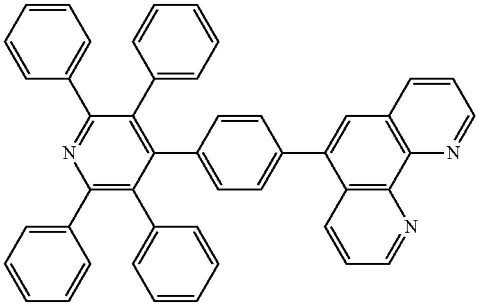

-continued

292

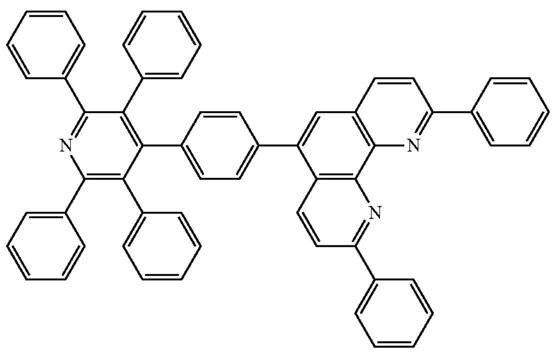

In addition, by introducing various substituents to the structure of Chemical Formula 1, heterocyclic compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the heterocyclic compound has a high glass transition temperature (Tg) and thereby has superior thermal stability. Such an increase in the thermal stability becomes an important factor in providing driving stability to a device.

The heterocyclic compound according to one embodiment of the present application may be prepared using a multi-step chemical reaction. Some intermediate compounds are prepared first, and from the intermediate compounds, the heterocyclic compound of Chemical Formula 1 may be prepared. More specifically, the heterocyclic compound according to one embodiment of the present application may be prepared based on preparation examples to describe later.

Another embodiment of the present application provides an organic light emitting device including the heterocyclic compound represented by Chemical Formula 1. The "organic light emitting device" may be expressed in terms such as an "organic light emitting diode", an "OLED", an "OLED device" and an "organic electroluminescent device".

One embodiment of the present application provides an organic light emitting device including a first electrode; a second electrode; and one or more organic material layers provided between the first electrode and the second electrode, wherein one or more layers of the organic material layers include the heterocyclic compound represented by Chemical Formula 1.

In one embodiment of the present application, the first electrode may be an anode, and the second electrode may be a cathode.

In another embodiment of the present application, the first electrode may be a cathode, and the second electrode may be an anode.

In one embodiment of the present application, the organic light emitting device may be a blue organic light emitting device, and the heterocyclic compound according to Chemical Formula 1 may be used as a material of the blue organic light emitting device.

In another embodiment of the present application, the organic light emitting device may be a green organic light emitting device, and the heterocyclic compound according to Chemical Formula 1 may be used as a material of the green organic light emitting device.

In another embodiment of the present application, the organic light emitting device may be a red organic light emitting device, and the heterocyclic compound according to Chemical Formula 1 may be used as a material of the red organic light emitting device.

Specific descriptions on the heterocyclic compound represented by Chemical Formula 1 are the same as the descriptions provided above.

The organic light emitting device of the present application may be manufactured using common organic light emitting device manufacturing methods and materials except that one or more of the organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present application may be formed in a single layer structure, but may be formed in a multilayer structure in which two or more organic material layers are laminated. For example, the organic light emitting device of the present disclosure may have a structure including a hole injection layer, a hole transfer layer, a hole auxiliary layer, a light emitting layer, an electron transfer layer, an electron injection layer and the like as the organic material layer. However, the structure of the organic light emitting device is not limited thereto, and may include a smaller number of organic material layers.

In the organic light emitting device of the present application, the organic material layer includes an electron transfer layer, and the electron transfer layer may include the heterocyclic compound. When using the heterocyclic compound in the electron transfer layer, proper energy level and band gap are formed increasing excitons in a light emitting area, and the device has enhanced driving voltage and efficiency. In addition, by having a high T1 value, a device with a long lifetime provided with excellent hole transfer ability and thermal stability may be obtained.

In the organic light emitting device of the present application, the organic material layer includes a hole blocking layer, and the hole blocking layer may include the heterocyclic compound. When using the heterocyclic compound in the hole blocking layer, proper energy level and band gap are formed increasing excitons in a light emitting area, and the device has enhanced driving voltage and efficiency. In addition, by having a high T1 value, a device with a long lifetime provided with excellent hole transfer ability and thermal stability may be obtained.

The organic light emitting device of the present disclosure may further include one, two or more layers selected from the group consisting of a light emitting layer, a hole injection layer, a hole transfer layer, an electron injection layer, an electron transfer layer, a hole auxiliary layer and a hole blocking layer.

FIG. 1 to FIG. 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 includes a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, layers other than the light emitting layer may not be included, and other necessary functional layers may be further added.

The organic material layer including the heterocyclic compound represented by Chemical Formula 1 may further include other materials as necessary.

In addition, the organic light emitting device according to one embodiment of the present application includes a first electrode; a first stack provided on the first electrode and including a first light emitting layer; a charge generation layer provided on the first stack; a second stack provided on the charge generation layer and including a second light emitting layer; and a second electrode provided on the second stack.

Herein, the charge generation layer may include the heterocyclic compound represented by Chemical Formula 1. When using the heterocyclic compound in a charge generation layer, the organic light emitting device may have superior driving, efficiency and lifetime.

In addition, the first stack and the second stack may each independently further include one or more types of the hole injection layer, the hole transfer layer, the hole blocking layer, the electron transfer layer, the electron injection layer and the like described above.

The charge generation layer may be an N-type charge generation layer, and the charge generation layer may further include a dopant known in the art in addition to the heterocyclic compound represented by Chemical Formula 1.

As the organic light emitting device according to one embodiment of the present application, an organic light emitting device having a 2-stack tandem structure is illustrated in FIG. 4.

Herein, the first electron blocking layer, the first hole blocking layer, the second hole blocking layer and the like described in FIG. 4 may not be included in some cases.

In the organic light emitting device according to one embodiment of the present application, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene](PEDOT), polypyrrole and polyaniline, and the like, but are not limited thereto.

As the cathode material, materials having relatively small work function may be used, and metals, metal oxides, conductive polymers or the like may be used. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrenesulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected and used as a host material of a light emitting layer.

In the organic light emitting device of the present application, the organic material layer includes a light emitting layer, and the light emitting layer may include the heterocyclic compound as a host material of a light emitting material.

In the organic light emitting device of the present application, the light emitting layer may include two or more host materials, and at least one of the host materials may include the heterocyclic compound as a host material of a light emitting material.

In the organic light emitting device of the present application, the light emitting layer may include two or more host materials, the two or more host materials each include one or more p-type host materials and n-type host materials, and at least one of the host materials may include the heterocyclic compound as a host material of a light emitting material. In this case, the organic light emitting device may have superior driving, efficiency and lifetime.

The organic light emitting device according to one embodiment of the present application may be a top-emission type, a bottom-emission type or a dual-emission type depending on the materials used.

The heterocyclic compound according to one embodiment of the present application may also be used in an organic electronic device including an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

Preparation Example 1

Preparation of Compound 1

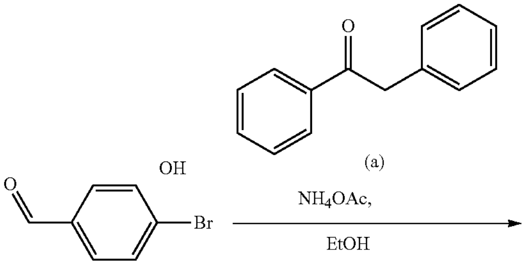

1-1

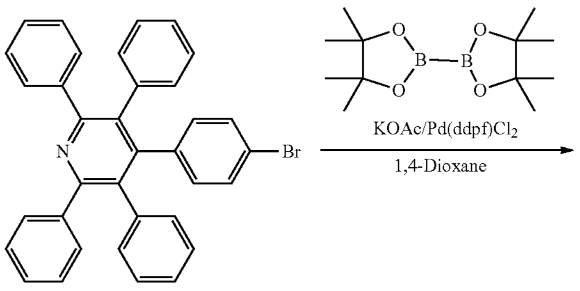

1-2

-continued

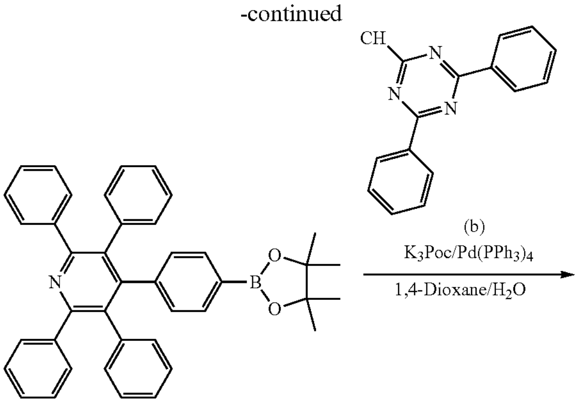

1-3

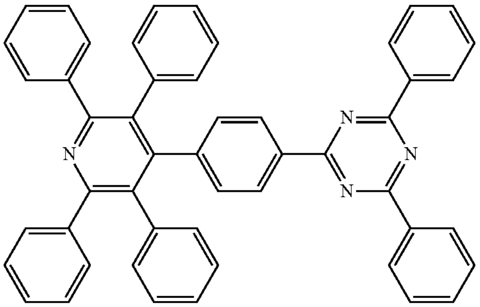

1

1) Preparation of Compound 1-2

EtOH (200 ml) was introduced to Intermediate (a) (20 g, 0.1 mol, 1 eq.), Intermediate (b) (42.4 g, 0.21 mol, 2 eq.), $NH_4OAc$ (7.5 g, 0.016 mol, 1.5 eq.) and ceric ammonium nitrate (CAN) (11.8 g, 0.02 mol, 0.2 eq.), and the mixture was stirred for 12 hours (h) at room temperature (abbreviated as “RT”). The reaction was terminated by introducing water thereto, and the result was extracted using methylene chloride (hereinafter, MC) and water. After that, moisture was removed using anhydrous $Na_2CO_3$. The result was separated using a silica gel column to obtain Compound 1-2 (24 g) in a 40% yield.

The room temperature means approximately 20° C. to approximately 30° C., approximately 22° C. to approximately 27° C., or approximately 25° C.

2) Preparation of Compound 1-3

Compound 1-2 (28 g. 0.052 mol, 1 eq.), bis(pinacolato) diboron (19.8 g, 0.077 mol, 1.5 eq.), KOAc (15.3 g, 0.155 mol, 3 eq.) and Pd(dppf)$Cl_2$ (3.8 g, 0.005 mol, 0.1 eq.) were introduced to 1,4-dioxane (280 ml), and the mixture was stirred for 7 hours at 100° C. The reaction was terminated by introducing water thereto, and the result was extracted using MC and water. After that, moisture was removed using anhydrous $Na_2CO_3$. The result was separated using a silica gel column to obtain Compound 1-3 (25 g) in an 82% yield.

3) Preparation of Compound 1

Compound 1-3 (8 g, 0.013 mol, 1 eq.), Intermediate (c) (4 g, 0.015 mol, 1.1 eq.), $K_3PO_4$ (5.8 g, 0.026 mol, 2 eq.) and Pd($PPh_3$)$_4$ (0.49 g, 0.0004 mol, 0.05 eq.) were introduced to 1,4-dioxane (160 ml) and $H_2O$ (40 ml), and the mixture was stirred for 5 hours at 80° C. Produced solids were filtered and dried to obtain Compound 1 (8 g) in an 85% yield.
Target compounds were synthesized in the same manner as in Preparation Example 1 except that Intermediates A and B of the following Table 1 were used instead of Intermediates (a), (b) and (c).
TABLE 1
| Target Compound | Intermediate A | Intermediate B | yield |
|---|---|---|---|
| 3 | 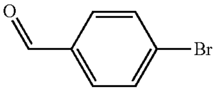 | 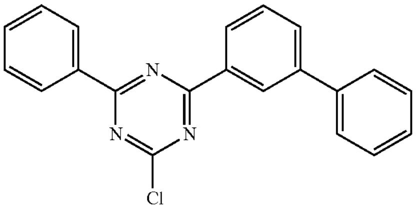 [SMILES: Clc1nc(-c2ccccc2)nc(-c2cccc(-c3ccccc3)c2)n1] | 73% |
| 7 | 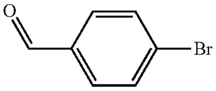 | 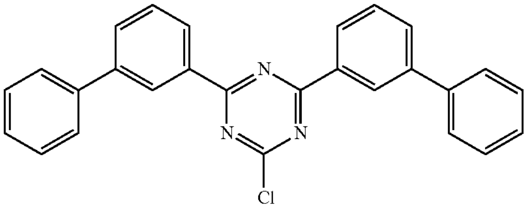 [SMILES: Clc1nc(-c2cccc(-c3ccccc3)c2)nc(-c2cccc(-c3ccccc3)c2)n1] | 68% |
| 14 | 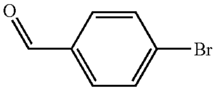 | 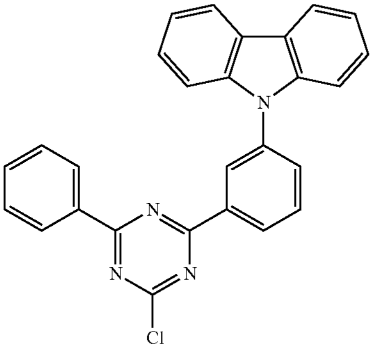 [SMILES: Clc1nc(-c2ccccc2)nc(-c2cccc(-n3c4ccccc4c4ccccc43)c2)n1] | 65% |
| 21 | 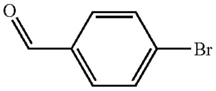 | 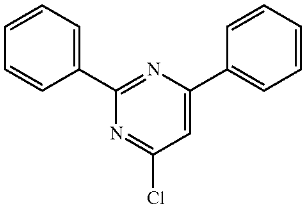 [SMILES: Clc1cc(-c2ccccc2)nc(-c2ccccc2)n1] | 70% |
| 26 | 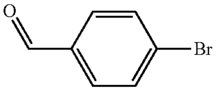 | 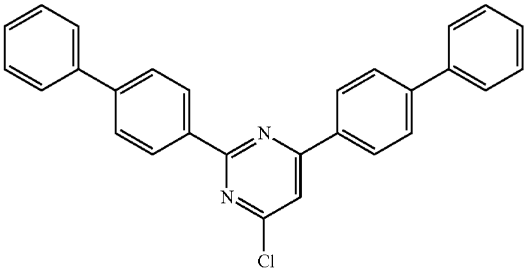 [SMILES: Clc1cc(-c2ccc(-c3ccccc3)cc2)nc(-c2ccc(-c3ccccc3)cc2)n1] | 72% |

TABLE 1-continued
| Target Compound | Intermediate A | Intermediate B | yield |
|---|---|---|---|
| 41 | 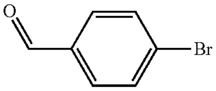 | 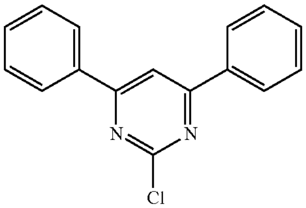 [SMILES: Clc1nc(-c2ccccc2)cc(-c2ccccc2)n1] | 68% |
| 77 | 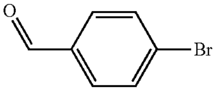 | 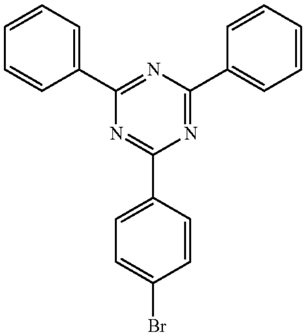 [SMILES: Brc1ccc(-c2nc(-c3ccccc3)nc(-c3ccccc3)n2)cc1] | 59% |
| 105 | 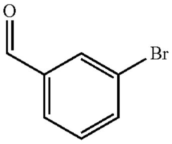 | 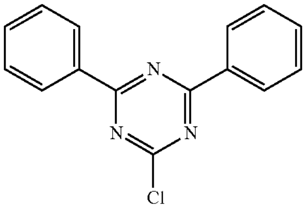 [SMILES: Clc1nc(-c2ccccc2)nc(-c2ccccc2)n1] | 70% |
| 114 | 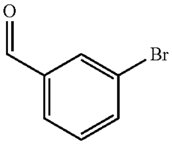 | 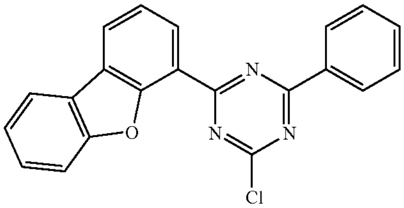 [SMILES: Clc1nc(-c2ccccc2)nc(-c2cccc3c2oc2ccccc23)n1] | 61% |
| 267 | 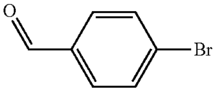 | 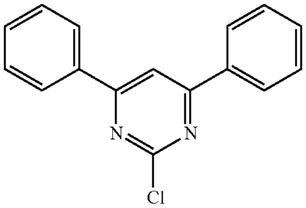 [SMILES: Clc1nc(-c2ccccc2)cc(-c2ccccc2)n1] | 55% |

Compounds were prepared in the same manner as in the preparation examples, and the synthesis identification results are shown in the following Table 2 and Table 3. The following Table 2 shows measurement values of ═H NMR ($CDCl_3$, 200 Mz), and the following Table 3 shows measurement values of FD-mass spectrometry (FD-MS: field desorption mass spectrometry).

TABLE 2

| Compound | $^1H$ NMR($CDCl_3$, 200 Mz) |
|---|---|
| 1 | δ = 8.30-8.28 (m, 8H), 7.85 (d, 2H), 7.54-7.41 (m, 22H), 7.25 (d, 2H) |
| 3 | δ = 8.30-8.24 (m, 9H), 7.79 (d, 2H), 7.54-7.41 (m, 22H), 7.25 (d, 2H) |
| 7 | δ = 8.30-8.24 (m, 6H), 7.85 (d, 2H), 7.70 (s, 2H), 7.54-7.41 (m, 30H), 7.25 (d, 2H) |
| 14 | δ = 8.55 (d, 1H), 8.30-8.28 (m, 7H), 8.09 (m, 2H), 7.94 (d, 1H), 7.85 (d, 2H), 7.63 (d, 1H), 7.54-7.41 (m, 27H) |
| 21 | δ = 8.30-8.24 (m, 9H), 7.79 (d, 2H), 7.54-7.41 (m, 22H), 7.25 (d, 2H) |
| 26 | δ = 8.30 (m, 8H), 8.23 (s, 1H), 7.85 (m, 4H), 7.54-7.41 (m, 26H), 7.25 (d, 4H) |
| 41 | δ = 8.30 (m, 4H), 8.23 (s, 1H), 7.85-7.79 (m, 6H), 7.54-7.41 (m, 22H), 7.25 (d, 2H) |
| 77 | δ = 8.30-8.28 (m, 8H), 7.85 (d, 2H), 7.54-7.41 (m, 22H), 7.25 (m, 6H) |
| 105 | δ = 8.30-8.24 (m, 9H), 7.52 (s, 1H), 7.54-7.41 (m, 24H) |
| 114 | δ = 8.30-8.24 (m, 7H), 7.89 (m, 3H), 7.66 (m, 2H), 7.54-7.32 (m, 24H) |
| 267 | δ = 8.23 (s, 1H), 7.94, (m, 4H), 7.85-7.79 (m, 6H), 7.54-7.41 (m, 12H), 7.25 (d, 2H), 2.31 (s, 6H) |

TABLE 3

| Compound | FD-MS | Compound | FD-MS |
|---|---|---|---|
| 1 | m/z = 690.28 (C50H34N4 = 690.83) | 3 | m/z = 766.31 (C56H38N4 = 766.93) |
| 7 | m/z = 842.32 (C62H42N4 = 843.02) | 14 | m/z = 855.34 (C62H41N5 = 856.02) |
| 21 | m/z = 689.28 (C51H35N3 = 689.84) | 26 | m/z = 841.35 (C63H43N3 = 842.04) |
| 41 | m/z = 689.28 (C51H35N3 = 689.84) | 77 | m/z = 766.31 (C56H38N4 = 766.93) |
| 105 | m/z = 690.28 (C50H34N4 = 690.83) | 114 | m/z = 780.29 (C56H36N4O = 780.91) |
| 267 | m/z = 565.25 (C41H31N3 = 565.70) | | |

EXPERIMENTAL EXAMPLE

Experimental Example 1

1) Manufacture of Organic Light Emitting Device

Comparative Example 1

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used. Next, the ITO substrate was installed in a substrate folder of a vacuum deposition apparatus, and the following 4,4',4"-tris(N, N-(2-naphthyl)-phenylamino)triphenylamine (2-TNATA) was introduced to a cell in the vacuum deposition apparatus.

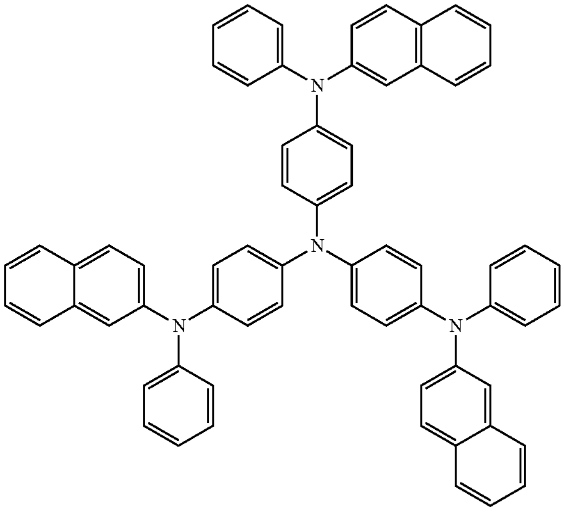

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate. To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

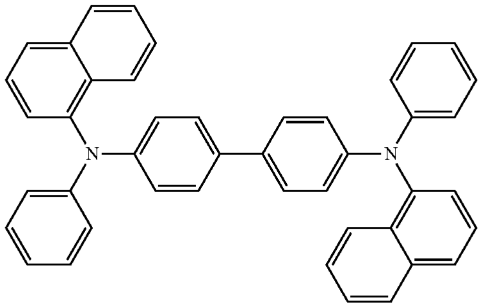

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5 wt % with respect to the host material.

H1

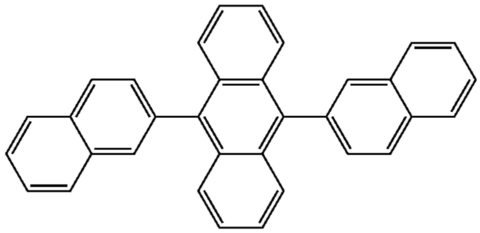

D1

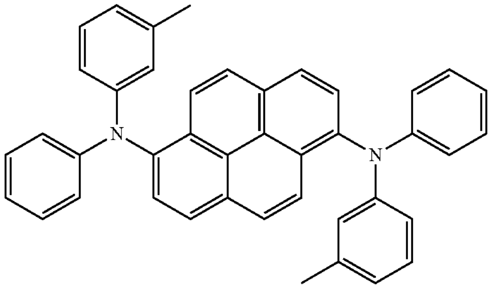

Subsequently, a compound of the following Structural Formula E1 was deposited to a thickness of 300 Å as an electron transfer layer.

E1

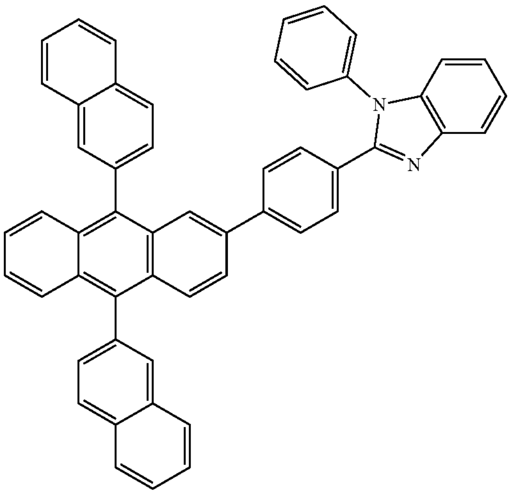

-continued

E2

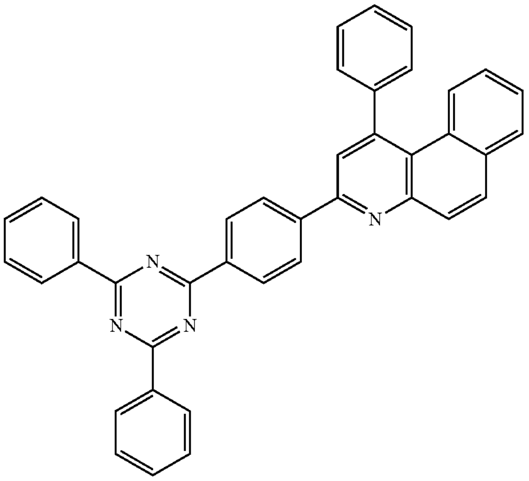

E3

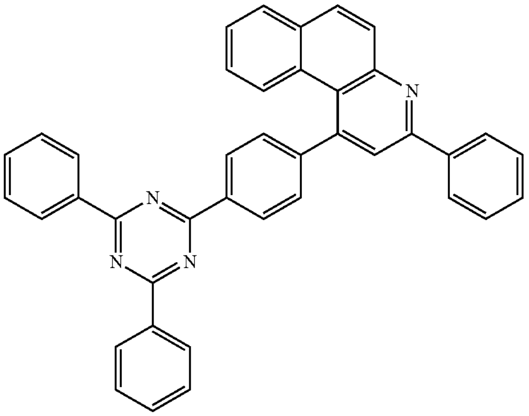

As an electron injection layer, lithium fluoride (LiF) was deposited to a thickness of 10 Å, and an Al cathode was employed to a thickness of 1,000 Å, and as a result, an OLED (Comparative Example 1) was manufactured.

Meanwhile, all the organic compounds required to manufacture the OLED were vacuum sublimation purified under $10^{-8}$ torr to $10^{-5}$ torr by each material to manufacture the OLED.

Organic light emitting devices of Examples 1 to 11 and Comparative Examples 2 and 3 were manufactured in the same manner as in Experimental Example 1 except that compounds shown in Table 4 were each used instead of E1 used when forming the electron transfer layer.

2) Driving Voltage and Light Emission Efficiency of Organic Light Emitting Device For each of the organic light emitting devices of Examples 1 to 11 and Comparative Examples 1 to 3 manufactured as above, electroluminescent (EL) properties were measured using M7000 manufactured by McScience Inc., and with the measurement results, $T_{95}$ was measured when standard luminance was 700 cd/$m^2$ through a lifetime measurement system (M6000) manufactured by McScience Inc. $T_{95}$ means a lifetime (unit: h, time), a time taken to become 95% with respect to initial luminance.

Results of measuring driving voltage, light emission efficiency, external quantum efficiency and color coordinate (CIE) of the blue organic light emitting devices manufactured according to the present disclosure are as shown in the following Table 4.

TABLE 4

| | Compound | Driving voltage (V) | Light emission efficiency (cd/A) | CIE (x, y) | Lifetime ($T_{95}$) |
|---|---|---|---|---|---|
| Example 1 | 1 | 4.62 | 6.88 | (0.134, 0.102) | 61 |
| Example 2 | 3 | 4.77 | 6.80 | (0.134, 0.102) | 59 |
| Example 3 | 7 | 4.68 | 6.90 | (0.134, 0.100) | 62 |
| Example 4 | 14 | 4.75 | 6.84 | (0.134, 0.100) | 58 |
| Example 5 | 21 | 4.80 | 6.83 | (0.134, 0.102) | 54 |
| Example 6 | 26 | 4.87 | 6.87 | (0.134, 0.102) | 52 |
| Example 7 | 41 | 4.66 | 6.91 | (0.134, 0.100) | 63 |
| Example 8 | 77 | 4.62 | 6.91 | (0.134, 0.102) | 65 |
| Example 9 | 105 | 4.80 | 6.85 | (0.134, 0.102) | 54 |
| Example 10 | 114 | 4.89 | 6.88 | (0.134, 0.101) | 55 |
| Example 11 | 267 | 4.72 | 6.95 | (0.134, 0.102) | 63 |
| Comparative Example 1 | E1 | 5.30 | 5.78 | (0.134, 0.102) | 38 |
| Comparative Example 2 | E2 | 5.48 | 5.59 | (0.134, 0.100) | 39 |
| Comparative Example 3 | E3 | 5.40 | 5.68 | (0.134, 0.101) | 40 |

As seen from the results of Table 4, the organic light emitting device using the electron transfer layer material of the blue organic light emitting device of the present disclosure had lower driving voltage and significantly improved light emission efficiency and lifetime compared to Comparative Examples 1, 2 and 3. Particularly, it was identified that the devices using Compounds 1, 7, 41, 77 and 267 were superior in all aspects of driving, efficiency and lifetime.

Such a result is considered to be due to the fact that, when using the disclosed compound having proper length and strength, and flatness as an electron transfer layer, a compound in an excited state is made by receiving electrons under a specific condition, and particularly when an excited state is formed in the hetero-skeleton site of the compound, excited energy will move to a stable state before the excited hetero-skeleton site goes through other reactions, and as a result, the relatively stabilized compound is capable of efficiently transferring electrons without the compound being decomposed or destroyed.

For reference, those that are stable when excited are considered to be aryl or acene-based compounds or polycyclic hetero-compounds. Accordingly, it is considered that excellent results in all aspects of driving, efficiency and lifetime were obtained by the compound of the present disclosure enhancing electron-transfer properties or stability.

Experimental Example 2

1) Manufacture of Organic Light Emitting Device

Comparative Example 4

A transparent indium tin oxide (ITO) electrode thin film obtained from glass for an OLED (manufactured by Samsung-Corning Co., Ltd.) was ultrasonic cleaned using 10 trichloroethylene, acetone, ethanol and distilled water consecutively for 5 minutes each, stored in isopropanol, and used. Next, the ITO substrate was installed in a substrate folder of a vacuum deposition apparatus, and the following 4,4',4"-tris(N, N-(2-naphthyl)-phenylamino)triphenylamine (2-TNATA) was introduced to a cell in the vacuum deposition apparatus.

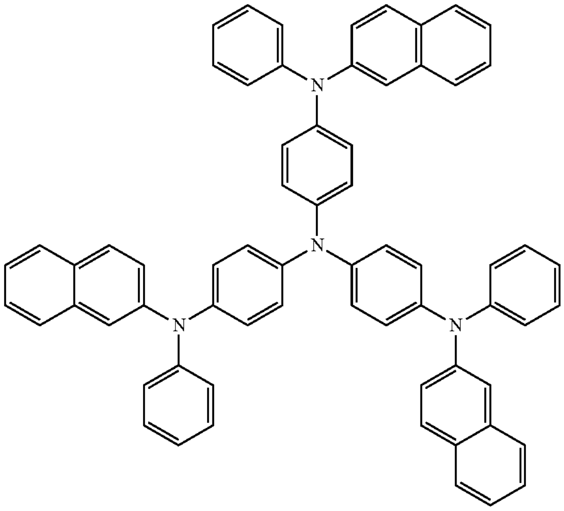

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate. To another cell in the vacuum deposition apparatus, the following N,N'-bis(α-naphthyl)-N, N'-diphenyl-4,4'-diamine (NPB) was introduced, and evaporated by applying a current to the cell to deposit a hole transfer layer having a thickness of 300 Å on the hole injection layer.

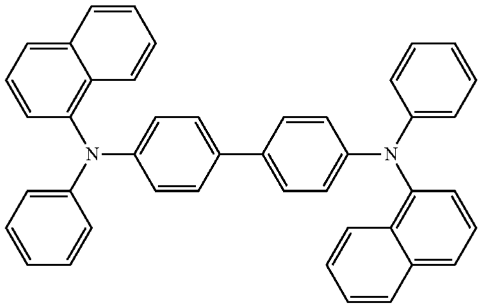

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5 wt % with respect to the host material.

H1

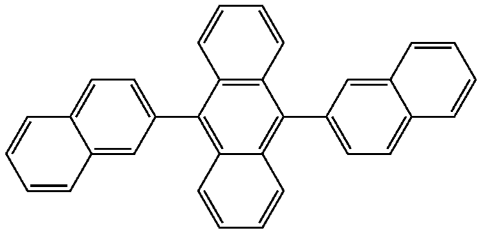

D1

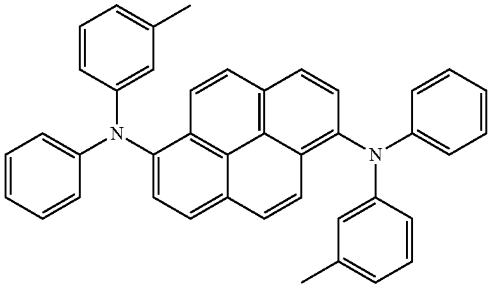

Subsequently, a compound of the following Structural Formula E1 was deposited to a thickness of 300 Å as an electron transfer layer.

E1

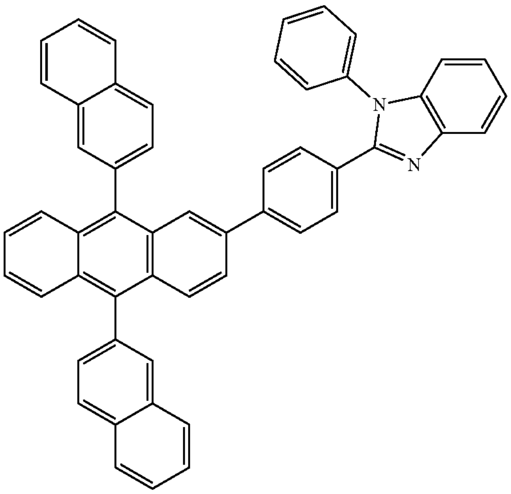

-continued

E2

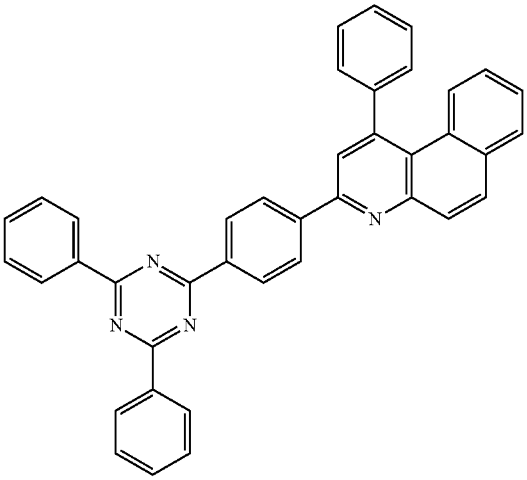

E3

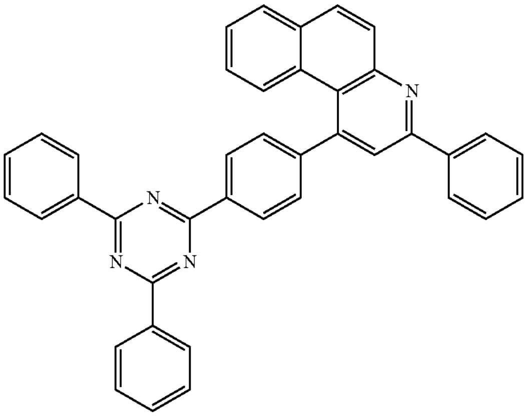

As an electron injection layer, lithium fluoride (LiF) was deposited to a thickness of 10 Å, and an Al cathode was employed to a thickness of 1,000 Å, and as a result, an OLED (Comparative Example 4) was manufactured. Meanwhile, all the organic compounds required to manufacture the OLED were vacuum sublimation purified under $10^{-8}$ torr to $10^{-6}$ torr by each material to manufacture the OLED.

Organic light emitting devices of Examples 12 to 22 and Comparative Examples 5 and 6 were manufactured in the same manner as in Experimental Example 2 except that, after depositing the light emitting layer, compounds shown in the following Table 5 were each employed to a thickness of 50 Å to form a hole blocking layer, and the electron transfer layer E1 was formed to a thickness of 250 Å on the hole blocking layer.

2) Driving Voltage and Light Emission Efficiency of Organic Light Emitting Device For each of the organic light emitting devices of Examples 12 to 22 and Comparative Examples 4 to 6 manufactured as above, electroluminescent (EL) properties were measured using M7000 manufactured by McScience Inc., and with the measurement results, $T_9$ was measured when standard luminance was 700 cd/$m^2$ through a lifetime measurement system (M6000) manufactured by McScience Inc. $T_{95}$ means a lifetime (unit: h, time), a time taken to become 95% with respect to initial luminance.

Results of measuring driving voltage, light emission efficiency, external quantum efficiency and color coordinate (CIE) of the blue organic light emitting devices manufactured according to the present disclosure are as shown in the following Table 5.

TABLE 5

| | Compound | Driving voltage (V) | Light emission efficiency (cd/A) | CIE (x, y) | Lifetime ($T_{95}$) |
|---|---|---|---|---|---|
| Example 12 | 1 | 5.00 | 6.66 | (0.134, 0.101) | 51 |
| Example 13 | 3 | 5.02 | 6.51 | (0.134, 0.100) | 54 |
| Example 14 | 7 | 5.01 | 6.40 | (0.134, 0.102) | 55 |
| Example 15 | 14 | 4.99 | 6.59 | (0.134, 0.101) | 61 |
| Example 16 | 21 | 4.97 | 6.71 | (0.134, 0.101) | 57 |
| Example 17 | 26 | 4.88 | 6.70 | (0.134, 0.100) | 60 |
| Example 18 | 41 | 4.80 | 6.65 | (0.134, 0.100) | 51 |
| Example 19 | 77 | 4.91 | 6.66 | (0.134, 0.101) | 60 |
| Example 20 | 105 | 4.88 | 6.69 | (0.134, 0.100) | 55 |
| Example 21 | 114 | 4.93 | 6.50 | (0.134, 0.100) | 62 |
| Example 22 | 267 | 4.95 | 6.55 | (0.134, 0.101) | 51 |
| Comparative Example 4 | E1 | 5.88 | 5.89 | (0.134, 0.101) | 43 |
| Comparative Example 5 | E2 | 5.69 | 6.00 | (0.134, 0.100) | 41 |
| Comparative Example 6 | E3 | 5.71 | 5.97 | (0.134, 0.100) | 41 |

As seen from the results of Table 5, the organic light emitting device using the hole blocking layer material of the blue organic light emitting device of the present disclosure had lower driving voltage and significantly improved light emission efficiency and lifetime compared to Comparative Examples 4, 5 and 6. When holes pass through an electron transfer layer and reach a cathode without binding in a light emitting layer, efficiency and lifetime decrease in an OLED. When using a compound having a deep HOMO level as a hole blocking layer in order to prevent such a phenomenon, the holes trying to pass through the light emitting layer and reach the cathode are blocked by an energy barrier of the hole blocking layer. As a result, probability of the holes and electrons forming excitons increases, and possibility of being emitted as light in the light emitting layer increases, and as a result, driving, efficiency and lifetime of the organic light emitting device may be enhanced.

In other words, it is considered that using the compound of the present disclosure having a deep HOMO level in a hole blocking layer increases possibility of forming excitons based on the above-described principle, and the compound of the present disclosure brings excellence in all aspects of driving, efficiency and lifetime of the organic light emitting device.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

The invention claimed is:

1. A heterocyclic compound represented by the following Chemical Formula 1:

[Chemical Formula 1]

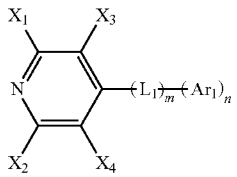

wherein, in Chemical Formula 1, $L_1$ is a direct bond; a substituted or unsubstituted arylene group having 6 to 60 carbon atoms; or a substituted or unsubstituted heteroarylene group having 2 to 60 carbon atoms;

$X_1$ to $X_4$ are the same as or different from each other, and each independently a substituted or unsubstituted aryl group having 6 to 20 carbon atoms;

$Ar_1$ is a substituted or unsubstituted heteroaryl group having 2 to 60 carbon atoms comprising N as a heteroatom; or a substituted or unsubstituted phosphine oxide group; and m and n are each independently an integer of 1 to 2, and when m and n are each 2, substituents in the parentheses are the same as or different from each other;

when Aris a substituted or unsubstituted heteroaryl group having 2 to 60 carbon atoms comprising N as a heteroatom, $L_1$ is a substituted or unsubstituted arylene group having 6 to 60 carbon atoms; or a substituted or unsubstituted heteroarylene group having 2 to 60 carbon atoms;

wherein the substituted or unsubstituted heteroaryl group having 2 to 60 carbon atoms comprising N as a heteroatom is a substituted or unsubstituted carbazolyl group, a substituted or unsubstituted benzocarbazolyl group, a substituted or unsubstituted dibenzocarbazolyl group, a substituted or unsubstituted indolocarbazolyl group, or a group represented by any one of the following Chemical Formulae 3 to 5,

[Chemical Formula 3]

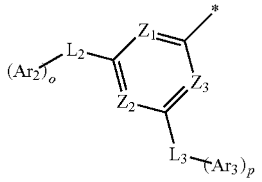

[Chemical Formula 4]

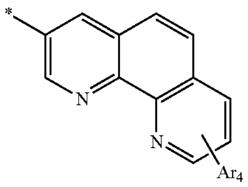

-continued

[Chemical Formula 5]

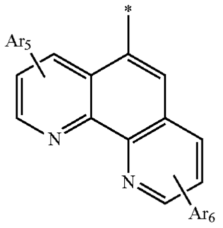

in Chemical Formulae 3 to 5,

* is a position bonding to $L_1$ of Chemical Formula 1;

$Z_1$ to $Z_3$ are the same as or different from each other and each independently N or CH, and at least two or more of $Z_1$ to $Z_3$ are N;

$L_2$ and $L_3$ are the same as or different from each other, and each independently a direct bond; a substituted or unsubstituted arylene group having 6 to 60 carbon atoms; or a substituted or unsubstituted heteroarylene group having 2 to 60 carbon atoms;

$Ar_2$ to $Ar_6$ are the same as or different from each other, and each independently hydrogen; deuterium; a substituted or unsubstituted aryl group having 6 to 60 carbon atoms; or a substituted or unsubstituted heteroaryl group having 2 to 60 carbon atoms; and o and p are each independently an integer of 0 to 2, and when o and p are each 2, substituents in the parentheses are the same as or different from each other; and wherein the "substituted or unsubstituted" means being substituted with one or more substituents selected from the group consisting of a monocyclic or polycyclic aryl group having 6 to 60 carbon atoms; a monocyclic or polycyclic heteroaryl group having 2 to 60 carbon atoms; a phosphine oxide group; and an amine group, or being unsubstituted, or being substituted with a substituent linking two or more substituents selected from among the substituents illustrated above, or being unsubstituted.

2. The heterocyclic compound of claim 1, wherein Chemical Formula 1 is represented by any one of the following compounds:

1

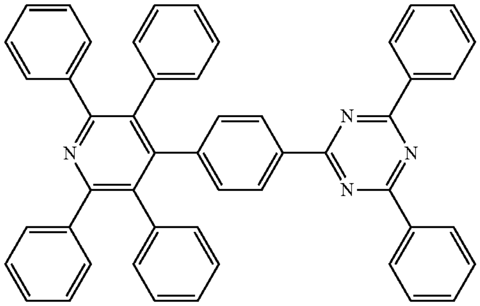

-continued

2

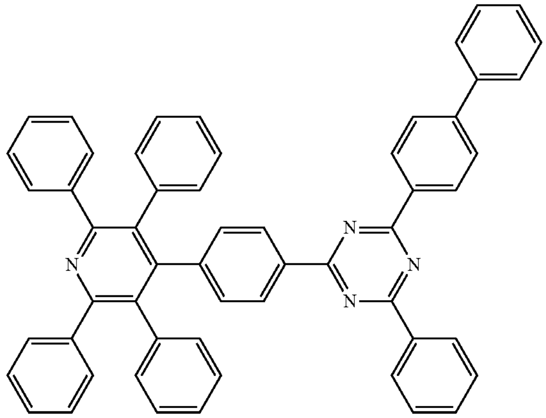

3

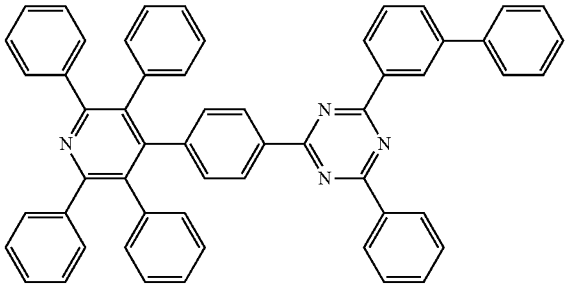

4

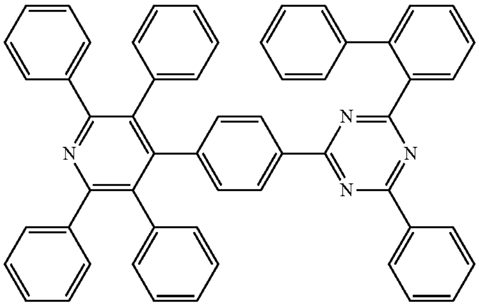

5

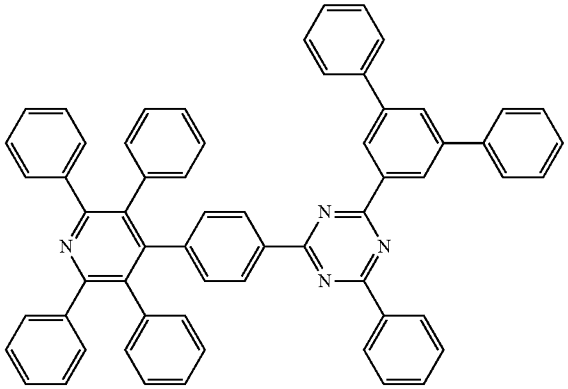

6
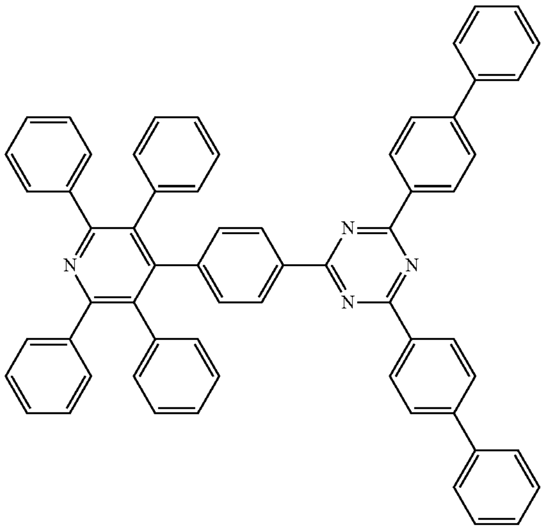
7
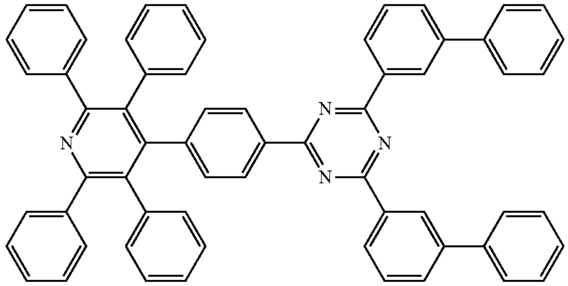
8
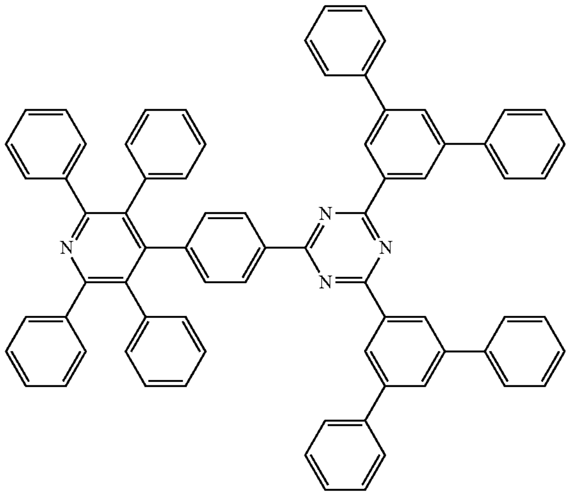
9
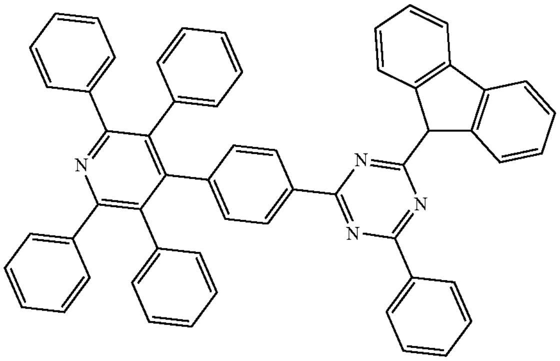
10
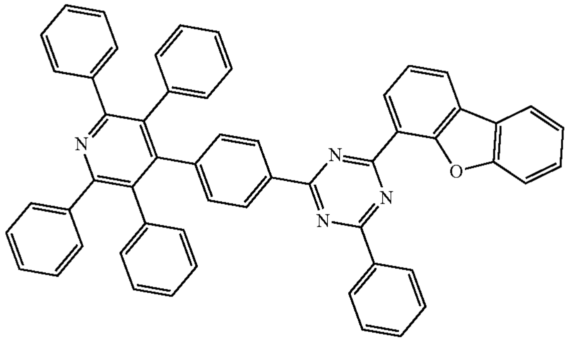
11
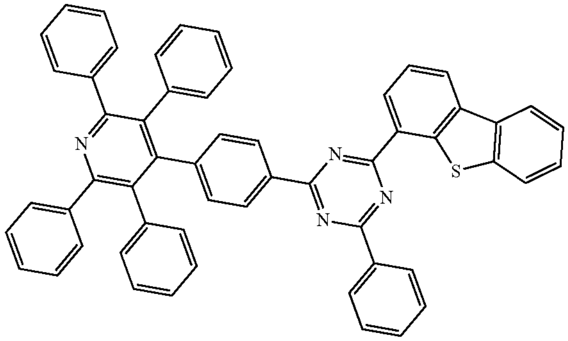
12
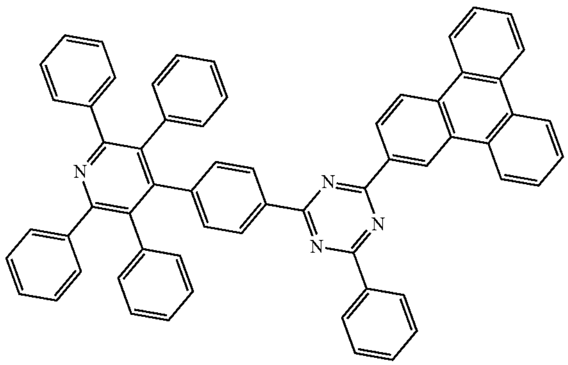

-continued
13
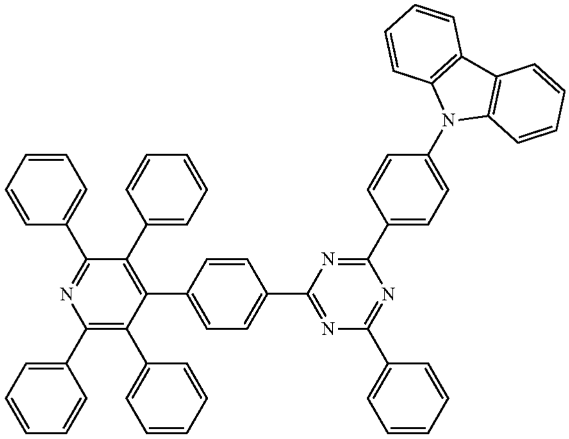
14
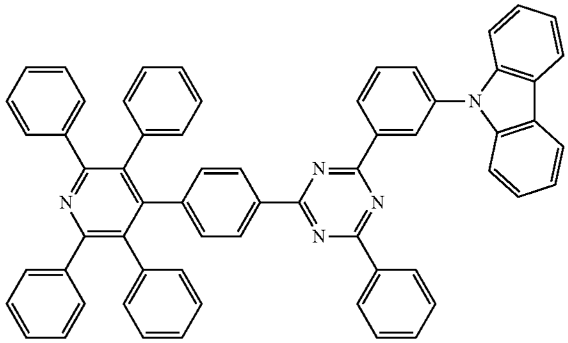
15
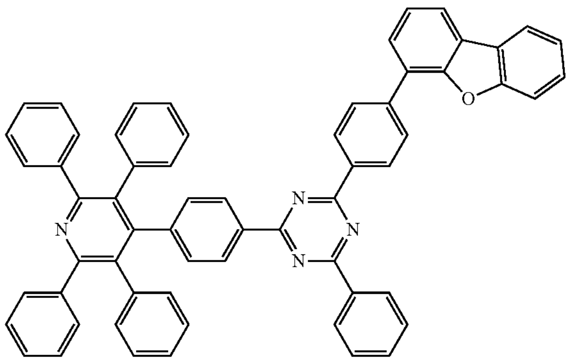
16
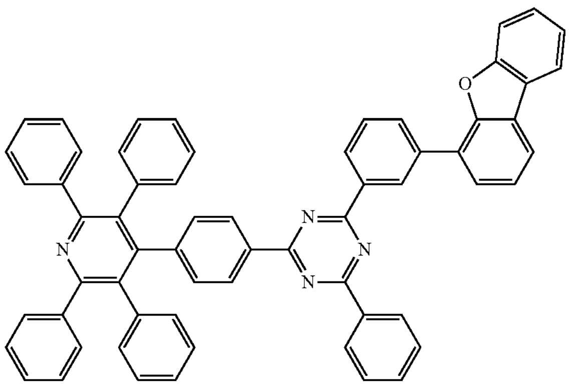
-continued
17
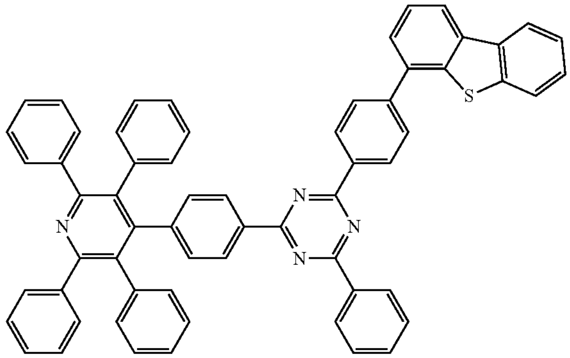
18
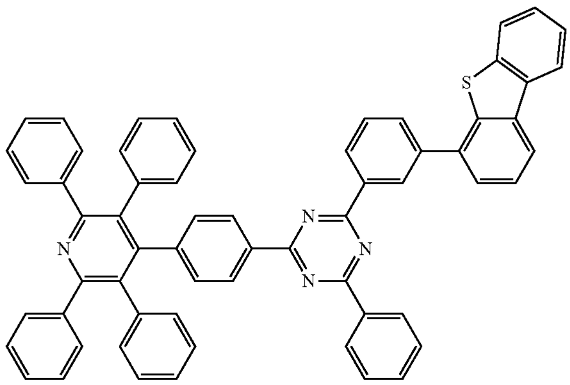
19
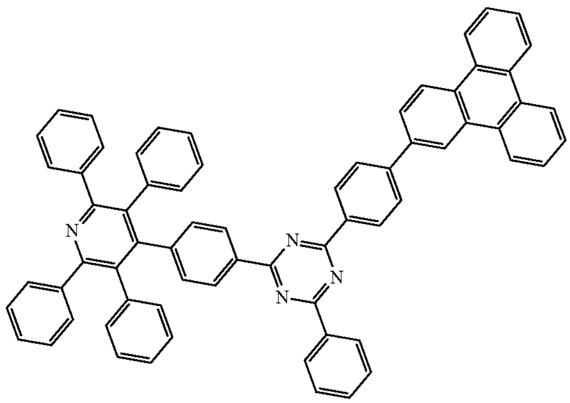
20
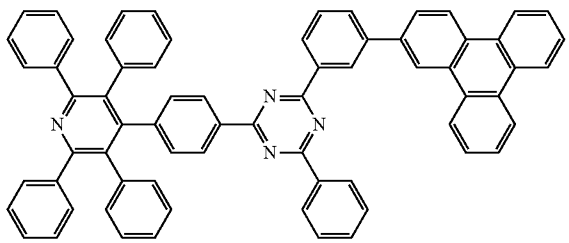

-continued
21
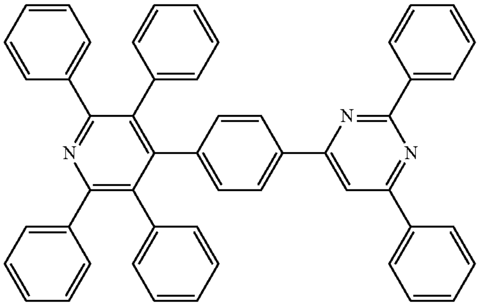
22
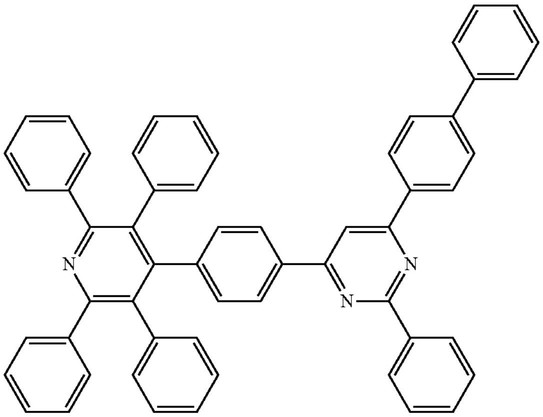
23
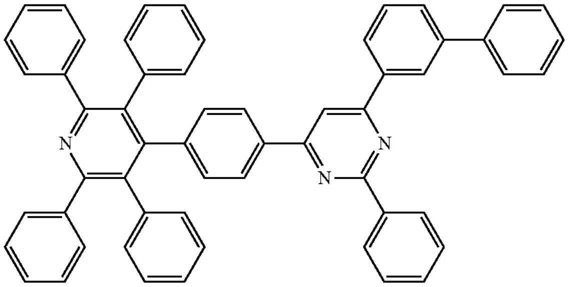
24
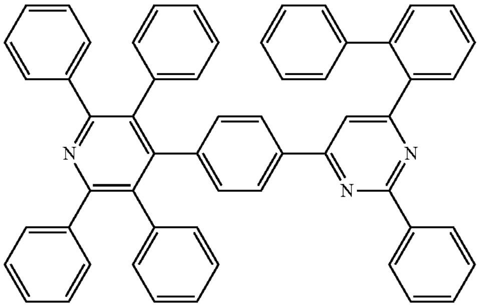
-continued
25
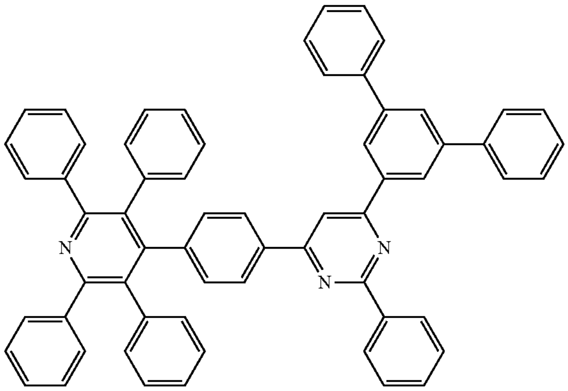
26
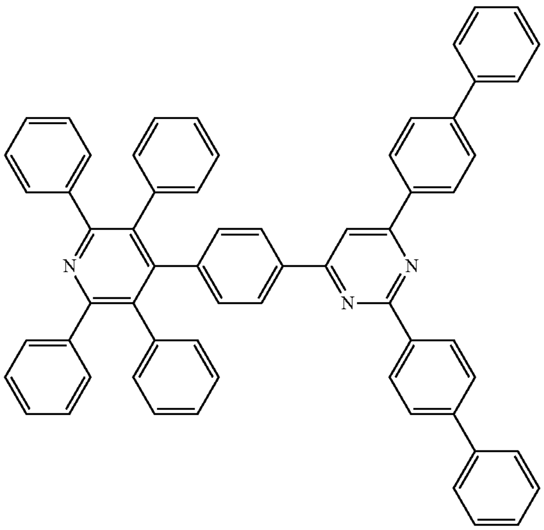
27
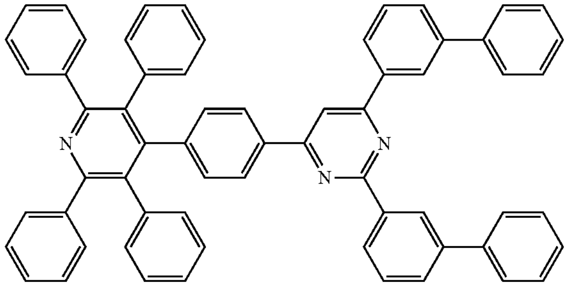

-continued
28
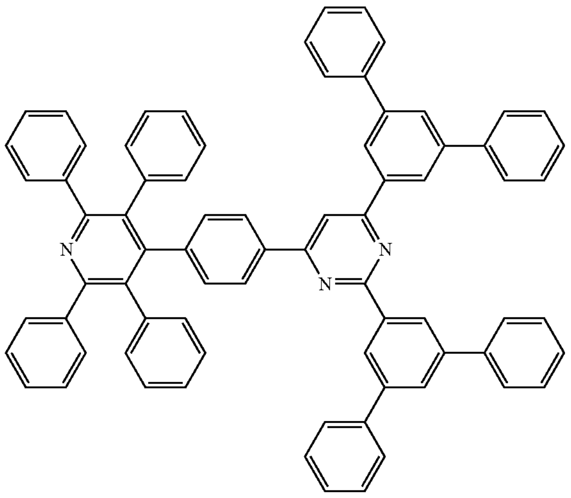
29
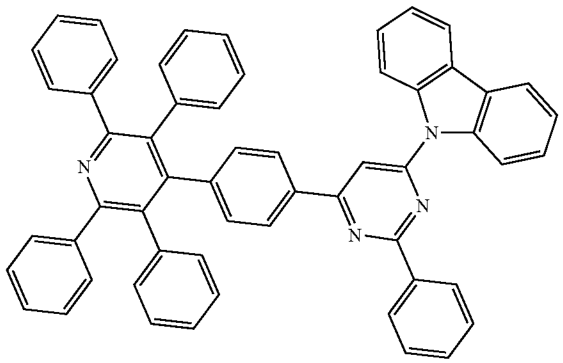
30
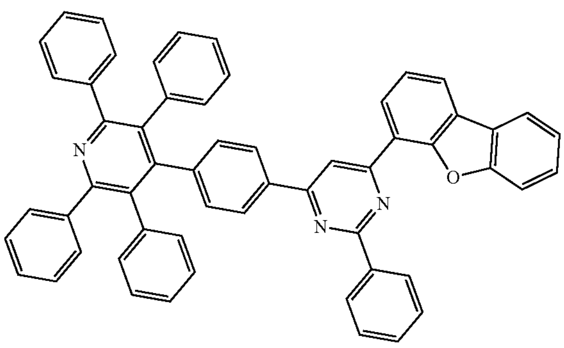
-continued
31
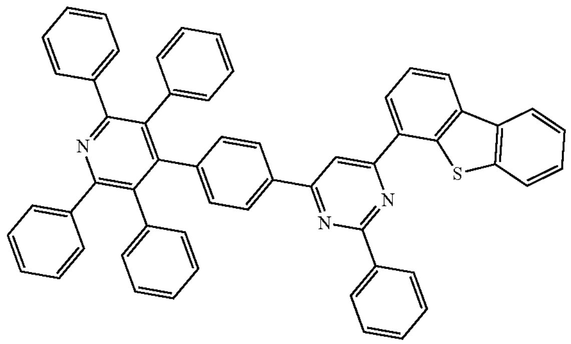
32
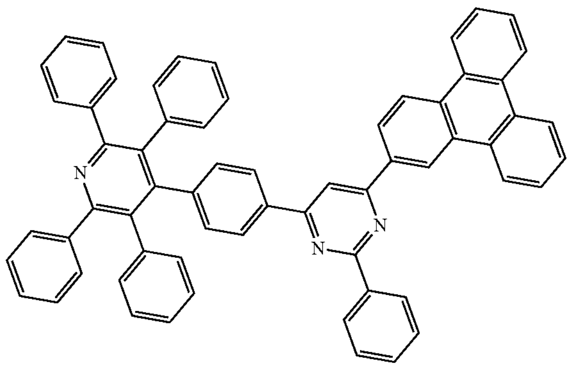
33
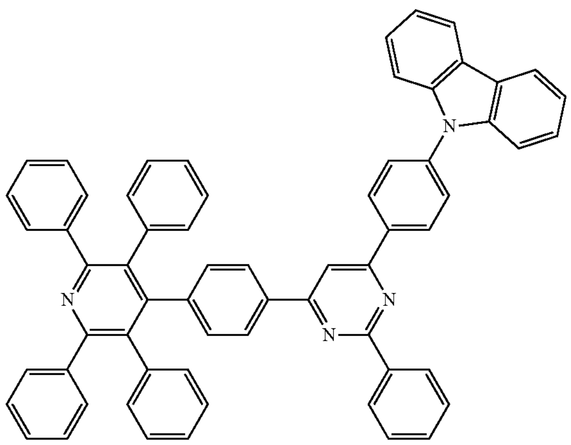
34
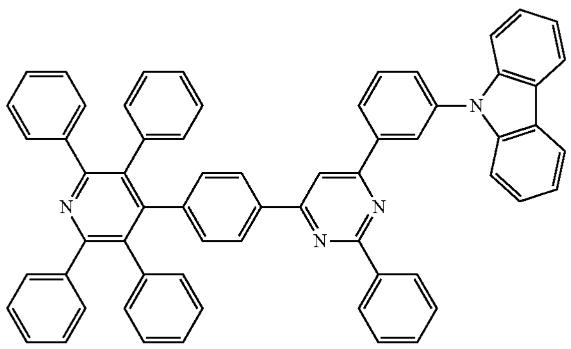

-continued
35
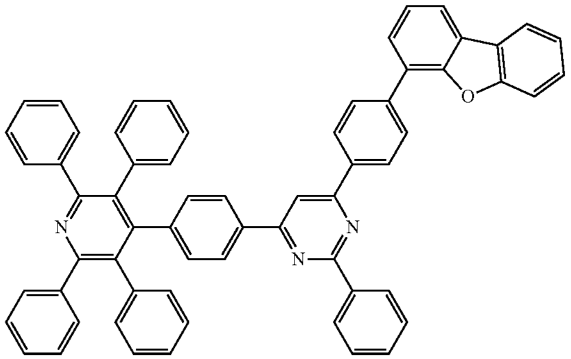
36
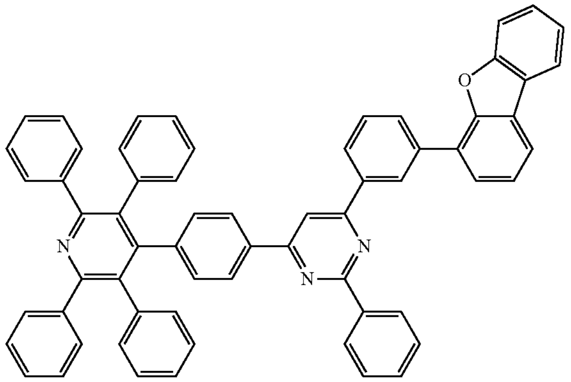
37
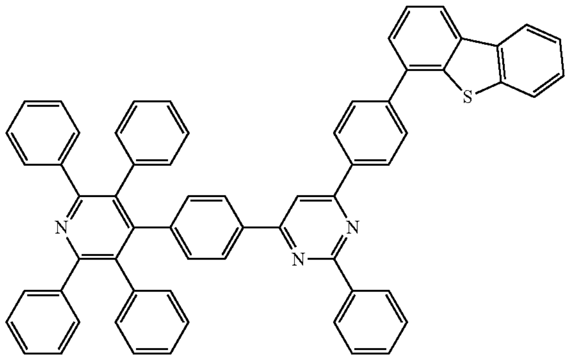
38
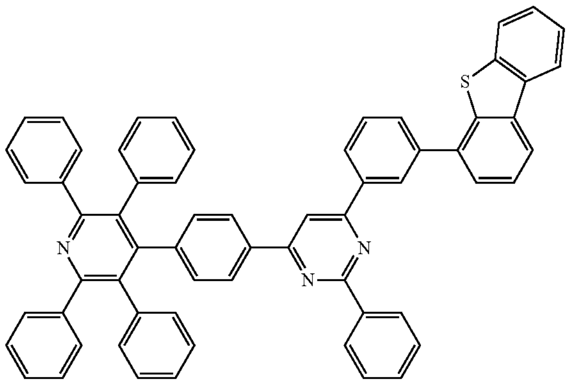
-continued
39
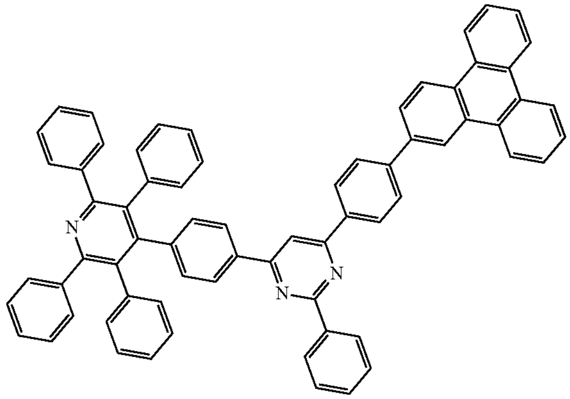
40
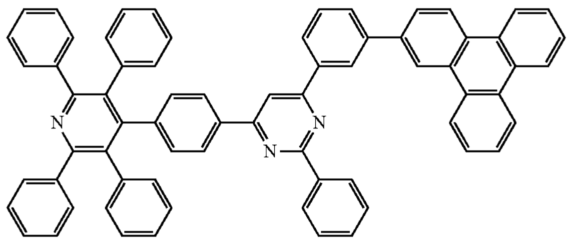
41
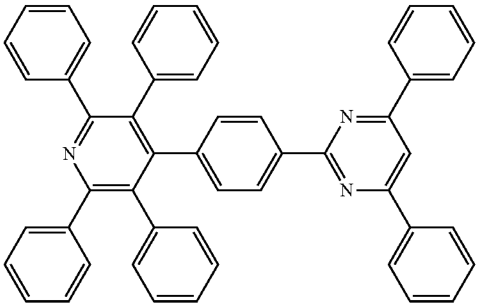
42
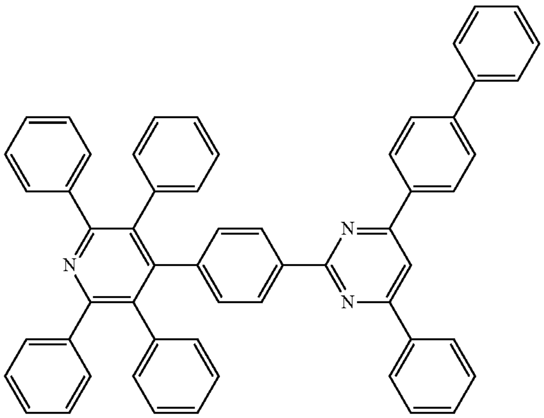

-continued
43
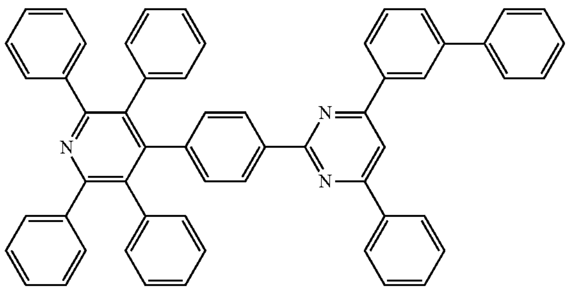
44
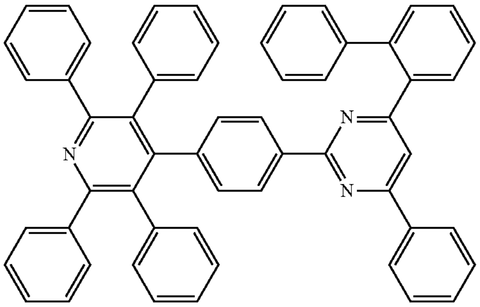
45
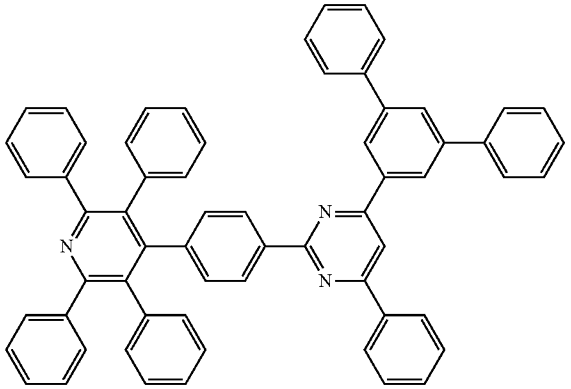
46
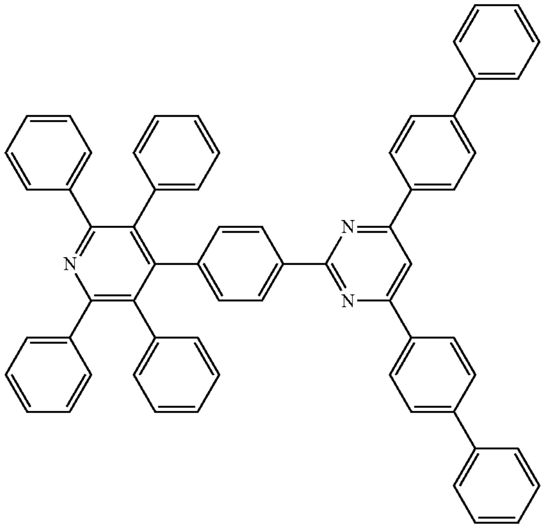
-continued
47
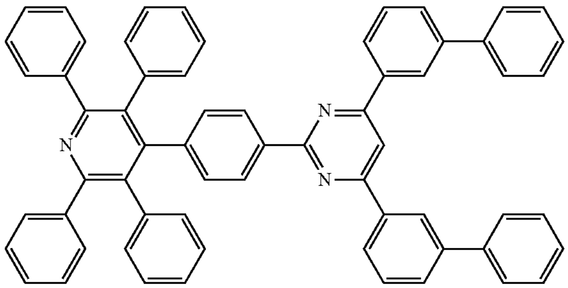
48
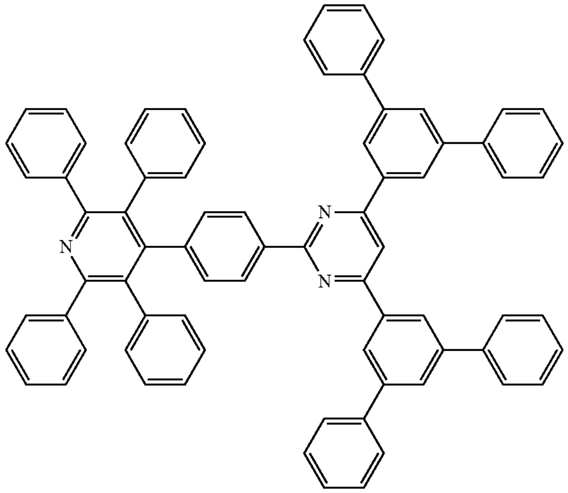
49
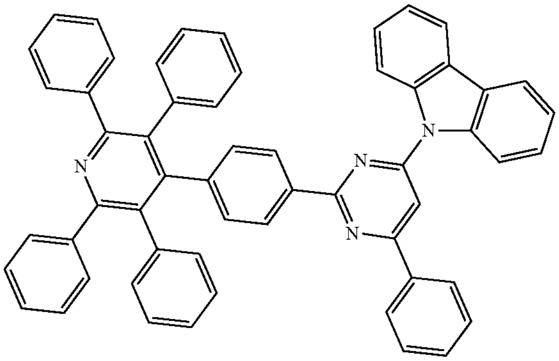
50
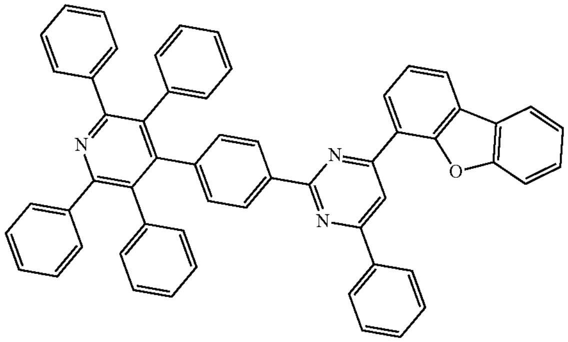

-continued
51
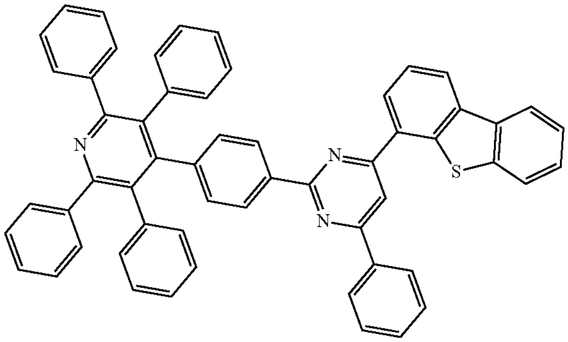
52
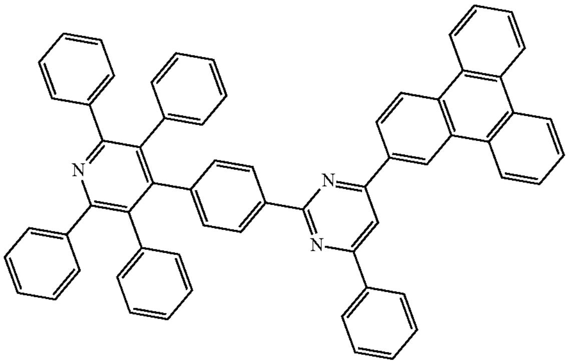
53
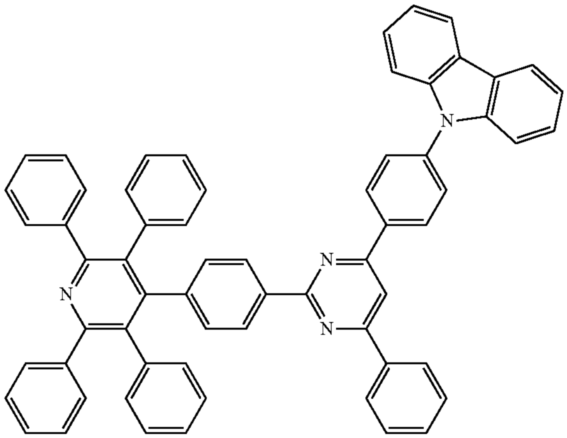
54
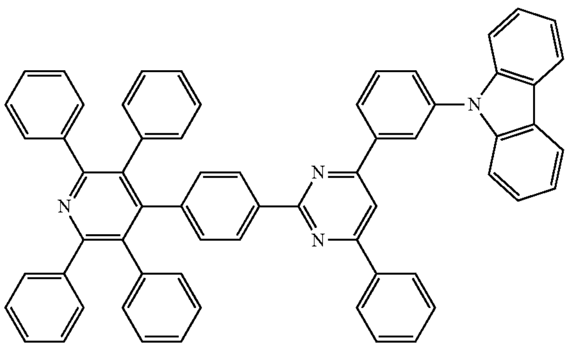
-continued
55
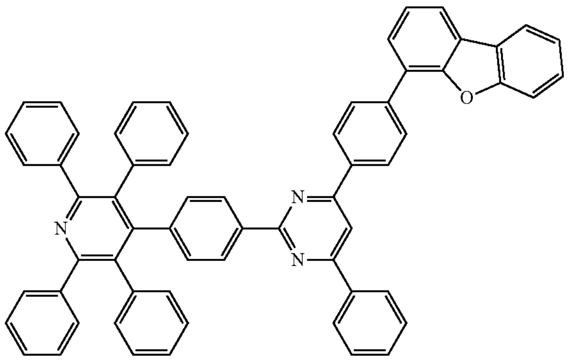
56
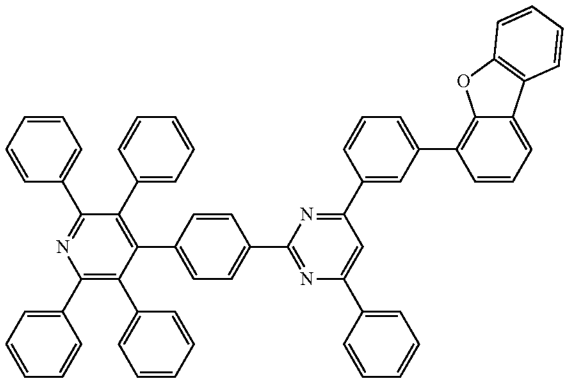
57
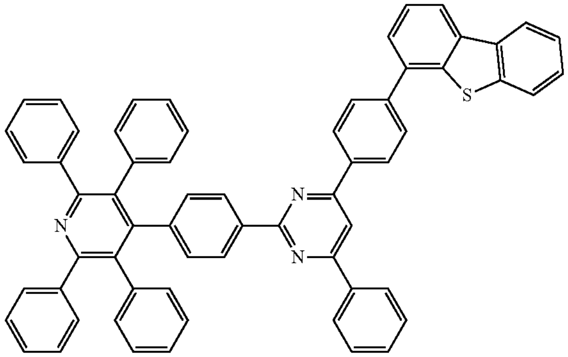
58
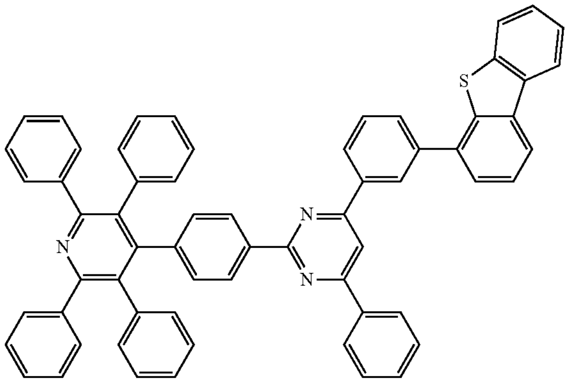

-continued
59
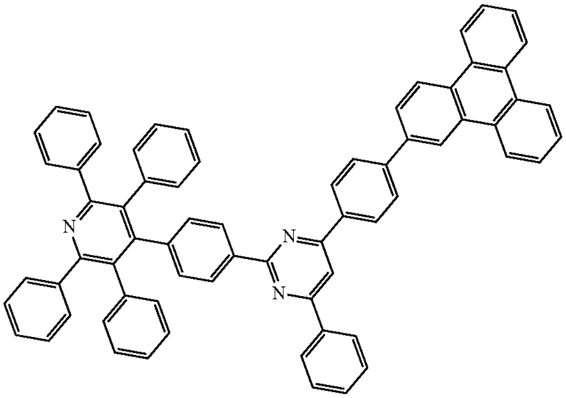
60
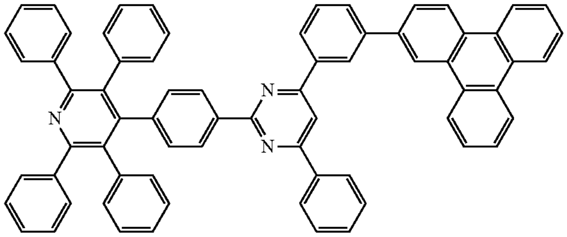
61
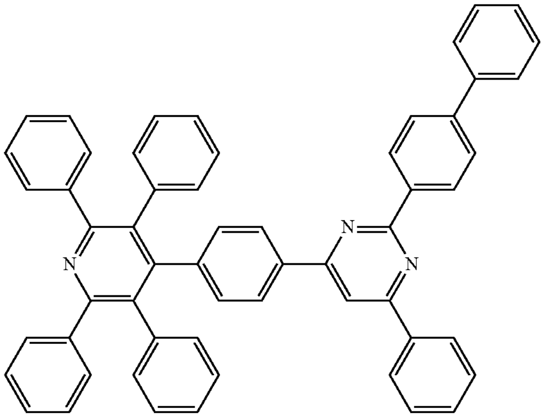
62
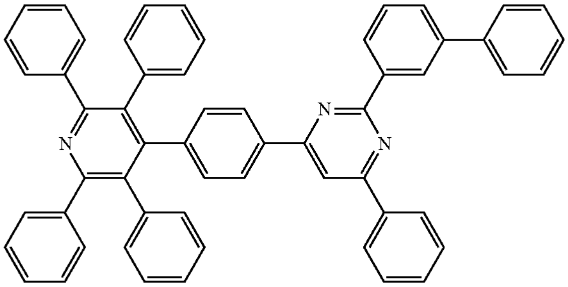
-continued
63
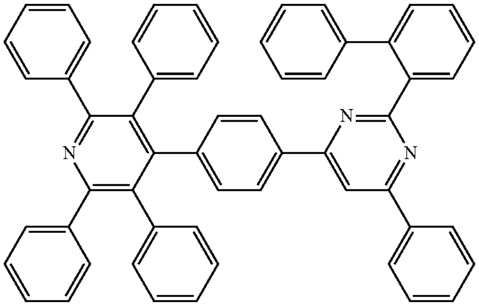
64
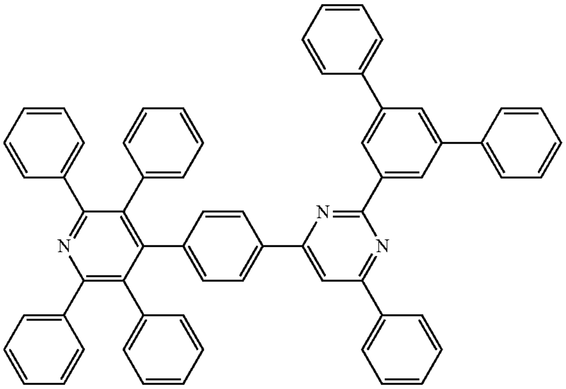
65
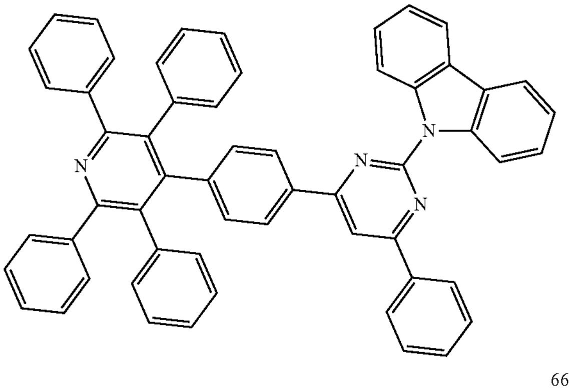
66
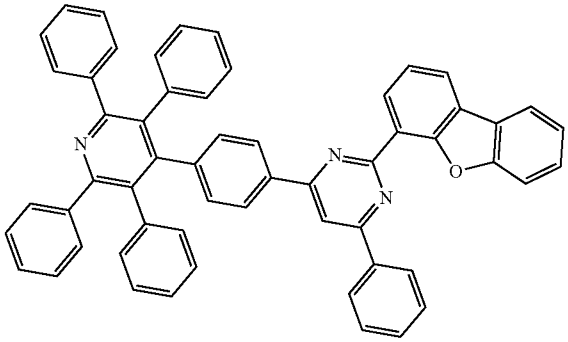

-continued
67
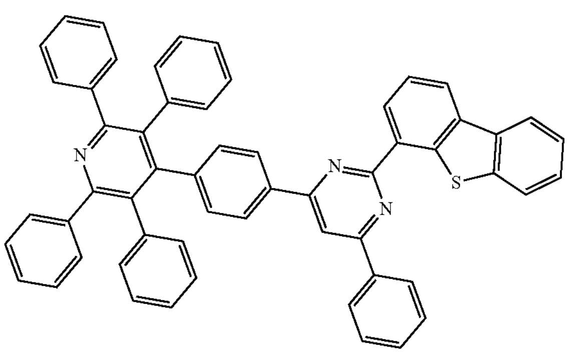
68
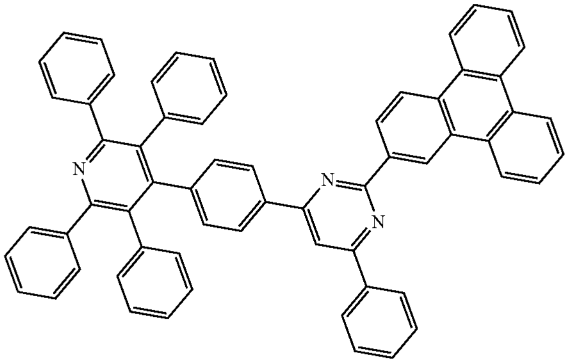
69
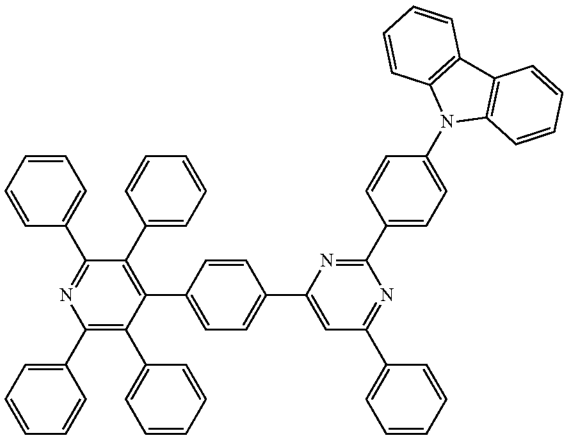
70
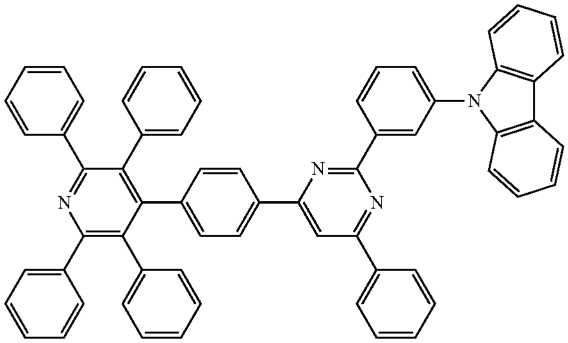
-continued
71
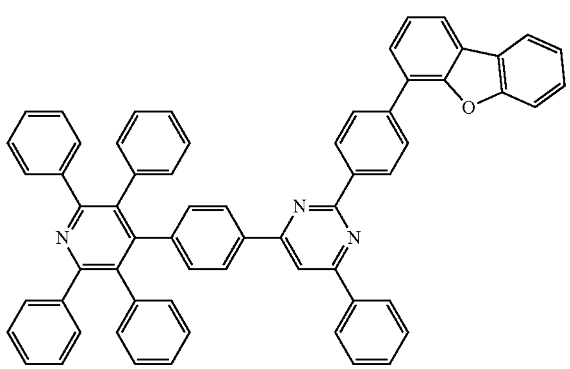
72
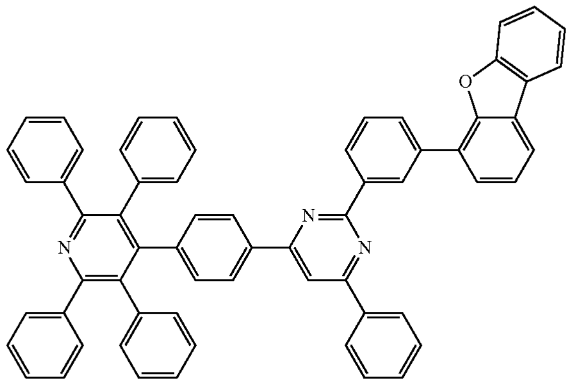
73
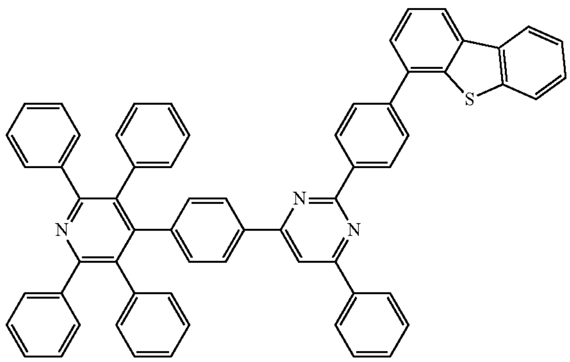
74
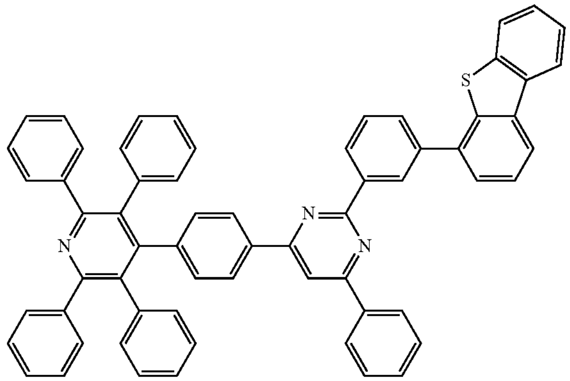

75
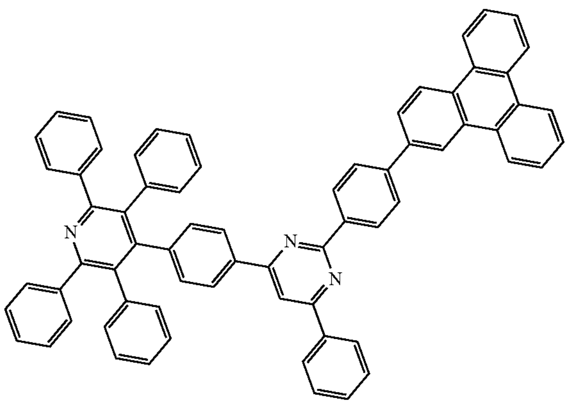
76
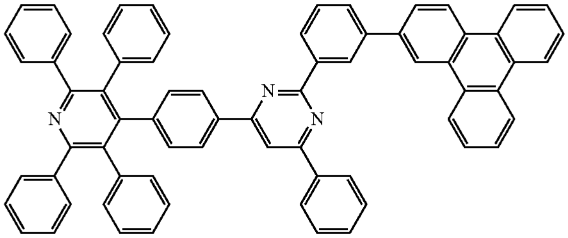
77
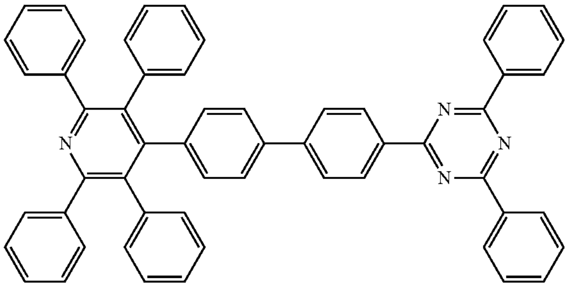
78
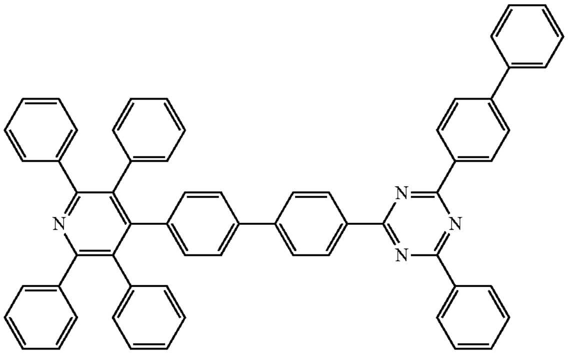
79
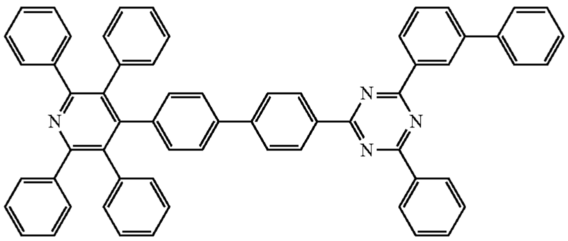
80
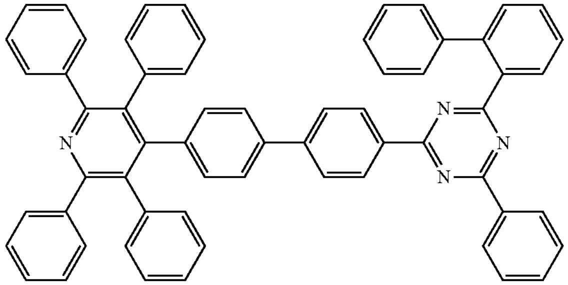
81
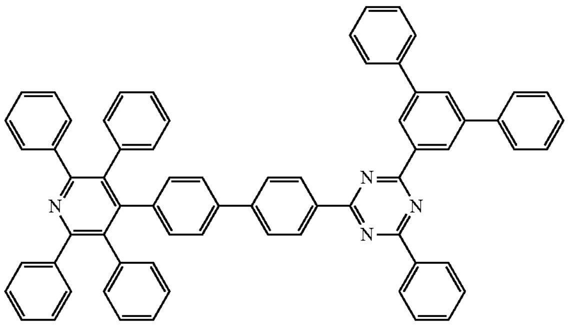
82
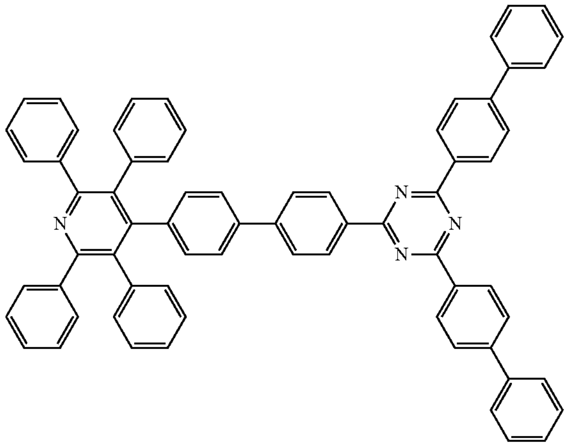
83
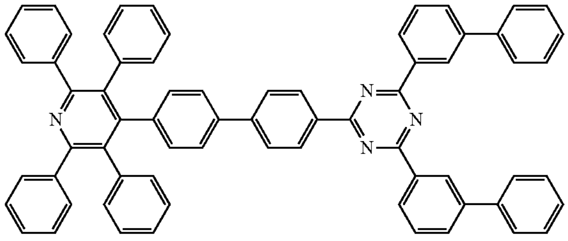

-continued
84
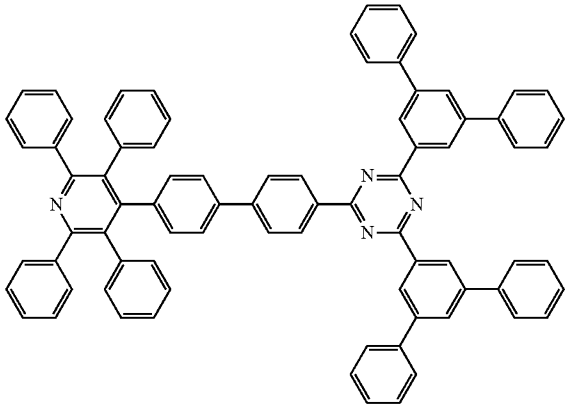
85
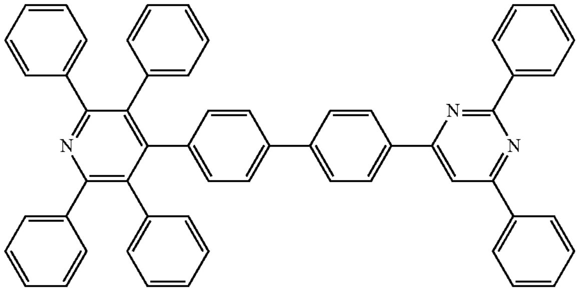
86
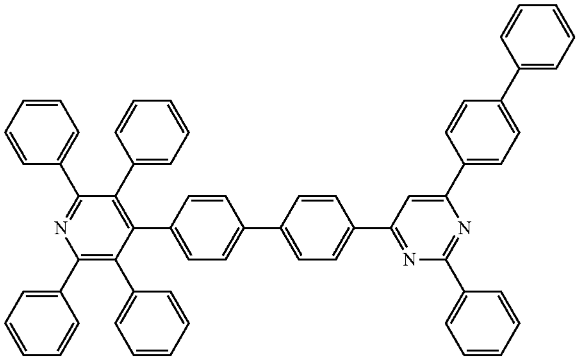
87
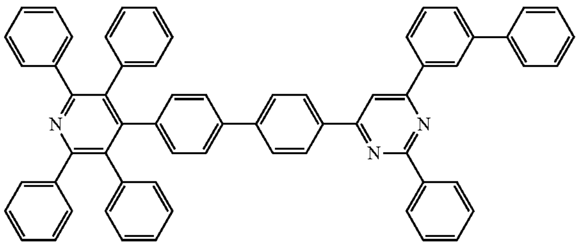
-continued
88
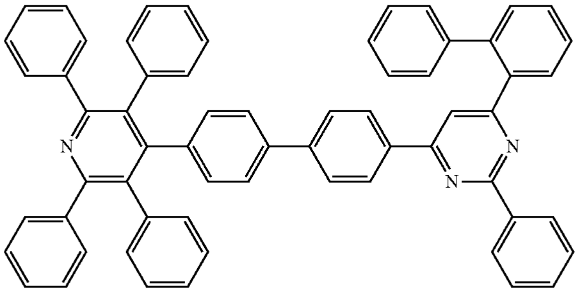
89
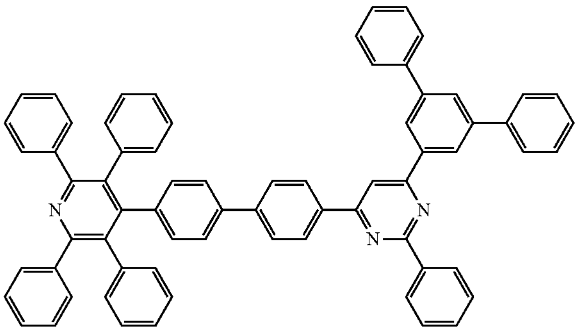
90
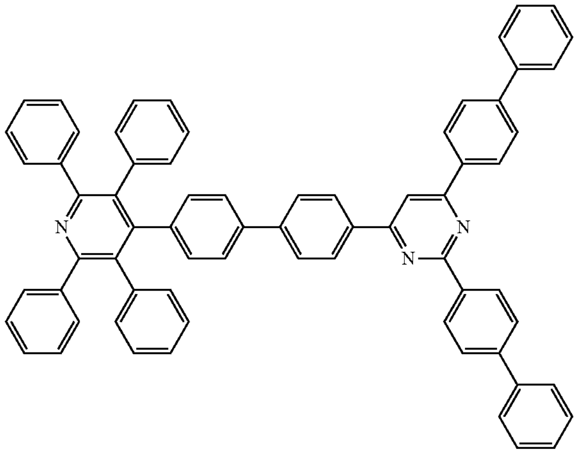
91
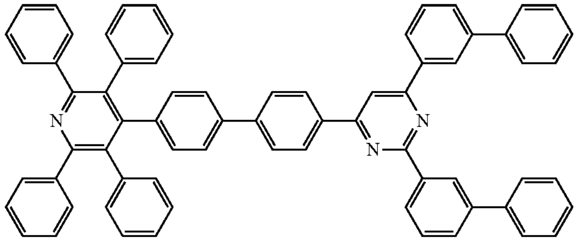

-continued
92
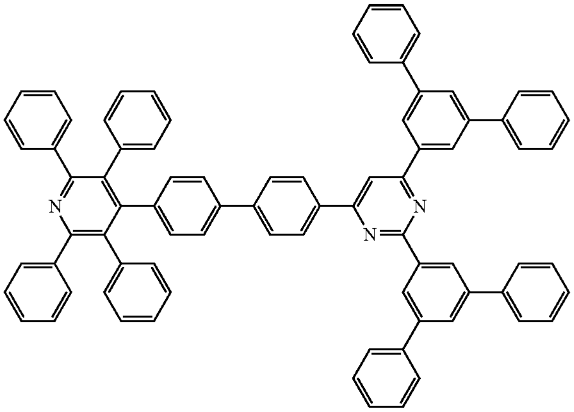
93
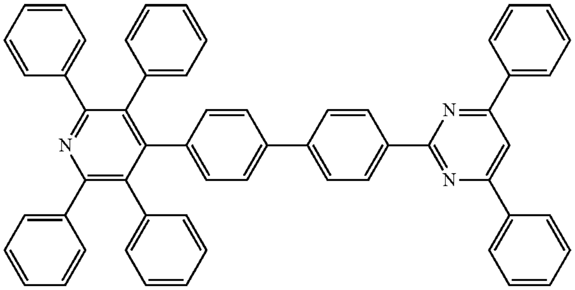
94
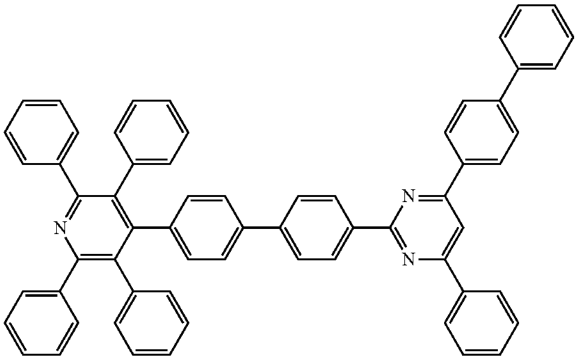
95
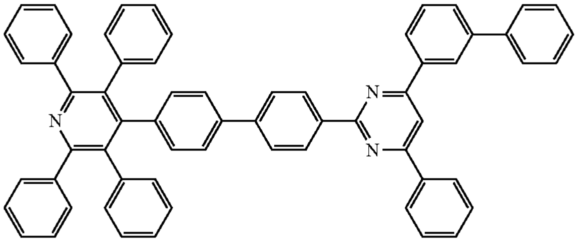
-continued
96
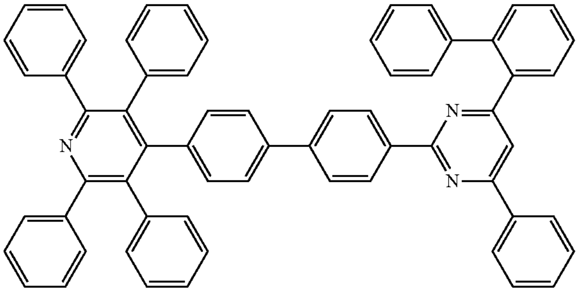
97
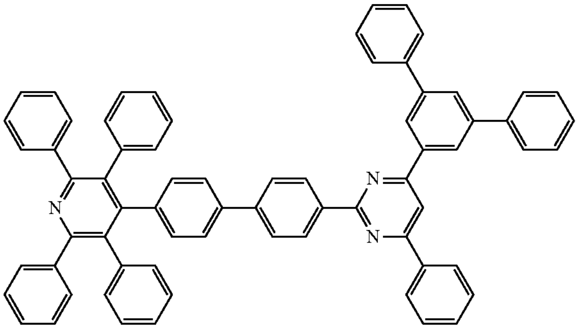
98
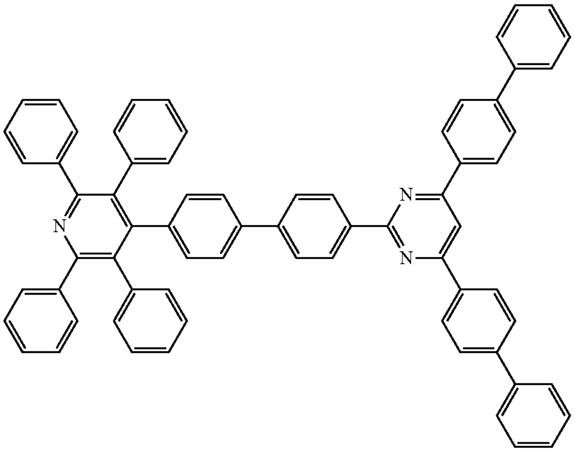
99
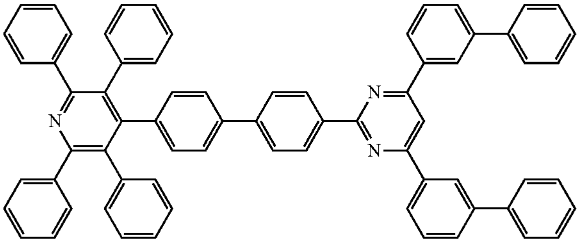

-continued
100
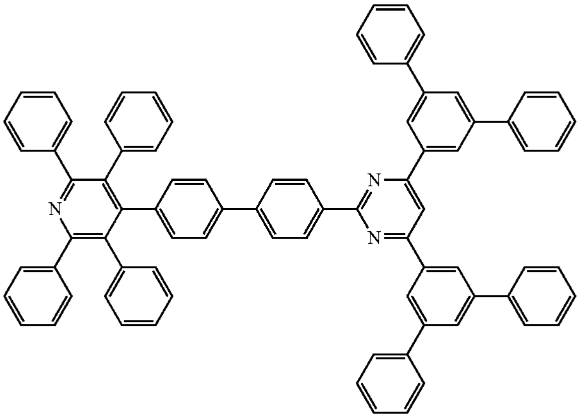
101
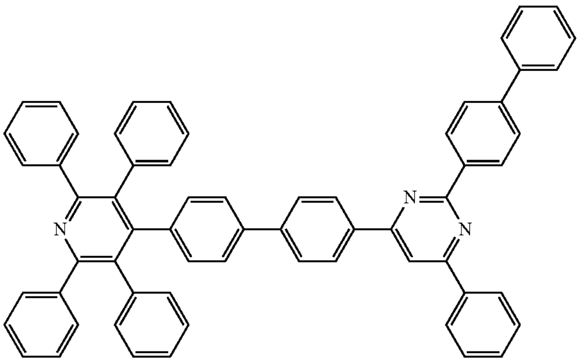
102
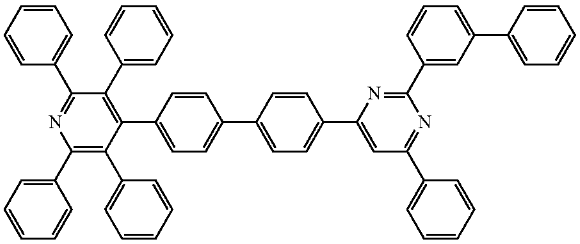
103
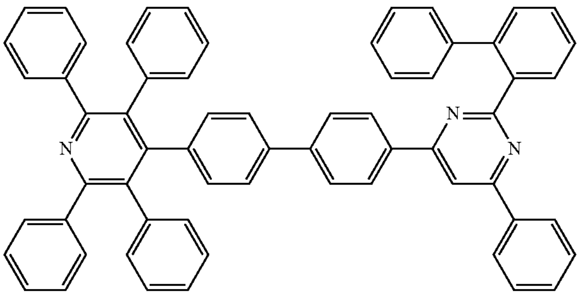
-continued
104
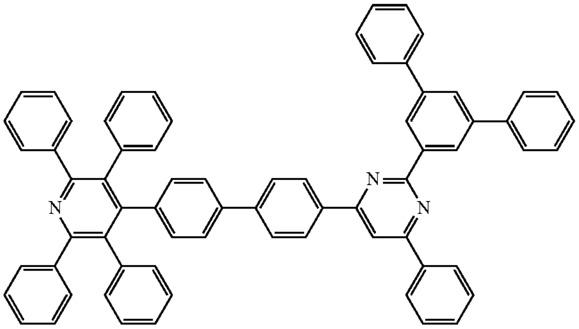
105
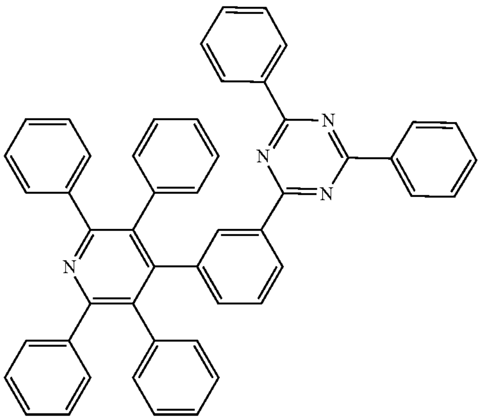
106
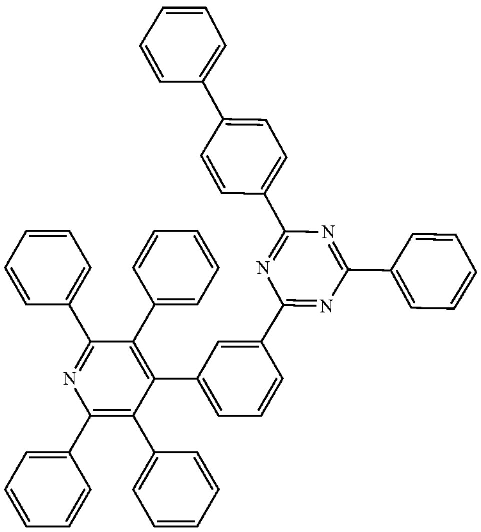

-continued
107
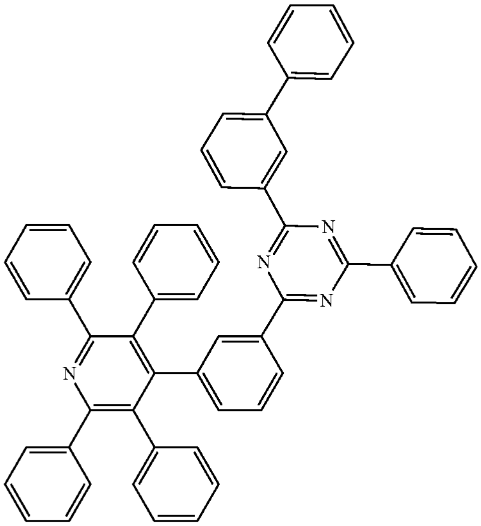
108
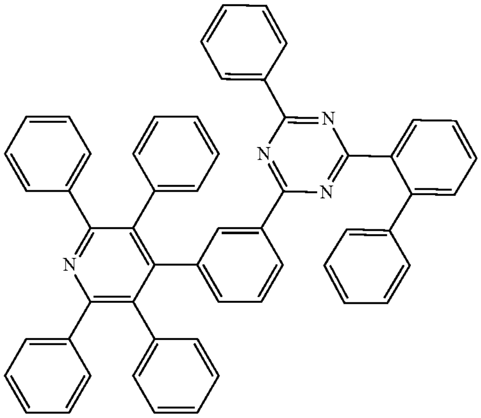
109
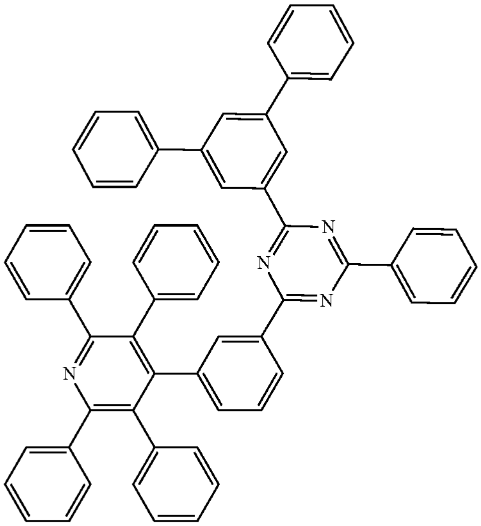
-continued
110
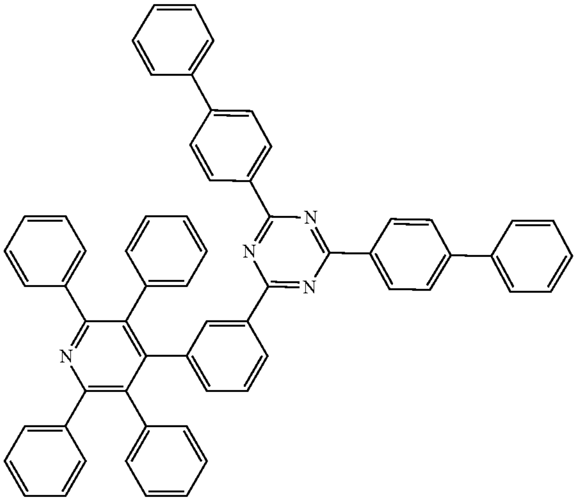
111
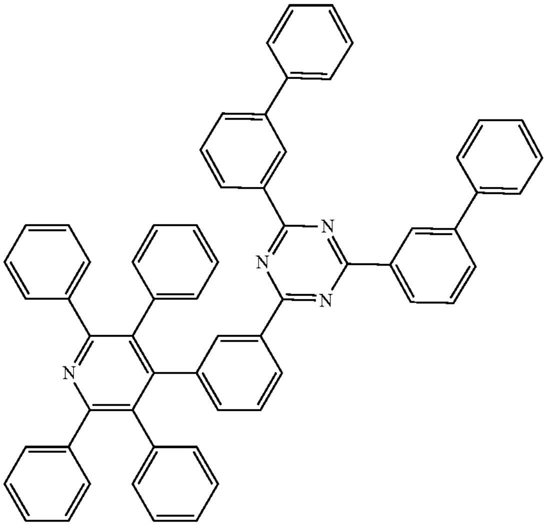
112
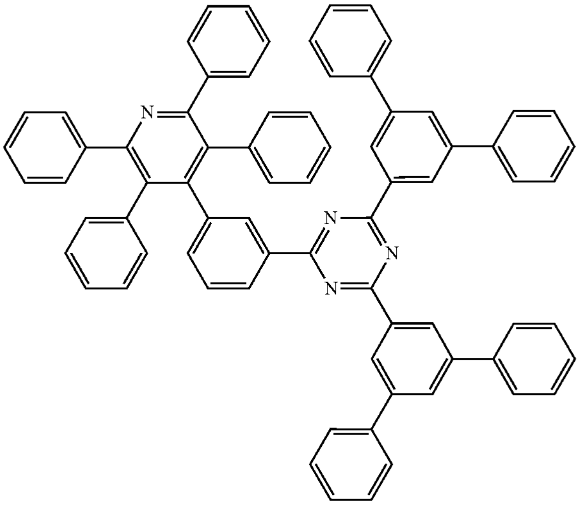

-continued
113
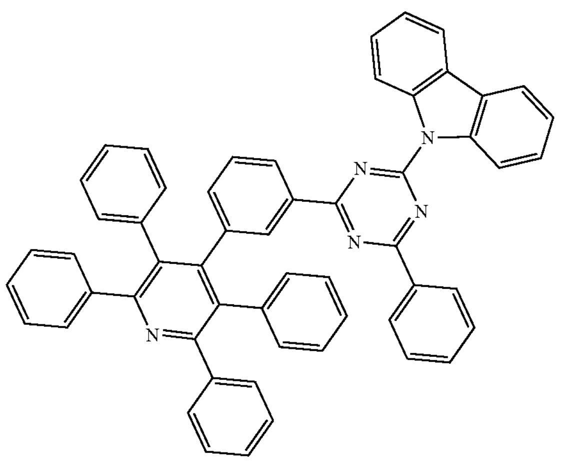
114
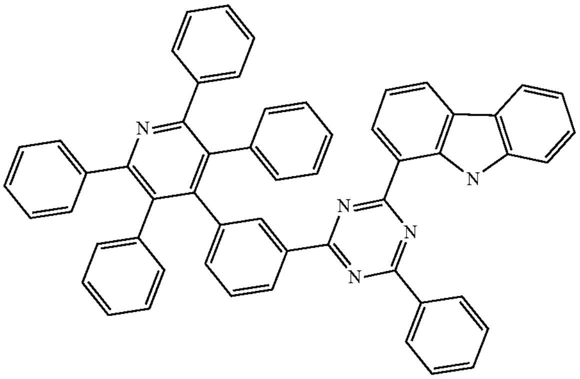
115
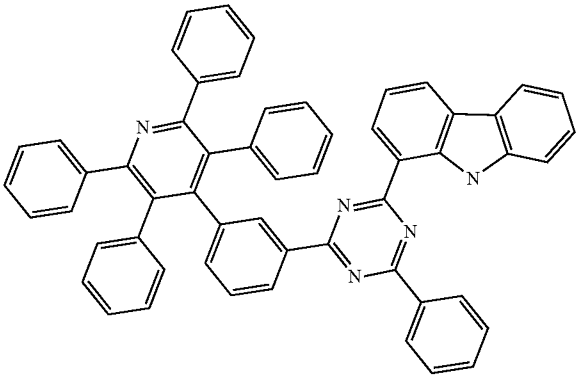
-continued
116
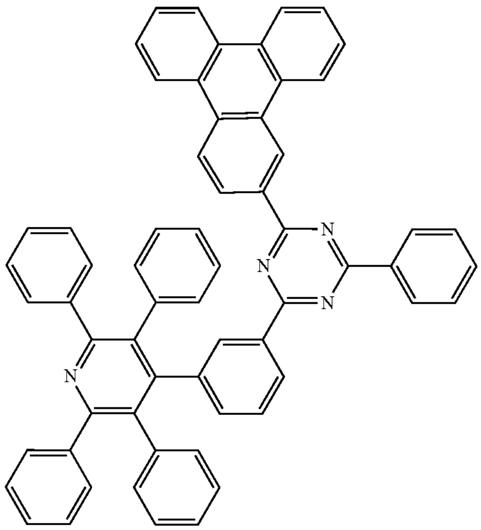
117
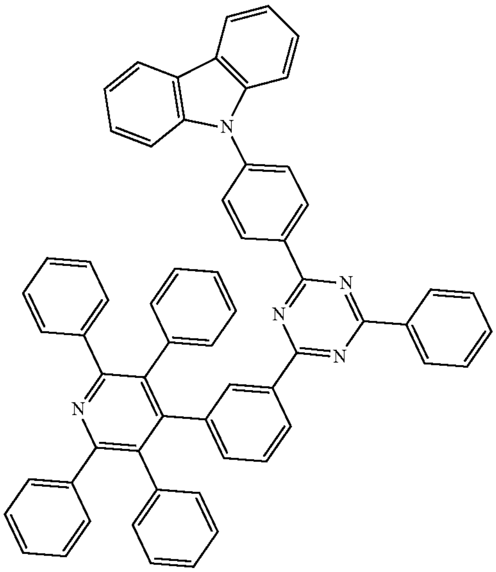

-continued
118
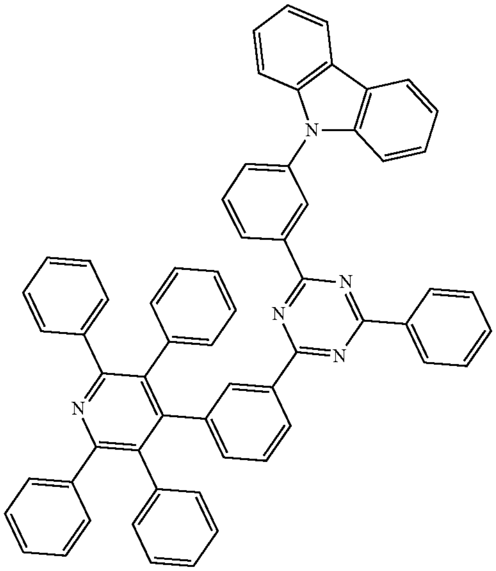
119
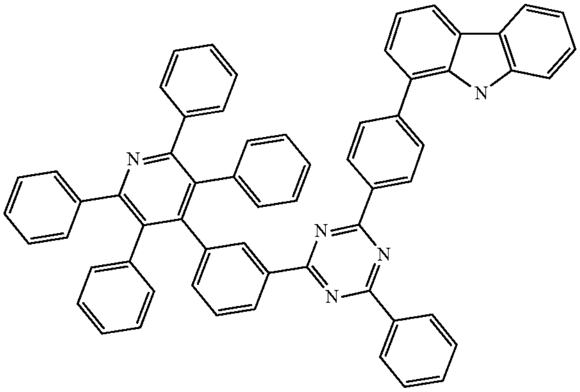
120
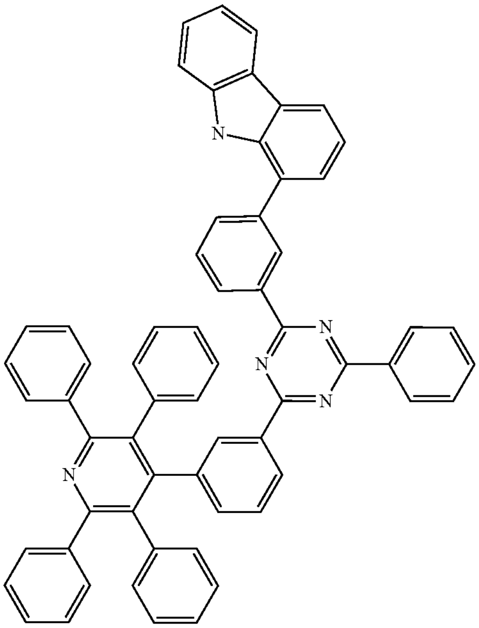
-continued
121
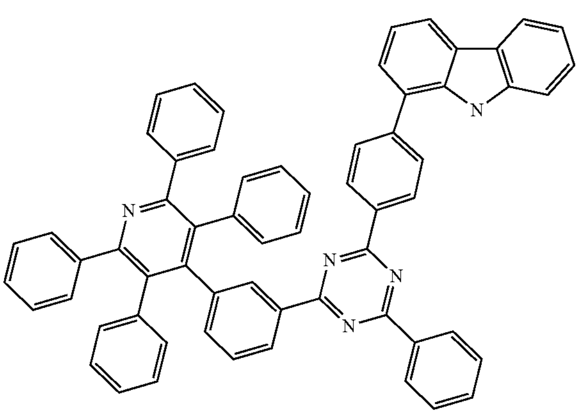
122
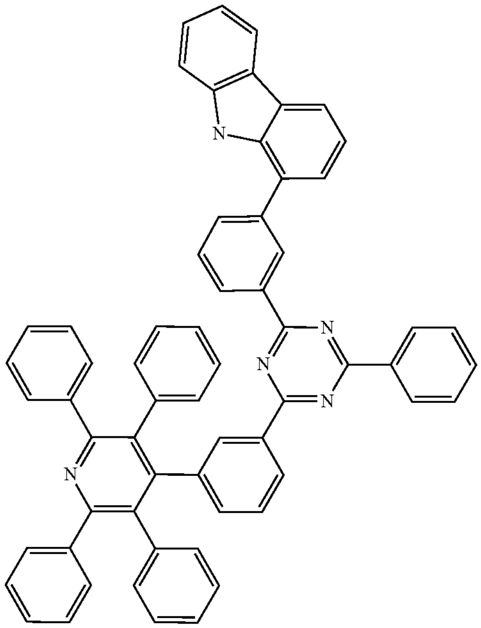
123
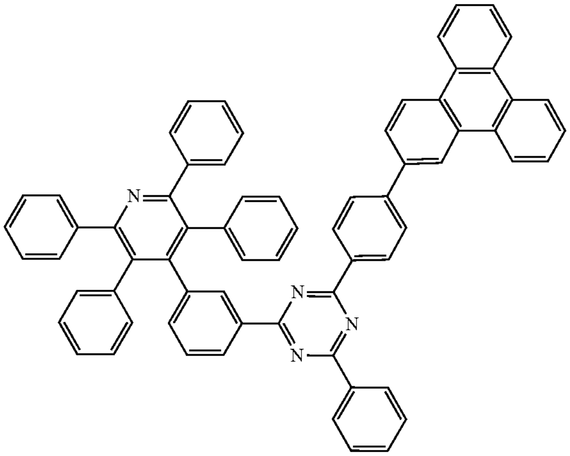

-continued
124
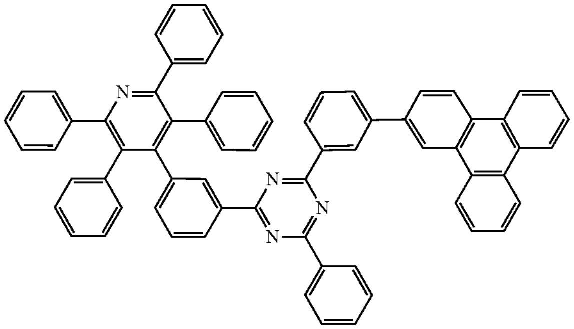
125
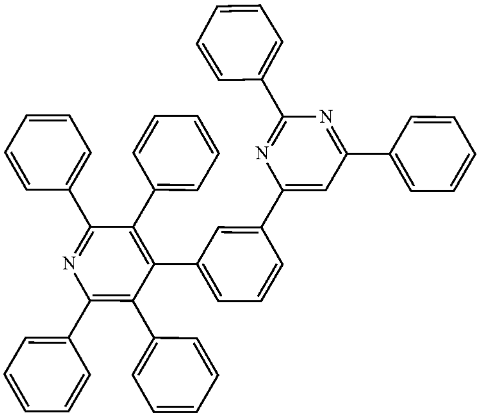
126
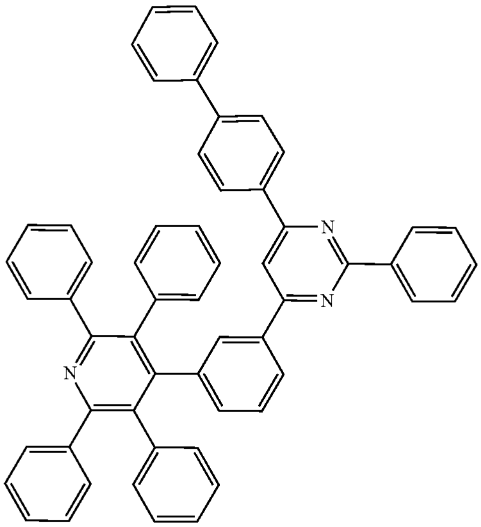
-continued
126
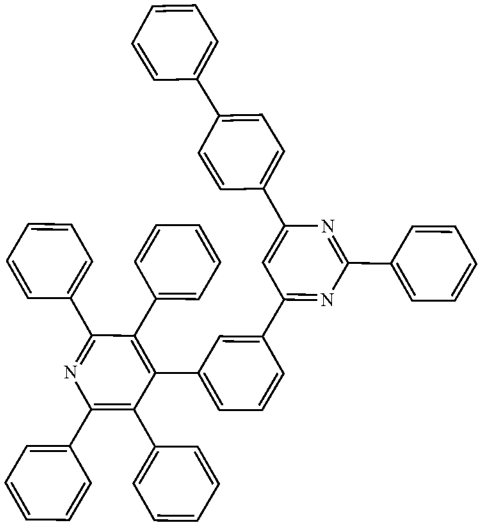
127
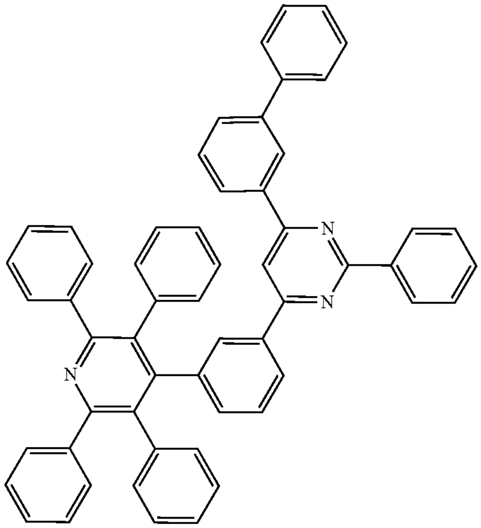
128
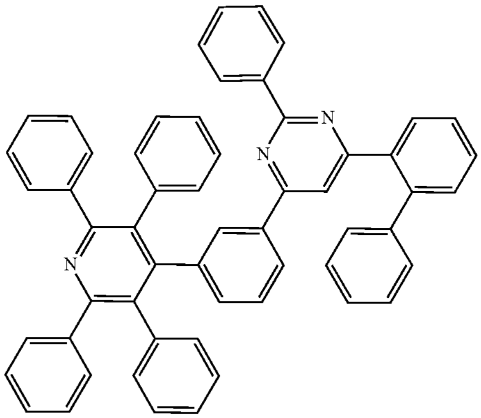

-continued
129
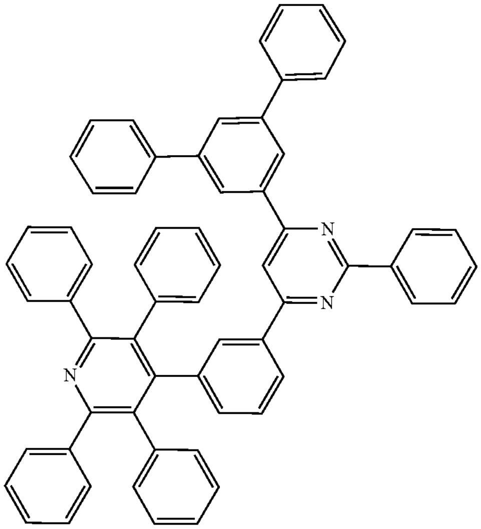
130
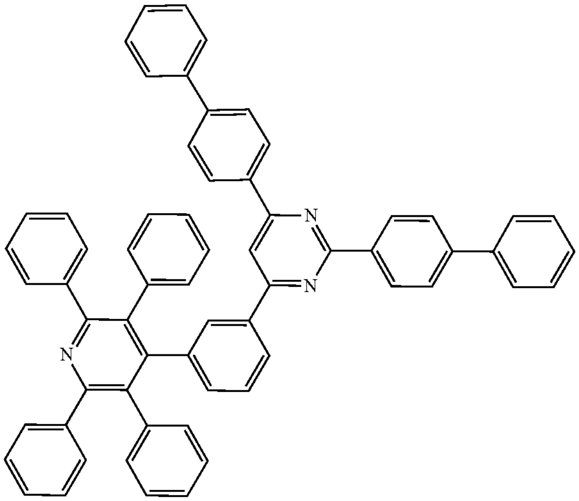
131
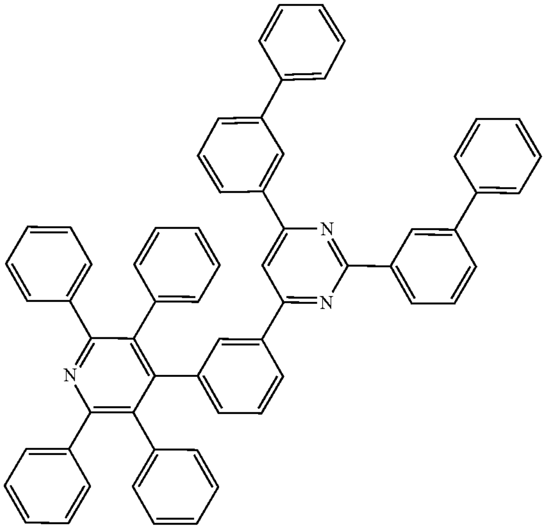
-continued
132
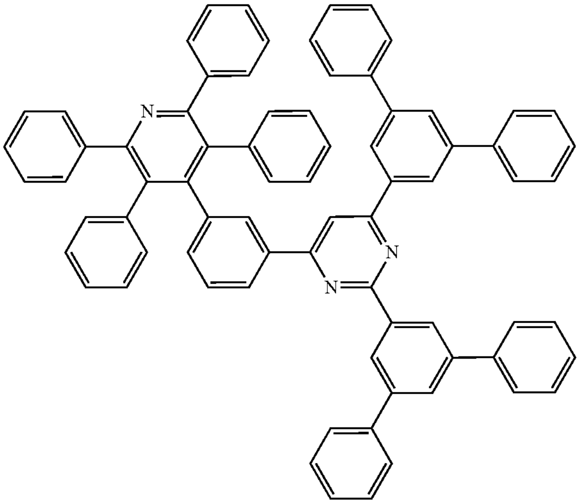
133
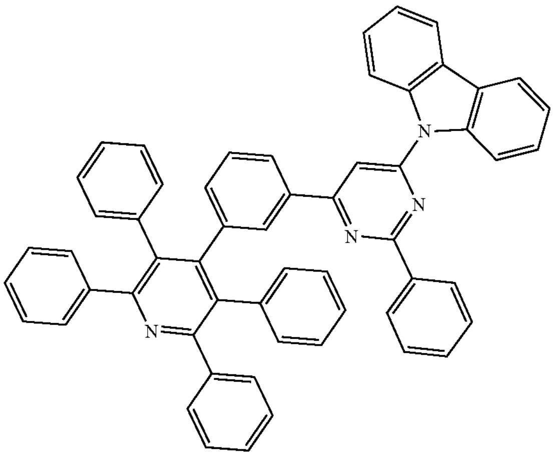
134
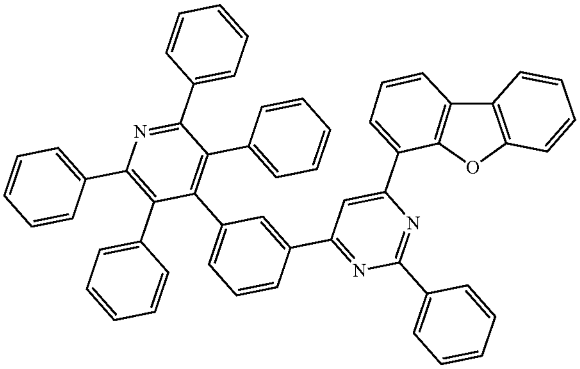

-continued
135
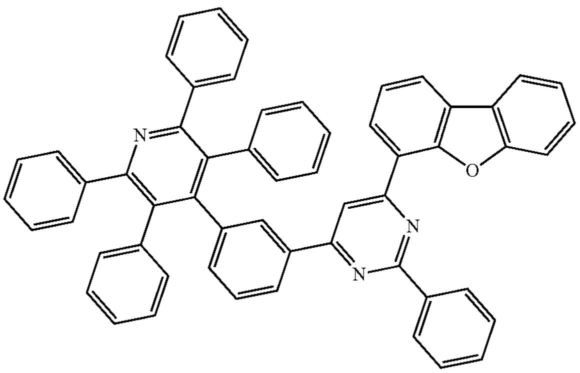
136
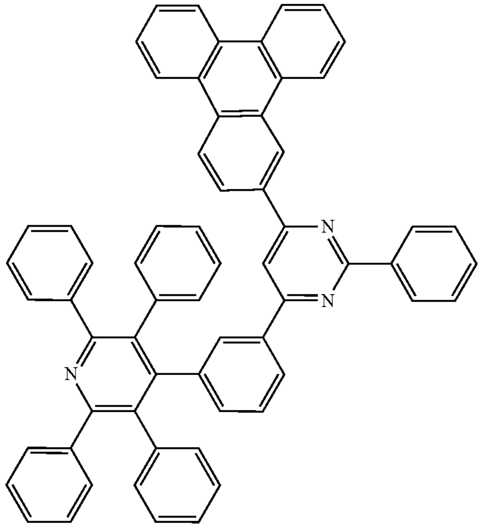
137
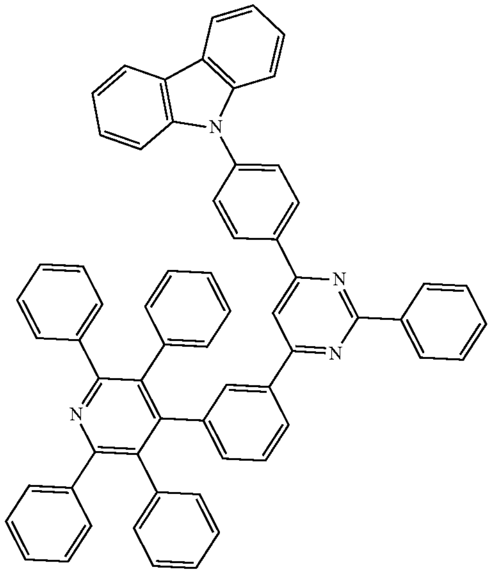
-continued
138
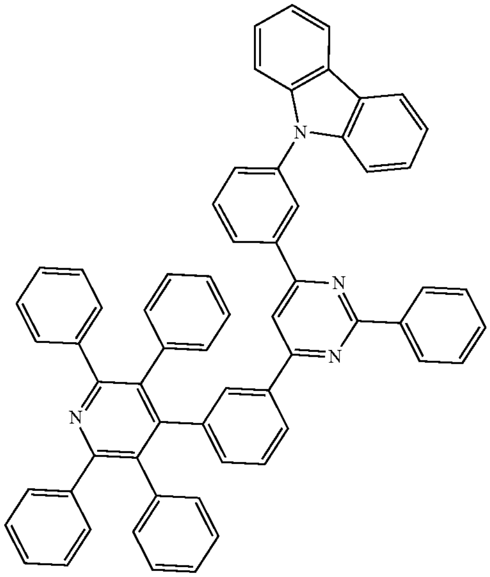
139
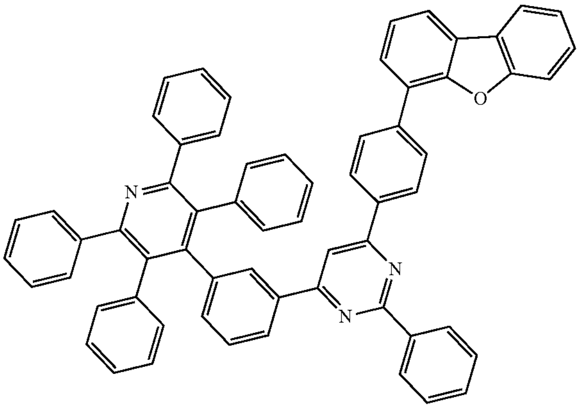
140
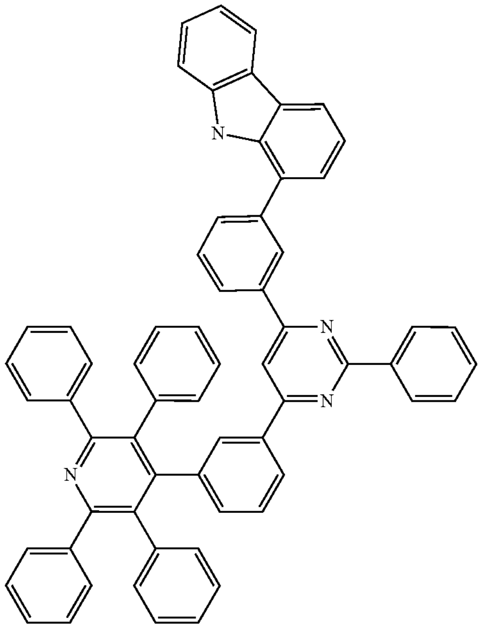

-continued
141
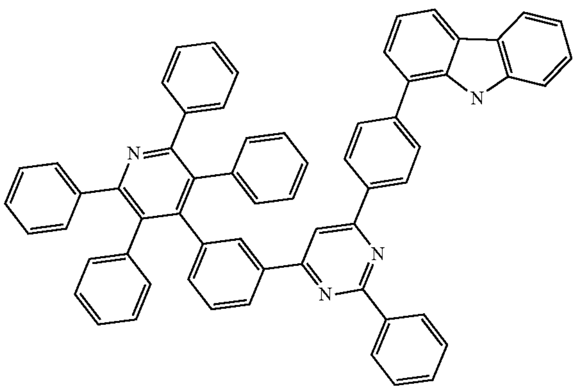
142
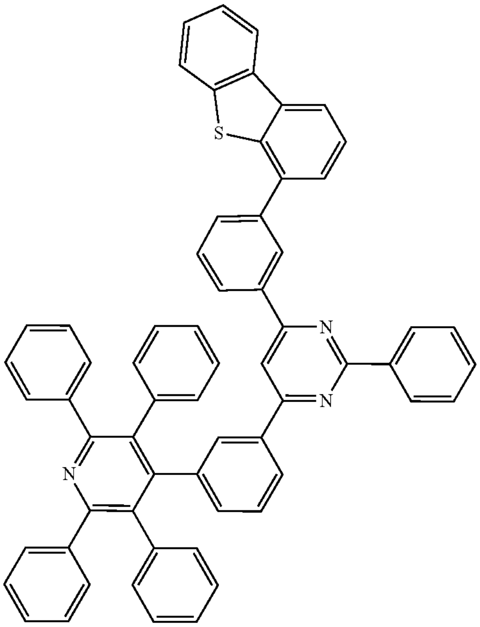
143
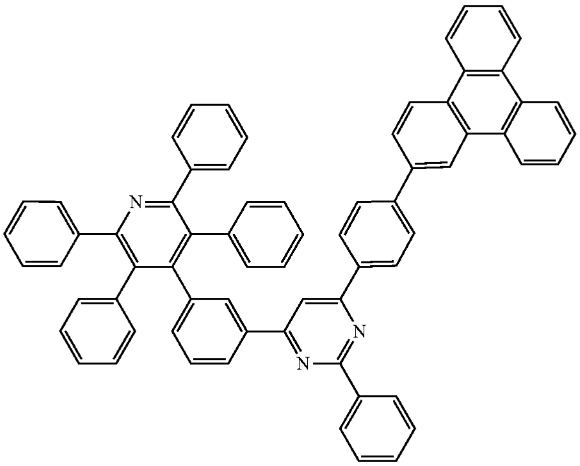
-continued
144
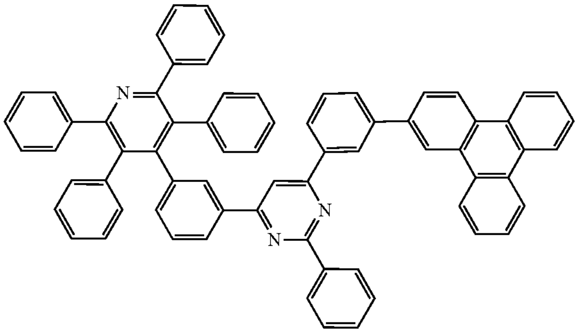
145
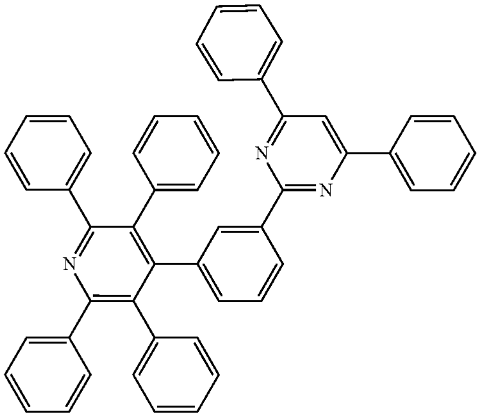
146
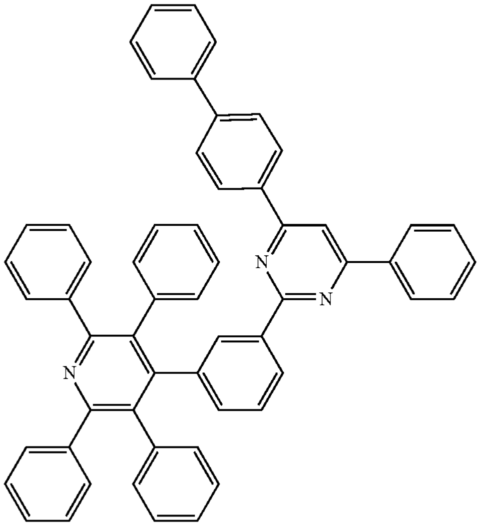

-continued
147
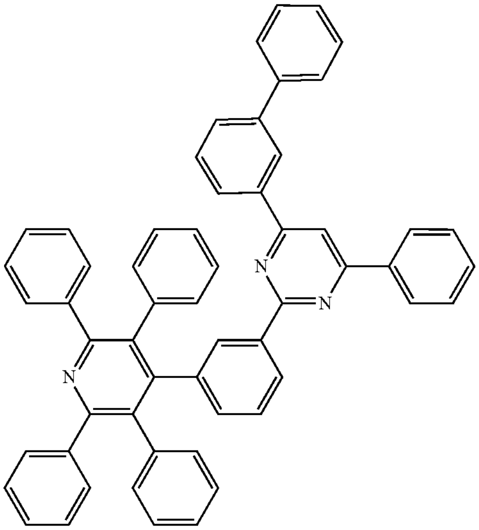
148
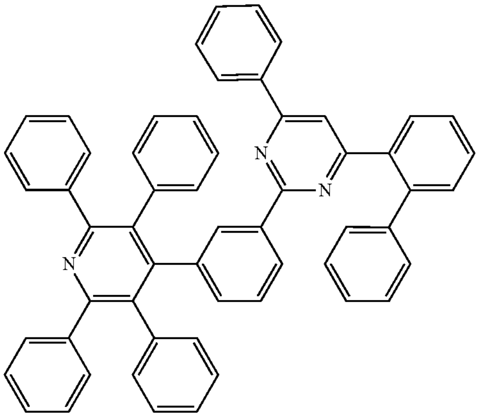
149
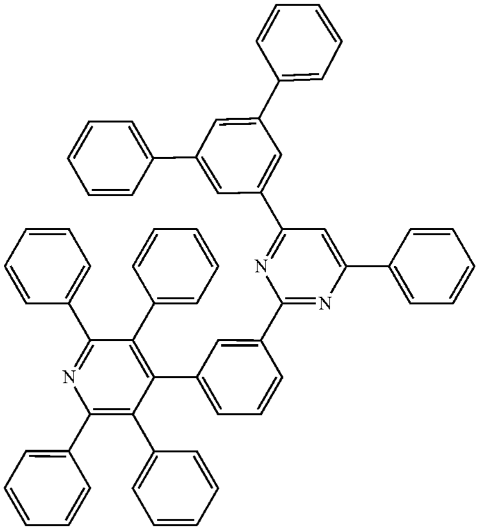
-continued
150
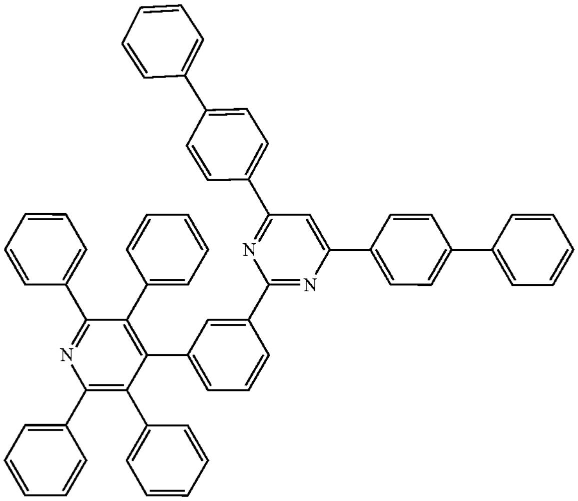
151
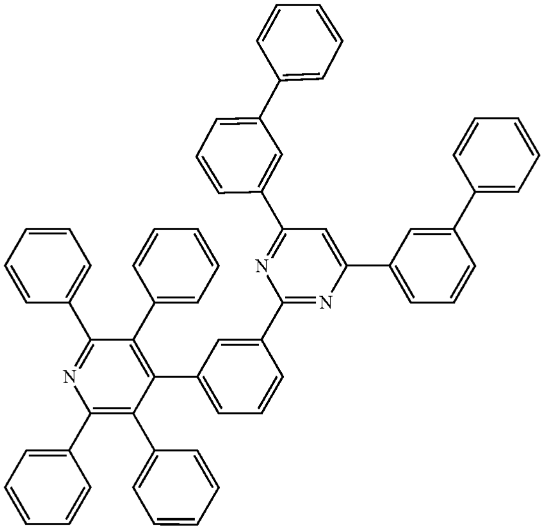
152
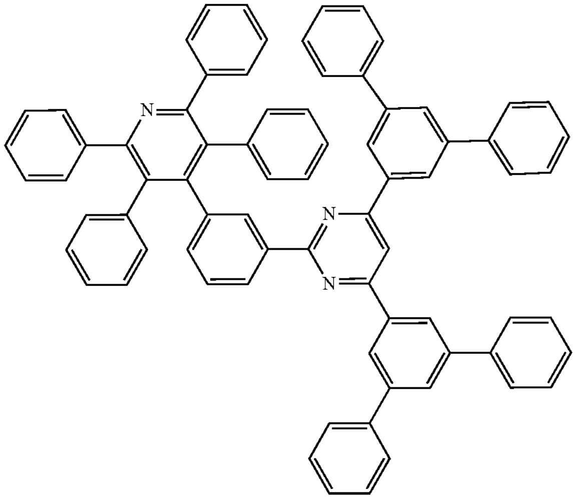

-continued
153
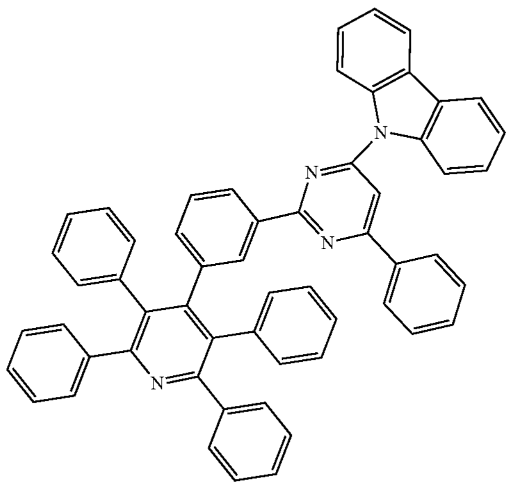
154
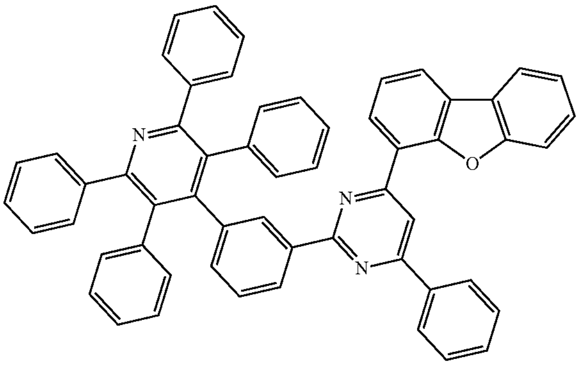
155
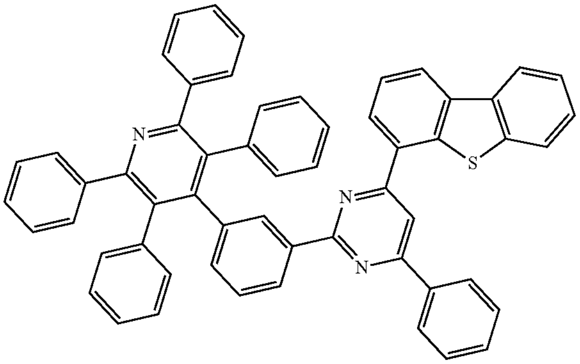
-continued
156
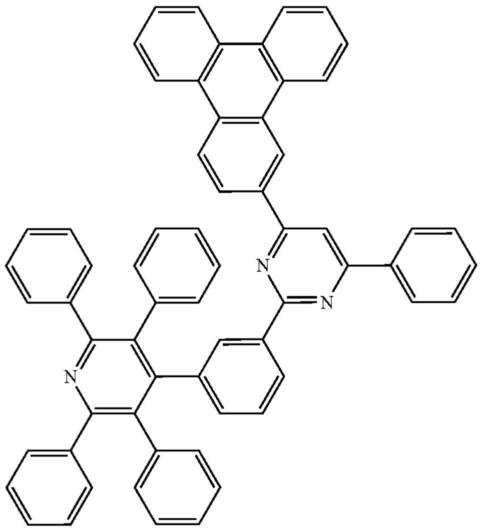
157
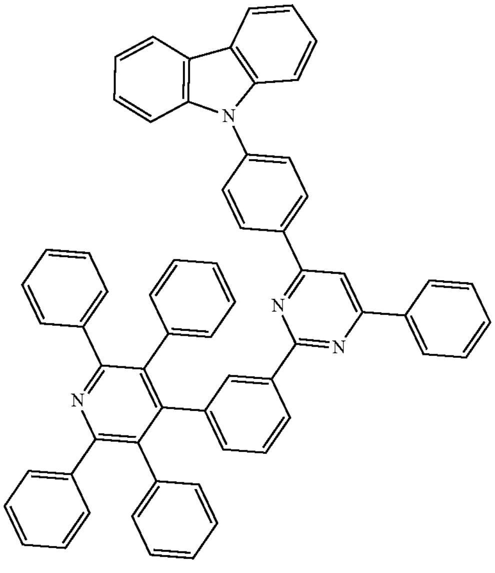

158
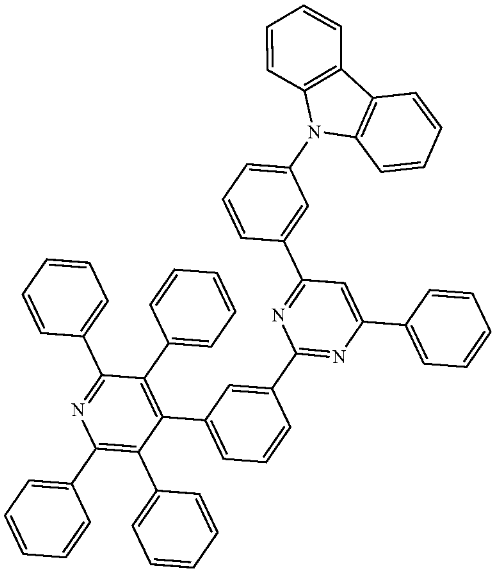
159
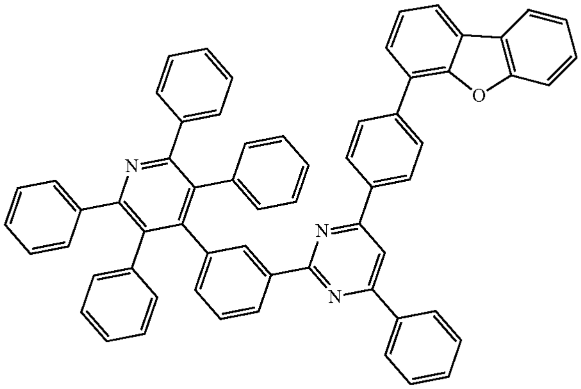
160
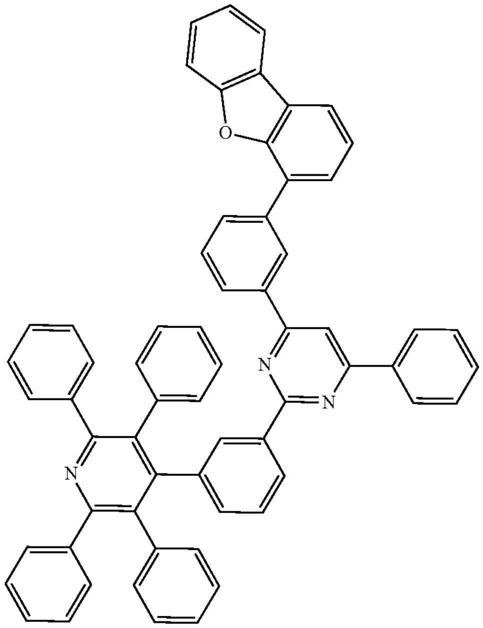
161
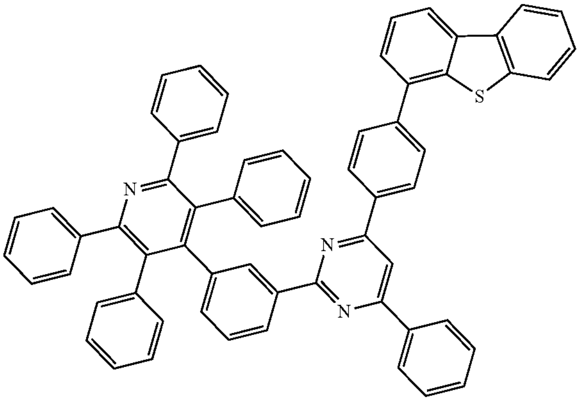
162
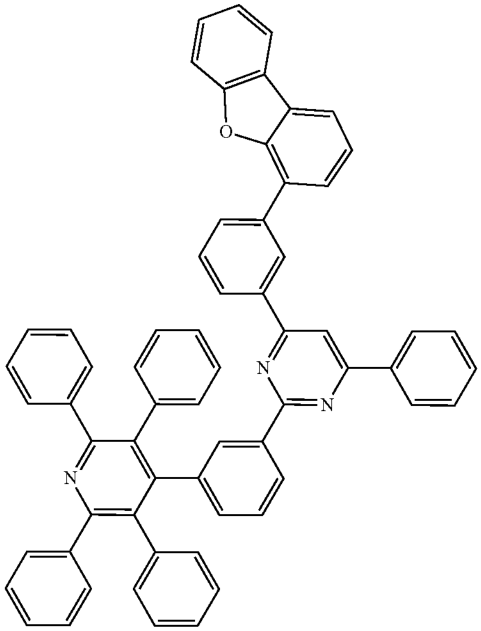
163
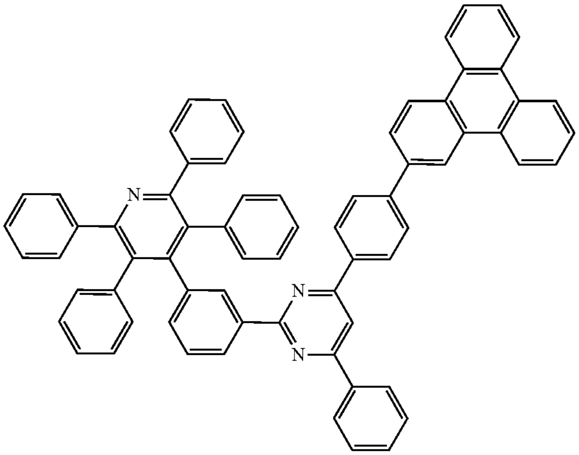

-continued
164
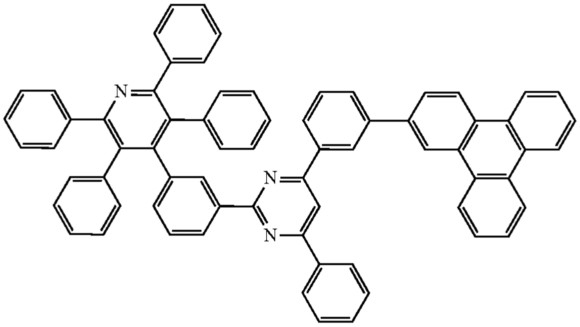
165
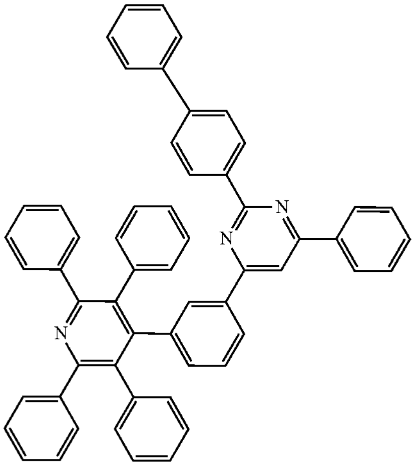
166
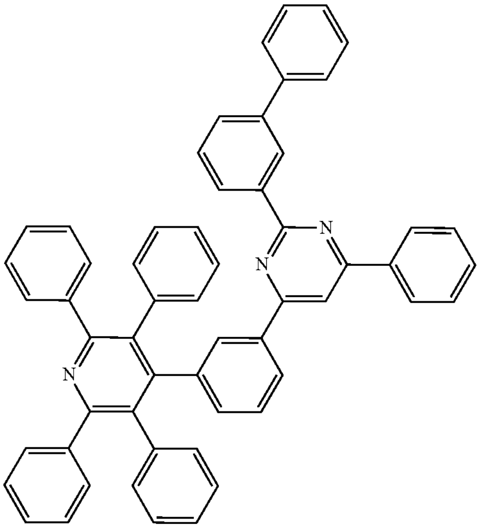
-continued
167
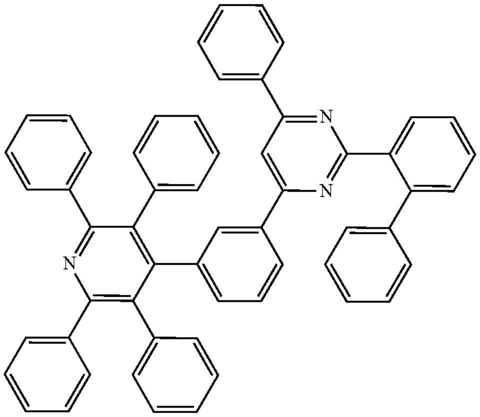
168
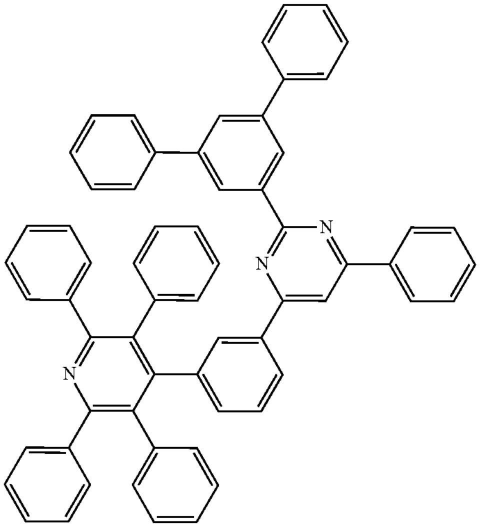
169
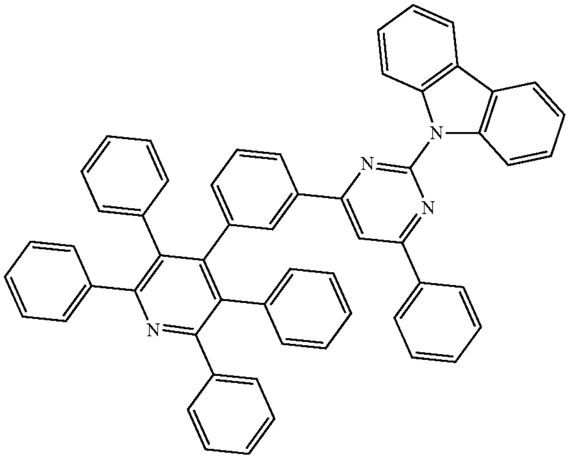

170
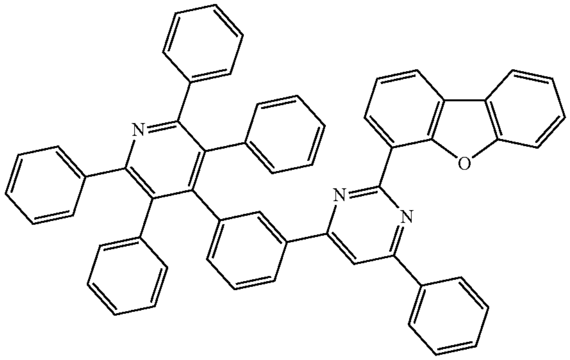
171
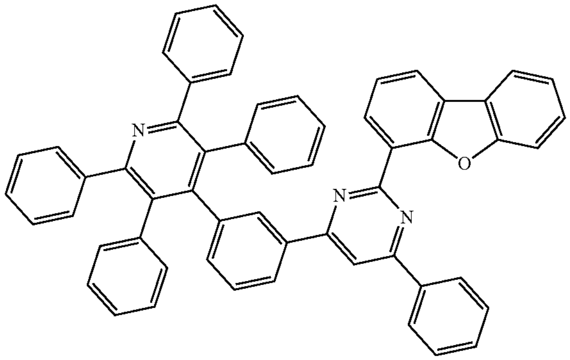
172
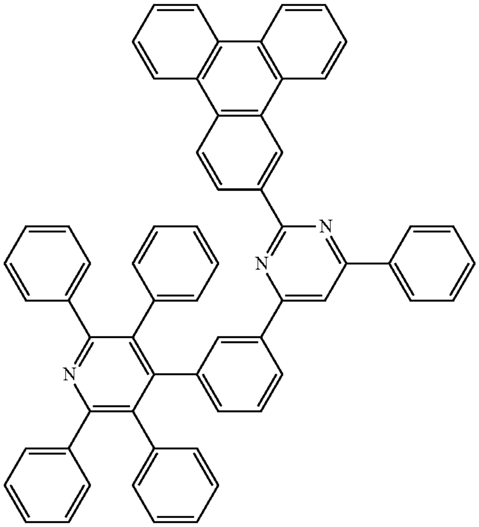
173
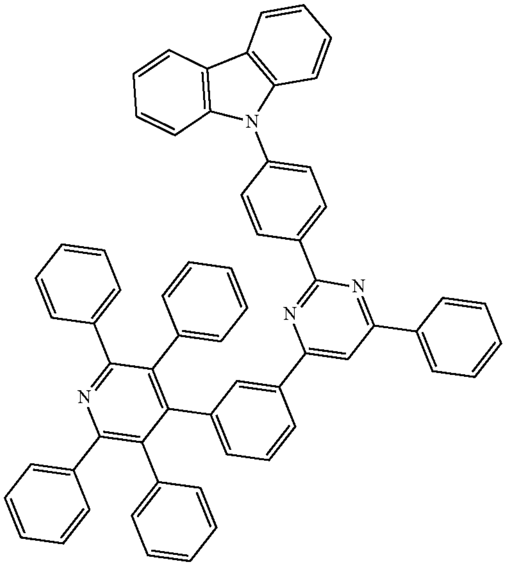
174
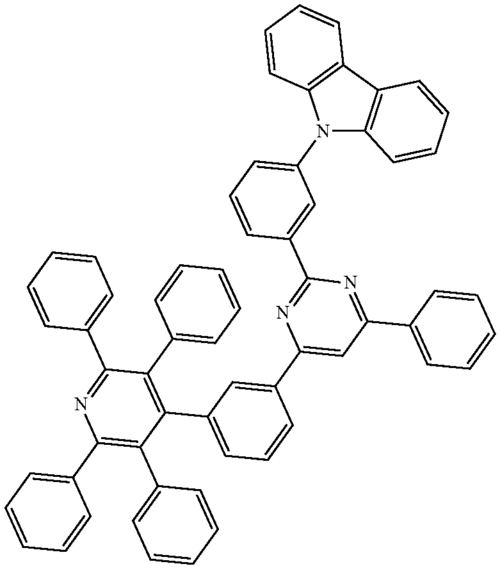
175
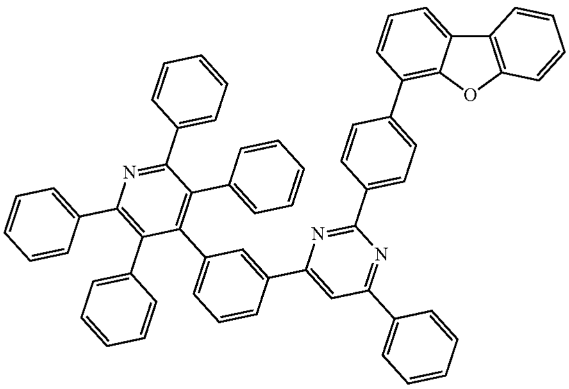

-continued
176
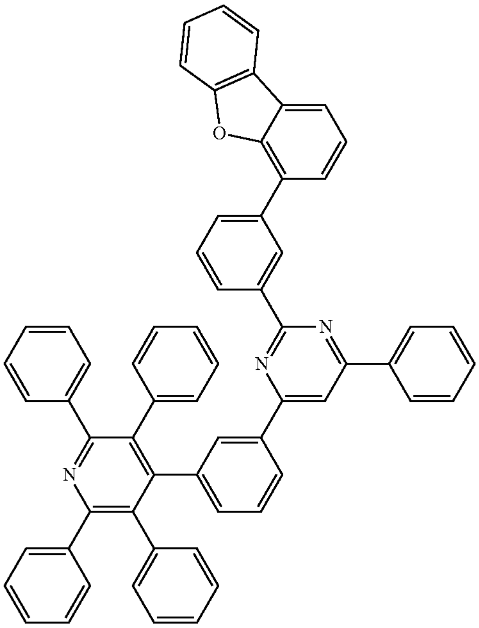
177
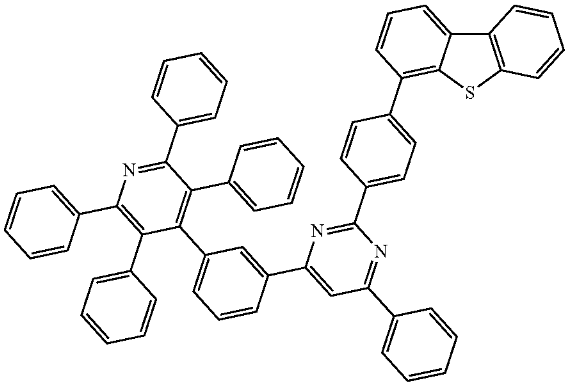
178
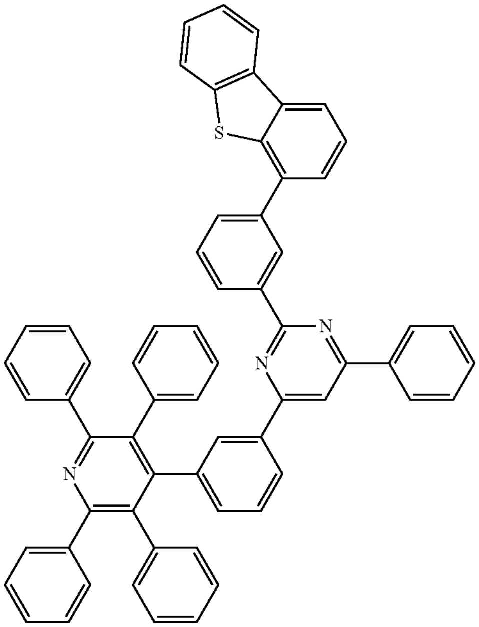
-continued
179
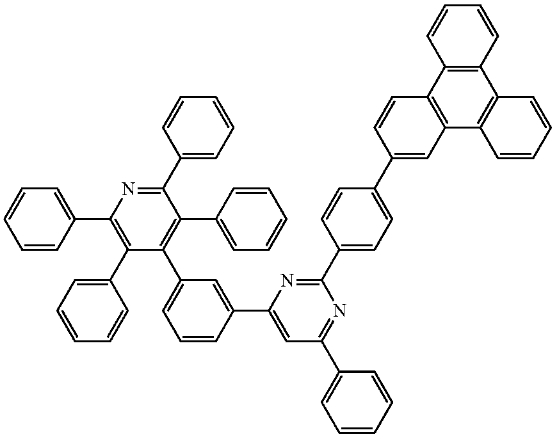
180
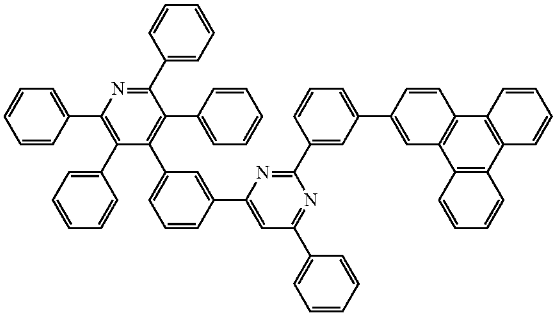
181
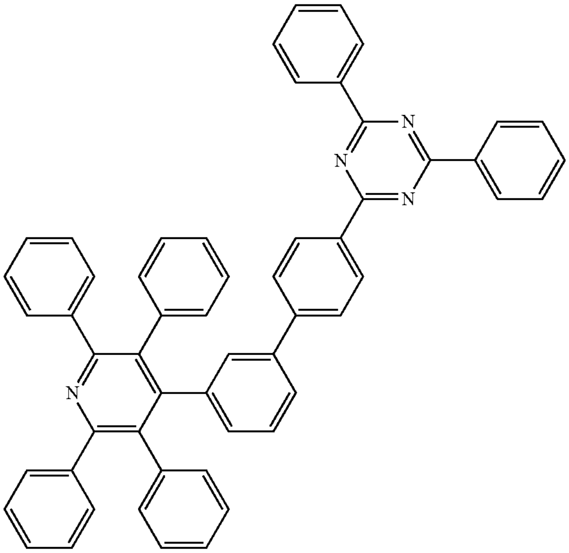

-continued
182
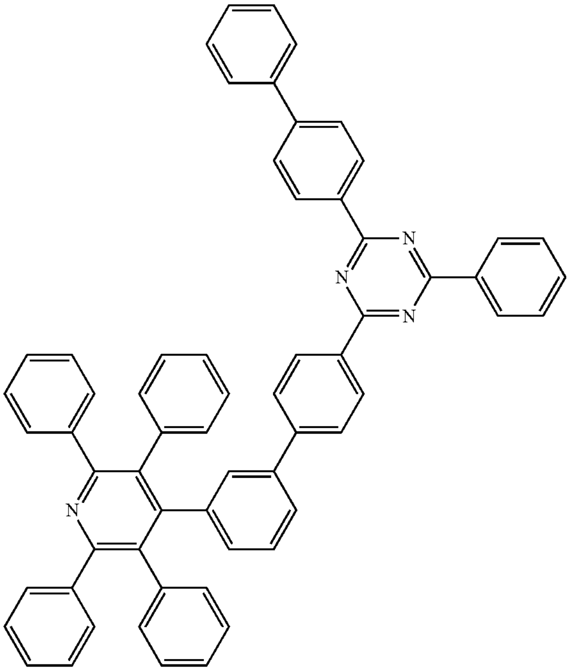
183
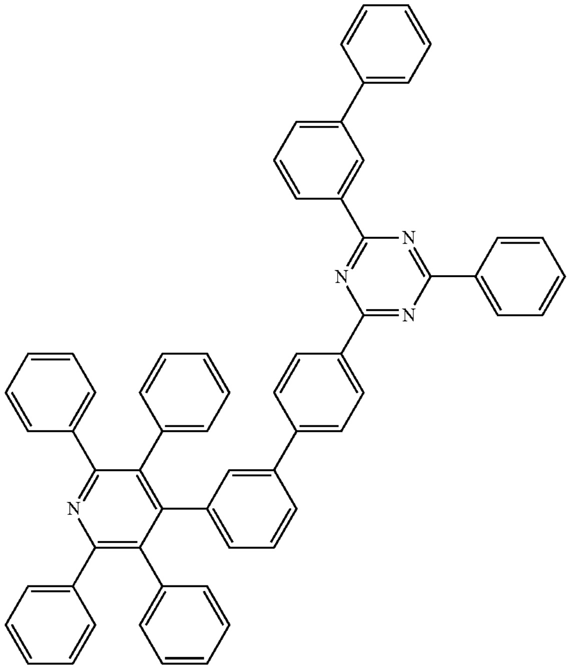
-continued
185
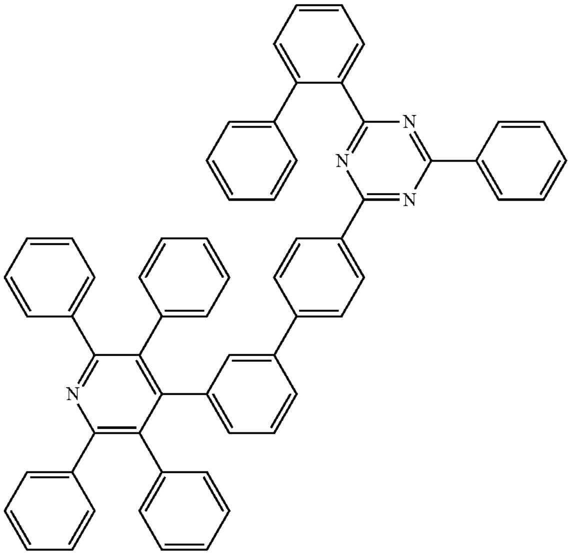
184
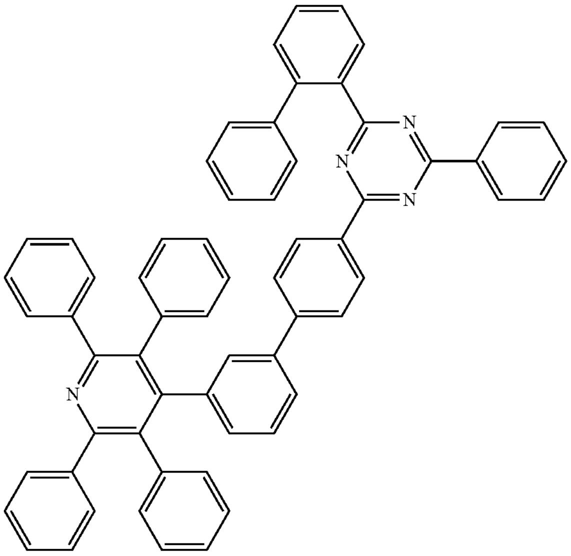

-continued
185
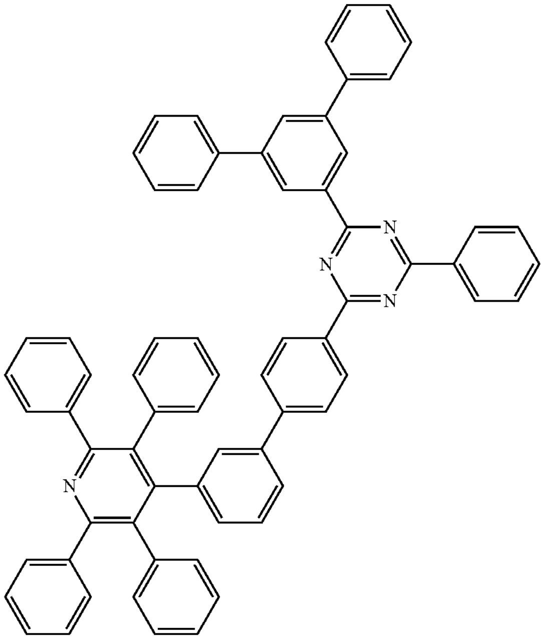
186
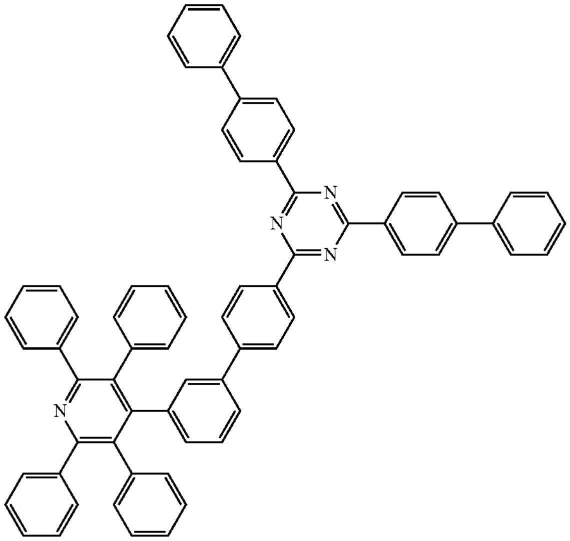
-continued
187
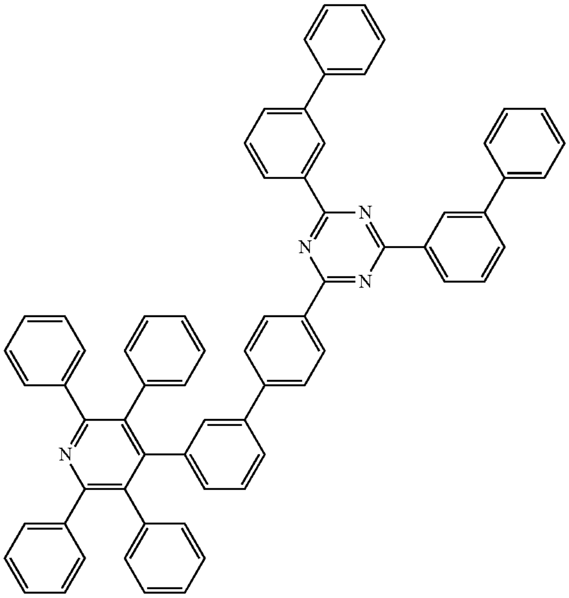
188
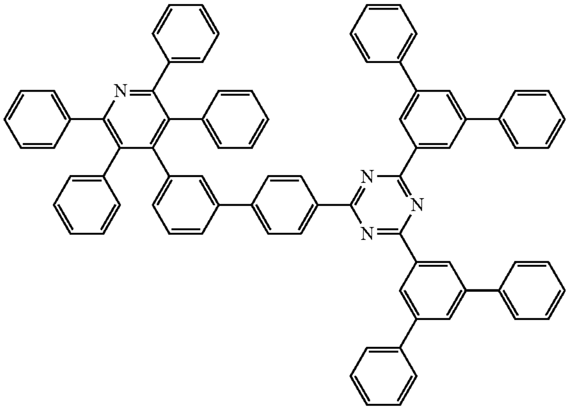
189
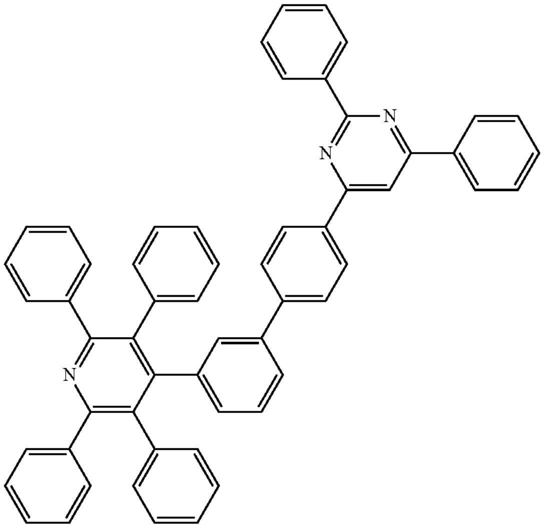

-continued
190
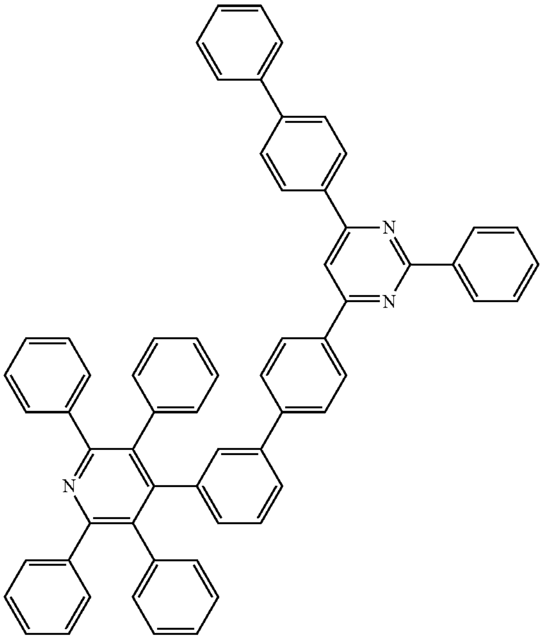
191
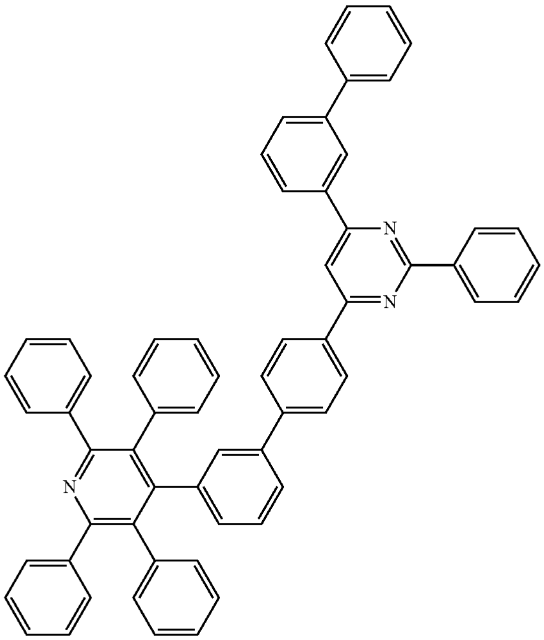
-continued
192
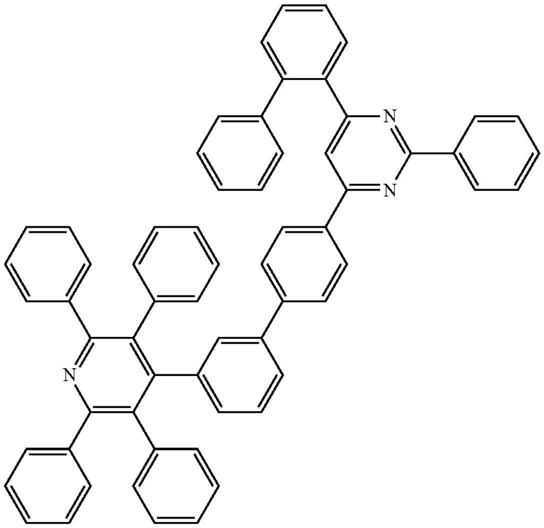
193
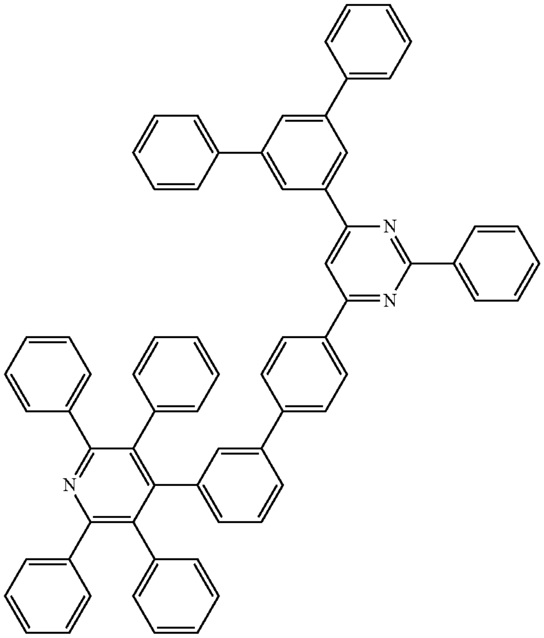

-continued
194
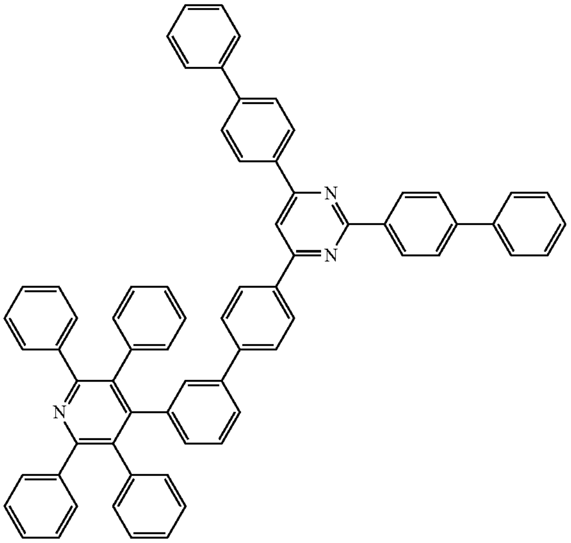
195
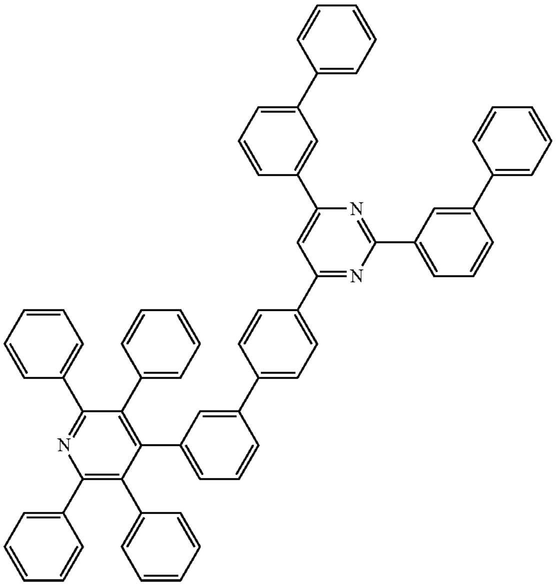
196
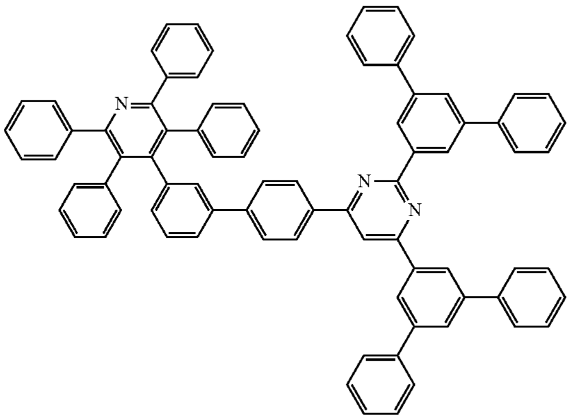
-continued
197
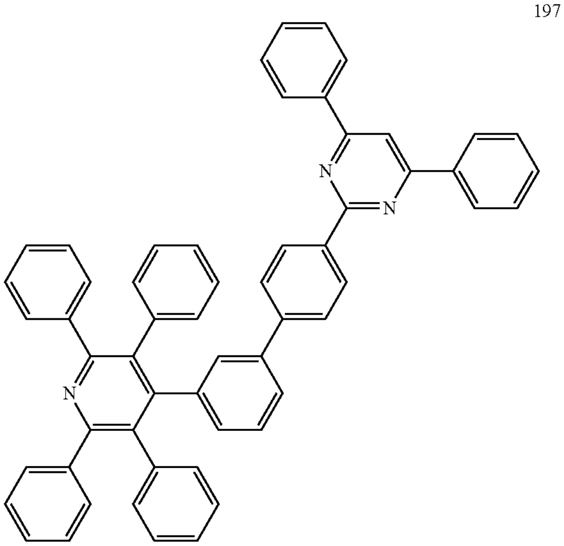
198
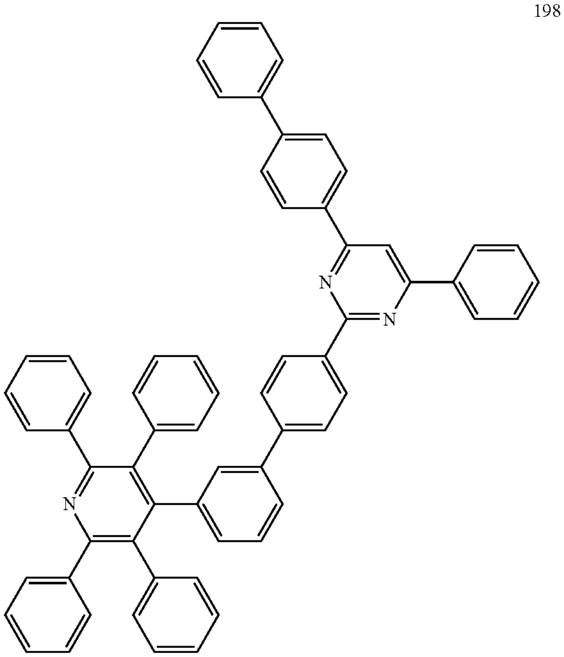

-continued
199
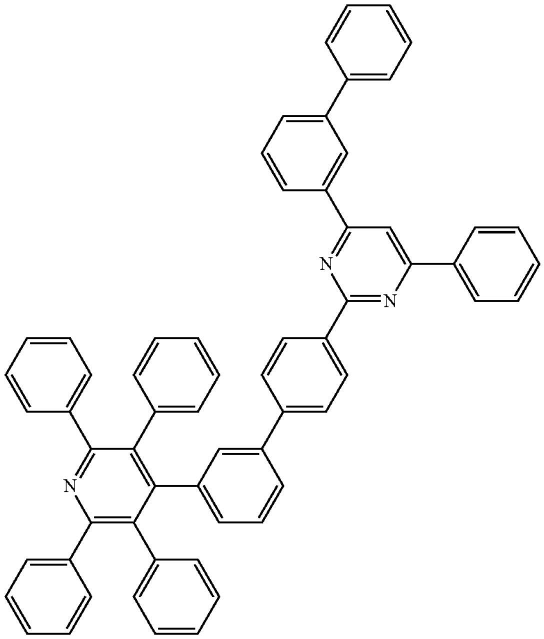
200
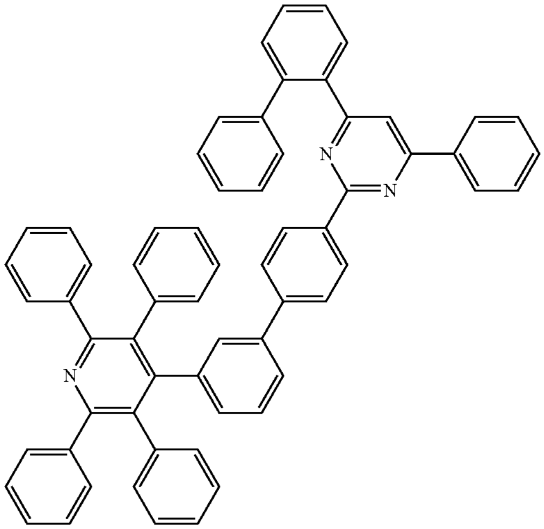
-continued
201
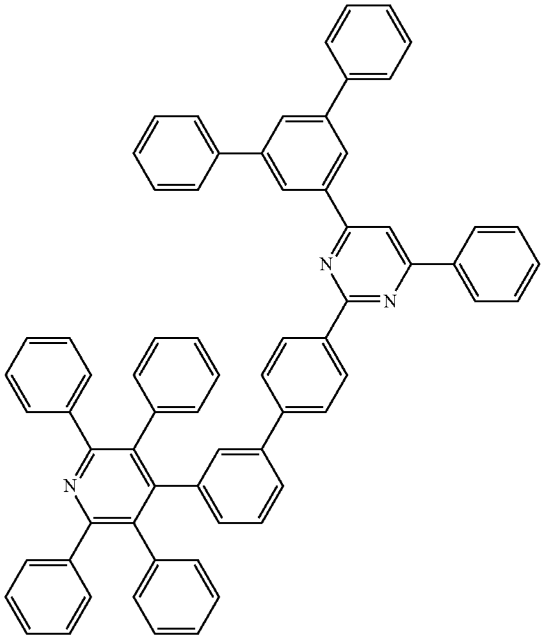
201
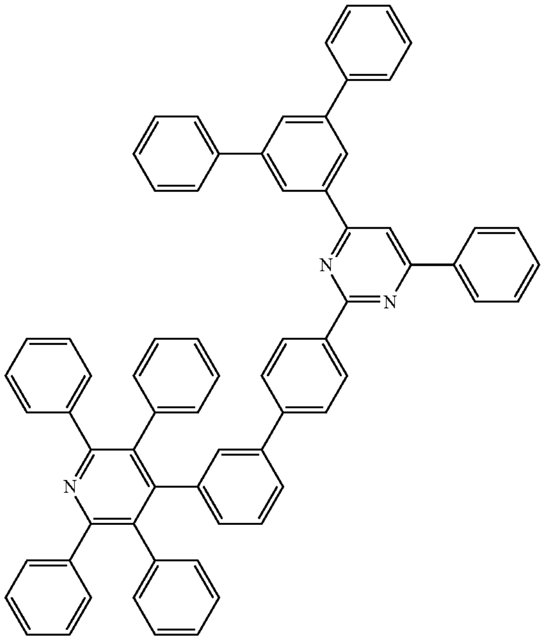

-continued
202
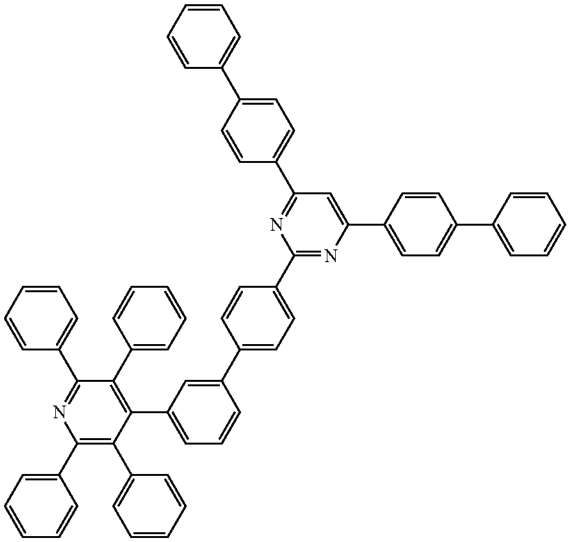
203
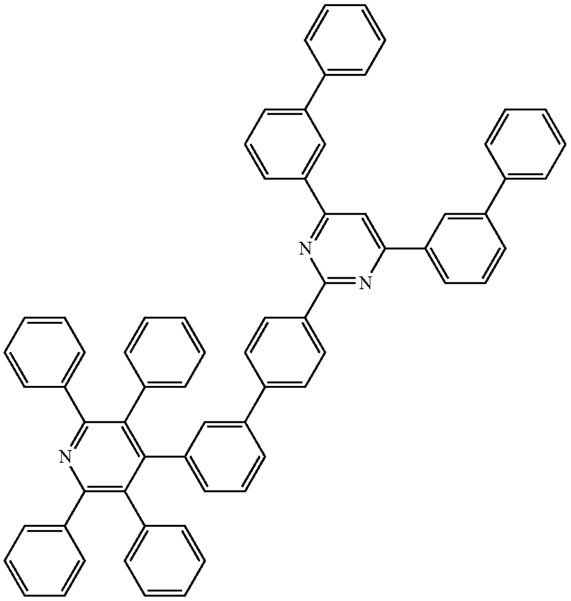
204
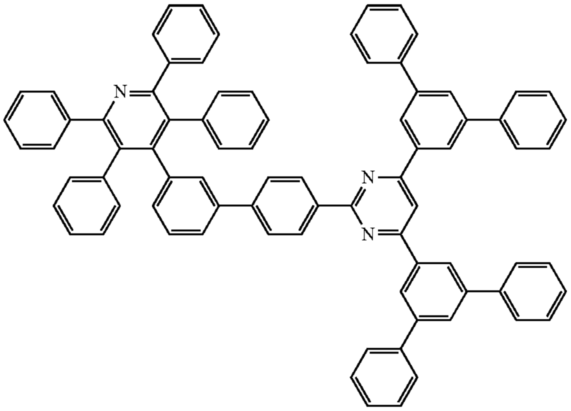
-continued
205
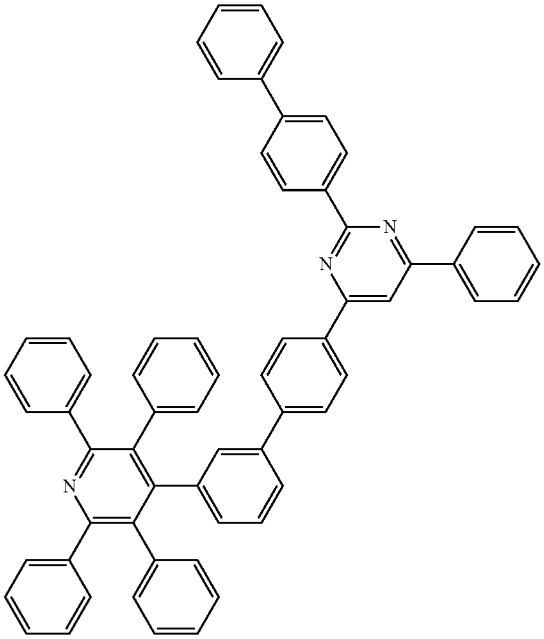
206
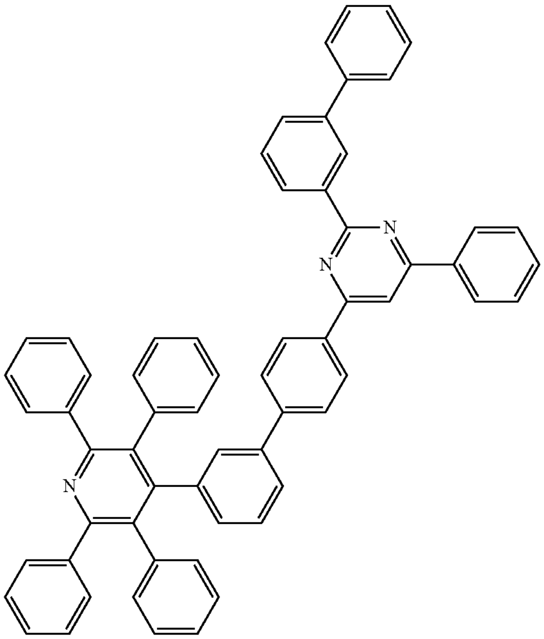

-continued
207
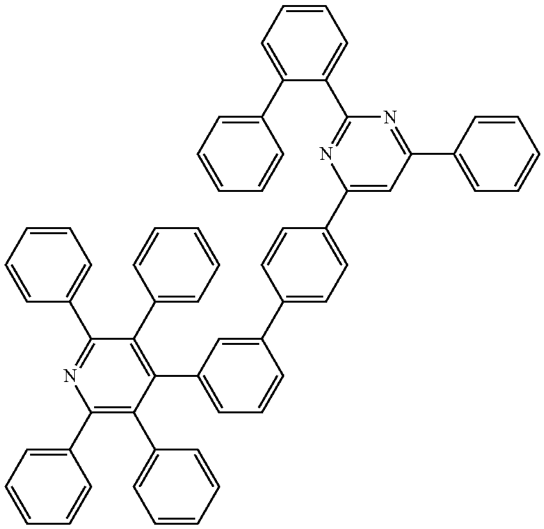
208
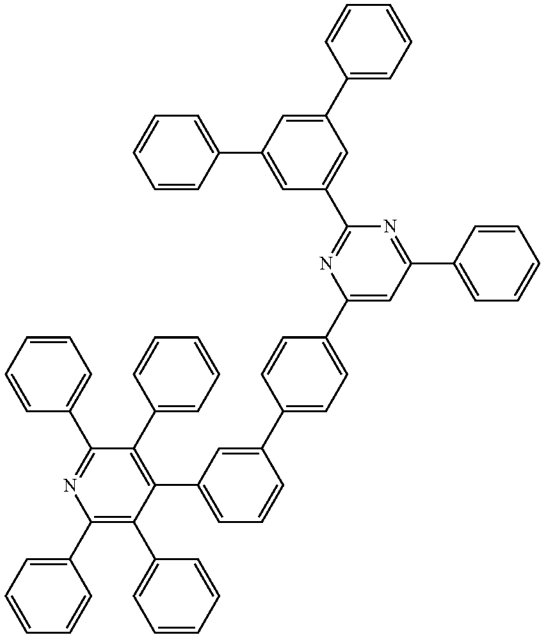
-continued
208
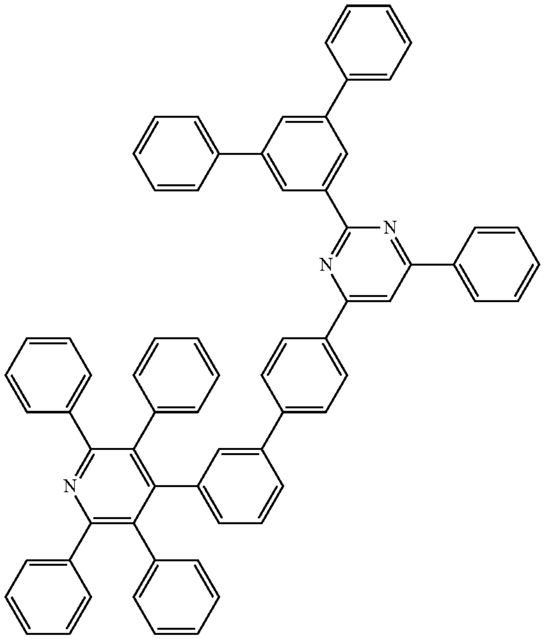
209
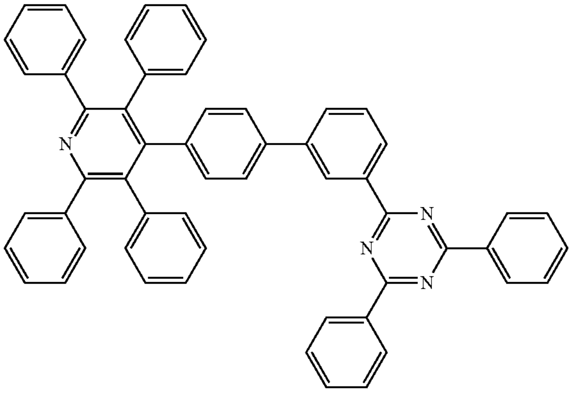
210
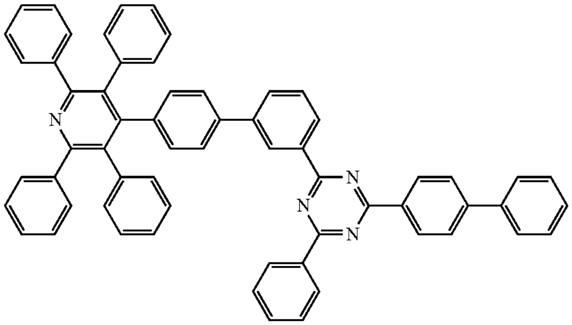

-continued
211
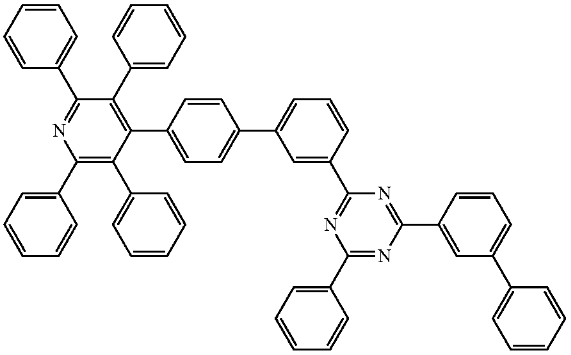
212
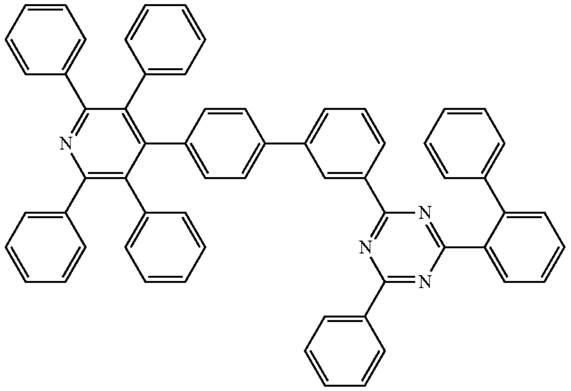
213
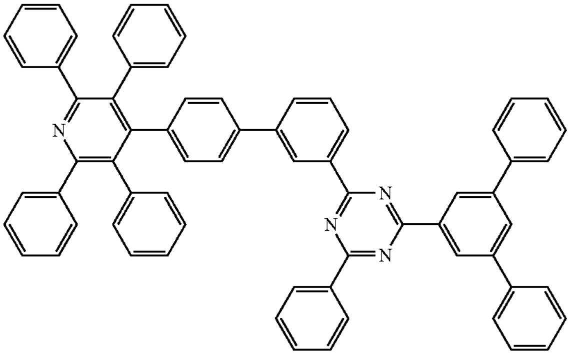
214
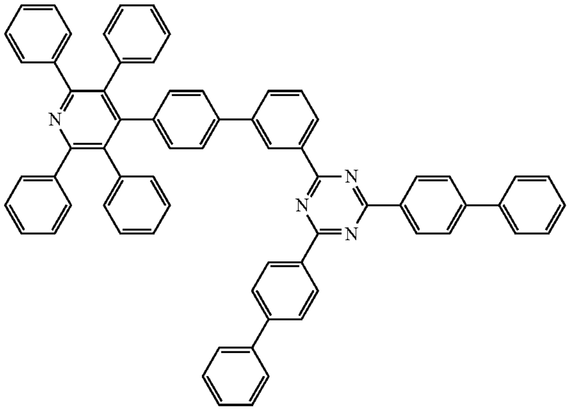
-continued
215
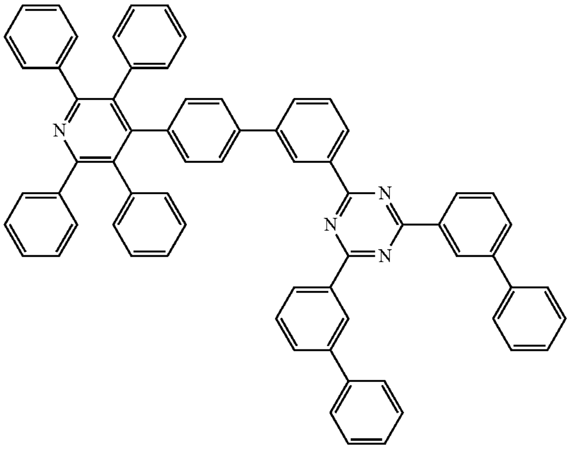
216
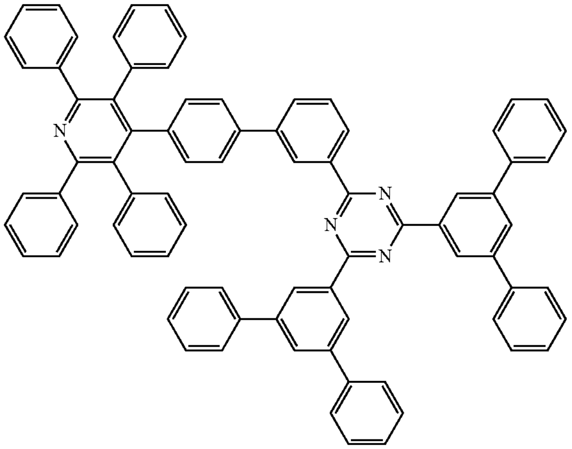
217
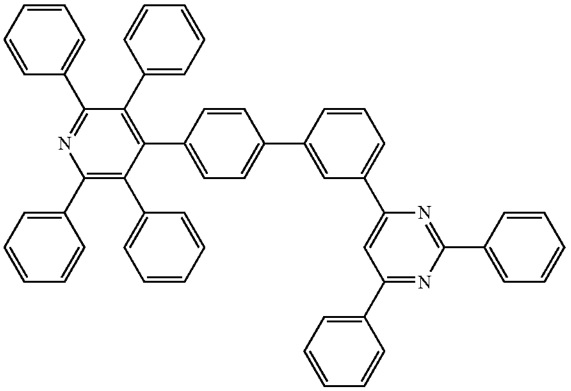

-continued
218
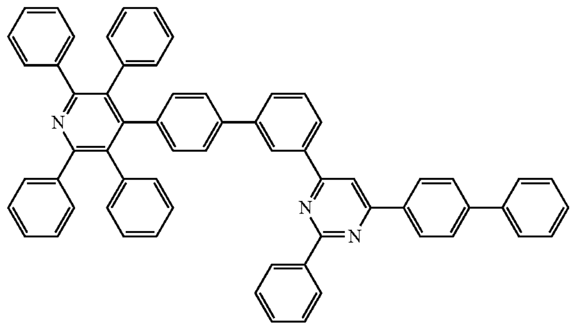
219
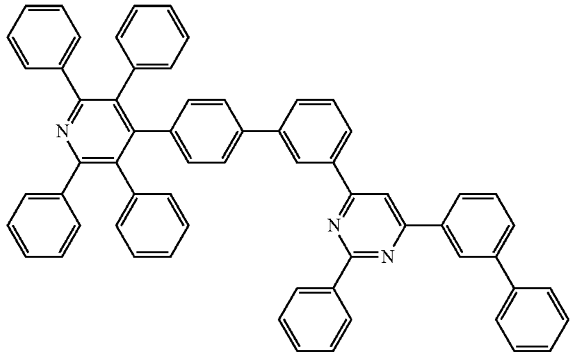
220
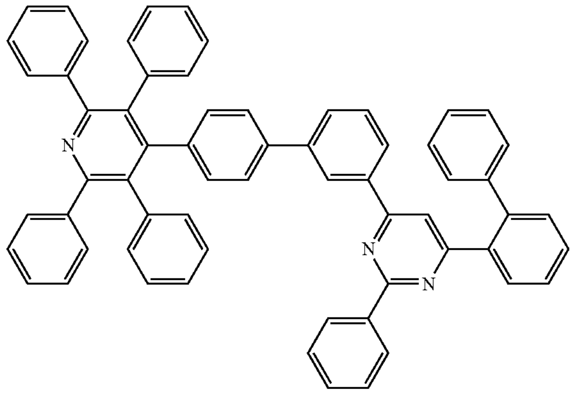
221
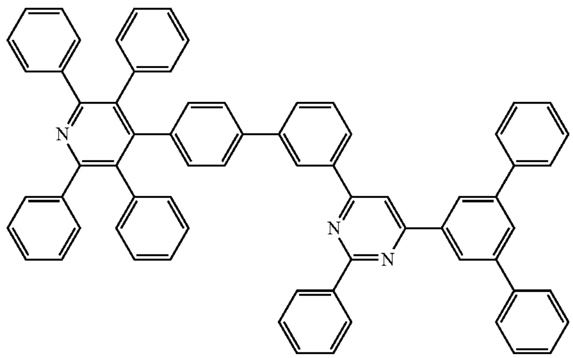
-continued
222
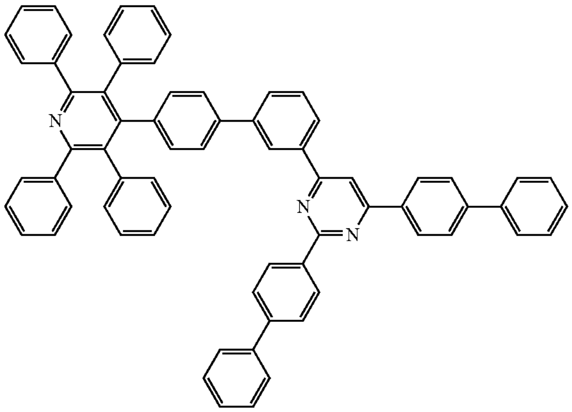
223
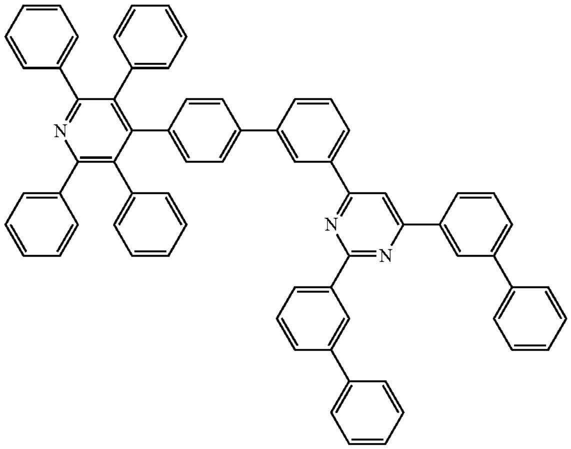
224
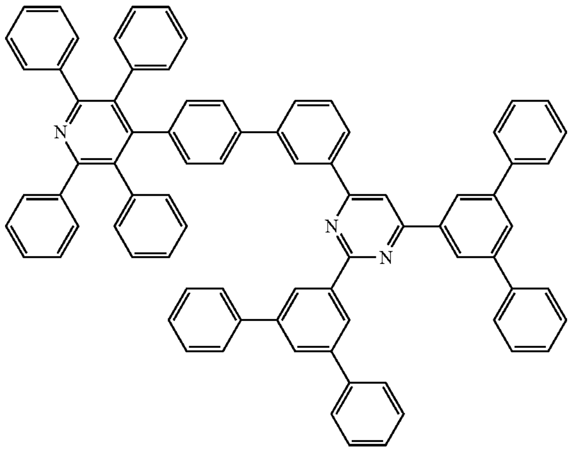

-continued
225
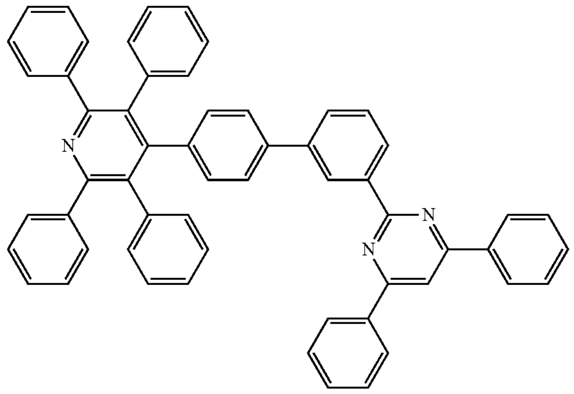
226
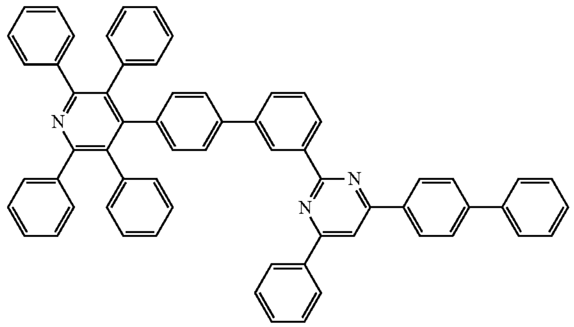
227
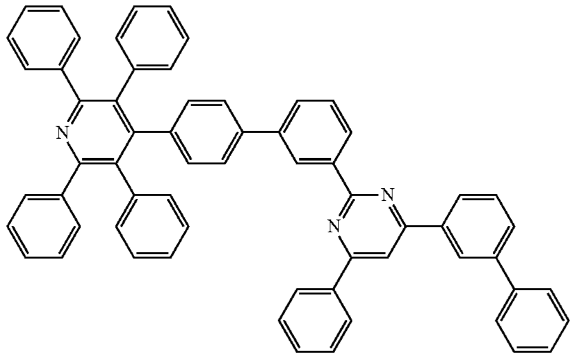
228
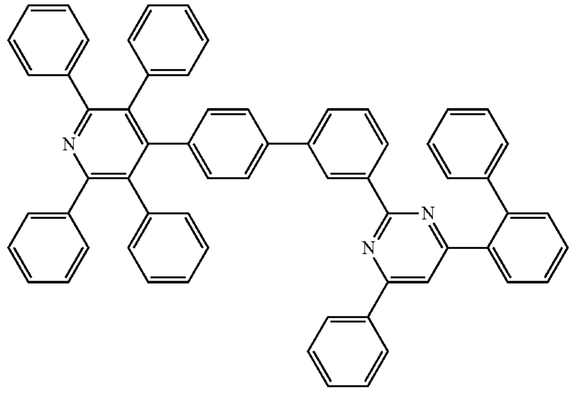
-continued
229
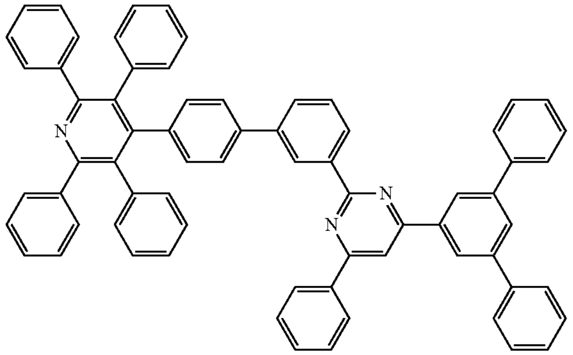
230
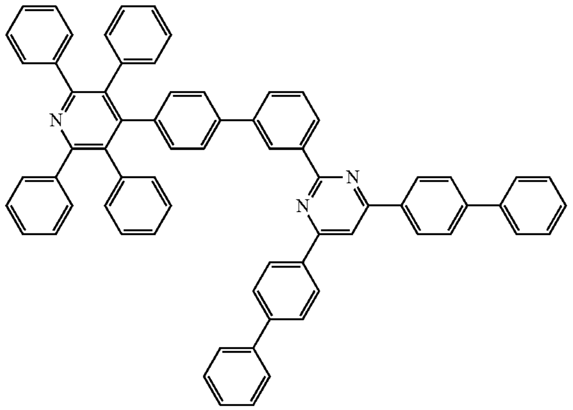
231
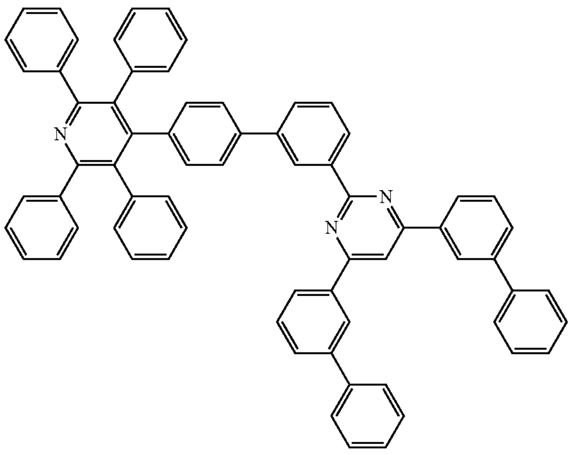

-continued
232
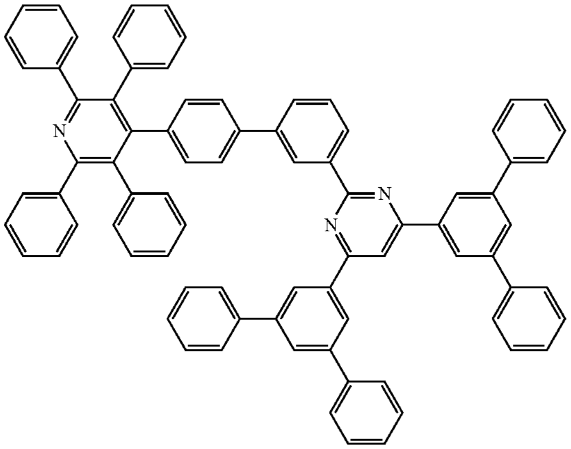
233
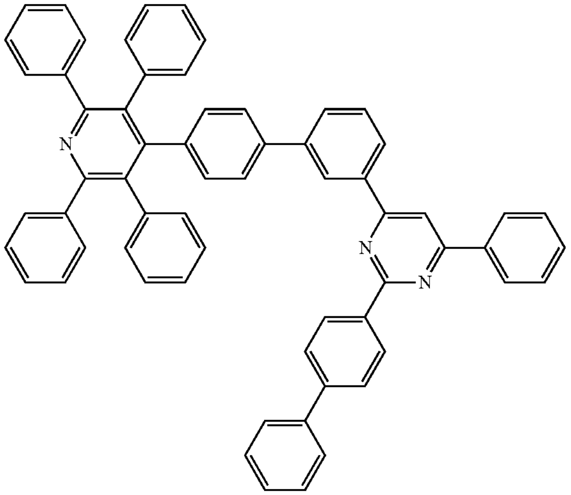
234
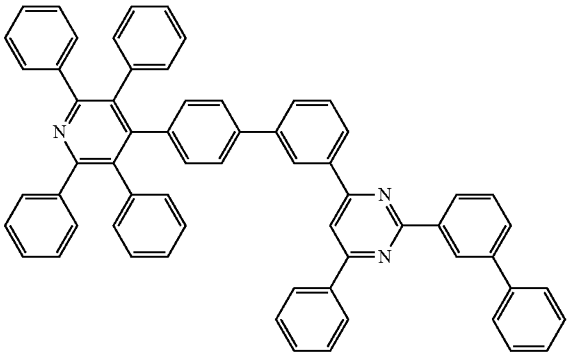
-continued
235
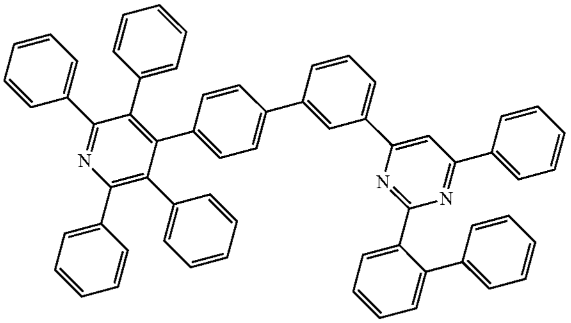
236
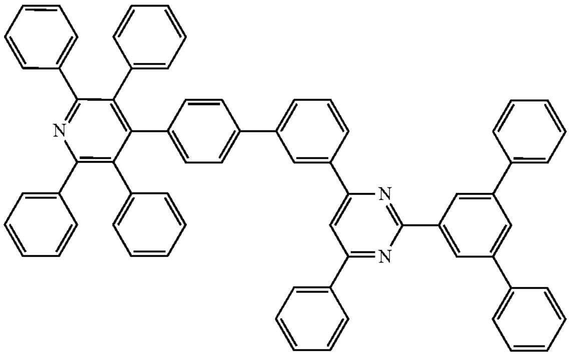
237
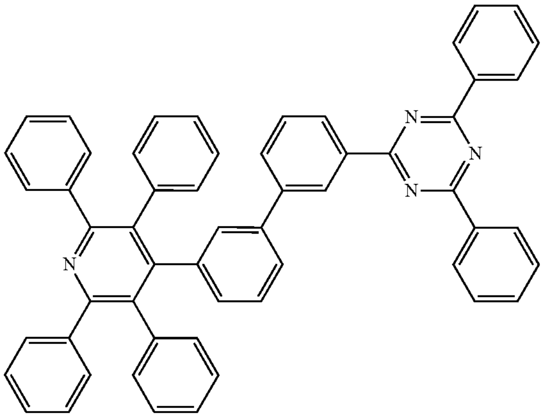

-continued
238
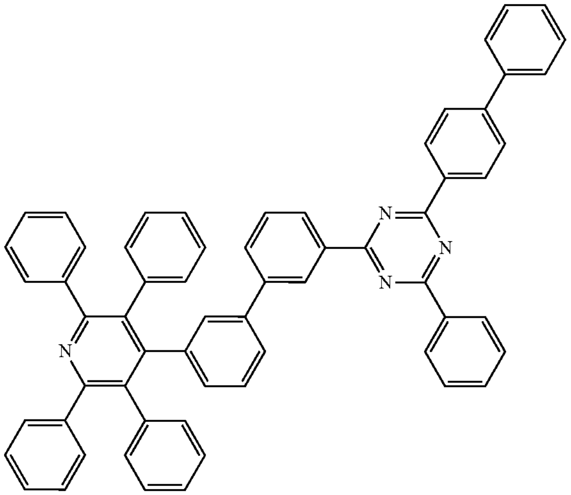
239
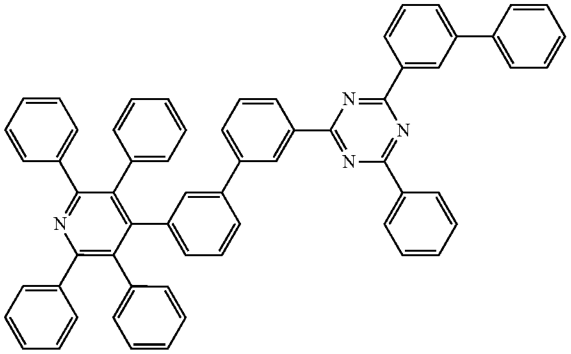
240
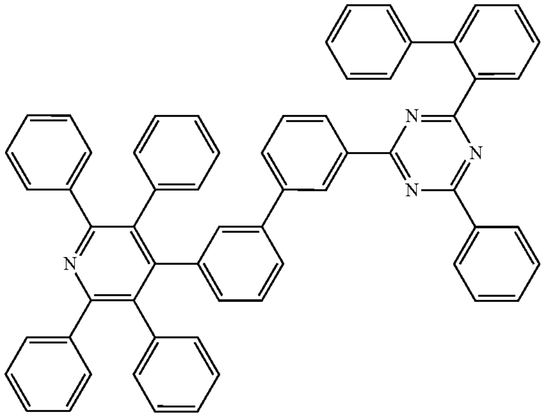
-continued
241
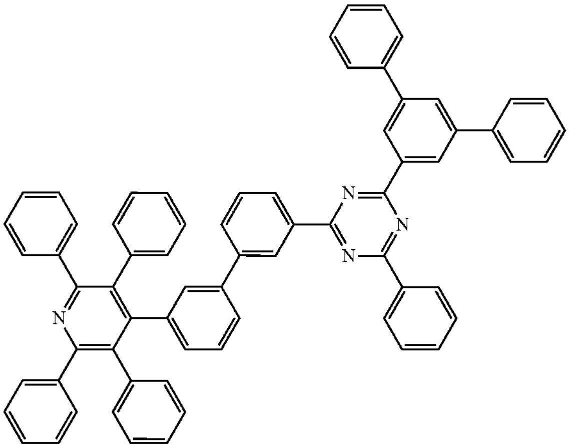
242
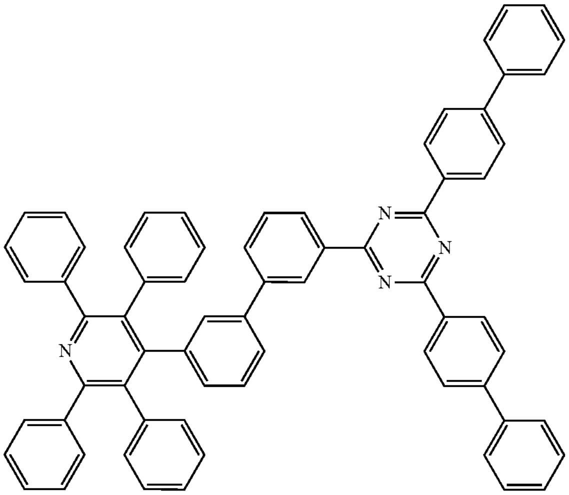
243
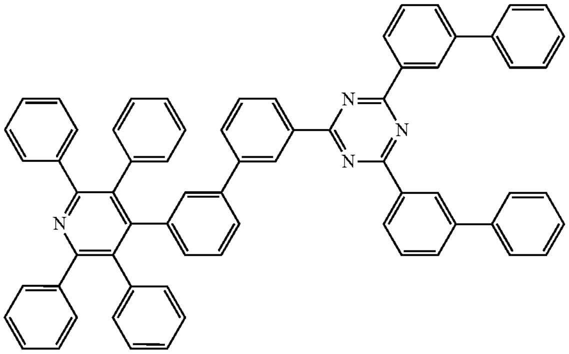

-continued
244
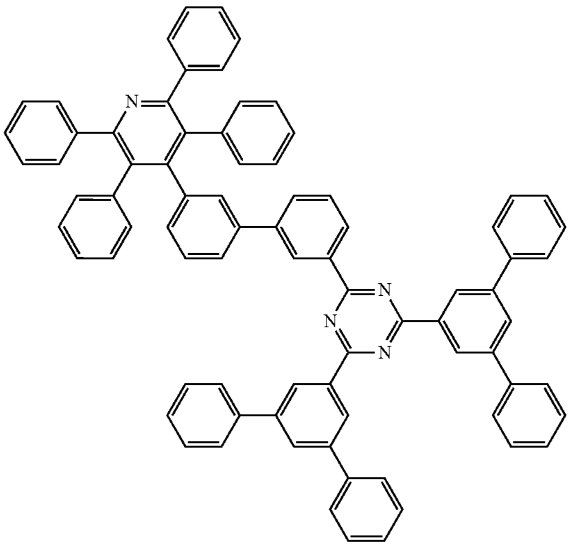
245
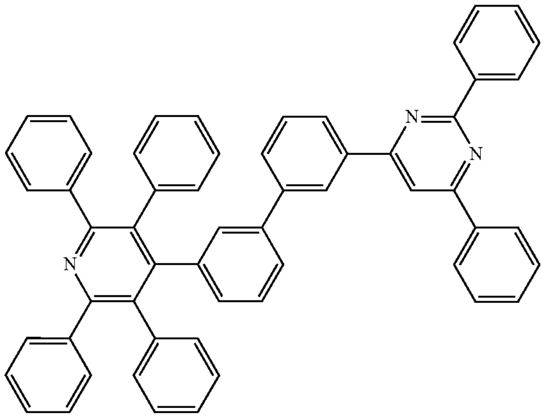
245
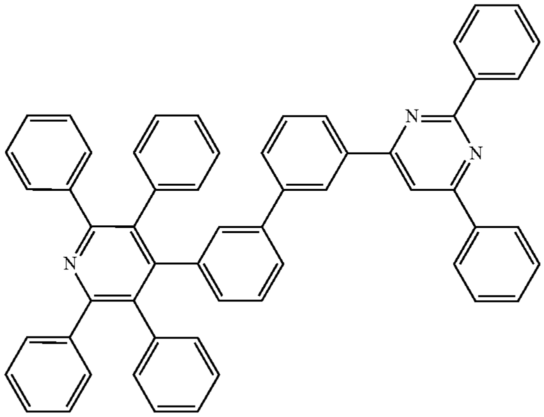
-continued
246
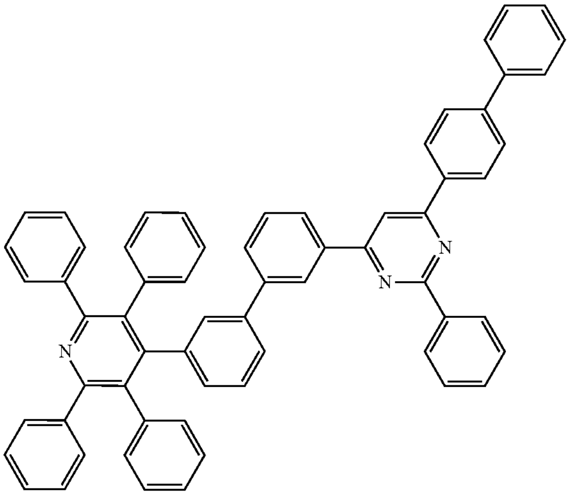
247
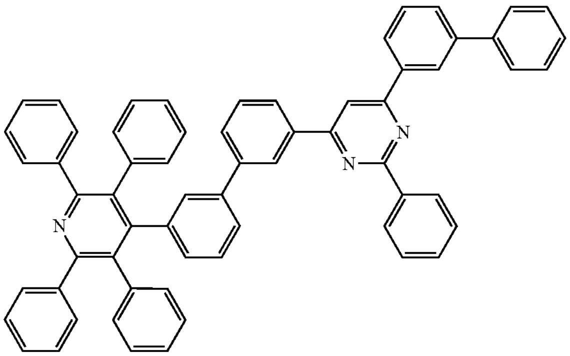
248
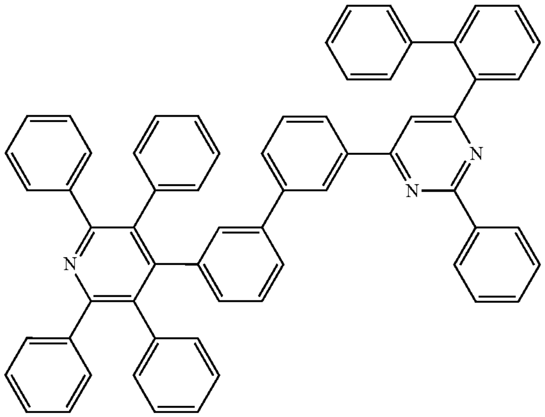

-continued
249
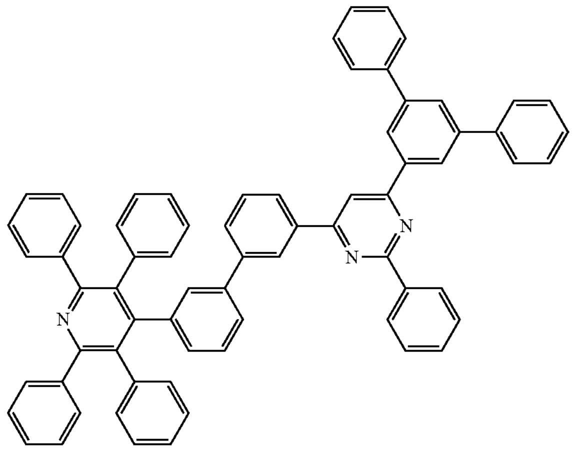
250
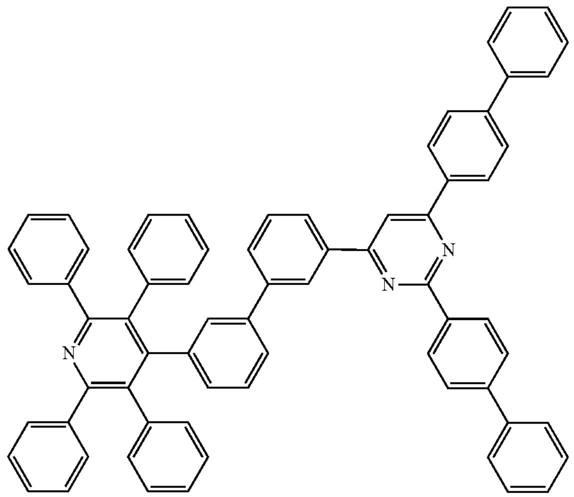
251
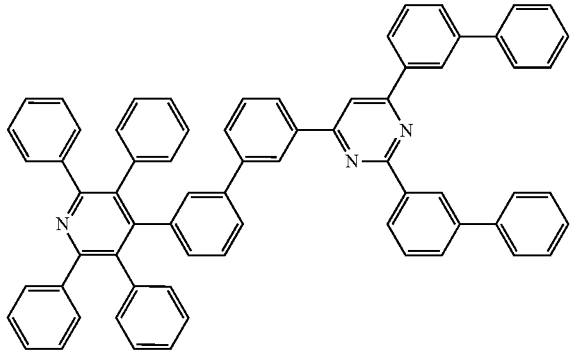
-continued
252
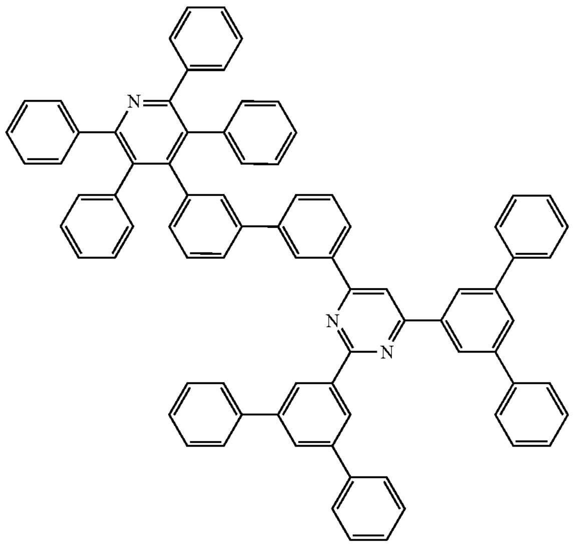
253
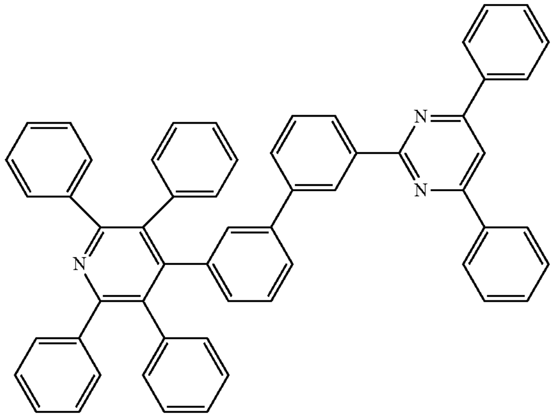
254
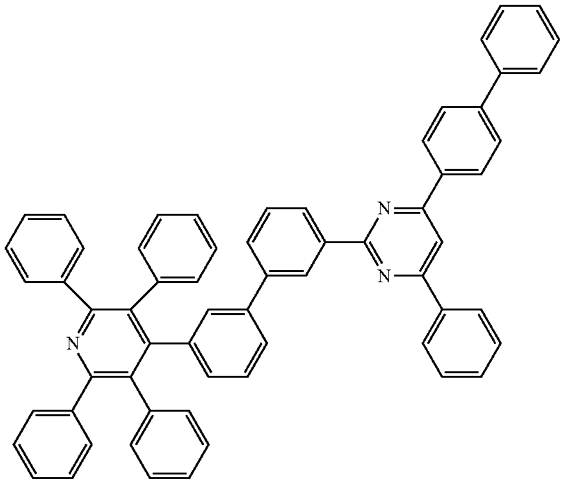

255
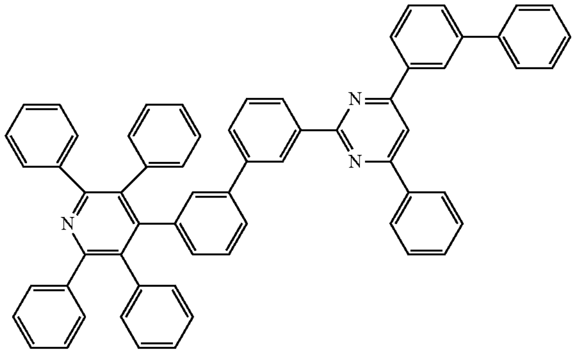
256
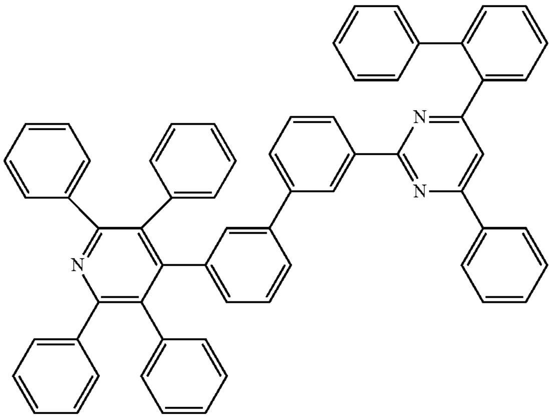
257
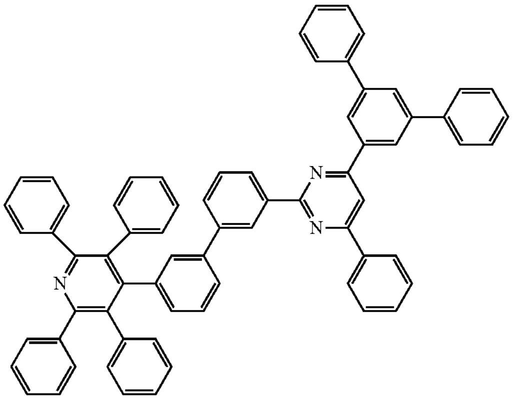
258
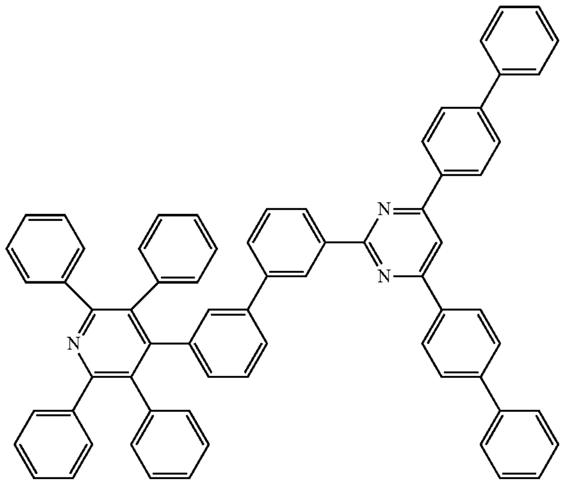
259
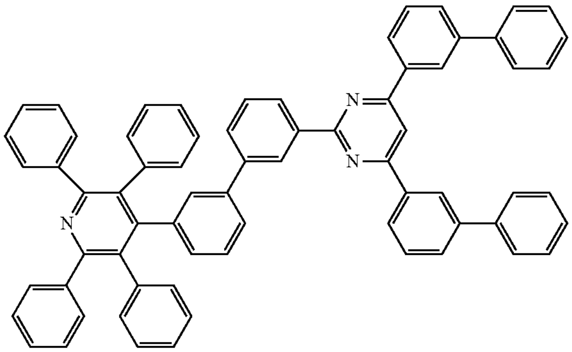
260
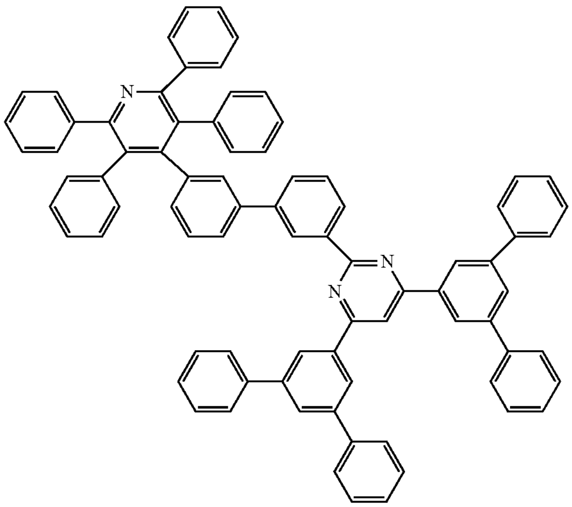

-continued
261
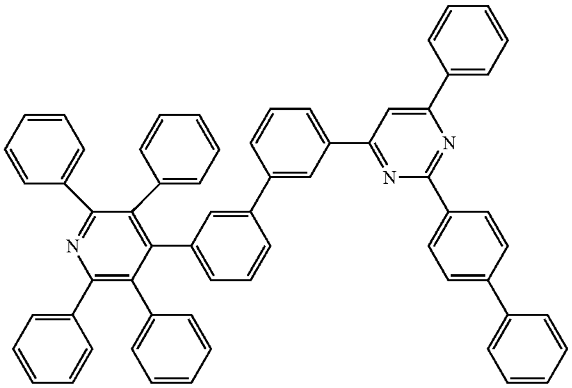
262
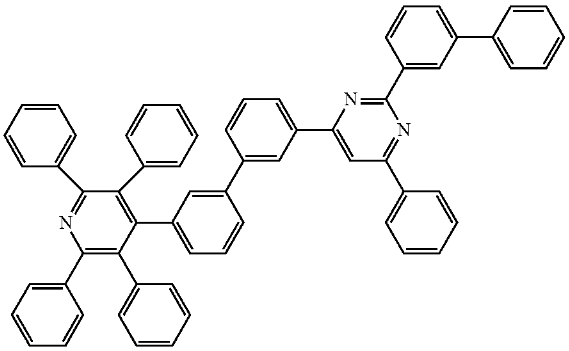
263
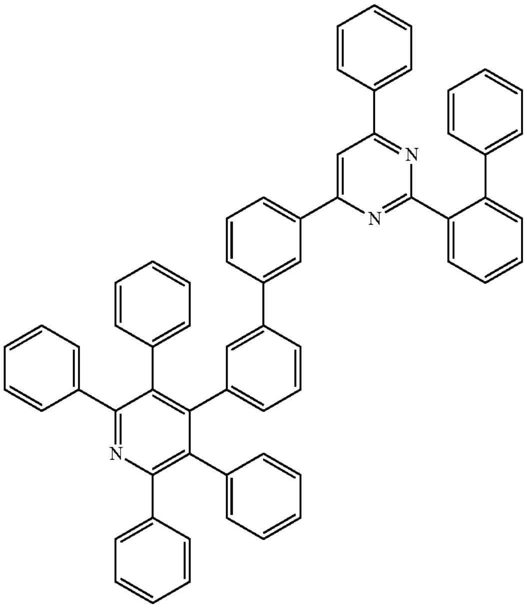
-continued
264
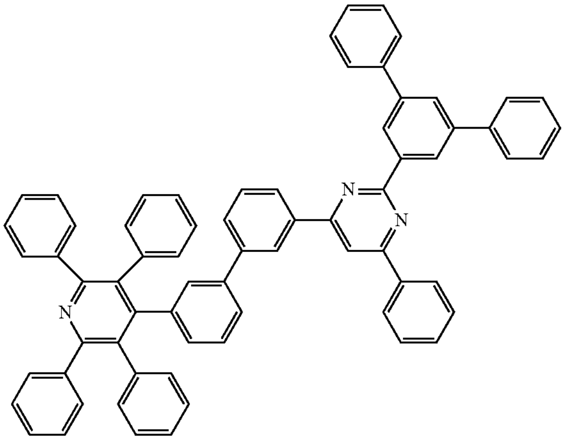
265
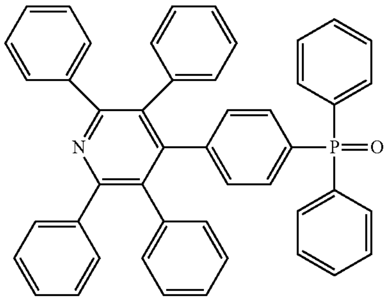
266
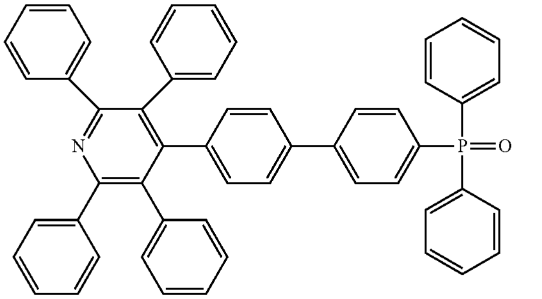
267
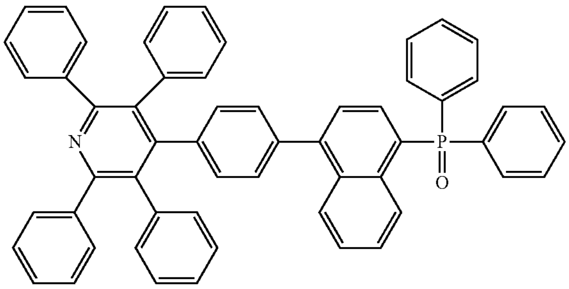

-continued
268
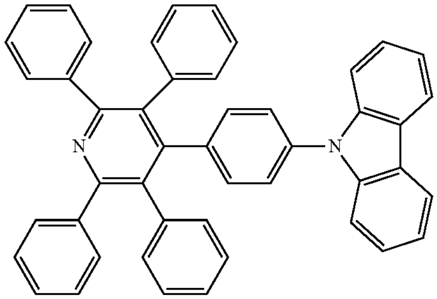
269
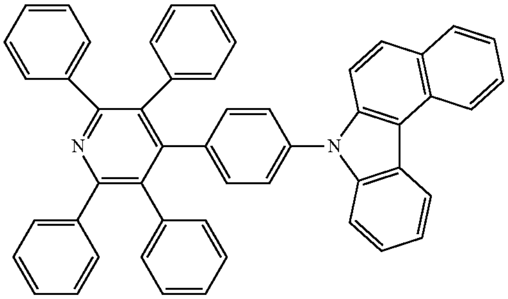
270
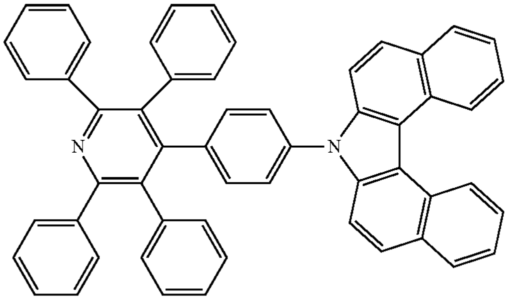
271
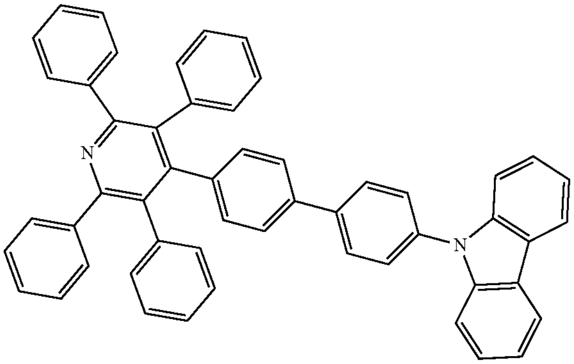
272
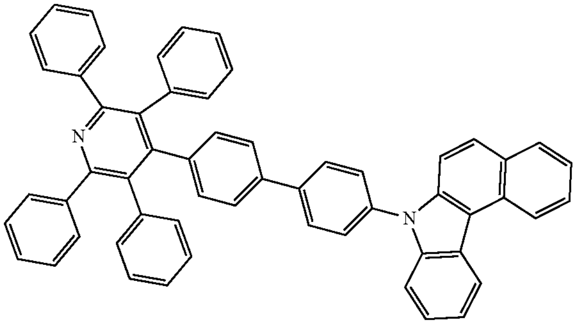
-continued
273
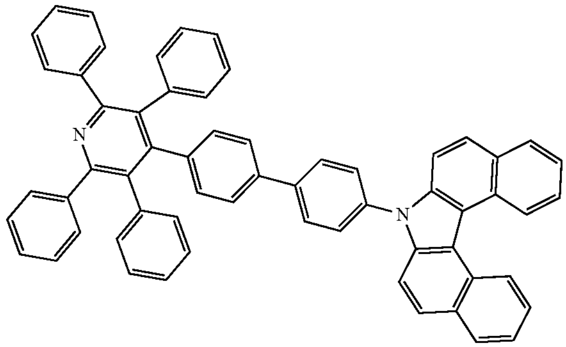
274
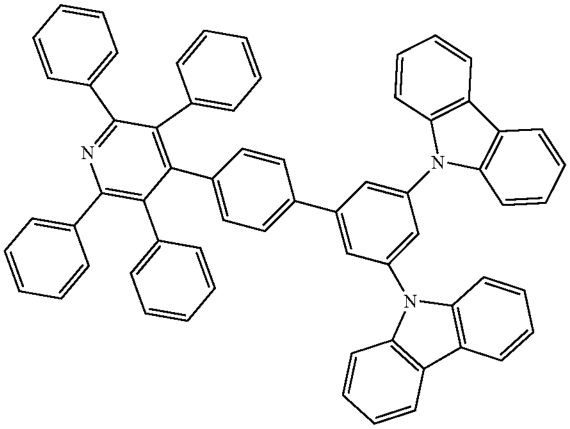
275
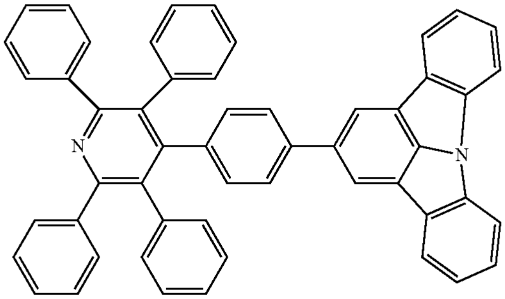
277
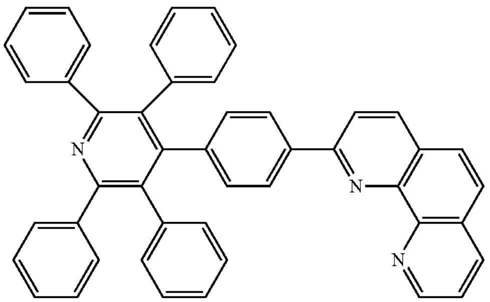

-continued
278
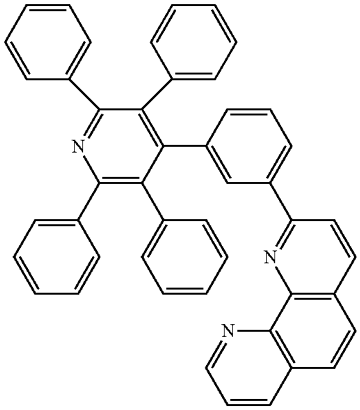
279
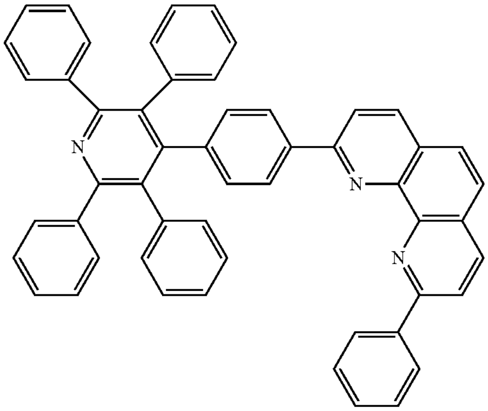
280
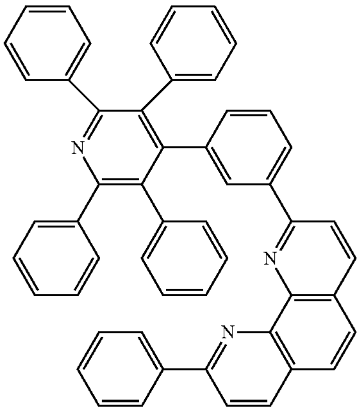
281
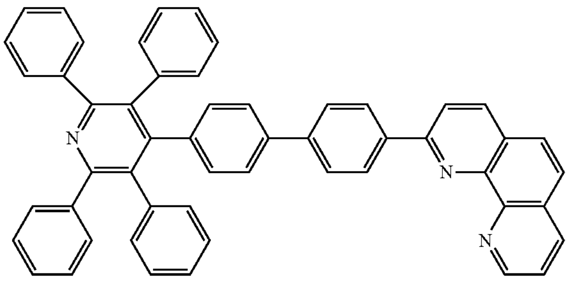
-continued
282
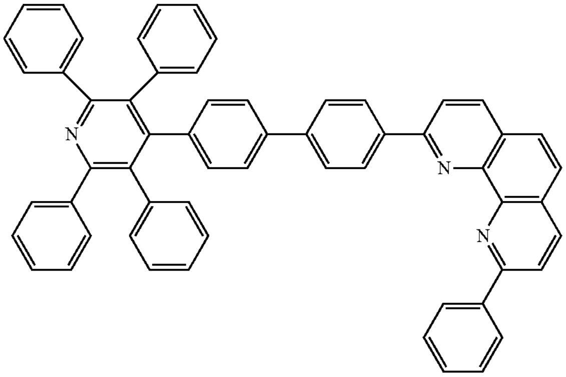
283
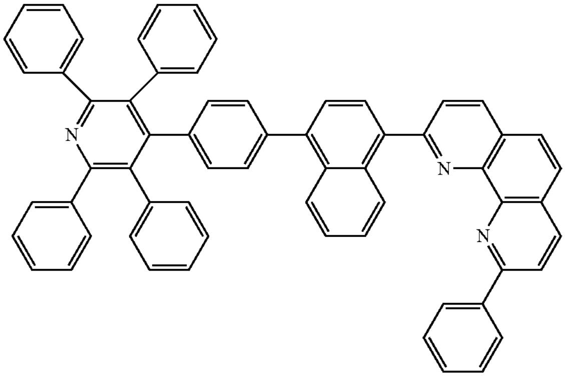
284
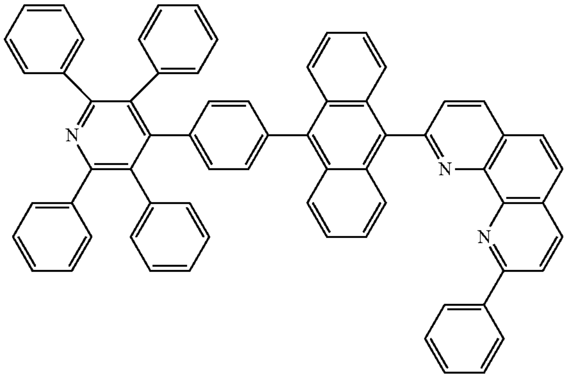

-continued
285
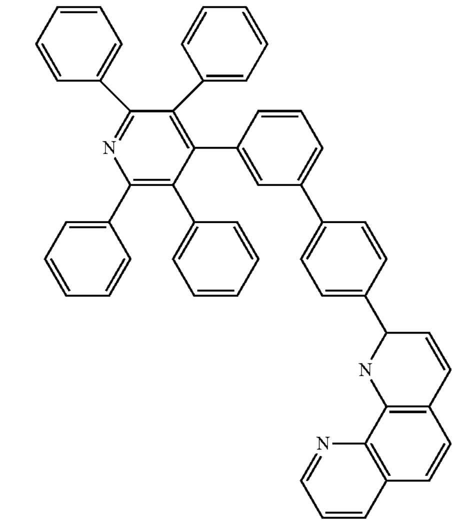
286
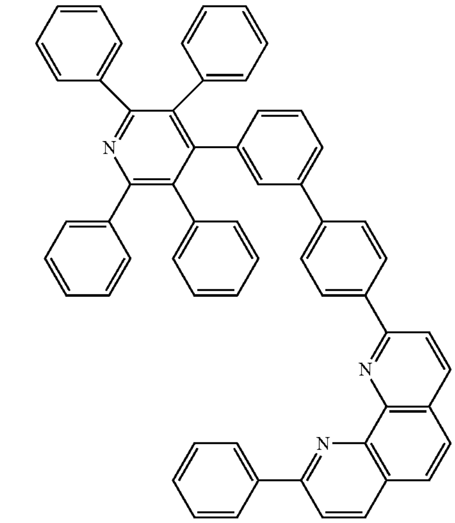
287
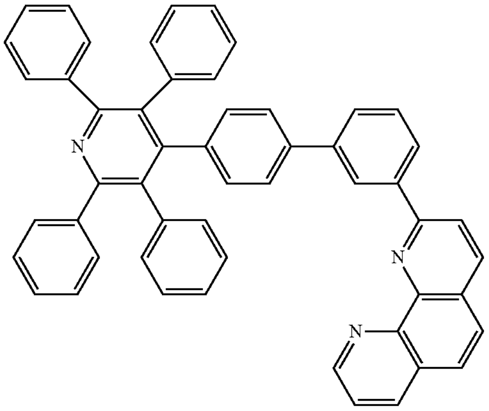
-continued
288
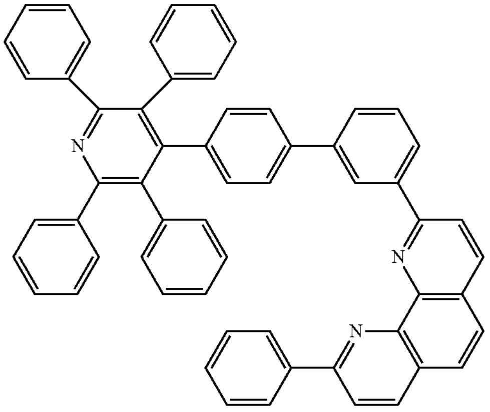
289
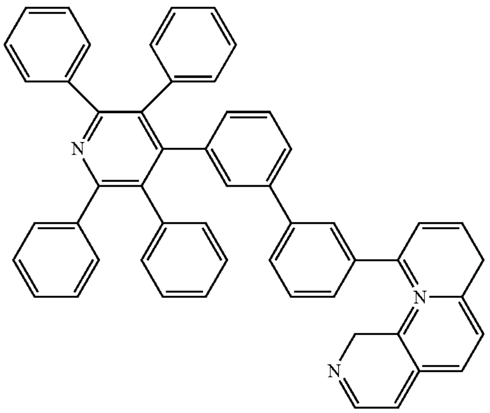
290
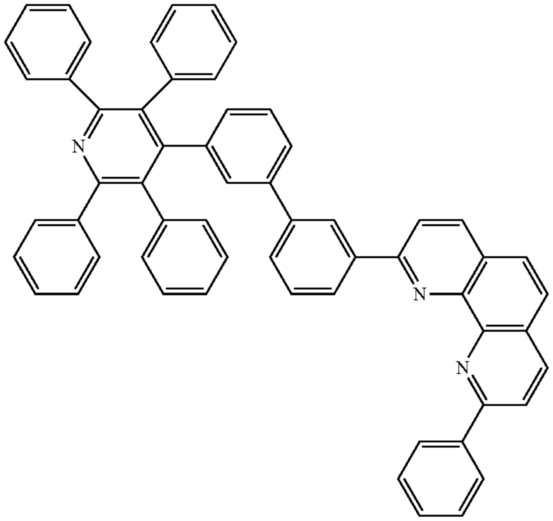
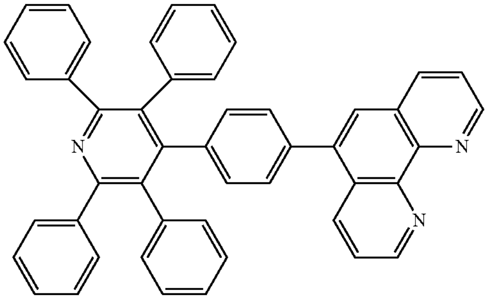

-continued

292

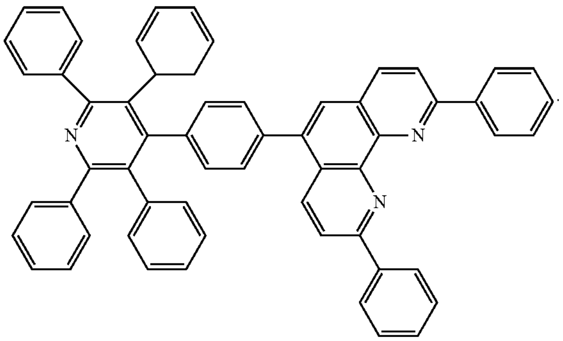

3. An organic light emitting device comprising:

a first electrode;

a second electrode; and one or more organic material layers provided between the first electrode and the second electrode, wherein one or more layers of the organic material layers comprise the heterocyclic compound of claim 1.

4. The organic light emitting device of claim 3, wherein the organic material layer comprises an electron transfer layer, and the electron transfer layer comprises the heterocyclic compound.

5. The organic light emitting device of claim 3, wherein the organic material layer comprises a hole blocking layer, and the hole blocking layer comprises the heterocyclic compound.

6. The organic light emitting device of claim 3, comprising:

the first electrode;

a first stack provided on the first electrode and comprising a first light emitting layer;

a charge generation layer provided on the first stack;

a second stack provided on the charge generation layer and comprising a second light emitting layer; and the second electrode provided on the second stack.

7. The organic light emitting device of claim 6, wherein the charge generation layer comprises the heterocyclic compound.

* * * * *